US012383609B2

(12) United States Patent
Lanzavecchia et al.

(10) Patent No.: US 12,383,609 B2
(45) Date of Patent: Aug. 12, 2025

(54) PLASMODIUM SPOROZOITE NPDP PEPTIDES AS VACCINE AND TARGET NOVEL MALARIA VACCINES AND ANTIBODIES BINDING TO

(71) Applicants: INSTITUTE FOR RESEARCH IN BIOMEDICINE, Bellinzona (CH); SEATTLE CHILDREN'S HOSPITAL, Seattle, WA (US); SCHWEIZERISCHES TROPEN—UND PUBLIC HEALTH-INSTITUT, Basel (CH)

(72) Inventors: Antonio Lanzavecchia, Porza (CH); Joshua Hoong Yu Tan, Shah Alam (MY); Claudia Daubenberger, Mülheim (DE); Brandon Wilder, Seattle, WA (US)

(73) Assignees: Institute for Research in Biomedicine, Bellinzona (CH); Seattle Children's Hospital, Seattle, WA (US); Schweizerisches Tropen-und Public Health-Institut, Basel (CH)

( * ) Notice: Subject to any disclaimer, the term of this patent is extended or adjusted under 35 U.S.C. 154(b) by 0 days.

(21) Appl. No.: 16/606,207

(22) PCT Filed: Apr. 19, 2018

(86) PCT No.: PCT/EP2018/060113
§ 371 (c)(1),
(2) Date: Oct. 17, 2019

(87) PCT Pub. No.: WO2018/193063
PCT Pub. Date: Oct. 25, 2018

(65) Prior Publication Data
US 2020/0093909 A1  Mar. 26, 2020

Related U.S. Application Data

(60) Provisional application No. 62/487,266, filed on Apr. 19, 2017.

(51) Int. Cl.
| | |
|---|---|
| *A61K 39/015* | (2006.01) |
| *A61K 39/00* | (2006.01) |
| *A61P 33/06* | (2006.01) |
| *C07K 16/20* | (2006.01) |

(52) U.S. Cl.
CPC ............ *A61K 39/015* (2013.01); *A61P 33/06* (2018.01); *C07K 16/205* (2013.01); *A61K 2039/505* (2013.01)

(58) Field of Classification Search
CPC . A61K 39/015; A61K 2039/505; A61P 33/06; C07K 16/205
See application file for complete search history.

(56) References Cited

U.S. PATENT DOCUMENTS

| | | | |
|---|---|---|---|
| 4,436,727 A | 3/1984 | Ribi | |
| 4,866,034 A | 9/1989 | Ribi | |
| 4,877,611 A | 10/1989 | Cantrell | |
| 4,912,094 A | 3/1990 | Myers et al. | |
| 5,057,540 A | 10/1991 | Kensil et al. | |
| 6,005,099 A | 12/1999 | Davies et al. | |
| 6,303,347 B1 | 10/2001 | Johnson et al. | |
| 6,764,840 B2 | 7/2004 | Johnson et al. | |
| 8,258,268 B2 | 9/2012 | Wu et al. | |
| 9,181,349 B2 | 11/2015 | Baurin et al. | |
| 9,676,857 B2 | 6/2017 | Dimitrov et al. | |
| 2003/0119733 A1 | 6/2003 | Cerami et al. | |
| 2005/0163783 A1 | 7/2005 | Braslawsky et al. | |
| 2009/0017055 A1 | 1/2009 | Duffy et al. | |
| 2009/0075404 A1 | 3/2009 | Matsunami | |
| 2016/0176955 A1 | 6/2016 | Gutierrez et al. | |
| 2017/0035871 A1 | 2/2017 | Ueno et al. | |
| 2018/0362628 A1* | 12/2018 | Liang | ..................... A61P 33/06 |

FOREIGN PATENT DOCUMENTS

| | | |
|---|---|---|
| CN | 101190946 A | 6/2008 |
| EP | 0 109 942 B1 | 3/1991 |
| EP | 0 362 279 B1 | 1/1995 |
| EP | 0 729 473 B1 | 8/2000 |
| WO | 94/21292 A1 | 9/1994 |
| WO | 95/09917 A1 | 4/1995 |
| WO | 95/14026 A1 | 5/1995 |
| WO | 96/11711 A1 | 4/1996 |

(Continued)

OTHER PUBLICATIONS

Skolnick et al. (Trends in Biotechnology 18: 34-39, 2000).*
Greenspan et al. (Nature Biotechnology 7: 936-937, 1999).*
Giusti et al. (Proc. Natl. Acad. Sci. USA. May 1987; 84 (9): 2926-2930).*
Winkler et al (J. Imm., 265:4505-4514, 2000).*
Sela-Culang et al. (Frontiers in Immunology, 2013 vol. 4, article 302, pp. 1-13).*
Tan et al. (Nature Medicine vol. 24 No. 4, pp. 401-407). (Year: 2018).*
Foquet et al. (Journal of Clinical Investigation, vol. 124 No. 1, pp. 140-144). Jan. 2014.*
Chien et al. (Proc. Natl. Acad. Sci. USA. Jul. 1989; 86 (14): 5532-5536).*

(Continued)

*Primary Examiner* — Robert A Zeman
(74) *Attorney, Agent, or Firm* — Fox Rothschild LLP

(57) ABSTRACT

The present invention provides a fragment of plasmodium circumsporozoite protein according to SEQ ID NO: 1, for example for use in a malaria vaccine. The present invention also provides nucleic acids encoding a fragment of plasmodium circumsporozoite protein according to SEQ ID NO: 1, compositions comprising a fragment of plasmodium circumsporozoite protein according to SEQ ID NO: 1 and antibodies binding to a fragment of plasmodium circumsporozoite protein according to SEQ ID NO: 1. The antibodies according to the present invention bind specifically to P. falciparum sporozoites and may be used in the treatment and/or prevention of malaria.

21 Claims, 8 Drawing Sheets

Specification includes a Sequence Listing.

(56) References Cited

FOREIGN PATENT DOCUMENTS

| WO | 96/33739 | A1 | 10/1996 | | |
|---|---|---|---|---|---|
| WO | 98/50399 | A1 | 11/1998 | | |
| WO | 99/64301 | A1 | 12/1999 | | |
| WO | 00/00462 | A1 | 1/2000 | | |
| WO | 01/46127 | A1 | 6/2001 | | |
| WO | 03/011223 | A2 | 2/2003 | | |
| WO | 03/043572 | A2 | 5/2003 | | |
| WO | 03/099195 | A2 | 12/2003 | | |
| WO | 2008/143954 | A2 | 11/2008 | | |
| WO | 2009/075404 | A1 | 6/2009 | | |
| WO | 2009/099961 | A2 | 8/2009 | | |
| WO | 2010/112193 | A1 | 10/2010 | | |
| WO | 2010/115589 | A1 | 10/2010 | | |
| WO | 2012/051097 | A1 | 4/2012 | | |
| WO | 2012/131555 | A2 | 10/2012 | | |
| WO | 2014/028644 | A1 | 2/2014 | | |
| WO | 2016/087416 | A1 | 6/2016 | | |
| WO | WO-2017163049 | A1 | * | 9/2017 | ........... C07K 16/205 |
| WO | 2017/193032 | A2 | 11/2017 | | |

OTHER PUBLICATIONS

Caldas et al. (Mol. Immunol. May 2003; 39 (15): 941-952).*
Casadevall et al. (PNAS vol. 109 No. 31, pp. 12272-12273). Jul. 31, 2012.*
Charoenvit et al., "Development of Two Monoclonal Antibodies against *Plasmodium falciparum* Sporozoite Surface Protein 2 and Mapping of B-Cell Epitopes," *Infection and Immunity* 65(8):3430-3437, 1997.
Clement et al., "Validation of an enzyme-linked immunosorbent assay for the quantification of human IgG directed against the repeat region of the circumsporozoite protein of the parasite *Plasmodium falciparum,*" *Malaria Journal* 11(384):1-15, 2012.
Foquet et al., "Vaccine-induced monoclonal antibodies targeting circumsporozoite protein prevent *Plasmodium falciparum* infection," *The Journal of Clinical Investigation* 124(1):140-144, 2014.
International Search Report and Written Opinion, dated Dec. 3, 2018, for International Application No. PCT/EP2018/060113, 21 pages.
López et al., "Immunogenicity of Synthetic Peptides Corresponding to the Nonrepeat Regions of the *Plasmodium falciparum* Circumsporozoite Protein," *Vaccines* 96:255-260, 1996.
Peng et al., "Breadth of humoral response and antigenic targets of sporozoite-inhibitory antibodies associated with sterile protection induced by controlled human malaria infection," *Cellular Microbiology* 18(12):1739-1750, 2016.
Swearingen et al., "Interrogating the *Plasmodium* Sporozoite Surface: Identification of Surface-Exposed Proteins and Demonstration of Glycosylation on CSP and TRAP by Mass Spectrometry-Based Proteomics," *PLOS Pathogens,* 2016. (33 pages).
Wilson et al., " Recognition of phage-expressed peptides containing Asx-Pro sequences by monoclonal antibodies produced against *Plasmodium falciparum* circumsporozoite protein," *Protein Engineering* 10(5):531-540, 1997.
Young et al., "Expression of *Plasmodium falciparum* Circumsporozoite Proteins in *Escherichia coli* for the Potential Use in a Human Malaria Vaccine," *Science* 228:958-962, 1985. (6 pages).
"Extract from the Clinical Evaluation Report for blinatumomab," AusPAR Attachment 2, Australian Government, Department of Health, Therapeutic Good Administration, 2018.
Ahmad et al., "scFv Antibody: Principles and Clinical Application," *Clinic Dev Immunol,* 2012, Article ID 980250, 2012.
Beiboer et al., "Guided Selection of a Pan Carcinoma Specific Antibody Reveals Similar Binding Characteristics yet Structural Divergence Between the Original Murine Antibody and its Human Equivalent," *J Mol. Biol.* 296:833-849, 2000.
Brinkmann et al., "The making of bispecific antibodies," *MABS* 9:2, 182-212, 2017.
Du et al. "Engineering Bifunctional Antibodies with Constant Region Fusion Architectures" *JACS* 139(51):18607-18615, 2017).
Giudicelli et al., "IMGT/GENE-DB: a comprehensive database for human and mouse immunoglobulin ant T cell receptor genes" *Nucleic Acids Res.* 33:D256-D261, 2005.
Golay et al. "Design and Validation of a Novel Generic Platform for the Production of Tetravalent IgG1-like Bispecific Antibodies", *J Immunol* 196:3199-3211, 2016.
Janeway's Immunobiology (Murphy, Kenneth and Weaver, Casey, Janeway's Immunobiology, 9th Ed. 2017, Garland Science, pp. 140-148 and 415.
Klimka et al., "Human anti-CD30 recombinant antibodies by guided phage antibody selection using cell panning," *British J. of Cancer,* 83:252-260, 2000.
Muda et al., "Therapeutic assessment of SEED: a new engineered antibody platform designed to generate mono- and bispecific antibodies", *PEDS* 24(5):447-454, 2011.
Product Package Insert, ABECMA® (idecabtagene vicleucel), suspension for intravenous infusion, 2021.
Product Package Insert, BLINCYTO® (blinatumomab) for injection for intravenous use, 2021.
Product Package Insert, BREYANZI® (lisocabtagene maraleucel) suspension for intravenous infusion, 2021.
Product Package Insert, KYMRIAH® (tisagenlecleucel) suspension for intravenous infusion, 2021.
Product Package Insert, TECARTUS™ (brexucabtagene autoleucel) suspension for intravenous infusion, 2021.
Product Package Insert, YESCARTA® (axicabtagene ciloleucel) suspension for intravenous infusion, 2021.
Rader et al. "A phage display approach for rapid antibody humanization: Designed combinatorial V gene libraries," *PNAS USA* 95:8910-8915, 1998.
Tudor et al. "Isotype modulates epitope specificity, affinity, and antiviral activities of anti-HIV-1 human broadly neutralizing 2F5 antibody," *PNAS* 109(31):12680-12685, 2012.
Wozniak-Knopp et al., "An antibody with Fab-constant domains exchanged for a pair of CH3 domains", *PLoS One* 13(4): e0195442, 2018, 19 pages.
Wu et al., "Blinatumomab: a bispecific T cell engage (BiTE) antibody against CD19/CD3 for refractory acute lymphoid leukemia," *J Hematol Oncol*.8(104): 2015, 7 pages.
ASTMH 63rd Annual Meeting, Nov. 2-6, 2014, pp. 491, 1607.
Armour et al., "Recombinant human IgG molecules lacking Fcγ receptor I binding and monocyte triggering activities," *Eur. J. Immunol.* 29:2613-2624, 1999.
Baker et al., "Structures of bovine and human papillomaviruses: Analysis by cryoelectron microscopy and three-dimensional image reconstruction," *Biophys. J.* 60:1445-1456, 1991.
Birkholz et al., "Targeting of DEC-205 on human dendritic cells results in efficient MHC class II-restricted antigen presentation," *Blood* 116(13):2277-2285, 2010.
Burton, "Immunoglobulin G: Functional sites," *Molecular Immunology* 22(3):161-206, 1985.
Capel et al., "Heterogeneity of human IgG Fc receptors," *Immunomethods* 4(1):25-34, 1994.
Casal, "Use of parvovirus-like particles for vaccination and induction of multiple immune responses," *Biotechnology and Applied Biochemistry* 29(2):141-150, 1999.
Chu et al., "Inhibition of B cell receptor-mediated activation of primary human B cells by coengagement of CD19 and FcγIIb with Fc-engineered antibodies," *Molecular Immunology* 45(15):3926-3933, 2008.
Coppi et al., "The *Plasmodium* circumsporozoite protein is proteolytically processed during cell invasion," *JEM* 201(1):27-33, 2005.
Crompton et al., "Malaria Immunity in Man and Mosquito: Insights into Unsolved Mysteries of a Deadly Infectious Disease," *Annu. Rev. Immunol.* 32:157-187, 2014.
De Haas et al., "Fcγ receptors of phagocytes," *J Lab Clin Med.* 126(4):330-341, 1995.
Duncan et al., "The binding site for Clq and IgG," *Nature* 332:738-740, 1988.
Flower, "Designing immunogenic peptides," *Nature Chemical Biology* 9:749-753, 2013.

(56) References Cited

OTHER PUBLICATIONS

Ganesan et al., "FcγRIIb on liver sinusoidal endothelium clears small immune complexes," *J Immunol* 189(10):4981-4988, 2012 (HHS Public Access Author manuscript, available in PMC Apr. 1, 2015)(23 pages).
Gessner et al., "The IgG Fc receptor family," *Ann Hematol* 76:231-248, 1998.
Goldmann et al., "Molecular Cloning and Expression of Major Structural Protein VP1 of the Human Polyomavirus JC Virus: Formation of Virus-Like Particles Useful for Immunological and Therapeutic Studies," *Journal of Virology* 73(5):4465-4469, 1999.
Hagensee et al., "Three-Dimensional Structure of Vaccinia Virus-Produced Human Papillomavirus Type 1 Capsids," *Journal of Virology* 68(7):4503-4505, 1994.
Hurtado et al., "Identification of Domains in Canine Parvovirus VP2 Essential for the Assembly of Virus-Like Particles," *Journal of Virology* 70(8):5422-5429, 1996.
Hutten et al., "CLEC12A-Mediated Antigen Uptake and Cross-Presentation by Human Dendritic Cell Subsets Efficiently Boost Tumor-Reactive T Cell Responses," *J Immunol* 197:2715-2725, 2016.
Huysamen et al., "CLEC9A Is a Novel Activation C-type Lectin-like Receptor Expressed on BDCA3+ Dendritic Cells and a Subset of Monocytes," *The Journal of Biological Chemistry* 283(24):16693-16701, 2008.
Izard et al., "Principles of quasi-equivalence and Euclidean geometry govern the assembly of cubic and dodecahedral cores of pyruvate dehydrogenase complexes," *Proc. Natl. Acad. Sci.* 96:1240-1245, 1999.
Jaoudé et al., "Role of the Antigenic Loop of the Hepatitis B Virus Envelope Proteins in Infectivity of Hepatitis Delta Virus," *Journal of Virology* 79(16):10460-10466, 2005.
Jiang et al., "Heterotypic protection from rotavirus infection in mice vaccinated with virus-like particles," *Vaccine* 17(7-8):1005-1013, 1999.
Kanekiyo et al., "Self-assembling influenza nanoparticle vaccines elicit broadly neutralizing H1N1 antibodies," *Nature* 499:102-106, 2013 (7 pages).
Kang et al., "Development of HIV/AIDS Vaccine Using Chimeric gag-env Virus-Like Particles," *Biological Chemistry* 380(3):353-364, 1999.
Li et al., "Expression and Self-Assembly of Empty Virus-Like Particles of Hepatitis E Virus," *Journal of Virology* 71(10):7207-7213, 1997.
Lohcharoenkal et al., "Protein Nanoparticles as Drug Delivery Carriers for Cancer Therapy," *BioMed Research International* 2014(180549):1-12, 2014.
Menard, "The journey of the malaria sporozite through its hosts: two parasite proteins lead the way," *Microbes and Infection* 2(6):633-642, 2000.
Notka et al., "Construction and Characterization of Recombinant VLPs and Semliki-Forest Virus live Vectors for Comparative Evaluation in the SHIV Monkey Model," *Biological Chemistry* 380(3):341-352, 1999.
Ravetch et al., "Fc Receptors," *Annu. Rev. Immunol.* 9:457-492, 1991.

Salisse et al., "A Functional Essential to Viral Entry Underlies the Hepatitis B Virus "a" Determinant," *Journal of Virology* 83(18):9321-9328, 2009.
Schneider-Ohrum et al., "Virus-like particles for antigen delivery at mucosal surfaces," *Curr Top Microbiol Immunol* 354:53-73, 2012.
Schreibelt et al., "The C-type lectin receptor CLEC9A mediates antigen uptake and cross- presentation by human blood BDCA3+ myeloid dendritic cells," *Blood* 119(10):2284-2292, 2012.
Shields et al., "High Resolution Mapping of the Binding Site on Human IgG1 for FcγRI, FcγRII, FcγRIII, and FcRn and Design of IgG1 Variants with Improved Binding to the FcγR," *The Journal of Biological Chemistry* 276(9):6591-6604, 2001.
Sinnis et al., "Sporozoite antigens: biology and immunology of the circumsporozoite protein and thrombospondin-related anonymous protein," *Chem Immunol.* 80:70-96, 2002.
Sutter et al., "Structural basis of enzyme encapsulation into a bacterial nanocompartment," *Nature Structural & Molecular Biology* 15(9):939-947, 2008.
Urich et al., "X-ray Structure of a Self-Compartmentalizing Sulfur Cycle Metalloenyzme," *Science* 311:996-1000, 2006.
Van de Winkel et al., "Biology of Human Immunoglobulin G Fc Receptors," *Journal of Leukocyte Biology* 49:511-524, 1991.
Vicente et al., "Large-scale production and purification of VLP-based vaccines," *Journal of Invertebrate Pathology* 107:S42-S48, 2011.
Ward et al., "The effector functions of immunoglobulins: implications for therapy," *Therapeutic Immunology* 2:77-94, 1995.
Wines et al., "The IgG Fc Contains Distinct Fc Receptor (FcR) Binding Sites: The Leukocyte Receptors FcγRI and FcγRIIa Bind to a Region in the Fc Distinct from That Recognized by Neonatal FcR and Protein A," *J Immunol* 164:5313-5318, 2000.
Wu, Jingjing, "Blinatumomab: a bispecific T cell engage (BiTE) antibody against CD19/CD3 for refractory acute lymphoid leukemia," *Journal of Hematology & Oncology* 8(104):1-7, 2015.
Zhang et al., "Self-Assembly in the Ferritin Nano-Cage Protein Superfamily," *Int. J. Mol. Sci.* 12:5406-5421, 2011.
Zhang et al., "X-ray structure analysis and crystallographic refinement of lumazine synthase from the hyperthermophile *Aquifex aeolicus* at 1.6A resolution: determinants of the thermostability revealed from structural comparisons," *Journal of Molecular Biology* 306(5):1099-1114, 2001.
Zhu et al., "QS-21: A Potent Vaccine Adjuvant," *Nat Prod Chem Res* 3(4):e113, 2016 (HHS Public Access Author manuscript, available in PMC May 20, 2016)(4 pages).
Espinosa et al., "Proteolytic Cleavage of the Plasmodium falciparum Circumsporozoite Protein is a Target of Protective Antibodies," Journal of Infectious Diseases, Oct. 1, 2015, 212(7):1111-1119, e-published Mar. 11, 2015, (9 pages).
Altshuler et al. "Production of recombinant antibodies and methods for increasing their affinity" [in Russian], Advances in Biological Chemistry, 2010, vol. 50, p. 203 (title page), 215, 216 and 219-228 and the English translation thereof ("Generation of Recombinant Antibodies and Means for Increasing Their Affinity," ISSN 0006-2979, Biochemistry (Moscow), Dec. 2010, vol. 75, No. 13, corresponding pp. 1584 (title page) and 1588-1593, (20 pages).

\* cited by examiner

FIG. 4A

*Plasmodium falciparum* circumsporozoite protein (PfCSP):

MMRKLAILSVSSFLFVEALFQEYQCYGSSSNTRVLNELNYDNAGTNLYNELEMNYYGKQE
NWYSLKKNSRSLGENDDGNNEDNEKLRKPKHKKLKQPADG<u>NPDP</u>NANPNVDPNANPNVD
PNANPNVDPNANPNANPNANPNANPNANPNANPNANPNANPNANPNANPNANPNANPN
ANPNANPNANPNANPNVDPNANPNANPNANPNANPNANPNANPNANPNANPNAN
PNANPNANPNANPNANPNANPNANPNANPNANPNKNNQGNGQGHNMPNDPNRN
VDENANANSAVKNNNNEEPSDKHIKEYLNKIQNSLSTEWSPCSVTCGNGIQVRIKPGSANKP
KDELDYANDIEKKICKMEKCSSVFNVVNSSIGLIMVLSFLFLN (SEQ ID NO.:24)

FIG. 4B

Peptide „22-110"

EYQCYGSSSNTRVLNELNYDNAGTNLYNELEMNYYGKQENWYSLKKNSRSLGENDDGNN
EDNEKLRKPKHKKLKQPADGNPDPNANPNV (SEQ ID NO.:27)

Peptide „NPDP"

KQPADG<u>NPDP</u>NANPNKNN (SEQ ID NO.:23)

Peptide „NANP"

NANPNANPNANPNANPNANPNANPNANPNANPNANP (SEQ ID NO.:26)

FIG. 4C

| Peptide | MGV3 | MGG4 | MGU5 | MGG1 |
|---|---|---|---|---|
| RKPKHKKLKQPADGN (SEQ ID NO.:333) | 0.0 | 0.0 | 0.0 | 0.0 |
| KPKHKKLKQPADGNP (SEQ ID NO.:334) | 0.0 | 0.0 | 0.0 | 0.0 |
| PKHKKLKQPADGNPD (SEQ ID NO.:335) | 65.5 | 0.0 | 0.0 | 0.0 |
| KHKKLKQPADGNPDP (SEQ ID NO.:336) | 353.0 | 0.0 | 0.0 | 0.0 |
| HKKLKQPADGNPDPN (SEQ ID NO.:337) | 65,305.0 | 0.0 | 0.0 | 0.0 |
| KKLKQPADGNPDPNA (SEQ ID NO.:338) | 25,218.8 | 0.0 | 0.0 | 0.0 |
| KLKQPADGNPDPNAN (SEQ ID NO.:339) | 19,858.8 | 14.0 | 0.0 | 49.0 |
| LKQPADGNPDPNANP (SEQ ID NO.:340) | 25,589.0 | 0.0 | 0.0 | 670.0 |
| KQPADGNPDPNANPN (SEQ ID NO.:341) | 16,479.5 | 3,647.5 | 2,858.8 | 131.5 |
| KQPADGNPDPNANPN (SEQ ID NO.:342) | 6,223.5 | 7,415.5 | 8,118.5 | 427.5 |
| QPADGNPDPNANPNV (SEQ ID NO.:343) | 8,418.0 | 7,365.8 | 3,256.5 | 8,164.3 |
| PADGNPDPNANPNVD (SEQ ID NO.:344) | 4,631.0 | 3,931.0 | 4,114.8 | 28,778.5 |
| ADGNPDPNANPNVDP (SEQ ID NO.:345) | 6,963.3 | 8,036.8 | 634.0 | 10,711.3 |
| DGNPDPNANPNVDPN (SEQ ID NO.:346) | 6,128.0 | 5,229.5 | 0.0 | 7,671.5 |
| GNPDPNANPNVDPNA (SEQ ID NO.:347) | 2,726.0 | 3,927.5 | 0.0 | 3,601.5 |
| NPDPNANPNVDPNAN (SEQ ID NO.:348) | 473.0 | 3,717.3 | 89.5 | 6,644.0 |
| PDPNANPNVDPNANP (SEQ ID NO.:349) | 32.0 | 10,003.8 | 4,878.5 | 1,525.0 |
| DPNANPNVDPNANPN (SEQ ID NO.:350) | 0.0 | 11,297.5 | 8,538.5 | 1,718.0 |
| PNANPNVDPNANPNV (SEQ ID NO.:351) | 0.0 | 10,546.8 | 3,049.5 | 14,591.3 |
| NANPNVDPNANPNVD (SEQ ID NO.:352) | 0.0 | 6,409.5 | 3,471.8 | 30,281.5 |
| ANPNVDPNANPNVDP (SEQ ID NO.:353) | 0.0 | 8,800.8 | 1,136.0 | 12,921.0 |
| NPNVDPNANPNVDPN (SEQ ID NO.:354) | 470.5 | 6,690.8 | 150.0 | 7,129.3 |
| PNVDPNANPNVDPNA (SEQ ID NO.:355) | 221.5 | 3,230.5 | 0.0 | 2,247.3 |
| NVDPNANPNVDPNAN (SEQ ID NO.:356) | 0.0 | 3,681.0 | 147.5 | 7,003.0 |
| PNANPNVDPNANPNA (SEQ ID NO.:357) | 0.0 | 12,183.8 | 18,119.5 | 900.0 |
| NANPNVDPNANPNAN (SEQ ID NO.:358) | 0.0 | 10,024.0 | 5,485.8 | 792.0 |
| ANPNVDPNANPNANP (SEQ ID NO.:359) | 0.0 | 8,529.5 | 7,731.8 | 604.5 |
| NPNVDPNANPNANPN (SEQ ID NO.:360) | 0.0 | 13,300.5 | 4,013.5 | 185.0 |
| PNVDPNANPNANPNA (SEQ ID NO.:361) | 0.0 | 13,697.0 | 11,744.0 | 118.0 |
| NVDPNANPNANPNAN (SEQ ID NO.:362) | 0.0 | 10,949.5 | 2,358.5 | 63.0 |
| VDPNANPNANPNANP (SEQ ID NO.:363) | 0.0 | 9,428.5 | 3,599.5 | 244.0 |
| DPNANPNANPNANPN (SEQ ID NO.:364) | 0.0 | 14,818.8 | 2,083.5 | 19.0 |
| PNANPNANPNANPNA (SEQ ID NO.:365) | 0.0 | 18,444.0 | 9,874.3 | 88.5 |
| NANPNANPNANPNAN (SEQ ID NO.:366) | 0.0 | 14,367.5 | 1,897.8 | 73.5 |
| ANPNANPNANPNANP (SEQ ID NO.:367) | 0.0 | 11,851.3 | 3,748.8 | 363.0 |
| NPNANPNANPNANPN (SEQ ID NO.:368) | 0.0 | 18,170.8 | 2,888.8 | 70.0 |
| PNANPNANPNANPNV (SEQ ID NO.:369) | 0.0 | 18,711.0 | 5,521.5 | 457.5 |
| NANPNANPNANPNVD (SEQ ID NO.:370) | 0.0 | 17,796.3 | 1,708.5 | 8,856.0 |
| ANPNANPNANPNVDP (SEQ ID NO.:371) | 0.0 | 12,414.8 | 620.0 | 18,103.3 |
| NPNANPNANPNVDPN (SEQ ID NO.:372) | 0.0 | 12,595.5 | 0.0 | 18,009.5 |
| PNANPNANPNVDPNA (SEQ ID NO.:373) | 0.0 | 12,657.3 | 57.0 | 5,421.5 |
| NANPNANPNVDPNAN (SEQ ID NO.:374) | 256.3 | 6,398.5 | 0.0 | 1,778.8 |
| ANPNANPNVDPNANP (SEQ ID NO.:375) | 310.0 | 7,064.0 | 65.5 | 5,238.5 |
| NPNANPNVDPNANPN (SEQ ID NO.:376) | 95.5 | 13,513.0 | 3,525.0 | 750.8 |
| PNANPNANPNANPNK (SEQ ID NO.:377) | 0.0 | 36,510.0 | 15,806.3 | 29.5 |
| NANPNANPNANPNKN (SEQ ID NO.:378) | 0.0 | 22,891.0 | 1,523.3 | 2.0 |
| ANPNANPNANPNKNN (SEQ ID NO.:379) | 0.0 | 18,718.0 | 2,221.8 | 0.0 |
| NPNANPNANPNKNNQ (SEQ ID NO.:380) | 0.0 | 12,025.8 | 360.0 | 0.0 |
| PNANPNANPNKNNQG (SEQ ID NO.:381) | 0.0 | 2,272.5 | 4.5 | 0.0 |
| NANPNANPNKNNQGN (SEQ ID NO.:382) | 0.0 | 243.5 | 0.0 | 0.0 |
| ANPNANPNKNNQGNG (SEQ ID NO.:383) | 0.0 | 68.5 | 0.0 | 0.0 |
| NPNANPNKNNQGNGQ (SEQ ID NO.:384) | 0.0 | 23.0 | 0.0 | 0.0 |
| PNANPNKNNQGNGQG (SEQ ID NO.:385) | 0.0 | 0.0 | 0.0 | 0.0 |

FIG. 6

PLASMODIUM SPOROZOITE NPDP PEPTIDES AS VACCINE AND TARGET NOVEL MALARIA VACCINES AND ANTIBODIES BINDING TO

STATEMENT OF GOVERNMENT INTEREST

This invention was made with government support under AI 114113 awarded by the National Institutes of Health. The government has certain rights in the invention.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 930485_411USPC_SEQUENCE_LISTING.txt. The text file is 129 KB, was created on Mar. 5, 2021, and is being submitted electronically via EFS-Web.

The present invention relates to the field of malaria medication, in particular to malaria vaccination and to antibodies binding to *Plasmodium* sporozoites, in particular to *Plasmodium* circumsporozoite protein.

Malaria is a mosquito-borne infectious disease affecting humans and other animals caused by parasitic protozoans of the genus *Plasmodium*. The genus *Plasmodium* includes about 200 species with five species regularly infecting humans, while other species infect birds, reptiles, rodents and various primates. *P. falciparum, P. vivax, P. ovale*, and *P. malariae* together account for nearly all human infections with *Plasmodium* species, with *P. falciparum* accounting for the overwhelming majority of malaria deaths. Malaria symptoms typically include fever, feeling tired, vomiting, and headaches. In severe cases it can cause yellow skin, seizures, coma, or death.

Malaria is most commonly transmitted by an infected female *Anopheles* mosquito. The mosquito bite introduces the parasites from the mosquito's saliva into a person's blood. Namely, during a *Plasmodium falciparum* infection, the female *Anopheles* mosquito injects a small number of sporozoites (~10-100) into the skin, after which they travel to the liver to invade hepatocytes (Crompton et al. (2014) *Annu Rev Immunol* 32, 157-187). In hepatocytes the sporozoites reproduces asexually (tissue schizogony), producing thousands of merozoites. These infect new red blood cells and initiate a series of asexual multiplication cycles (blood schizogony) that produce 8 to 24 new infective merozoites, at which point the cells burst and the infective cycle begins anew. Other merozoites develop into immature gametocytes, which are the precursors of male and female gametes. When a fertilized mosquito bites an infected person, gametocytes are taken up with the blood and mature in the mosquito gut.

The male and female gametocytes fuse and form an ookinete—a fertilized, motile zygote. Ookinetes develop into new sporozoites that migrate to the insect's salivary glands, ready to infect a new vertebrate host.

Although sporozoites are not associated with clinical symptoms, this is a time when parasite numbers in the host are low and their eradication can completely abrogate infection. Accordingly, the sporozoite and liver stages of the *P. falciparum* parasite are key targets of current malaria vaccine candidates, as a vaccine that successfully protects against these stages would be able to prevent both malaria infection and transmission. Therefore, subunit vaccines based on circumsporozoite protein (CSP), such as RTS,S, are at the center of the malaria vaccine effort.

The *Plasmodium* circumsporozoite protein (CSP) is an approximately 42 kD soluble protein that can readily be made using an *E. coli* expression system. CSP is a secreted protein of the sporozoite stage of *Plasmodium*. CSP forms a dense coat on the parasite surface and has been hypothesized to mediate many of the initial interactions between the sporozoite and its two hosts (Ménard R., 2000, *Microbes Infect.* 2:633-642; Sinnis P. and Nardin E., 2002, Sporozoite antigens: biology and immunology of the circumsporozoite protein and thrombospondin related anonymous protein. In Malaria Immunology. P. Perlmann and M. Troye-Blomberg, editors. S. Karger AG, Basel, Switzerland. 70-96). The structure and function of CSP is highly conserved across the various strains of malaria that infect humans, non-human primates and rodents. The amino-acid sequence of CSP comprises an immunodominant central repeat region, that is diverse across *Plasmodium* species (NANP-repeat region in case of *P. falciparum*). Flanking the repeats are two conserved motifs at the N- and C-termini, namely region I, a 5-aa sequence at the N terminus of the repeats, and a known cell-adhesive motif C-terminal to the repeats termed the type I thrombospondin repeat (TSR). Those conserved motifs are implicated in protein processing as the parasite travels from the mosquito to the mammalian vector.

CSP is known to play a crucial role in the migration of the sporozoites from the midgut walls of infected mosquitoes to the mosquito salivary glands. Additionally, CSP is involved in hepatocyte binding in the mammalian host with the N-terminus and central repeat region of CSP initially facilitate parasite binding. On the hepatocyte surface proteolytic cleavage at region 1 of the N-terminus exposes the adhesive domain of the C-terminus, thereby priming the parasites for invasion of the liver (Coppi et al. (2005) *J Exp Med* 201, 27-33).

At present, the leading malaria vaccine is RTS,S/AS01 (trade name Mosquirix), which is a recombinant protein-based malaria vaccine. RTS,S is a hybrid protein particle, formulated in a multi-component adjuvant named AS01. The RTS,S vaccine antigen consists of 19 NANP amino acid repeat units followed by the complete C-terminal domain minus the GPI anchor of the CS antigen, fused to the Hepatitis B virus S protein. The S protein corresponds to the surface antigen of Hepatitis B virus (HBsAg). Approved for use by European regulators in July 2015, it is not only the world's first licensed malaria vaccine, but the first vaccine licensed for use against a parasitic disease of any kind. Even though RTS,S causes the production of antibodies capable of preventing the invasion of hepatocytes and additionally elicits a cellular response enabling the destruction of infected hepatocytes, RTS,S presented problems in trials due to its poor immunogenicity. RTS,S attempted to avoid these by fusing the protein with a surface antigen from hepatitis B, hence creating a more potent and immunogenic vaccine. Moreover, the RTS,S protein had to be formulated in the potent adjuvant AS01, a liposome-based formulation comprising the immunostimulants monophosphoryl lipid A (MPL, a toll-like receptor 4 agonist) and QS-21 (a derivative of Quill A). However, the level of efficacy of RTS,S/AS01 remained behind expectations. In particular, the protective effect of the vaccine is known to decline rapidly after vaccination. The effects of a booster dose were positive, even though overall efficacy seem to wane with time. After four years reductions were 36 percent for children who received three shots and a booster dose. Missing the booster dose reduced the efficacy against severe malaria to a negligible effect. The vaccine was shown to be less effective for infants. Three doses of vaccine plus a booster reduced the risk of clinical episodes by 26 percent over three years, but offered no significant protection against severe malaria.

Moreover, another factor that has complicated the development of such vaccines is the difficulty in identifying robust correlates of protection. Antibodies have been shown to inhibit sporozoite invasion of hepatocytes in in vitro functional assays, but their role in the protection of malaria-vaccinated individuals remains unclear.

Accordingly, there is still a need of a more potent malaria vaccine preventing malaria infection and transmission. Moreover, there is still a need of specific antibodies, in particular of antibodies potently inhibiting sporozoite invasion and liver stage parasite multiplication in vivo.

In view of the above, it is the object of the present invention to overcome the drawbacks of current malaria antibodies and vaccines outlined above. In particular, it is the object of the present invention to provide a malaria vaccine, which is superior to the malaria vaccines of the prior art, for example due to its potency. Moreover, it is an object of the present invention to provide antibodies, which are superior to the malaria antibodies of the prior art, for example by potently inhibiting sporozoite invasion and liver stage parasite multiplication in vivo.

This object is achieved by means of the subject-matter set out below and in the appended claims.

Although the present invention is described in detail below, it is to be understood that this invention is not limited to the particular methodologies, protocols and reagents described herein as these may vary. It is also to be understood that the terminology used herein is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements may be listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Throughout this specification and the claims which follow, unless the context requires otherwise, the term "comprise", and variations such as "comprises" and "comprising", will be understood to imply the inclusion of a stated member, integer or step but not the exclusion of any other non-stated member, integer or step. The term "consist of" is a particular embodiment of the term "comprise", wherein any other non-stated member, integer or step is excluded. In the context of the present invention, the term "comprise" encompasses the term "consist of". The term "comprising" thus encompasses "including" as well as "consisting" e.g., a composition "comprising" X may consist exclusively of X or may include something additional e.g., X+Y.

The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. No language in the specification should be construed as indicating any non-claimed element essential to the practice of the invention.

The word "substantially" does not exclude "completely" e.g., a composition which is "substantially free" from Y may be completely free from Y. Where necessary, the word "substantially" may be omitted from the definition of the invention.

The term "about" in relation to a numerical value x means x±10%.

The term "disease" as used herein is intended to be generally synonymous, and is used interchangeably with, the terms "disorder" and "condition" (as in medical condition), in that all reflect an abnormal condition of the human or animal body or of one of its parts that impairs normal functioning, is typically manifested by distinguishing signs and symptoms, and causes the human or animal to have a reduced duration and/or quality of life.

As used herein, reference to "treatment" of a subject or patient is intended to include prevention, prophylaxis, attenuation, amelioration and therapy. The terms "subject" or "patient" are used interchangeably herein to mean all mammals including humans. Examples of subjects include humans, cows, dogs, cats, horses, goats, sheep, pigs, and rabbits. Preferably, the subject or patient is a human.

As used herein, the terms "peptide", "polypeptide", and "protein" are used interchangeably. The terms "peptide", "polypeptide", and "protein" and variations of these terms typically refer to a molecule, in particular a peptide, an oligopeptide, a polypeptide or a protein, such as a fusion protein, comprising at least two amino acids joined to each other by a normal peptide bond, or by a modified peptide bond, such as for example in the cases of isosteric peptides. For example, a "classical" peptide, polypeptide or protein is typically composed of amino acids selected from the 20 amino acids defined by the genetic code, linked to each other by a normal peptide bond. A peptide, polypeptide or protein can be composed of L-amino acids and/or D-amino acids. Preferably, a peptide, polypeptide or protein is either (entirely) composed of L-amino acids or (entirely) of D-amino acids. In particular, the terms "peptide", "polypeptide", "protein" also include "peptidomimetics" which are defined as peptide analogs containing non-peptidic structural elements, which peptides are capable of mimicking or antagonizing the biological action(s) of a natural parent peptide. A peptidomimetic lacks classical peptide characteristics such as enzymatically scissile peptide bonds. In particular, a peptide, polypeptide or protein may comprise amino acids other than the 20 amino acids defined by the genetic code in addition to these amino acids, or it can be composed of amino acids other than the 20 amino acids defined by the genetic code. In particular, a peptide, polypeptide or protein in the context of the present invention can equally be composed of amino acids modified by natural processes, such as post-translational maturation processes or by chemical processes, which are well known to a person skilled in the art. Such modifications are fully detailed in the literature. These modifications can appear anywhere in the polypeptide: in the peptide skeleton, in the amino acid chain or even at the carboxy- or amino-terminal ends. In particular, a peptide or polypeptide can be branched following an ubiquitination or be cyclic with or without branching. This type of modification can be the result of natural or synthetic post-translational processes that are well known to a person skilled in the art. The terms "peptide", "polypeptide", "protein" in the context of the present invention in particular also include modified peptides, polypeptides and proteins. For example, peptide, polypeptide or protein modifications can include acetylation, acylation, ADP-ribosylation, amidation, covalent fixation of a nucleotide or of a nucleotide derivative, covalent fixation of a lipid or of a lipidic derivative, the covalent fixation of a phosphatidylinositol, covalent or non-covalent cross-linking, cyclization, disulfide bond formation, demethylation, glycosylation including pegylation, hydroxylation, iodization, methylation, myristoylation, oxidation, proteolytic processes, phosphorylation, prenylation, racemization, seneloylation, sulfatation, amino acid addition such as arginylation or ubiquitination. Such modifications are fully detailed in the literature (Proteins Structure and Molecular Properties (1993) 2nd Ed., T. E. Creighton, New York; Post-translational Covalent Modifications of Proteins (1983) B. C. Johnson, Ed., Academic Press, New York; Seifter et al. (1990) Analysis for protein modifications and nonprotein cofactors, Meth. Enzymol. 182: 626-646 and Rattan et al., (1992) Protein Synthesis: Post-translational Modifications and Aging, Ann NY Acad Sci, 663: 48-62). Accordingly, the terms "peptide", "polypeptide", "protein" preferably include for example lipopeptides, lipoproteins, glycopeptides, glycoproteins and the like.

As used herein a "(poly)peptide" comprises a single chain of amino acid monomers linked by peptide bonds as explained above. A "protein", as used herein, comprises one or more, e.g. 1, 2, 3, 4, 5, 6, 7, 8, 9 or 10 (poly)peptides, i.e. one or more chains of amino acid monomers linked by peptide bonds as explained above. Preferably, a protein according to the present invention comprises 1, 2, 3, or 4 polypeptides.

The term "recombinant protein", as used herein, refers to any protein which is prepared, expressed, created or isolated by recombinant means, and which is in particular not occurring in nature.

As used herein, the term "antibody" encompasses various forms of antibodies including, without being limited to, whole antibodies, antibody fragments, in particular antigen binding fragments, human antibodies, chimeric antibodies, humanized antibodies, recombinant antibodies and genetically engineered antibodies (variant or mutant antibodies) as long as the characteristic properties according to the invention are retained. Human antibodies and monoclonal antibodies are preferred and especially preferred are human monoclonal antibodies, in particular as recombinant human monoclonal antibodies.

Human antibodies are well-known in the art (van Dijk, M. A., and van de Winkel, J. G., Curr. Opin. Chem. Biol. 5 (2001) 368-374). In particular, human antibodies can also be produced in transgenic animals (e.g., mice) that are capable, upon immunization, of producing a full repertoire or a selection of human antibodies in the absence of endogenous immunoglobulin production. Transfer of the human germ-line immunoglobulin gene array in such germ-line mutant mice will result in the production of human antibodies upon antigen challenge (see, e.g., Jakobovits, A., et al., Proc. Natl. Acad. Sci. USA 90 (1993) 2551-2555; Jakobovits, A., et al., Nature 362 (1993) 255-258; Bruggemann, M., et al., Year Immunol. 7 (1993) 3340). Human antibodies can also be produced in phage display libraries (Hoogenboom, H. R., and Winter, G., J. Mol. Biol. 227 (1992) 381-388; Marks, J. D., et al., J. Mol. Biol. 222 (1991) 581-597). The techniques of Cole et al. and Boerner et al. are also available for the preparation of human monoclonal antibodies (Cole et al., Monoclonal Antibodies and Cancer Therapy, Alan R. Liss, p. 77 (1985); and Boerner, P., et al., J. Immunol. 147 (1991) 86-95). Most preferably, human monoclonal antibodies are prepared by using improved EBV-B cell immortalization as described in Traggiai E, Becker S, Subbarao K, Kolesnikova L, Uematsu Y, Gismondo M R, Murphy B R, Rappuoli R, Lanzavecchia A. (2004): An efficient method to make human monoclonal antibodies from memory B cells: potent neutralization of SARS coronavirus. Nat Med. 10(8):871-5. The term "human antibody" as used herein also comprises such antibodies which are modified, e.g. in the variable region, to generate the properties according to the invention as described herein. As used herein, the term "variable region" (variable region of a light chain ($V_L$), variable region of a heavy chain ($V_H$)) denotes each of the pair of light and heavy chains which is involved directly in binding the antibody to the antigen.

Antibodies of the invention can be of any isotype (e.g., IgA, IgG, IgM i.e. an α, γ or μ heavy chain), but will preferably be IgG. Within the IgG isotype, antibodies may be of IgG1, IgG2, IgG3 or IgG4 subclass, whereby IgG1 is preferred. Antibodies of the invention may have a κ or a λ light chain.

Preferably, the antibody according to the present invention, or the antigen binding fragment thereof, is a purified antibody, a single chain antibody, Fab, Fab', F(ab')2, Fv or scFv.

The antibodies of the invention may thus preferably be human antibodies, monoclonal antibodies, human monoclonal antibodies, recombinant antibodies or purified antibodies. The invention also provides fragments of the antibodies of the invention, particularly fragments that retain the antigen-binding activity of the antibodies. Such fragments include, but are not limited to, single chain antibodies, Fab, Fab', F(ab')2, Fv or scFv. Although the specification, including the claims, may, in some places, refer explicitly to antigen binding fragment(s), antibody fragment(s), variant(s) and/or derivative(s) of antibodies, it is understood that the term "antibody" includes all categories of antibodies, namely, antigen binding fragment(s), antibody fragment(s), variant(s) and derivative(s) of antibodies.

As used herein, the terms "antigen binding fragment," "fragment," and "antibody fragment" are used interchangeably to refer to any fragment of an antibody of the invention that retains the antigen-binding activity of the antibody. Examples of antibody fragments include, but are not limited to, a single chain antibody, Fab, Fab', F(ab')$_2$, Fv or scFv. Fragments of the antibodies of the invention can be obtained from the antibodies by methods that include digestion with enzymes, such as pepsin or papain, and/or by cleavage of disulfide bonds by chemical reduction. Alternatively, fragments of the antibodies can be obtained by cloning and expression of part of the sequences of the heavy or light chains. Antibody "fragments" include Fab, Fab', F(ab')2 and Fv fragments. The invention also encompasses single-chain Fv fragments (scFv) derived from the heavy and light chains of an antibody of the invention. For example, the invention includes a scFv comprising the CDRs from an antibody of the invention. Also included are heavy or light chain monomers and dimers, single domain heavy chain antibodies, single domain light chain antibodies, as well as single chain antibodies, e.g., single chain Fv in which the heavy and light chain variable domains are joined by a peptide linker.

Antibody fragments of the invention may impart monovalent or multivalent interactions and be contained in a variety of structures as described above. For instance, scFv molecules may be synthesized to create a trivalent "triabody" or a tetravalent "tetrabody". The scFv molecules may include a domain of the Fc region resulting in bivalent minibodies. In addition, the sequences of the invention may be a component of multispecific molecules in which the sequences of the invention target the epitopes of the invention and other regions of the molecule bind to other targets. Exemplary molecules include, but are not limited to, bispecific Fab2, trispecific Fab3, bispecific scFv, and diabodies (Holliger and Hudson, 2005, *Nature Biotechnology* 9: 1126-1136).

Antibodies according to the present invention may be provided in purified form. Typically, the antibody will be present in a composition that is substantially free of other polypeptides e.g., where less than 90% (by weight), usually less than 60% and more usually less than 50% of the composition is made up of other polypeptides.

Antibodies according to the present invention may be immunogenic in human and/or in non-human (or heterologous) hosts e.g., in mice. For example, the antibodies may have an idiotype that is immunogenic in non-human hosts, but not in a human host. Antibodies of the invention for human use include those that cannot be easily isolated from hosts such as mice, goats, rabbits, rats, non-primate mammals, etc. and cannot generally be obtained by humanization or from xeno-mice.

As used herein, a "neutralizing antibody" is one that can neutralize, i.e., prevent, inhibit, reduce, impede or interfere with, the ability of a pathogen to initiate and/or perpetuate an infection in a host. The terms "neutralizing antibody" and "an antibody that neutralizes" or "antibodies that neutralize" are used interchangeably herein. These antibodies can be used alone, or in combination, as prophylactic or therapeutic agents upon appropriate formulation, in association with active vaccination, as a diagnostic tool, or as a production tool as described herein.

As used herein, the terms "nucleic acid", "nucleic acid molecule" and "polynucleotide" are used interchangeably and are intended to include DNA molecules and RNA molecules. A nucleic acid molecule may be single-stranded or double-stranded, but preferably is double-stranded DNA.

As used herein, the terms "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included. Where distinct designations are intended, it will be clear from the context.

Doses are often expressed in relation to the bodyweight. Thus, a dose which is expressed as [g, mg, or other unit]/kg (or g, mg etc.) usually refers to [g, mg, or other unit] "per kg (or g, mg etc.) bodyweight", even if the term "bodyweight" is not explicitly mentioned.

The terms "binding" and, in particular, "specifically binding" and similar reference does not encompass non-specific sticking.

The term "vaccine" as used herein is typically understood to be a prophylactic or therapeutic material providing at least one antigen, preferably an immunogen. The antigen or immunogen may be derived from any material that is suitable for vaccination. For example, the antigen or immunogen may be derived from a pathogen, such as from bacteria, virus particles or protozoa, parasites etc., or from a tumor or cancerous tissue. The antigen or immunogen can typically stimulate the body's adaptive immune system to provide an adaptive immune response. In particular, an "antigen" or an "immunogen" refers typically to a substance which may be recognized by the immune system, preferably by the adaptive immune system, and which is capable of triggering an antigen-specific immune response, e.g. by formation of antibodies and/or antigen-specific T cells as part of an adaptive immune response. Typically, an antigen may be or may comprise a peptide or protein which may be presented by the MHC to T-cells.

As used herein, "sequence variant" (also referred to as "variant") refers to any alteration in a reference sequence, whereby a reference sequence is any of the sequences listed in the "Tables of Sequences and SEQ ID Numbers" (sequence listing), i.e. SEQ ID NO: 1 to SEQ ID NO: 332. Thus, the term "sequence variant" includes nucleotide sequence variants and amino acid sequence variants. In particular, in a "sequence variant" the functionality (of the reference sequence) is preserved, i.e. the sequence variant is functional (also referred to as "functional sequence variant"). Sequence variants typically maintain the biological function of, for example, the antibody or an antigen/immunogen. In the context of the present invention such a maintained biological function is preferably the binding of the antibody to *P. falciparum* sporozoites, in particular to *Plasmodium* circumsporozoite protein (CSP) or the ability of a peptide/protein to elicit an immune response, in particular the production of antibodies.

Preferred sequence variants are thus functional sequence variants having at least 70%, at least 75%, at least 80%, at least 85%, at least 88%, at least 90%, at least 92%, at least 95%, at least 96%, at least 97%, at least 98% or at least 99% sequence identity to a reference sequence. The phrase "functional sequence variant thereof having at least 70%9, at least 75%, at least 80%, at least 85%, at least 88%, at least 90%, at least 92%, at least 95%, at least 96%, at least 97%, at least 98% or at least 99% sequence identity", as used herein, means (i) that the sequence variant is functional as described herein and (ii) the higher the % sequence identity, the more preferred the sequence variant. In other words, the phrase "functional sequence variant thereof having at least 70%, at least 75%, at least 80%, at least 85%, at least 88%, at least 90%, at least 92%, at least 95%, at least 96%, at least 97%, at least 98% or at least 99% sequence identity", means in particular that the functional sequence variant has at least 70% sequence identity, preferably at least 75% sequence identity, preferably at least 80% sequence identity, more preferably at least 85% sequence identity, more preferably at least 88% sequence identity, even more preferably at least 90% sequence identity, even more preferably at least 92% sequence identity, still more preferably at least 95% sequence identity, still more preferably at least 96% sequence identity, particularly preferably at least 97% sequence identity, particularly preferably at least 98% sequence identity and most preferably at least 99% sequence identity to the respective reference sequence.

Sequence identity is usually calculated with regard to the full length of the reference sequence (i.e. the sequence recited in the application). Percentage identity, as referred to herein, can be determined, for example, using BLAST using the default parameters specified by the NCBI (the National Center for Biotechnology Information; http:// www.ncbi.nlm.nih.gov/) [Blosum 62 matrix; gap open penalty=11 and gap extension penalty=1].

A nucleotide "sequence variant" (i.e., a "sequence variant" of a nucleotide sequence) in the context of a nucleotide sequence has an altered sequence in which one or more of the nucleotides in the reference sequence is deleted, or substituted, or one or more nucleotides are inserted into the sequence of the reference nucleotide sequence. Nucleotides are referred to herein by the standard one-letter designation (A, C, G, or T). Due to the degeneracy of the genetic code, a "sequence variant" of a nucleic acid (nucleotide) sequence can either result in a change in the respective reference amino acid sequence, i.e. in a "sequence variant" of the respective amino acid sequence or not. Preferred sequence variants are such nucleotide sequence variants, which do not result in amino acid sequence variants (silent mutations), but other non-silent mutations are within the scope as well, in particular mutant nucleotide sequences, which result in an amino acid sequence, which is at least 70% identical to the reference sequence, preferably at least 80% identical to the reference sequence, more preferably at least 90% identical, even more preferably at least 95% identical, and particularly preferably at least 99% identical to the reference sequence.

An amino acid "sequence variant" (i.e., a "sequence variant" of an amino acid sequence) in the context of an amino acid has an altered sequence in which one or more of the amino acids in the reference sequence is deleted or substituted, or one or more amino acids are inserted into the sequence of the reference amino acid sequence. As a result of the alterations, the amino acid sequence variant has an amino acid sequence which is at least 70% identical to the reference sequence, preferably at least 80% identical to the reference sequence, more preferably at least 90% identical, even more preferably at least 95% identical, and particularly preferably at least 99% identical to the reference sequence. Variant sequences which are at least 90% identical have no more than 10 alterations, i.e. any combination of deletions, insertions or substitutions, per 100 amino acids of the reference sequence.

In the context of peptides/proteins, a "linear sequence" or a "sequence" is the order of amino acids in a peptide/protein in an amino to carboxyl terminal direction in which residues that neighbor each other in the sequence are contiguous in the primary structure of the peptide/protein.

While it is possible to have non-conservative amino acid substitutions in a "sequence variant", it is preferred in a "sequence variant" that the substitutions are conservative amino acid substitutions, in which the substituting amino acid has similar structural and/or chemical properties as the corresponding substituted amino acid (i.e. the amino acid in the original sequence which was substituted). By way of example, conservative amino acid substitutions involve substitution of one aliphatic or hydrophobic amino acid, e.g. alanine, valine, leucine and isoleucine, with another; substitution of one hydroxyl-containing amino acid, e.g. serine and threonine, with another; substitution of one acidic residue, e.g. glutamic acid or aspartic acid, with another; replacement of one amide-containing residue, e.g. asparagine and glutamine, with another; replacement of one aromatic residue, e.g. phenylalanine and tyrosine, with another; replacement of one basic residue, e.g. lysine, arginine and histidine, with another; and replacement of one small amino acid, e.g., alanine, serine, threonine, methionine, and glycine, with another.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include the fusion to the N- or C-terminus of an amino acid sequence to a reporter molecule or an enzyme.

Importantly, the sequence variants are usually functional sequence variants, i.e. the alterations in the sequence variants do not abolish the functionality of the respective reference sequence as described above. Guidance in determining which nucleotides and amino acid residues, respectively, may be substituted, inserted or deleted without abolishing such functionality are found by using computer programs well known in the art.

As used herein, a nucleic acid sequence or an amino acid sequence "derived from" a designated nucleic acid, peptide, polypeptide or protein refers to the origin of the nucleic acid, peptide, polypeptide or protein. Preferably, the nucleic acid sequence or amino acid sequence which is derived from a particular sequence has an amino acid sequence that is essentially identical to that sequence or a portion thereof, from which it is derived, whereby "essentially identical" includes sequence variants as defined above. Preferably, the nucleic acid sequence or amino acid sequence which is derived from a particular peptide or protein, is derived from the corresponding domain in the particular peptide or protein. Thereby, "corresponding" refers in particular to the same functionality. For example, an "extracellular domain" corresponds to another "extracellular domain" (of another protein), or a "transmembrane domain" corresponds to another "transmembrane domain" (of another protein). "Corresponding" parts of peptides, proteins and nucleic acids are thus easily identifiable to one of ordinary skill in the art. Likewise, sequences "derived from" other sequence are usually easily identifiable to one of ordinary skill in the art as having its origin in the sequence.

Preferably, a nucleic acid sequence or an amino acid sequence derived from another nucleic acid, peptide, polypeptide or protein may be identical to the starting nucleic acid, peptide, polypeptide or protein (from which it is derived). However, a nucleic acid sequence or an amino acid sequence derived from another nucleic acid, peptide, polypeptide or protein may also have one or more mutations relative to the starting nucleic acid, peptide, polypeptide or protein (from which it is derived), in particular a nucleic acid sequence or an amino acid sequence derived from another nucleic acid, peptide, polypeptide or protein may be a functional sequence variant as described above of the starting nucleic acid, peptide, polypeptide or protein (from which it is derived). For example, in a peptide/protein one or more amino acid residues may be substituted with other amino acid residues or one or more amino acid residue insertions or deletions may occur.

As used herein, the term "mutation" relates to a change in the nucleic acid sequence and/or in the amino acid sequence in comparison to a reference sequence, e.g. a corresponding genomic sequence. A mutation, e.g. in comparison to a genomic sequence, may be, for example, a (naturally occurring) somatic mutation, a spontaneous mutation, an induced mutation, e.g. induced by enzymes, chemicals or radiation, or a mutation obtained by site-directed mutagenesis (molecular biology methods for making specific and intentional changes in the nucleic acid sequence and/or in the amino acid sequence). Thus, the terms "mutation" or "mutating" shall be understood to also include physically making a mutation, e.g. in a nucleic acid sequence or in an amino acid sequence. A mutation includes substitution, deletion and insertion of one or more nucleotides or amino acids as well as inversion of several successive nucleotides or amino acids. To achieve a mutation in an amino acid sequence, preferably a mutation may be introduced into the nucleotide sequence encoding said amino acid sequence in order to express a (recombinant) mutated polypeptide. A mutation may be achieved e.g., by altering, e.g., by site-directed mutagenesis, a codon of a nucleic acid molecule encoding one amino acid to result in a codon encoding a different amino acid, or by synthesizing a sequence variant, e.g., by knowing the nucleotide sequence of a nucleic acid molecule encoding a polypeptide and by designing the synthesis of a nucleic acid molecule comprising a nucleotide sequence encoding a variant of the polypeptide without the need for mutating one or more nucleotides of a nucleic acid molecule.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

It is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

The present invention is based, amongst other findings, on the surprising finding of extremely potent antibodies binding to malaria circumsporozoite protein (CSP). In particular, those antibodies were surprisingly found to bind to an epitope on the malaria circumsporozoite protein, which is located in/spanning the junction between the N-terminus and the NANP-repeats, close to the functionally important Region I. Interestingly, that region is not included in the currently only approved malaria vaccine RTS,S/AS01.

Peptide Comprising or Consisting of the Amino Acid According to SEQ ID NO: 1

In a first aspect the present invention provides a peptide comprising or consisting of the amino acid according to SEQ ID NO: 1:

[SEQ ID NO: 1]
NPDP

This motif can be found in the *Plasmodium* circumsporozoite protein C-terminally of region I and N-terminally of the NANP-repeats. Surprisingly it was found that antibodies binding to that motif according to SEQ ID NO: 1 are extremely potent and significantly reduce liver parasite burden (of *Plasmodium* sporozoites) in vivo, indicating the ability of such antibodies to potently inhibit (i) sporozoite invasion and (ii) liver stage parasite multiplication in vivo. Since the peptide according to the present invention is able to give rise to such potent antibodies, it is useful, for example, to generate a potent vaccine against malaria, which leads to inhibition of (i) sporozoite invasion and (ii) liver stage parasite multiplication in vivo. Thereby, not only the disease in an individual can be prevented and/or treated, but also the spreading of the disease in a population can be inhibited.

Preferably, the peptide according to the present invention comprises or consists of an amino acid sequence according to any of SEQ ID NOs: 2-5, preferably the peptide comprises the amino acid sequence according to SEQ ID NO: 5.

For example, the peptide according to the present invention preferably comprises or consists of an amino acid sequence according to SEQ ID NO: 2:

[SEQ ID NO: 2]
NPDPN

For example, the peptide according to the present invention preferably comprises or consists of an amino acid sequence according to SEQ ID NO: 3:

[SEQ ID NO: 3]
NPDPNA

For example, the peptide according to the present invention preferably comprises or consists of an amino acid sequence according to SEQ ID NO: 4:

[SEQ ID NO: 4]
NPDPNAN

More preferably, the peptide according to the present invention comprises or consists of an amino acid sequence according to SEQ ID NO: 5:

[SEQ ID NO: 5]
NPDPNANP

Such a peptide according to SEQ ID NO: 5 comprises, in addition to the motif according to SEQ ID NO: 1, the first "NANP"-sequence (i.e. the very N-terminal part of the NANP-repeats).

Moreover, the peptide according to the present invention may preferably comprise or consist of an amino acid sequence according to any of SEQ ID NOs: 6-22.

For example, the peptide according to the present invention preferably comprises or consists of an amino acid sequence according to SEQ ID NO: 6:

[SEQ ID NO: 6]
NPDPNANPN

For example, the peptide according to the present invention preferably comprises or consists of an amino acid sequence according to SEQ ID NO: 7:

[SEQ ID NO: 7]
GNPDPNANP

For example, the peptide according to the present invention preferably comprises or consists of an amino acid sequence according to SEQ ID NO: 8:

[SEQ ID NO: 8]
GNPDPNANPN

For example, the peptide according to the present invention preferably comprises or consists of an amino acid sequence according to SEQ ID NO: 9:

DGNPDPNANP [SEQ ID NO: 9]

For example, the peptide according to the present invention preferably comprises or consists of an amino acid sequence according to SEQ ID NO: 10:

NPDPNANPNK [SEQ ID NO: 10]

For example, the peptide according to the present invention preferably comprises or consists of an amino acid sequence according to SEQ ID NO: 11:

DGNPDPNANPN [SEQ ID NO: 11]

For example, the peptide according to the present invention preferably comprises or consists of an amino acid sequence according to SEQ ID NO: 12:

GNPDPNANPNK [SEQ ID NO: 12]

For example, the peptide according to the present invention preferably comprises or consists of an amino acid sequence according to SEQ ID NO: 13:

DGNPDPNANPNK [SEQ ID NO: 13]

For example, the peptide according to the present invention preferably comprises or consists of an amino acid sequence according to SEQ ID NO: 14:

ADGNPDPNANPN [SEQ ID NO: 14]

For example, the peptide according to the present invention preferably comprises or consists of an amino acid sequence according to SEQ ID NO: 15:

QPADGNPDPNANPNK [SEQ ID NO: 15]

For example, the peptide according to the present invention preferably comprises or consists of an amino acid sequence according to SEQ ID NO: 16:

ADGNPDPNANPNK [SEQ ID NO: 16]

For example, the peptide according to the present invention preferably comprises or consists of an amino acid sequence according to SEQ ID NO: 17:

PADGNPDPNANPNK [SEQ ID NO: 17]

For example, the peptide according to the present invention preferably comprises or consists of an amino acid sequence according to SEQ ID NO: 18:

ADGNPDPNANPNKN [SEQ ID NO: 18]

For example, the peptide according to the present invention preferably comprises or consists of an amino acid sequence according to SEQ ID NO: 19:

PADGNPDPNANPNKN [SEQ ID NO: 19]

For example, the peptide according to the present invention preferably comprises or consists of an amino acid sequence according to SEQ ID NO: 20:

QPADGNPDPNANPNKN [SEQ ID NO: 20]

For example, the peptide according to the present invention preferably comprises or consists of an amino acid sequence according to SEQ ID NO: 21:

PADGNPDPNANPNKNN [SEQ ID NO: 21]

For example, the peptide according to the present invention preferably comprises or consists of an amino acid sequence according to SEQ ID NO: 22:

QPADGNPDPNANPNKNN [SEQ ID NO: 22]

More preferably, the peptide according to the present invention comprises or consists of an amino acid sequence according to SEQ ID NO: 23 or sharing at least 72%, preferably at least 77%, more preferably at least 83%, even more preferably at least 88%, most preferably at least 94% sequence identity with SEQ ID NO. 23.

KQPADGNPDPNANPNKNN [SEQ ID NO: 23]

In general, the peptide according to the present invention preferably consists of a fragment of *Plasmodium* circumsporozoite protein (CSP), more preferably of a fragment of *Plasmodium falciparum* circumsporozoite protein, or, preferably, shares at least 70%, preferably at least 80%, more preferably at least 90%, even more preferably at least 95%, most preferably at least 98% sequence identity with a fragment of *Plasmodium* circumsporozoite protein (over the entire length of the peptide according to the present invention), more preferably with a fragment of *Plasmodium falciparum* circumsporozoite protein (over the entire length of the peptide according to the present invention). In other words, the peptide preferably either consists of a fragment of *Plasmodium* circumsporozoite protein (CSP), more preferably of a fragment of *Plasmodium falciparum* circumsporozoite protein, or of a (functional) sequence variant thereof as described herein. This means that a particularly preferred peptide (i) comprises a "core" motif according to any of SEQ ID NOs 1-23 as described above, wherein core motifs according to SEQ ID NOs 1 or 5 are particularly preferred, and (ii) "outside" the core motif the peptide is still a sequence variant of CSP as described herein. To this end, sequence identity is calculated over the complete length of the peptide in comparison to a (corresponding) CSP fragment as reference sequence. A preferred CSP reference sequence is the amino acid sequence according to SEQ ID NO: 24. Accordingly, the fragment of *Plasmodium* circumsporozoite protein (as referred to above) is preferably a fragment of SEQ ID NO: 24. The fragment of *Plasmodium* (*falciparum*) circumsporozoite protein (CSP), as referred to above, has preferably a length of at least 8 or 10 amino acids, preferably at least 15 amino acids, preferably at least 20 amino acids, more preferably at least 25 amino acids, more preferably at least 30 amino acids, more preferably at least 40 amino acids, even more preferably at least 50 amino acids, even more preferably at least 75 amino acids, even more preferably at least 100 amino acids, still more preferably at least 150 amino acids, still more preferably at least 200 amino acids, most preferably at least 300 amino acids.

Preferably, the peptide according to the present invention has a length of no more than 380 amino acids, preferably of no more than 350 amino acids, preferably of no more than 320 amino acids, more preferably of no more than 300 amino acids, more preferably of no more than 275 amino acids, more preferably of no more than 250 amino acids, even more preferably of no more than 225 amino acids, even more preferably of no more than 200 amino acids, even more preferably of no more than 200 amino acids, even more preferably of no more than 175 amino acids, still more preferably of no more than 150 amino acids, still more preferably of no more than 125 amino acids, still more preferably of no more than 100 amino acids, particularly preferably of no more than 75 amino acids, and most preferably of no more than 50 amino acids.

More preferably, the peptide according to the present invention has a length from 4 to 380 amino acids, preferably the peptide has a length from 5 to 350 amino acids, preferably the peptide has a length from 5 to 300 amino acids, preferably the peptide has a length from 5 to 250 amino acids, more preferably the peptide has a length from 5 to 200 amino acids, more preferably the peptide has a length from 5 to 150 amino acids, more preferably the peptide has a length from 5 to 100 amino acids, even more preferably the peptide has a length from 6 to 80 amino acids, even more preferably the peptide has a length from 7 to 70 amino acids, even more preferably the peptide has a length from 8 to 60 amino acids, still more preferably the peptide has a length from 9 to 50 amino acids, still more preferably the peptide has a length from 10 to 40 amino acids, still more preferably the peptide has a length from 11 to 30 amino acids, most preferably the peptide has a length from 12 to 25 amino acids.

The peptide according to any one of the previous claims, wherein the peptide is a recombinant peptide. A recombinant peptide is a peptide, which does not occur in nature. For example, the peptide may be modified as described herein, such that the resulting modified peptide is a peptide, which does not occur in nature. This may be achieved either by a non-natural (or synthetic) modification or by a modification, which does in nature not occur at the peptide according to the present invention. Alternatively or additionally, the recombinant peptide may also differ in its length from peptides occurring in nature.

Moreover, the peptide preferably includes one or more mutations in comparison to the corresponding reference fragment of *Plasmodium* circumsporozoite protein (CSP). Preferably, the peptide according to the present invention comprises (i) exactly one or (ii) one or more mutations in comparison to the corresponding reference fragment of *Plasmodium* circumsporozoite protein (CSP). It is also preferred that the peptide according to the present invention comprises (i) exactly two or (ii) two or more mutations in comparison to the corresponding reference fragment of *Plasmodium* circumsporozoite protein (CSP). Preferably, the peptide according to the present invention comprises (i) exactly three or (ii) three or more mutations in comparison to the corresponding reference fragment of *Plasmodium* circumsporozoite protein (CSP). It is also preferred that the peptide according to the present invention comprises (i) exactly four or (ii) four or more mutations in comparison to the corresponding reference fragment of *Plasmodium* circumsporozoite protein (CSP). Preferably, the peptide according to the present invention comprises (i) exactly five or (ii) five or more mutations in comparison to the corresponding reference fragment of *Plasmodium* circumsporozoite protein (CSP). It is also preferred that the peptide according to the present invention comprises (i) exactly six or (ii) six or more mutations in comparison to the corresponding reference fragment of *Plasmodium* circumsporozoite protein (CSP). Preferably, the peptide according to the present invention comprises (i) exactly seven or (ii) seven or more mutations in comparison to the corresponding reference fragment of *Plasmodium* circumsporozoite protein (CSP). It is also preferred that the peptide according to the present invention comprises (i) exactly eight or (ii) eight or more mutations in comparison to the corresponding reference fragment of *Plasmodium* circumsporozoite protein (CSP). Preferably, the peptide according to the present invention comprises (i) exactly nine or (ii) nine or more mutations in comparison to the corresponding reference fragment of *Plasmodium* circumsporozoite protein (CSP). It is also preferred that the peptide according to the present invention comprises (i) exactly ten or (ii) ten or more mutations in comparison to the corresponding reference fragment of *Plasmodium* circumsporozoite protein (CSP). Preferably, the peptide according to the present invention comprises (i) exactly eleven or (ii) eleven or more mutations in comparison to the corresponding reference fragment of *Plasmodium* circumsporozoite protein (CSP). It is also preferred that the peptide according to the present invention comprises (i) exactly twelve or (ii) twelve or more mutations in comparison to the corresponding reference fragment of *Plasmodium* circumsporozoite protein (CSP). Preferably, the peptide according to the present invention comprises (i) exactly thirteen or (ii) thirteen or more mutations in comparison to the corresponding reference fragment of *Plasmodium* circumsporozoite protein (CSP). It is also preferred that the peptide according to the present invention comprises (i) exactly fourteen or (ii) fourteen or more mutations in comparison to the corresponding reference fragment of *Plasmodium* circumsporozoite protein (CSP). Preferably, the peptide according to the present invention comprises (i) exactly fifteen or (ii) fifteen or more mutations in comparison to the corresponding reference fragment of *Plasmodium* circumsporozoite protein (CSP). It is also preferred that the peptide according to the present invention comprises (i) exactly sixteen or (ii) sixteen or more mutations in comparison to the corresponding reference fragment of *Plasmodium* circumsporozoite protein (CSP). Preferably, the peptide according to the present invention comprises (i) exactly seventeen or (ii) seventeen or more mutations in comparison to the corresponding reference fragment of *Plasmodium* circumsporozoite protein (CSP). It is also preferred that the peptide according to the present invention comprises (i) exactly eighteen or (ii) eighteen or more mutations in comparison to the corresponding reference fragment of *Plasmodium* circumsporozoite protein (CSP). Preferably, the peptide according to the present invention comprises (i)

exactly nineteen or (ii) nineteen or more mutations in comparison to the corresponding reference fragment of *Plasmodium* circumsporozoite protein (CSP). It is also preferred that the peptide according to the present invention comprises (i) exactly twenty or (ii) twenty or more mutations in comparison to the corresponding reference fragment of *Plasmodium* circumsporozoite protein (CSP).

Preferably, the peptide according to the present invention comprises 1, 2, 3, 4, or 5 mutations in comparison to the corresponding reference fragment of *Plasmodium* circumsporozoite protein (CSP), more preferably in comparison to the corresponding reference fragment of SEQ ID NO: 24.

The peptide according to the present invention is preferably for use in the prevention and/or treatment of malaria as described herein. In other words, it is preferred that the peptide according to the present invention is used for the manufacture of a medicament, preferably for the prevention and/or treatment of malaria as described herein.

Protein Comprising the Peptide According to the Invention, Virus-Like Particle and Protein Nanoparticle In a further aspect the present invention provides a protein comprising the peptide according to the present invention. Accordingly, the protein may consist of the peptide according to the present invention. However, it is preferred that the protein comprises (i) the peptide according to the present invention and (ii) an additional amino acid sequence, preferably providing a synergistic functionality and/or an additional functionality to the protein. In other words, such an additional amino acid sequence may preferably provide a functionality, in addition to the peptide's functionality (as immunogen/antigen), which is preferably synergistic with to the peptide's functionality (as immunogen/antigen). Non-limiting examples of such functionalities include (i) targeting, e.g. as described below, and (ii) immunogenicity, e.g. as described below.

To this end, the protein according to the present invention is preferably a fusion protein. Fusion proteins typically comprise two or more distinct functionalities. Accordingly, fusion proteins typically comprise "parts" from different sources, for example a fusion protein comprises distinct proteins/peptides encoded by at least two distinct genes or parts of (distinct) genes. Accordingly, fusion proteins may be also referred to as "chimeric proteins". Even though fusion proteins may, in general, occur in nature, e.g., when a complex mutation, such as a chromosomal translocation, tandem duplication, or retrotransposition creates a novel coding sequence containing parts of the coding sequences from two different genes (for example in cancer cells), recombinant fusion proteins (which do not occur in nature) are preferred. Recombinant fusion proteins do not occur in nature in that combination.

For example, the protein according to the present invention may comprise—in addition to the peptide according to the present invention HBsAg or a fragment of HBsAg. HBsAg is the surface antigen of the hepatitis B virus (HBV).

The hepatitis B virus (HBV) consists of (i) an envelope containing three related surface proteins (hepatitis B surface antigen, HBsAg) and lipid and (ii) an icosahedral nucleocapsid enclosing the viral DNA genome and DNA polymerase. The HBV capsid is formed in the cytosol of the infected cell during packaging of an RNA pregenome replication complex and gains the ability to bud during synthesis of the viral DNA genome by reverse transcription of the pregenome in the lumen of the particle. The three HBV envelope proteins S-HBsAg, M-HBsAg, and L-HBsAg shape a complex transmembrane fold at the endoplasmic reticulum, and form disulfide-linked homo- and heterodimers.

A "fragment" of HBsAg typically has a length of at least 5, preferably at least 10 amino acids, preferably at least 15 amino acids, preferably at least 20 amino acids, more preferably at least 25 amino acids, more preferably at least 30 amino acids, more preferably at least 40 amino acids, even more preferably at least 50 amino acids, even more preferably at least 75 amino acids, still more preferably at least 100 amino acids, still more preferably at least 150 amino acids, most preferably at least 200 amino acids. In other words, the longer the fragment, the more preferred.

For example, the fragment of HBsAg may at least contain the antigenic loop region of HBsAg. The envelope of the hepatitis B virus contains three "HBV envelope proteins" (also known as "HBsAg", "hepatitis B surface antigen"): S protein (for "small", also referred to as S-HBsAg), M protein (for "middle", also referred to as M-HBsAg) and L protein (for "large", also referred to as L-HBsAg). S-HBsAg, M-HBsAg and L-HBsAg share the same C-terminal extremity (also referred to as "S domain", 226 amino acids), which corresponds to the S protein (S-HBsAg) and which is crucial for virus assembly and infectivity. S-HBsAg, M-HBsAg and L-HBsAg are synthesized in the endoplasmic reticulum (ER), assembled, and secreted as particles through the Golgi apparatus. The S domain comprises four predicted transmembrane (TM) domains, whereby both, the N-terminus as well as the C-terminus of the S domain are exposed to the lumen. The transmembrane domains TM1 and TM2 are both necessary for cotranslational protein integration into the ER membrane and the transmembrane domains TM3 and TM4 are located in the C-terminal third of the S domain. The "antigenic loop region" of HBsAg is located between the predicted TM3 and TM4 transmembrane domains of the S domain of HBsAg, whereby the antigenic loop region comprises amino acids 101-172 of the S domain, which contains 226 amino acids in total (Salisse J. and Sureau C., 2009, journal of Virology 83: 9321-9328). It is important to note that a determinant of infectivity resides in the antigenic loop region of HBV envelope proteins. In particular, residues between 119 and 125 of the HBsAg contained a CXXC motif, which had been demonstrated to be the most important sequence required for the infectivity of HBV and HDV (Jaoude G A, Sureau C, Journal of Virology, 2005; 79:10460-6).

Preferably, the protein according to the present invention comprises the S domain of HBsAg or a sequence variant thereof as described herein. More preferably, the protein according to the present invention comprises SEQ ID NO: 319 or a sequence variant thereof as described herein:

(SEQ ID NO: 319)
MENITSGFLGPLLVLQAGFFLLTRILTIPQSLDSWWTSLNFLGGTTVCLG

QNSQSPTSNHSPTSCPPTCPGYRWMCLRRFIIFLFILLLCLIFLLVLLDY

QGMLPVCPLIPGSSTTSTGPCRTCMTTAQGTSMYPSCCCTKPSDGNCTCI

PIPSSWAFGKFLWEWASARFSWLSLLVPFVQWFVGLSPTVWLSVIWMMWY

WGPSLYSILSPFLPLLPIFFCLWVYI

SEQ ID NO: 319 shows an exemplified amino acid sequence of an S domain of HBsAg.

Preferably, the protein according to the present invention further comprises targeting moiety, such as a targeting peptide. In general, a targeting peptide is peptide chain that directs the transport of a protein to a specific location, for example to a specific cell type, into cells or to a specific region in the cell, including the nucleus, mitochondria, endoplasmic reticulum (ER), chloroplast, apoplast, peroxisome and plasma membrane. Targeting peptides may optionally be cleaved from the protein, e.g. by signal peptidases, after the proteins are transported to the specific location. Preferred targeting peptides include antibodies and fragments thereof, such as scFV. For example, such antibodies or antibody fragments may be directed to surface molecules of specific cell types.

For example, the targeting peptide may have a length of no more than 1000 amino acids, preferably of no more than 500 amino acids, more preferably of no more than 200 amino acids, even more preferably of no more than 100 amino acids, still more preferably of no more than 80 amino acids, particularly preferably of no more than 70 amino acids and most preferably of no more than 50 amino acids. For example, the targeting peptide may have a length from 3 to 70 amino acids.

Preferably the targeting moiety, in particular the targeting peptide, targets the protein according to the present invention to a specific cell type. More preferably, the targeting moiety, in particular the targeting peptide, targets the protein according to the present invention to antigen-presenting cells, such as to dendritic cells. An antigen-presenting cell (APC) typically displays an antigen complexed with major histocompatibility complexes (MHCs) on their surfaces; a process known as "antigen presentation". T cells may recognize these complexes using their T cell receptors (TCRs). Accordingly, APCs process antigens and present them to T-cells. Antigen-presenting cells are vital for effective adaptive immune response, as the functioning of both cytotoxic and helper T cells is dependent on APCs. Antigen presentation allows for specificity of adaptive immunity and can contribute to immune responses against both intracellular and extracellular pathogens.

Preferably, the targeted APC is a professional APC. Professional antigen-presenting cells specialize in presenting antigen to T cells and are very efficient at internalizing antigens, for example by phagocytosis (macrophages and dendritic cells) or by receptor-mediated endocytosis (B cells), processing the antigen into peptide fragments and then displaying those peptides, bound to a class II MHC molecule, on their membrane. Preferred examples of APCs to be targeted include macrophages, B cells and dendritic cells.

Most preferably, the targeted APC is a dendritic cell (DC). Dendritic cells have the broadest range of antigen presentation and are necessary for activation of naive T cells. DCs present antigen to both helper and cytotoxic T cells. They can also perform cross-presentation, a process by which they present an exogenous antigen on MHC class I molecules to cytotoxic T cells. Cross-presentation allows for the activation of these T cells. Dendritic cells may be recognized by a targeting moiety, such as a targeting peptide, by their specific receptors including DEC-205, Clec9A and Clec12A.

Preferably, the targeting moiety, in particular the targeting peptide, targets DEC-205. DEC-205 is a type I cell surface protein expressed by dendritic cells (DC). Targeting of DEC-205 may be achieved by DEC-205 antibodies or fragments thereof, such as anti-DEC-205scFv, for example as described in Birkholz K. et al., 2010, Blood 116(13): 2277-85 (however, with the peptide according to the present invention as antigen/epitope).

It is also preferred that the targeting moiety, in particular the targeting peptide, targets Clec9A. Clec9A is a group V C-type lectin-like receptor (CTLR) that functions as an activation receptor and is expressed on myeloid lineage cells. In humans, this receptor is selectively expressed by BDCA3(+) myeloid dendritic cells (mDCs), which have been proposed to be the main human cross-presenting mDCs and may represent the human homologue of murine CD8(+) DCs. Targeting of Clec9A may be achieved by a Clec9A antibodies or fragments thereof, for example as described in Huysamen C. et al., 2008, J. Biol. Chem. 283(24):16693-16701 or in Schreibelt G. et al., 2012, Blood 119(10):2284-92.

Preferably, the targeting moiety, in particular the targeting peptide, targets Clec12A. Clec12A (also known as CD371 DCAL-2, MICL or CLL-1), is a 30 kD type II transmembrane protein with extracellular C-type lectin domains, which belongs to the C-type lectin family. Targeting of Clec12A may be achieved by a Clec12A antibodies or fragments thereof, for example as described in Hutten T. J. A. et al., 2016, J. Immunol. 197 (7) 2715-2725.

Accordingly, it is preferred that the targeting moiety, in particular the targeting peptide, targets DEC-205, Clec9A and/or Clec12A. Thereby, the protein is typically directed to dendritic cells, which may then process the protein and present the antigen/immunogen, such as the peptide according to the present invention, in order to trigger an immune response.

It is also preferred that the targeting moiety, in particular the targeting peptide, targets the protein to hepatocytes. To this end, the targeting moiety, in particular the targeting peptide, may comprise, for example, an antibody or a fragment thereof, directed against any specific hepatocyte surface molecule.

It is also preferred that the targeting moiety, in particular the targeting peptide, comprises an N-terminal region of *Plasmodium* circumsporozoite protein, in particular of a *Plasmodium falciparum* circumsporozoite protein. In this context, an N-terminal region of *Plasmodium* circumsporozoite protein may be any fragment of the N-terminus of CSP (wherein the "N-terminus of CSP" extends until the central repeat region/NANP-repeat region of CSP; i.e. the "N-terminus of CSP" refers to all amino acids N-terminal of the central repeat region/NANP-repeat region of CSP), or a sequence variant thereof as described herein. A fragment of the N-terminus of CSP typically has a length of at least 3 amino acids, preferably at least 5 amino acids, more preferably at least 8 amino acids, even more preferably at least 10 amino acids, still more preferably at least 12 amino acids, particularly preferably at least 15 amino acids and most preferably at least 20 amino acids. Preferred fragments and sequence variants thereof provide targeting to hepatocytes. A preferred example of an "N-terminus of CSP" is shown in SEQ ID NO: 320:

(SEQ ID NO: 320)
MMRKLAILSVSSFLFVEALFQEYQCYGSSSNTRVLNELNYDNAGTNLYNE

LEMNYYGKQENWYSLKKNSRSLGENDDGNNEDNEKLRKPKHKKLKQPADG

NPDP

Particularly preferably, the N-terminal region of *Plasmodium* circumsporozoite protein comprises or consists of CSP region I, in particular the N-terminal region of *Plasmodium* circumsporozoite protein thus comprises or consists of an amino acid sequence according to SEQ ID NO: 25.

It is also preferred that the N-terminal region of *Plasmodium* circumsporozoite protein comprises or consists of an amino acid sequence according to SEQ ID NO: 321 or of a sequence variant thereof as described herein:

KKLKQPA (SEQ ID NO: 321)

It is also preferred that the N-terminal region of *Plasmodium* circumsporozoite protein comprises or consists of an amino acid sequence according to SEQ ID NO: 322 or of a sequence variant thereof as described herein:

HKKLKQPAD (SEQ ID NO: 322)

It is also preferred that the N-terminal region of *Plasmodium* circumsporozoite protein comprises or consists of an amino acid sequence according to SEQ ID NO: 323 or of a sequence variant thereof as described herein:

KHKKLKQPADG (SEQ ID NO: 323)

Moreover, the N-terminal region of *Plasmodium* circumsporozoite protein preferably comprises or consists of an amino acid sequence according to SEQ ID NO: 324 or of a sequence variant thereof as described herein:

KHKKLKQP (SEQ ID NO: 324)

It is also preferred that the N-terminal region of *Plasmodium* circumsporozoite protein comprises or consists of an amino acid sequence according to SEQ ID NO: 325 or of a sequence variant thereof as described herein:

RKPKHKKLKQP (SEQ ID NO: 325)

It is also preferred that the N-terminal region of *Plasmodium* circumsporozoite protein comprises or consists of an amino acid sequence according to SEQ ID NO: 326 or of a sequence variant thereof as described herein:

PKHKKLKQPADGN (SEQ ID NO: 326)

It is also preferred that the N-terminal region of *Plasmodium* circumsporozoite protein comprises or consists of an amino acid sequence according to SEQ ID NO: 327 or of a sequence variant thereof as described herein:

KPKHKKLKQPADGNP (SEQ ID NO: 327)

It is also preferred that the N-terminal region of *Plasmodium* circumsporozoite protein comprises or consists of an amino acid sequence according to SEQ ID NO: 328 or of a sequence variant thereof as described herein:

RKPKHKKLKQPADGNPD (SEQ ID NO: 328)

It is also preferred that the N-terminal region of *Plasmodium* circumsporozoite protein comprises or consists of an amino acid sequence according to SEQ ID NO: 329 or of a sequence variant thereof as described herein:

NEKLRKPKHKKLKQP (SEQ ID NO: 329)

It is also preferred that the N-terminal region of *Plasmodium* circumsporozoite protein comprises or consists of an amino acid sequence according to SEQ ID NO: 330 or of a sequence variant thereof as described herein:

NEKLRKPKHKKLKQPADG (SEQ ID NO: 330)

Preferably, the protein according to the present invention protein further comprises an immunogenic peptide. In general, an immunogenic peptide increases the immunogenicity of the peptide according to the present invention. To this end, an immunogenic peptide is, by itself, immunogenic, i.e. able to elicit an immune response. For example, an immunogenic peptide may comprise an antigen/immunogen distinct from the peptide according to the present invention, such as HBsAg as described above. Many immunogenic peptides are known in the art. Moreover, it is well known to the skilled person how immunogenic peptides can be designed, for example as described in Flower D. R., 2013, Nature Chemical Biology 9(12): 749-753: Designing immunogenic peptides.

The protein according to the present invention may further comprise linker sequences, as known in the art, for example "GS-linkers".

The protein according to the present invention has preferably a length of at least 20 amino acids, preferably at least 50 amino acids, preferably at least 60 amino acids, more preferably at least 70 amino acids, more preferably at least 80 amino acids, more preferably at least 90 amino acids, even more preferably at least 100 amino acids, even more preferably at least 150 amino acids, even more preferably at least 200 amino acids, still more preferably at least 250 amino acids, still more preferably at least 300 amino acids, most preferably at least 350 or at least 400 amino acids.

In a further aspect the present invention also provides a virus-like particle comprising the comprising the peptide according to the present invention as described herein or the protein according to the present invention as described herein.

As used herein, a "virus-like particle" (also "VLP") refers in particular to a non-replicating, viral shell, derived from any of several viruses. VLPs are generally composed of one or more viral proteins, such as, but not limited to, those proteins referred to as capsid, coat, shell, surface and/or envelope proteins, or particle-forming polypeptides derived from these proteins. VLPs can form spontaneously upon recombinant expression of the protein in an appropriate expression system. Methods for producing particular VLPs are known in the art.

The presence of VLPs following recombinant expression of viral proteins can be detected using conventional techniques known in the art, such as by electron microscopy, biophysical characterization, and the like. Further, VLPs can be isolated by known techniques, e.g., density gradient centrifugation and identified by characteristic density banding. See, for example, Baker et al. (1991) Biophys. J. 60: 1445-1456; and Hagensee et al. (1994) J. Viral. 68:4503-

4505; Vincente, J Invertebr Pathol., 2011; Schneider-Ohrum and Ross, Curr. Top. Microbial. Immunol., 354: 53073, 2012).

For example, if HBsAg or another viral protein is present at sufficient concentrations, virus-like particles spontaneously assemble without DNA, resulting in a noninfectious immunogenic construct. Coadministration enables activation of the immune system and increases antibody response to the peptide according to the present invention.

A virus-like particle comprising the peptide according to the present invention or the protein according to the present invention as described herein is thus in particular a virus-like particle (VLP) that includes the peptide or the protein according to the present invention, which comprises SEQ ID NO: 1. Preferred embodiments of the VLP comprising the peptide according to the present invention or the protein according to the present invention correspond to preferred embodiments of the peptide according to the present invention or the protein according to the present invention.

In general, VLPs lack the viral components that are required for virus replication and thus represent a highly attenuated form of a virus. The VLP can display a polypeptide (e.g., the peptide according to the present invention or the protein according to the present invention) that is capable of eliciting an immune response to *Plasmodium* when administered to a subject. Virus like particles and methods of their production are known and familiar to the person of ordinary skill in the art, and viral proteins from several viruses are known to form VLPs, including human papillomavirus, HIV (Kang et al., Biol. Chem. 380: 353-64 (1999)), Semliki-Forest virus (Notka et al., Biol. Chem. 380: 341-52 (1999)), human polyomavirus (Goldmann et al., J. Virol. 73: 4465-9 (1999)), rota virus (Jiang et al., Vaccine 17: 1005-13 (1999)), parvovirus (Casal, Biotechnology and Applied Biochemistry, Vol 29, Part 2, pp 141-150 (1999)), canine parvovirus (Hurtado et al., J. Viral. 70: 5422-9 (1996)), hepatitis E virus (Li et al., J. Viral. 71: 35 7207-13 (1997)), and Newcastle disease virus. For example, a chimeric VLP containing the peptide according to the present invention can be a HBsAg-based VLP. The formation of such VLPs can be detected by any suitable technique. Examples of suitable techniques known in the art for detection of VLPs in a medium include, e.g., electron microscopy techniques, dynamic light scattering (DLS), selective chromatographic separation (e.g., ion exchange, hydrophobic interaction, and/or size exclusion chromatographic separation of the VLPs) and density gradient centrifugation.

In a further aspect the present invention also provides a protein nanoparticle comprising the peptide according to the present invention or the protein according to the present invention.

As used herein, a "protein nanoparticle" refers in particular to a multi-subunit, protein-based polyhedron shaped structure. The subunits are each composed of proteins or polypeptides (for example a glycosylated polypeptide), and, optionally of single or multiple features of the following: nucleic acids, prosthetic groups, organic and inorganic compounds. Non-limiting examples of protein nanoparticles include ferritin nanoparticles (see, e.g., Zhang, Y. Int. *J. Mol. Sci.,* 12:5406-5421, 2011, incorporated by reference herein), encapsulin nanoparticles (see, e.g., Sutter et al., *Nature Struct. and Mol. Biol.,* 15:939-947, 2008, incorporated by reference herein), Sulfur Oxygenase Reductase (SOR) nanoparticles (see, e.g., Urich et al., *Science,* 311:996-1000, 2006, incorporated by reference herein), lumazine synthase nanoparticles (see, e.g., Zhang et al., *J. Mol. Biol.,* 306: 1099-1114, 2001) or pyruvate dehydrogenase nanoparticles (see, e.g., Izard et al., PNAS 96:1240-1245, 1999, incorporated by reference herein). Ferritin, encapsulin, SOR, lumazine synthase, and pyruvate dehydrogenase are monomeric proteins that self-assemble into globular protein complexes that in some cases consists of 24, 60, 24, 60, and 60 protein subunits, respectively. Preferably, ferritin, encapsulin, SOR, lumazine synthase, or pyruvate dehydrogenase monomers are linked to the peptide according to the present invention or to the protein according to the present invention and self-assembled into a protein nanoparticle presenting the disclosed antigen/epitope on its surface, which can be administered to a subject to stimulate an immune response to the peptide according to the present invention or to the protein according to the present invention.

A protein nanoparticle particle comprising the immunogen according to the present invention as described herein is thus in particular a protein nanoparticle that includes the peptide according to the present invention or the protein according to the present invention. Preferred embodiments of the protein nanoparticle comprising the peptide according to the present invention or the protein according to the present invention correspond to preferred embodiments of the peptide according to the present invention or of the protein according to the present invention.

For example, the protein nanoparticle may include one or more of any of the disclosed peptides, wherein the protein nanoparticle preferably specifically binds to an antibody according to the present invention as described herein.

Non-limiting example of nanoparticles include ferritin nanoparticles, encapsulin nanoparticles and Sulfur Oxygenase Reductase (SOR) nanoparticles, which are comprised of an assembly of monomeric subunits including ferritin proteins, encapsulin proteins and SOR proteins, respectively. To construct protein nanoparticles including the peptide according to the present invention or the protein according to the present invention, the peptide according to the present invention or the protein according to the present invention is usually linked to a subunit of the protein nanoparticle (such as a ferritin protein, an encapsulin protein or a SOR protein). The fusion protein self-assembles into a nanoparticle under appropriate conditions.

Preferably, the protein nanoparticle is thus a ferritin nanoparticle, an encapsulin nanoparticle, a Sulfur Oxygenase Reductase (SOR) nanoparticle, a lumazine synthase nanoparticle or a pyruvate dehydrogenase nanoparticle. More preferably, the protein nanoparticle is a ferritin nanoparticle.

Ferritin nanoparticles and their use for immunization purposes (e.g., for immunization against influenza antigens) has been disclosed in the art (see, e.g., Kanekiyo et al., Nature, 499: 102-106, 2013, incorporated by reference herein in its entirety). Accordingly, a preferred protein nanoparticle is a ferritin nanoparticle. For example, any of the disclosed immunogens (in particular the peptide according to the present invention or the protein according to the present invention) may be linked to a ferritin polypeptide or hybrid of different ferritin polypeptides to construct a ferritin protein nanoparticle. Accordingly, the protein nanoparticle comprising the peptide according to the present invention or the protein according to the present invention is preferably a ferritin nanoparticle.

Ferritin is a globular protein that is found in all animals, bacteria, and plants, and which acts primarily to control the rate and location of polynuclear $Fe(III)_2O_3$ formation through the transportation of hydrated iron ions and protons to and from a mineralized core. The globular form of ferritin is made up of monomeric subunits, which are polypeptides having a molecule weight of approximately 17-20 kDa. An example of the sequence of one such monomeric subunit is represented by SEQ ID NO: 331:

ferritin polypeptide:
(SEQ ID NO: 331)
MLSKDIIKLLNEQVNKEMNSSNLYMSMSSWCYTHSLDGAGLFLFDHAAEE

YEHAKKLIVFLNENNVPVQLTSISAPEHKFEGLTQIFQKAYEHEQHISES

INNIVDHAIKGKDHATFNFLQWYVAEQHEEEVLFKDILDKIELIGNENHG

LYLADQYVKGIAKSRKS

The globular form of ferritin comprises 24 monomeric, subunit proteins, and has a capsid-like structure having 432 symmetry. Methods of constructing ferritin nanoparticles are known to the person of ordinary skill in the art and are further described herein (see, e.g., Zhang, Int. J. Mol. Sci., 12:5406-5421, 2011, which is incorporated herein by reference in its entirety).

For example, the ferritin polypeptide may be *E. coli* ferritin, *Helicobacter pylori* ferritin, human light chain ferritin, bullfrog ferritin or a hybrid thereof, such as *E. coli*-human hybrid ferritin, *E. coli*-bullfrog hybrid ferritin, or human-bullfrog hybrid ferritin. Exemplary amino acid sequences of ferritin polypeptides and nucleic acid sequences encoding ferritin polypeptides to be combined with the peptide according to the present invention or the protein according to the present invention can be found in GENBANK®, for example at accession numbers ZP 03085328, ZP 06990637, EjB64322. I, AAA35832, NP 000137 AAA49532, AAA49525, AAA49524 and AAA49523, which are specifically incorporated by reference herein in their entirety as available Apr. 19, 2017. Preferably, the peptide according to the present invention or the protein according to the present invention is linked to a ferritin protein including an amino acid sequence at least 80% (such as at least 85%, at least 90%, at least 95%, or at least 97%) identical to amino acid sequence set forth as SEQ ID NO: 331.

Preferably, the ferritin polypeptide is a *Helicobacter pylori* ferritin (such as a ferritin polypeptide set forth as SEQ ID NO: 331). More preferably, the ferritin polypeptide includes a substitution of the cysteine residue at position 31, such as a C31S, C31A or C31V substitution. The peptide according to the present invention or the protein according to the present invention can be linked to a *Helicobacter pylori* ferritin (such as a ferritin polypeptide set forth as SEQ ID NO: 331) that preferably further includes a substitution of the cysteine residue at position 31 of the ferritin polypeptide, such as a C31 S, C31A or C31V substitution.

Preferably, the peptide according to the present invention or the protein according to the present invention may be linked to an encapsulin polypeptide to construct an encapsulin nanoparticle. Accordingly, the protein nanoparticle comprising the peptide according to the present invention or the protein according to the present invention is preferably an encapsulin nanoparticle. Encapsulin proteins are a conserved family of bacterial proteins also known as lincocin-like proteins that form large protein assemblies that function as a minimal compartment to package enzymes. The encapsulin assembly is made up of monomeric subunits, which are polypeptides having a molecule weight of approximately 30 kDa. An example of the sequence of one such monomeric subunit is provided as SEQ ID NO: 332:

encapsulin polypeptide:
(SEQ ID NO: 332)
MEFLKRSFAPLTEKQWQEIDNRAREIFKTQLYGRKFVDVEGPYGWEYAAH

PLGEVEVLSDENEVVKWGLRKSLPLIELRATFTLDLWELDNLERGKPNVD

LSSLEETVRKVAEFEDEVIFRGCEKSGVKGLLSFEERKIECGSTPKDLLE

AIVRALSIFSKDGIEGPYTLVINTDRWINFLKEEAGHYPLEKRVEECLRG

GKIITTPRIEDALVVSERGGDFKLILGQDLSIGYEDREKDAVRLFITETF

TFQVVNPEALILLKF

Following production, the monomeric subunits self-assemble into the globular encapsulin assembly including 60 monomeric subunits. Methods of constructing encapsulin nanoparticles are known to the person of ordinary skill in the art, and further described herein (see, for example, Sutter et al., Nature Struct. and Mol. Biol., 15:939-947, 2008, which is incorporated by reference herein in its entirety). In specific examples, the encapsulin polypeptide is bacterial encapsulin, such as *E. coli* or *Thermotoga maritime* encapsulin.

An exemplary encapsulin sequence to be combined with the peptide according to the present invention or the protein according to the present invention is set forth as SEQ ID NO: 332.

Preferably, the peptide according to the present invention or the protein according to the present invention may be linked to a Sulfur Oxygenase Reductase (SOR) polypeptide to construct a SOR nanoparticle. Accordingly, the protein nanoparticle comprising the peptide according to the present invention or the protein according to the present invention is preferably an SOR nanoparticle. SOR proteins are microbial proteins (for example from the thermoacidophilic archaeon *Acidianus ambivalens* that form 24 subunit protein assemblies. Methods of constructing SOR nanoparticles are known to the person of ordinary skill in the art (see, e.g., Urich et al., Science, 311:996-1000, 2006, which is incorporated by reference herein in its entirety).

Furthermore, the peptide according to the present invention or the protein according to the present invention may also be linked to a Lumazine synthase polypeptide to construct a Lumazine synthase nanoparticle. Accordingly, the protein nanoparticle comprising the peptide according to the present invention or the protein according to the present invention is preferably an Lumazine synthase nanoparticle.

Moreover, the peptide according to the present invention or the protein according to the present invention may also be linked to a pyruvate dehydrogenase polypeptide to construct a pyruvate dehydrogenase nanoparticle. Accordingly, the protein nanoparticle comprising the peptide according to the present invention or the protein according to the present invention is preferably a pyruvate dehydrogenase nanoparticle.

Further preferred examples of protein nanoparticles, and methods for obtaining the same, are disclosed in Warangkana Lohcharoenkal, Liying Wang, Yi Charlie Chen, and Yon Rojanasakul, "Protein Nanoparticles as Drug Delivery Carriers for Cancer Therapy," BioMed Research International, vol. 2014, Article ID 180549, 12 pages, 2014. doi: 10.1155/2014/180549, which is incorporated herein by reference.

Preferably, the peptide according to the present invention or the protein according to the present invention is linked to the N- or C-terminus of a nanoparticle protein, such as a ferritin, encapsulin, SOR, lumazine synthase or pyruvate dehydrogenase protein, for example with a linker, such as a GS-linker known in the art. Constructs are preferably made in HEK 293 cells, in particular since fusion proteins may be secreted from those cells and self-assemble into nanoparticles. The nanoparticles can be purified using known techniques, for example by a few different chromatography procedures, e.g. Mono Q (anion exchange) followed by size exclusion (SUPEROSE® 6) chromatography.

The present invention also provides a fusion protein comprising (i) the peptide according to the present invention and (ii) a monomeric subunit of a nanoparticle protein, such as ferritin, encapsulin, SOR, lumazine synthase or pyruvate dehydrogenase protein, or any portion thereof which is capable of directing self-assembly of monomeric subunits into the globular form of the protein. Amino acid sequences from monomeric subunits of any known nanoparticle protein, such as ferritin, encapsulin, SOR, lumazine synthase or pyruvate dehydrogenase protein, can be used to produce fusion proteins with the peptide according to the present invention or the protein according to the present invention, in particular so long as the monomeric subunit is capable of self-assembling into a nanoparticle displaying the peptide according to the present invention on its surface.

The fusion proteins need not comprise the full-length sequence of a monomeric subunit polypeptide of a nanoparticle protein, such as ferritin, encapsulin, SOR, lumazine synthase or pyruvate dehydrogenase protein. Portions, or regions, of the monomeric subunit polypeptide can be utilized so long as the portion comprises amino acid sequences that direct self assembly of monomeric subunits into the globular form of the protein.

In some embodiments, it may be useful to engineer mutations into the amino acid sequence of the monomeric ferritin, encapsulin, SOR, lumazine synthase or pyruvate dehydrogenase subunits. For example, it may be useful to alter sites such as enzyme recognition sites or glycosylation sites in order to give the fusion protein beneficial properties (e.g., half-life).

It will be understood by those skilled in the art that fusion of the peptide according to the present invention or the protein according to the present invention to the ferritin, encapsulin, SOR, lumazine synthase or pyruvate dehydrogenase protein should be done such that the portion of the fusion protein containing the peptide according to the present invention or the protein according to the present invention does not interfere with self-assembly of the monomeric ferritin, encapsulin, SOR, lumazine synthase or pyruvate dehydrogenase subunits into the globular protein, and that the ferritin, encapsulin, SOR, lumazine synthase or pyruvate dehydrogenase protein portion of the fusion protein does not interfere with the ability of the peptide according to the present invention or the protein according to the present invention to elicit an immune response.

In general, the nanoparticle protein and the peptide according to the present invention or the protein according to the present invention can be joined together directly without affecting the activity of either portion. Alternatively, the nanoparticle protein and the peptide according to the present invention or the protein according to the present invention are joined using a linker (also referred to as a spacer) sequence. For example, the ferritin, encapsulin, SOR, lumazine synthase or pyruvate dehydrogenase protein and the peptide according to the present invention or the protein according to the present invention can be joined together directly without affecting the activity of either portion. Alternatively, the ferritin, encapsulin, SOR, lumazine synthase or pyruvate dehydrogenase protein and the peptide according to the present invention or the protein according to the present invention are joined using a linker (also referred to as a spacer) sequence.

The linker sequence may be designed to position the ferritin, encapsulin, SOR, lumazine synthase or pyruvate dehydrogenase portion of the fusion protein and the portion of the fusion protein containing the peptide according to the present invention or the protein according to the present invention, with regard to one another, such that the fusion protein maintains the ability to assemble into nanoparticles, and also elicits an immune response to *Plasmodium*.

Preferably, the linker sequences comprise amino acids. Preferable amino acids to use are those having small side chains and/or those which are not charged. Such amino acids are less likely to interfere with proper folding and activity of the fusion protein. Accordingly, preferred amino acids to use in linker sequences, either alone or in combination are serine, glycine and alanine. One example of such a linker sequence is SGG. Amino acids can be added or subtracted as needed. Those skilled in the art are capable of determining appropriate linker sequences for construction of protein nanoparticles.

Preferably, the protein nanoparticles has a molecular weight of from 100 to 5000 kDa, such as approximately 500 to 4600 kDa. More preferably, a Ferritin nanoparticle has an approximate molecular weight of about 650 kDa, an Encapsulin nanoparticle has an approximate molecular weight of about 2100 kDa, a SOR nanoparticle has an approximate molecular weight of about 1000 kDa, a lumazine synthase nanoparticle has an approximate molecular weight of about 4000 kDa, and a pyruvate dehydrogenase nanoparticle has an approximate molecular weight of about 4600 kDa, when the protein nanoparticle includes the peptide according to the present invention or the protein according to the present invention.

The peptide according to the present invention or the protein according to the present invention linked to ferritin, encapsulin, SOR, lumazine synthase or pyruvate dehydrogenase proteins can self-assemble into multi-subunit protein nanoparticles, typically termed ferritin nanoparticles, encapsulin nanoparticles, SOR nanoparticles, lumazine synthase nanoparticles, and pyruvate dehydrogenase nanoparticles, respectively. The nanoparticles including the peptide according to the present invention or the protein according to the present invention have substantially the same structural characteristics as the native ferritin, encapsulin, SOR, lumazine synthase or pyruvate dehydrogenase nanoparticles that do not include the peptide according to the present invention or the protein according to the present invention. That is, they contain 24, 60, 24, 60, or 60 subunits (respectively) and have similar corresponding symmetry.

It is also preferred that the peptide according to the present invention, the protein according to the present invention, the virus-like particle according to the present invention, or the protein nanoparticle according to the present invention specifically bind to the antibodies according to the present invention as described below, preferably with a $K_d$ of 1 µM or less.

As used herein, "$K_d$" refers to the dissociation constant for a given interaction, such as a polypeptide-ligand interaction or an antibody-antigen interaction. For example, for the bimolecular interaction of an antibody (such as the antibodies according to the present invention as described below) and an antigen (such as the peptide according to the present invention or the protein according to the present invention), it is the concentration of the individual components of the bimolecular interaction divided by the concentration of the complex. Methods of determining the $K_d$ of an antibody:antigen interaction are familiar to the person of ordinary skill in the art.

Antibodies According to the Present Invention

Antibody Binding to the Peptide According to the Invention

In a further aspect the present invention provides an antibody, or an antigen-binding fragment thereof, that (specifically) binds to a peptide according to the present invention. In other words, the antibody according to the present invention, or the antigen-binding fragment thereof, is able to recognize an epitope, in particular a CSP epitope, which corresponds to the peptide according to the present invention. Accordingly, the antibodies according to the present invention bind to a CSP epitope, which is located at the junction between the N-terminus of CSP and the NANP-repeat region, close to the functionally important region I of CSP.

Antibodies binding to that epitope, and thus to a peptide according to the present invention, were surprisingly found to greatly reduce liver parasite burden in vivo, indicating that such antibodies are able to potently inhibit (i) sporozoite invasion and (ii) liver stage parasite multiplication in vivo. Thereby, not only the disease in an individual can be prevented and/or treated, but also the spreading of the disease in a population can be inhibited.

Preferably, the antibody, or an antigen binding fragment thereof, according to the present invention is a human antibody. It is also preferred that the antibody, or an antigen binding fragment thereof, according to the present invention is a monoclonal antibody, preferably a human monoclonal antibody. Furthermore, it is also preferred that the antibody, or an antigen binding fragment thereof, according to the present invention is a recombinant antibody.

Preferably, the antibody according to the present invention, or an antigen binding fragment thereof, comprises an Fc moiety. More preferably, the Fc moiety is derived from human origin, e.g. from human IgG1, IgG2, IgG3, and/or IgG4, whereby human IgG1 is particularly preferred.

As used herein, the term "Fc moiety" refers to a sequence derived from the portion of an immunoglobulin heavy chain beginning in the hinge region just upstream of the papain cleavage site (e.g., residue 216 in native IgG, taking the first residue of heavy chain constant region to be 114) and ending at the C-terminus of the immunoglobulin heavy chain. Accordingly, an Fc moiety may be a complete Fc moiety or a portion (e.g., a domain) thereof. A complete Fc moiety comprises at least a hinge domain, a CH2 domain, and a CH3 domain (e.g., EU amino acid positions 216-446). An additional lysine residue (K) is sometimes present at the extreme C-terminus of the Fc moiety, but is often cleaved from a mature antibody. Each of the amino acid positions within an Fc moiety have been numbered according to the art-recognized EU numbering system of Kabat, see e.g., by Kabat et al., in "Sequences of Proteins of Immunological Interest", U.S. Dept. Health and Human Services, 1983 and 1987.

Preferably, in the context of the present invention an Fc moiety comprises at least one of: a hinge (e.g., upper, middle, and/or lower hinge region) domain, a CH2 domain, a CH3 domain, or a variant, portion, or fragment thereof. In preferred embodiments, an Fc moiety comprises at least a hinge domain, a CH2 domain or a CH3 domain. More preferably, the Fc moiety is a complete Fc moiety. The Fc moiety may also comprises one or more amino acid insertions, deletions, or substitutions relative to a naturally-occurring Fc moiety. For example, at least one of a hinge domain, CH2 domain or CH3 domain (or portion thereof) may be deleted. For example, an Fc moiety may comprise or consist of: (i) hinge domain (or portion thereof) fused to a CH2 domain (or portion thereof), (ii) a hinge domain (or portion thereof) fused to a CH3 domain (or portion thereof), (iii) a CH2 domain (or portion thereof) fused to a CH3 domain (or portion thereof), (iv) a hinge domain (or portion thereof), (v) a CH2 domain (or portion thereof), or (vi) a CH3 domain or portion thereof.

It will be understood by one of ordinary skill in the art that the Fc moiety may be modified such that it varies in amino acid sequence from the complete Fc moiety of a naturally occurring immunoglobulin molecule, while retaining at least one desirable function conferred by the naturally-occurring Fc moiety. Such functions include Fc receptor (FcR) binding, antibody half-life modulation, ADCC function, protein A binding, protein G binding, and complement binding. The portions of naturally occurring Fc moieties, which are responsible and/or essential for such functions are well known by those skilled in the art.

For example, to activate the complement cascade C1q binds to at least two molecules of IgG1 or one molecule of IgM, attached to the antigenic target (Ward, E. S., and Ghetie, V., *Ther. Immunol.* 2 (1995) 77-94). Burton, D. R., described (*Mol. Immunol.* 22 (1985) 161-206) that the heavy chain region comprising amino acid residues 318 to 337 is involved in complement fixation. Duncan, A. R., and Winter, G. (*Nature* 332 (1988) 738-740), using site directed mutagenesis, reported that Glu318, Lys320 and Lys322 form the binding site to C1q. The role of Glu318, Lys320 and Lys322 residues in the binding of C1q was confirmed by the ability of a short synthetic peptide containing these residues to inhibit complement mediated lysis.

For example, FcR binding can be mediated by the interaction of the Fc moiety (of an antibody) with Fc receptors (FcRs), which are specialized cell surface receptors on hematopoietic cells. Fc receptors belong to the immunoglobulin superfamily, and were shown to mediate both the removal of antibody-coated pathogens by phagocytosis of immune complexes, and the lysis of erythrocytes and various other cellular targets (e.g. tumor cells) coated with the corresponding antibody, via antibody dependent cell mediated cytotoxicity (ADCC; Van de Winkel, J. G., and Anderson, C. L., *J. Leukoc. Biol.* 49 (1991) 511-524). FcRs are defined by their specificity for immunoglobulin classes; Fc receptors for IgG antibodies are referred to as FcγR, for IgE as FcεR, for IgA as FcαR and so on and neonatal Fc receptors are referred to as FcRn. Fc receptor binding is described for example in Ravetch, J. V., and Kinet, J. P., *Annu. Rev. Immunol.* 9 (1991) 457-492; Capel, P. J., et al., *Immunomethods* 4 (1994) 25-34; de Haas, M., et al., *J Lab. Clin. Med.* 126 (1995) 330-341; and Gessner, J. E., et al., *Ann. Hematol.* 76 (1998) 231-248.

Cross-linking of receptors by the Fc domain of native IgG antibodies (FcγR) triggers a wide variety of effector functions including phagocytosis, antibody-dependent cellular cytotoxicity, and release of inflammatory mediators, as well as immune complex clearance and regulation of antibody production. Therefore, Fc moieties providing cross-linking of receptors (FcγR) are preferred. In humans, three classes of FcγR have been characterized, which are: (i) FcγRI (CD64), which binds monomeric IgG with high affinity and is expressed on macrophages, monocytes, neutrophils and eosinophils; (ii) FcγRII (CD32), which binds complexed IgG with medium to low affinity, is widely expressed, in particular on leukocytes, is known to be a central player in antibody-mediated immunity, and which can be divided into FcγRIIA, FcγRIIB and FcγRIIC, which perform different functions in the immune system, but bind with similar low affinity to the IgG-Fc, and the ectodomains of these receptors are highly homologous; and (iii) FcγRIII (CD16), which binds IgG with medium to low affinity and exists as two types: FcγRIIIA found on NK cells, macrophages, eosinophils and some monocytes and T cells and mediating ADCC and FcγRIIIB, which is highly expressed on neutrophils. FcγRIIA is found on many cells involved in killing (e.g. macrophages, monocytes, neutrophils) and seems able to activate the killing process. FcγRIIB seems to play a role in inhibitory processes and is found on B-cells, macrophages and on mast cells and eosinophils. Importantly, 75% of all FcγRIIB is found in the liver (Ganesan, L. P. et al., 2012: FcγRIIb on liver sinusoidal endothelium clears small immune complexes. Journal of Immunology 189: 4981-4988). FcγRIIB is abundantly expressed on Liver Sinusoidal Endothelium, called LSEC, and in Kupffer cells in the liver and LSEC are the major site of small immune complexes clearance (Ganesan, L. P. et al., 2012: FcγRIIb on liver sinusoidal endothelium clears small immune complexes. Journal of Immunology 189: 4981-4988).

Accordingly, in the present invention such antibodies, and antigen binding fragments thereof, are preferred, which are able to bind to FcγRIIb, for example antibodies comprising an Fc moiety for binding to FcγRIIb, in particular an Fc region, such as, for example IgG-type antibodies. Moreover, it is possible to engineer the Fc moiety to enhance FcγRIIB binding by introducing the mutations S267E and L328F as described by Chu, S. Y. et al., 2008: Inhibition of B cell receptor-mediated activation of primary human B cells by coengagement of CD19 and FcγRIIb with Fc-engineered antibodies. Molecular Immunology 45, 3926-3933. Thereby, the clearance of immune complexes can be enhanced (Chu, S., et al., 2014: Accelerated Clearance of IgE In Chimpanzees Is Mediated By Xmab7195, An Fc-Engineered Antibody With Enhanced Affinity For Inhibitory Receptor FcγRIIb. Am J Respir Crit, American Thoracic Society International Conference Abstracts). Accordingly, in the context of the present invention such antibodies, or antigen binding fragments thereof, are preferred, which comprise an engineered Fc moiety with the mutations S267E and L328F, in particular as described by Chu, S. Y. et al., 2008: Inhibition of B cell receptor-mediated activation of primary human B cells by coengagement of CD19 and FcγRIIb with Fc-engineered antibodies. Molecular Immunology 45, 3926-3933.

On B-cells it seems to function to suppress further immunoglobulin production and isotype switching to say for example the IgE class. On macrophages, FcγRIIB acts to inhibit phagocytosis as mediated through FcγRIIA. On eosinophils and mast cells the b form may help to suppress activation of these cells through IgE binding to its separate receptor.

Regarding FcγRI binding, modification in native IgG of at least one of E233-G236, P238, D265, N297, A327 and P329 reduces binding to FcγRI. IgG2 residues at positions 233-236, substituted into IgG1 and IgG4, reduces binding to FcγRI by $10^3$-fold and eliminated the human monocyte response to antibody-sensitized red blood cells (Armour, K. L., et al. Eur. J. Immunol. 29 (1999) 2613-2624). Regarding FcγRII binding, reduced binding for FcγRIIA is found e.g. for IgG mutation of at least one of E233-G236, P238, D265, N297, A327, P329, D270, Q295, A327, R292 and K414. Regarding FcγRIII binding, reduced binding to FcγRIIIA is found e.g. for mutation of at least one of E233-G236, P238, D265, N297, A327, P329, D270, Q295, A327, S239, E269, E293, Y296, V303, A327, K338 and D376. Mapping of the binding sites on human IgG1 for Fc receptors, the above mentioned mutation sites and methods for measuring binding to FcγRI and FcγRIIA are described in Shields, R. L., et al., J. Biol. Chem. 276 (2001) 6591-6604.

Regarding binding to the crucial FcγRII, two regions of native IgG Fc appear to be critical for interactions of FcγRIIs and IgGs, namely (i) the lower hinge site of IgG Fc, in particular amino acid residues L, L, G, G (234-237, EU numbering), and (ii) the adjacent region of the CH2 domain of IgG Fc, in particular a loop and strands in the upper CH2 domain adjacent to the lower hinge region, e.g. in a region of P331 (Wines, B. D., et al., J. Immunol. 2000; 164: 5313-5318). Moreover, FcγRI appears to bind to the same site on IgG Fc, whereas FcRn and Protein A bind to a different site on IgG Fc, which appears to be at the CH2-CH3 interface (Wines, B. D., et al., J. Immunol. 2000; 164: 5313-5318).

For example, the Fc moiety may comprise or consist of at least the portion of an Fc moiety that is known in the art to be required for FcRn binding or extended half-life. Alternatively or additionally, the Fc moiety of the antibody of the invention comprises at least the portion of known in the art to be required for Protein A binding and/or the Fc moiety of the antibody of the invention comprises at least the portion of an Fc molecule known in the art to be required for protein G binding. A preferred Fc moiety comprises at least the portion known in the art to be required for FcγR binding. As outlined above, a preferred Fc moiety may thus at least comprise (i) the lower hinge site of native IgG Fc, in particular amino acid residues L, L, G, G (234-237, EU numbering), and (ii) the adjacent region of the CH2 domain of native IgG Fc, in particular a loop and strands in the upper CH2 domain adjacent to the lower hinge region, e.g. in a region of P331, for example a region of at least 3, 4, 5, 6, 7, 8, 9, or 10 consecutive amino acids in the upper CH2 domain of native IgG Fc around P331, e.g. between amino acids 320 and 340 (EU numbering) of native IgG Fc.

Preferably, the antibody, or antigen binding fragment thereof, according to the present invention comprises an Fc region. As used herein, the term "Fc region" refers to the portion of an immunoglobulin formed by two or more Fc moieties of antibody heavy chains. For example, the Fc region may be monomeric or "single-chain" Fc region (i.e., a scFc region). Single chain Fc regions are comprised of Fc moieties linked within a single polypeptide chain (e.g., encoded in a single contiguous nucleic acid sequence). Exemplary scFc regions are disclosed in WO 2008/143954 A2. Preferably, the Fc region is a dimeric Fc region. A "dimeric Fc region" or "dcFc" refers to the dimer formed by the Fc moieties of two separate immunoglobulin heavy chains. The dimeric Fc region may be a homodimer of two identical Fc moieties (e.g., an Fc region of a naturally occurring immunoglobulin) or a heterodimer of two non-identical Fc moieties.

The Fc moieties of the Fc region may be of the same or different class and/or subclass. For example, the Fc moieties may be derived from an immunoglobulin (e.g., a human immunoglobulin) of an IgG1, IgG2, IgG3 or IgG4 subclass. Preferably, the Fc moieties of Fc region are of the same class and subclass. However, the Fc region (or one or more Fc moieties of an Fc region) may also be chimeric, whereby a chimeric Fc region may comprise Fc moieties derived from different immunoglobulin classes and/or subclasses. For example, at least two of the Fc moieties of a dimeric or single-chain Fc region may be from different immunoglobulin classes and/or subclasses. Additionally or alternatively, the chimeric Fc regions may comprise one or more chimeric Fc moieties. For example, the chimeric Fc region or moiety may comprise one or more portions derived from an immunoglobulin of a first subclass (e.g., an IgG1, IgG2, or IgG3 subclass) while the remainder of the Fc region or moiety is of a different subclass. For example, an Fc region or moiety of an Fc polypeptide may comprise a CH2 and/or CH3 domain derived from an immunoglobulin of a first subclass (e.g., an IgG1, IgG2 or IgG4 subclass) and a hinge region from an immunoglobulin of a second subclass (e.g., an IgG3 subclass). For example, the Fc region or moiety may comprise a hinge and/or CH2 domain derived from an immunoglobulin of a first subclass (e.g., an IgG4 subclass) and a CH3 domain from an immunoglobulin of a second subclass (e.g., an IgG1, IgG2, or IgG3 subclass). For example, the chimeric Fc region may comprise an Fc moiety (e.g., a complete Fc moiety) from an immunoglobulin for a first subclass (e.g., an IgG4 subclass) and an Fc moiety from an immunoglobulin of a second subclass (e.g., an IgG1, IgG2 or IgG3 subclass). For example, the Fc region or moiety may comprise a CH2 domain from an IgG4 immunoglobulin and a CH3 domain from an IgG1 immunoglobulin. For example, the Fc region or moiety may comprise a CH1 domain and a CH2 domain from an IgG4 molecule and a CH3 domain from an IgG1 molecule. For example, the Fc region or moiety may comprise a portion of a CH2 domain from a particular subclass of antibody, e.g., EU positions 292-340 of a CH2 domain. For example, an Fc region or moiety may comprise amino acids a positions 292-340 of CH2 derived from an IgG4 moiety and the remainder of CH2 derived from an IgG1 moiety (alternatively, 292-340 of CH2 may be derived from an IgG1 moiety and the remainder of CH2 derived from an IgG4 moiety).

Moreover, an Fc region or moiety may (additionally or alternatively) for example comprise a chimeric hinge region. For example, the chimeric hinge may be derived, e.g. in part, from an IgG1, IgG2, or IgG4 molecule (e.g., an upper and lower middle hinge sequence) and, in part, from an IgG3 molecule (e.g., an middle hinge sequence). In another example, an Fc region or moiety may comprise a chimeric hinge derived, in part, from an IgG1 molecule and, in part, from an IgG4 molecule. In another example, the chimeric hinge may comprise upper and lower hinge domains from an IgG4 molecule and a middle hinge domain from an IgG1 molecule. Such a chimeric hinge may be made, for example, by introducing a proline substitution (Ser228Pro) at EU position 228 in the middle hinge domain of an IgG4 hinge region. In another embodiment, the chimeric hinge can comprise amino acids at EU positions 233-236 are from an IgG2 antibody and/or the Ser228Pro mutation, wherein the remaining amino acids of the hinge are from an IgG4 antibody (e.g., a chimeric hinge of the sequence ESKYGPPCPPCPAPPVAGP). Further chimeric hinges, which may be used in the Fc moiety of the antibody according to the present invention are described in US 2005/0163783 A1.

In the present invention it is preferred that the Fc moiety, or the Fc region, comprises or consists of an amino acid sequence derived from a human immunoglobulin sequence (e.g., from an Fc region or Fc moiety from a human IgG molecule). However, polypeptides may comprise one or more amino acids from another mammalian species. For example, a primate Fc moiety or a primate binding site may be included in the subject polypeptides. Alternatively, one or more murine amino acids may be present in the Fc moiety or in the Fc region.

Preferably, the antibody according to the present invention comprises, in particular in addition to an Fc moiety as described above, other parts derived from a constant region, in particular from a constant region of IgG, preferably from a constant region of IgG1, more preferably from a constant region of human IgG1. More preferably, the antibody according to the present invention comprises, in particular in addition to an Fc moiety as described above, all other parts of the constant regions, in particular all other parts of the constant regions of IgG, preferably all other parts of the constant regions of IgG1, more preferably all other parts of the constant regions of human IgG1.

Particularly preferred sequences of constant regions are the amino acid sequences according to SEQ ID NOs: 313-315 (nucleic acid sequences according to SEQ ID NOs: 316-318). Preferably, the amino acid sequence of IgG1 CH1-CH2-CH3 is according to SEQ ID NO: 313 or a functional sequence variant thereof, as described herein.

As outlined above, a particularly preferred antibody according to the present invention comprises a (complete) Fc region derived from human IgG1. More preferably, the antibody according to the present invention comprises, in particular in addition to a (complete) Fc region derived from human IgG1 also all other parts of the constant regions of IgG, preferably all other parts of the constant regions of IgG1, more preferably all other parts of the constant regions of human IgG1.

Preferably, the antibody according to the present invention comprises a (complete) Fc moiety/Fc region, wherein the interaction/binding with FcR is not compromised. In general, binding of the antibody to an Fc receptor may be assessed by various methods known to the skilled person, such as ELISA (Hessell A J, Hangartner L, Hunter M, Havenith C E G, Beurskens F J, Bakker J M, Lanigan C M S, Landucci G, Forthal D N, Parren P W H I, et al.: Fc receptor but not complement binding is important in antibody protection against HIV. Nature 2007, 449:101-104; Grevys A, Bern M, Foss S, Bratlie D B, Moen A, Gunnarsen K S, Aase A, Michaelsen T E, Sandlie I, Andersen J T: Fc Engineering of Human IgG1 for Altered Binding to the Neonatal Fc Receptor Affects Fc Effector Functions. 2015, 194:5497-5508) or flow-cytometry (Perez L G, Costa M R, Todd C A, Haynes B F, Montefiori D C: Utilization of immunoglobulin G Fc receptors by human immunodeficiency virus type 1: a specific role for antibodies against the membrane-proximal external region of gp41. J Virol 2009, 83:7397-7410; Piccoli L, Campo I, Fregni C S, Rodriguez B M F, Minola A, Sallusto F, Luisetti M, Corti D, Lanzavecchia A: Neutralization and clearance of GM-CSF by autoantibodies in pulmonary alveolar proteinosis. Nat Commun 2015, 6:1-9).

In general, the antibody according to the present invention may be glycosylated. N-linked glycans attached to the CH2 domain of a heavy chain, for instance, can influence C1q and FcR binding, with glycosylated antibodies having lower affinity for these receptors. Accordingly, the CH2 domain of the Fc moiety of the antibody according to the present invention may comprise one or more mutations, in which a glycosylated residue is substituted by a non-glycosylated residue. The glycan structure can also affect activity e.g. differences in complement-mediated cell death may be seen depending on the number of galactose sugars (0, 1 or 2) at the terminus of a glycan's biantennary chain. Preferably, the antibody's glycans do not lead to a human immunogenic response after administration.

Furthermore, the antibody according to the present invention can be modified by introducing random amino acid mutations into particular region of the CH2 or CH3 domain of the heavy chain in order to alter their binding affinity for FcR and/or their serum half-life in comparison to unmodified antibodies. Examples of such modifications include, but are not limited to, substitutions of at least one amino acid from the heavy chain constant region selected from the group consisting of amino acid residues 250, 314, and 428.

Preferably, the antibody, or an antigen-binding fragment thereof, according to according to the present invention comprises a variable region of the heavy chain of the antibody, or of the antigen-binding fragment thereof, (VH), which is encoded by a nucleic acid comprising a gene (segment) of the VH3 gene family, preferably the gene (segment) VH3-30.

In general, the antibody according to the present invention, or the antigen binding fragment thereof, preferably comprises (at least) three complementarity determining regions (CDRs) on a heavy chain and (at least) three CDRs on a light chain. In general, complementarity determining regions (CDRs) are the hypervariable regions present in heavy chain variable domains and light chain variable domains. Typically, the CDRs of a heavy chain and the connected light chain of an antibody together form the antigen receptor. Usually, the three CDRs (CDR1, CDR2, and CDR3) are arranged non-consecutively in the variable domain. Since antigen receptors are typically composed of two variable domains (on two different polypeptide chains, i.e. heavy and light chain), there are six CDRs for each antigen receptor (heavy chain: CDRH1, CDRH2, and CDRH3; light chain: CDRL1, CDRL2, and CDRL3). A single antibody molecule usually has two antigen receptors and therefore contains twelve CDRs. The CDRs on the heavy and/or light chain may be separated by framework regions, whereby a framework region (FR) is a region in the variable domain which is less "variable" than the CDR. For example, a chain (or each chain, respectively) may be composed of four framework regions, separated by three CDR's.

The sequences of the heavy chains and light chains of exemplary antibodies of the invention, comprising three different CDRs on the heavy chain and three different CDRs on the light chain were determined. The position of the CDR amino acids are defined according to the IMGT numbering system (IMGT: http://www.imgt.org/; cf. Lefranc, M.-P. et al. (2009) Nucleic Acids Res. 37, D1006-D1012).

Preferably, the antibody, or the antigen binding fragment thereof, according to the present invention comprises a heavy chain comprising at least one CDRH1, at least one CDRH2 and at least one CDRH3 and a light chain comprising at least one CDRL1, at least one CDRL2 and at least one CDRL3, wherein at least one CDR, preferably the at least one heavy chain CDRH3, comprises or consists of an amino acid sequence according to any of SEQ ID NOs: 66, 84, 138, 156, 208, 226, 260, 278 and 296, or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

More preferably, the antibody, or the antigen binding fragment thereof, according to the present invention comprises a heavy chain comprising at least one CDRH1, at least one CDRH2 and at least one CDRH3 and a light chain comprising at least one CDRL1, at least one CDRL2 and at least one CDRL3, wherein at least one CDR, preferably the at least one heavy chain CDRH3, comprises or consists of an amino acid sequence according to any of SEQ ID NOs: 66, 84, 138, 208, 226 and 278, or a functional sequence variant thereof having at least 70%, at least 75%, at least 80%, at least 85%, at least 88%, at least 90%, at least 92%, at least 95%, at least 96%, at least 97%, at least 98% or at least 99% sequence identity. Even more preferably, the antibody, or the antigen binding fragment thereof, according to the present invention comprises a heavy chain comprising at least one CDRH1, at least one CDRH2 and at least one CDRH3 and a light chain comprising at least one CDRL1, at least one CDRL2 and at least one CDRL3, wherein at least one CDR, preferably the at least one heavy chain CDRH3, comprises or consists of an amino acid sequence according to SEQ ID NO: 66 or according to SEQ ID NO: 226; or of a functional sequence variant thereof having at least 70%, at least 75%, at least 80%, at least 85%, at least 88%, at least 90%, at least 92%, at least 95%, at least 96%, at least 97%, at least 98% or at least 99% sequence identity. Still more preferably, the antibody, or the antigen binding fragment thereof, according to the present invention comprises a heavy chain comprising at least one CDRH1, at least one CDRH2 and at least one CDRH3 and a light chain comprising at least one CDRL1, at least one CDRL2 and at least one CDRL3, wherein at least one CDR, preferably the at least one heavy chain CDRH3, comprises or consists of an amino acid sequence according to SEQ ID NO: 208 or according to SEQ ID NO: 278; or of a functional sequence variant thereof having at least 70%, at least 75%, at least 80%, at least 85%, at least 88%, at least 90%, at least 92%, at least 95%, at least 96%, at least 97%, at least 98% or at least 99% sequence identity. Most preferably, the antibody, or the antigen binding fragment thereof, according to the present invention comprises a heavy chain comprising at least one CDRH1, at least one CDRH2 and at least one CDRH3 and a light chain comprising at least one CDRL1, at least one CDRL2 and at least one CDRL3, wherein at least one CDR, preferably the at least one heavy chain CDRH3, comprises or consists of an amino acid sequence according to SEQ ID NO: 84 or according to SEQ ID NO: 138; or of a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

Preferably, the antibody, or the antigen binding fragment thereof, according to the present invention comprises a heavy chain comprising at least one CDRH1, at least one CDRH2 and at least one CDRH3 and a light chain comprising at least one CDRL1, at least one CDRL2 and at least one CDRL3, wherein
  (i) the at least one heavy chain CDRH1 comprises an amino acid sequence according to any of SEQ ID NOs: 64, 82, 136, 154, 206, 224, 258, 276, and 294, or a functional sequence variant thereof having at least 70%, at least 75%, at least 80%, at least 85%, at least 88%, at least 90%, at least 92%, at least 95%, at least 96%, at least 97%, at least 98% or at least 99% sequence identity;
  (ii) the at least one CDRH2 comprises an amino acid sequence according to any of SEQ ID NOs: 65, 83, 137, 155, 207, 225, 259, 277, and 295, or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; and/or
  (iii) the at least one heavy chain CDRH3 comprises an amino acid sequence according to any of SEQ ID NOs: 66, 84, 138, 156, 208, 226, 260, 278 and 296, or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

More preferably, the antibody, or the antigen binding fragment thereof, according to the present invention comprises a heavy chain comprising at least one CDRH1, at least one CDRH2 and at least one CDRH3 and a light chain comprising at least one CDRL1, at least one CDRL2 and at least one CDRL3, wherein
(i) the at least one heavy chain CDRH1 comprises an amino acid sequence according to any of SEQ ID NOs: 64, 82, 136, 206, 224, and 276, or a functional sequence variant thereof having at least 70%, at least 75%, at least 80%, at least 85%, at least 88%, at least 90%, at least 92%, at least 95%, at least 96%, at least 97%, at least 98% or at least 99% sequence identity;
(ii) the at least one CDRH2 comprises an amino acid sequence according to any of SEQ ID NOs: 65, 83, 137, 207, 225, and 277, or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; and/or
(iii) the at least one heavy chain CDRH3 comprises an amino acid sequence according to any of SEQ ID NOs: 66, 84, 138, 208, 226, and 278, or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

Even more preferably, the antibody, or the antigen binding fragment thereof, according to the present invention comprises a heavy chain comprising at least one CDRH1, at least one CDRH2 and at least one CDRH3 and a light chain comprising at least one CDRL1, at least one CDRL2 and at least one CDRL3, wherein
(i) the at least one heavy chain CDRH1 comprises an amino acid sequence according to SEQ ID NO: 64 or according to SEQ ID NO: 224; or a functional sequence variant thereof having at least 70%, at least 75%, at least 80%, at least 85%, at least 88%, at least 90%, at least 92%, at least 95%, at least 96%, at least 97%, at least 98% or at least 99% sequence identity;
(ii) the at least one CDRH2 comprises an amino acid sequence according to SEQ ID NO: 65 or according to SEQ ID NO: 225; or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; and/or
(iii) the at least one heavy chain CDRH3 comprises an amino acid sequence according to SEQ ID NO: 66 or according to SEQ ID NO: 226; or a functional sequence variant thereof having at least 70%, at least 75%, at least 80%, at least 85%, at least 88%, at least 90%/0, at least 92%, at least 95%, at least 96%, at least 97%, at least 98% or at least 99% sequence identity.

Still more preferably, the antibody, or the antigen binding fragment thereof, according to the present invention comprises a heavy chain comprising at least one CDRH1, at least one CDRH2 and at least one CDRH3 and a light chain comprising at least one CDRL1, at least one CDRL2 and at least one CDRL3, wherein
(i) the at least one heavy chain CDRH1 comprises an amino acid sequence according to SEQ ID NO: 206 or according to SEQ ID NO: 276; or a functional sequence variant thereof having at least 70%, at least 75%, at least 80%, at least 85%, at least 88%, at least 90%, at least 92%, at least 95%, at least 96%, at least 97%, at least 98% or at least 99% sequence identity;
(ii) the at least one CDRH2 comprises an amino acid sequence according to SEQ ID NO: 207 or according to SEQ ID NO: 277; or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; and/or
(iii) the at least one heavy chain CDRH3 comprises an amino acid sequence according to SEQ ID NO: 208 or according to SEQ ID NO: 278; or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

Most preferably, the antibody, or the antigen binding fragment thereof, according to the present invention comprises a heavy chain comprising at least one CDRH1, at least one CDRH2 and at least one CDRH3 and a light chain comprising at least one CDRL1, at least one CDRL2 and at least one CDRL3, wherein
(i) the at least one heavy chain CDRH1 comprises an amino acid sequence according to SEQ ID NO: 82 or according to SEQ ID NO: 136; or a functional sequence variant thereof having at least 70%, at least 75%, at least 80%, at least 85%, at least 88%, at least 90%, at least 92%, at least 95%, at least 96%, at least 97%, at least 98% or at least 99% sequence identity;
(ii) the at least one CDRH2 comprises an amino acid sequence according to SEQ ID NO: 83 or according to SEQ ID NO: 137; or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; and/or
(iii) the at least one heavy chain CDRH3 comprises an amino acid sequence according to SEQ ID NO: 84 or according to SEQ ID NO: 138; or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

It is also preferred that the antibody, or the antigen binding fragment thereof, according to the present invention comprises a heavy chain comprising at least one CDRH1, at least one CDRH2 and at least one CDRH3 and a light chain comprising at least one CDRL1, at least one CDRL2 and at least one CDRL3, wherein
(i) the at least one CDRL1 comprises an amino acid sequence according to any of SEQ ID NOs: 67, 85, 139, 157, 209, 227, 261, 279, and 297, or a functional sequence variant thereof having at least 70%, at least 75%, at least 80%, at least 85%, at least 88%, at least 90%, at least 92%, at least 95%, at least 96%, at least 97%, at least 98% or at least 99% sequence identity;
(ii) the at least one CDRL2 comprises an amino acid sequence according to any of SEQ ID NOs: 68, 69, 86, 87, 140, 141, 158, 159, 210, 211, 228, 229, 262, 263, 280, 281, 298 and 299, or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; and/or
(iii) the at least one CDRL3 amino comprises an amino acid sequence according to any of SEQ ID NOs: 70, 88, 142, 160, 212, 230, 264, 282, and 300 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

More preferably, the antibody, or the antigen binding fragment thereof, according to the present invention comprises a heavy chain comprising at least one CDRH1, at least one CDRH2 and at least one CDRH3 and a light chain comprising at least one CDRL1, at least one CDRL2 and at least one CDRL3, wherein
  (i) the at least one CDRL1 comprises an amino acid sequence according to any of SEQ ID NOs: 67, 85, 139, 209, 227, and 279; or a functional sequence variant thereof having at least 70%, at least 75%, at least 80%, at least 85%, at least 88%, at least 90%, at least 92%, at least 95%, at least 96%, at least 97%, at least 98% or at least 99% sequence identity;
  (ii) the at least one CDRL2 comprises an amino acid sequence according to any of SEQ ID NOs: 68, 69, 86, 87, 140, 141, 210, 211, 228, 229, 280, and 281; or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; and/or
  (iii) the at least one CDRL3 amino comprises an amino acid sequence according to any of SEQ ID NOs: 70, 88, 142, 212, 230, and 282; or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

Even more preferably, the antibody, or the antigen binding fragment thereof, according to the present invention comprises a heavy chain comprising at least one CDRH1, at least one CDRH2 and at least one CDRH3 and a light chain comprising at least one CDRL1, at least one CDRL2 and at least one CDRL3, wherein
  (i) the at least one CDRL1 comprises an amino acid sequence according to SEQ ID NO: 67; or a functional sequence variant thereof having at least 70%, at least 75%, at least 80%, at least 85%, at least 88%, at least 90%, at least 92%, at least 95%, at least 96%, at least 97%, at least 98% or at least 99% sequence identity;
  (ii) the at least one CDRL2 comprises an amino acid sequence according to SEQ ID NO: 68 or 69; or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; and/or
  (iii) the at least one CDRL3 amino comprises an amino acid sequence according to SEQ ID NO: 70; or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

Still more preferably, the antibody, or the antigen binding fragment thereof, according to the present invention comprises a heavy chain comprising at least one CDRH1, at least one CDRH2 and at least one CDRH3 and a light chain comprising at least one CDRL1, at least one CDRL2 and at least one CDRL3, wherein
  (i) the at least one CDRL1 comprises an amino acid sequence according to SEQ ID NO: 209; or a functional sequence variant thereof having at least 70%, at least 75%, at least 80%, at least 85%, at least 88%, at least 90%, at least 92%, at least 95%, at least 96%, at least 97%, at least 98% or at least 99% sequence identity;
  (ii) the at least one CDRL2 comprises an amino acid sequence according to SEQ ID NO: 210 or 211; or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; and/or
  (iii) the at least one CDRL3 amino comprises an amino acid sequence according to SEQ ID NO: 212; or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

Even more preferably, the antibody, or the antigen binding fragment thereof, according to the present invention comprises a heavy chain comprising at least one CDRH1, at least one CDRH2 and at least one CDRH3 and a light chain comprising at least one CDRL1, at least one CDRL2 and at least one CDRL3, wherein
  (i) the at least one CDRL1 comprises an amino acid sequence according to SEQ ID NO: 227; or a functional sequence variant thereof having at least 70%, at least 75%, at least 80%, at least 85%, at least 88%, at least 90%, at least 92%, at least 95%, at least 96%, at least 97%, at least 98% or at least 99% sequence identity;
  (ii) the at least one CDRL2 comprises an amino acid sequence according to SEQ ID NO: 228 or 229; or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; and/or
  (iii) the at least one CDRL3 amino comprises an amino acid sequence according to SEQ ID NO: 230; or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

Still more preferably, the antibody, or the antigen binding fragment thereof, according to the present invention comprises a heavy chain comprising at least one CDRH1, at least one CDRH2 and at least one CDRH3 and a light chain comprising at least one CDRL1, at least one CDRL2 and at least one CDRL3, wherein
  (i) the at least one CDRL1 comprises an amino acid sequence according to SEQ ID NO: 279; or a functional sequence variant thereof having at least 70%, at least 75%, at least 80%, at least 85%, at least 88%, at least 90%, at least 92%, at least 95%, at least 96%, at least 97%, at least 98% or at least 99% sequence identity;
  (ii) the at least one CDRL2 comprises an amino acid sequence according to SEQ ID NO: 280 or 281; or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; and/or
  (iii) the at least one CDRL3 amino comprises an amino acid according to SEQ ID NO: 282; or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

Particularly preferably, the antibody, or the antigen binding fragment thereof, according to the present invention comprises a heavy chain comprising at least one CDRH1, at least one CDRH2 and at least one CDRH3 and a light chain comprising at least one CDRL1, at least one CDRL2 and at least one CDRL3, wherein
  (i) the at least one CDRL1 comprises an amino acid sequence according to SEQ ID NO: 139; or a functional sequence variant thereof having at least 70%, at least 75%, at least 80%, at least 85%, at least 88%, at least 90%, at least 92%, at least 95%, at least 96%, at least 97%, at least 98% or at least 99% sequence identity;
  (ii) the at least one CDRL2 comprises an amino acid sequence according to SEQ ID NO: 140 or 141; or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; and/or
  (iii) the at least one CDRL3 amino comprises an amino acid sequence according to SEQ ID NO: 142; or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

Most preferably, the antibody, or the antigen binding fragment thereof, according to the present invention comprises a heavy chain comprising at least one CDRH1, at least one CDRH2 and at least one CDRH3 and a light chain comprising at least one CDRL1, at least one CDRL2 and at least one CDRL3, wherein
  (i) the at least one CDRL1 comprises an amino acid sequence according to SEQ ID NO: 85; or a functional sequence variant thereof having at least 70%, at least 75%, at least 80%, at least 85%, at least 88%, at least 90%, at least 92%, at least 95%, at least 96%, at least 97%, at least 98% or at least 99% sequence identity;
  (ii) the at least one CDRL2 comprises an amino acid sequence according to SEQ ID NO: 86 or 87; or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; and/or
  (iii) the at least one CDRL3 amino comprises an amino acid sequence according to SEQ ID NO: 88; or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

Preferably, the antibody, or the antigen binding fragment thereof, according to the present invention comprises CDRH1, CDRH2, and CDRH3 amino acid sequences (i) according to SEQ ID NOs: 64-66; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (ii) according to SEQ ID NOs: 82-84; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (iii) according to SEQ ID NOs: 136-138; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (iv) according to SEQ ID NOs: 154-156; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (v) according to SEQ ID NOs: 206-208; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (vi) according to SEQ ID NOs: 224-226; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (vii) according to SEQ ID NOs: 258-260; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (viii) according to SEQ ID NOs: 276-278; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (ix) according to SEQ ID NOs: 294-296; or functional sequence variants thereof having at least 70%, at least 75%, at least 80%, at least 85%, at least 88%, at least 90%, at least 92%, at least 95%, at least 96%, at least 97%, at least 98% or at least 99% sequence identity.

It is also preferred that the antibody, or the antigen binding fragment thereof, according to the present invention comprises CDRH1, CDRH2, and CDRH3 amino acid sequences and CDRL1, CDRL2, and CDRL3 amino acid sequences (i) according to SEQ ID NOs: 64-68 and 70; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (ii) according to SEQ ID NOs: 64-67 and 69-70; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (iii) according to SEQ ID NOs: 82-86 and 88; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (iv) according to SEQ ID NOs: 82-85 and 87-88; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (v) according to SEQ ID NOs: 136-140 and 142; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (vi) according to SEQ ID NOs: 136-139 and 141-142; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (vii) according to SEQ ID NOs: 154-158 and 160; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (viii) according to SEQ ID NOs: 154-157 and 159-160; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (ix) according to SEQ ID NOs: 206-210 and 212; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; or (x) according to SEQ ID NOs: 206-209 and 211-212; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; or (xi) according to SEQ ID NOs: 224-228 and 230; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; or (xii) according to SEQ ID NOs: 224-227 and 229-230; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; or (xiii) according to SEQ ID NOs: 258-262 and 264; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; or (xiv) according to SEQ ID NOs: 258-261 and 263-264; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; or (xv) according to SEQ ID NOs: 276-280 and 282; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; or (xvi) according to SEQ ID NOs: 276-279 and 281-282; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; or (xvii) according to SEQ ID NOs: 294-298 and 300; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; or (xviii) according to SEQ ID NOs: 294-297 and 299-300; or functional sequence variants thereof having at least 70%, at least 75%, at least 80%, at least 85%, at least 88%, at least 90%, at least 92%, at least 95%, at least 96%, at least 97%, at least 98% or at least 99% sequence identity.

More preferably, the antibody, or the antigen binding fragment thereof, according to the present invention comprises CDRH1, CDRH2, and CDRH3 amino acid sequences and CDRL1, CDRL2, and CDRL3 amino acid sequences (i) according to SEQ ID NOs: 64-68 and 70, respectively; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; or (ii) according to SEQ ID NOs: 64-67 and 69-70; or functional sequence variants thereof having at least 70%, at least 75%, at least 80%, at least 85%, at least 88%, at least 90%, at least 92%, at least 95%, at least 96%, at least 97%, at least 98% or at least 99% sequence identity.

More preferably, the antibody, or the antigen binding fragment thereof, according to the present invention comprises CDRH1, CDRH2, and CDRH3 amino acid sequences and CDRL1, CDRL2, and CDRL3 amino acid sequences (i) according to SEQ ID NOs: 224-228 and 230; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; or (ii) according to SEQ ID NOs: 224-227 and 229-230; or functional sequence variants thereof having at least 70%, at least 75%, at least 80%, at least 85%, at least 88%, at least 90%, at least 92%, at least 95%, at least 96%, at least 97%, at least 98% or at least 99% sequence identity.

Even more preferably, the antibody, or the antigen binding fragment thereof, according to the present invention comprises CDRH1, CDRH2, and CDRH3 amino acid sequences and CDRL1, CDRL2, and CDRL3 amino acid sequences (i) according to SEQ ID NOs: 276-280 and 282; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; or (ii) according to SEQ ID NOs: 276-279 and 281-282; or functional sequence variants thereof having at least 70%, at least 75%, at least 80%, at least 85%, at least 88%, at least 90%, at least 92%, at least 95%, at least 96%, at least 97%, at least 98% or at least 99% sequence identity.

Still more preferably, the antibody, or the antigen binding fragment thereof, according to the present invention comprises CDRH1, CDRH2, and CDRH3 amino acid sequences and CDRL1, CDRL2, and CDRL3 amino acid sequences (i) according to SEQ ID NOs: 206-210 and 212; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; or (ii) according to SEQ ID NOs: 206-209 and 211-212; or functional sequence variants thereof having at least 70%, at least 75%, at least 80%, at least 85%, at least 88%, at least 90%, at least 92%, at least 95%, at least 96%, at least 97%, at least 98% or at least 99% sequence identity.

Particularly preferably, the antibody, or the antigen binding fragment thereof, according to the present invention comprises CDRH1, CDRH2, and CDRH3 amino acid sequences and CDRL1, CDRL2, and CDRL3 amino acid sequences (i) according to SEQ ID NOs: 136-140 and 142; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (ii) according to SEQ ID NOs: 136-139 and 141-142; or functional sequence variants thereof having at least 70%, at least 75%, at least 80%, at least 85%, at least 88%, at least 90%, at least 92%, at least 95%, at least 96%, at least 97%, at least 98% or at least 99% sequence identity.

Most preferably, the antibody, or the antigen binding fragment thereof, according to the present invention comprises CDRH1, CDRH2, and CDRH3 amino acid sequences and CDRL1, CDRL2, and CDRL3 amino acid sequences (i) according to SEQ ID NOs: 82-86 and 88; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (ii) according to SEQ ID NOs: 82-85 and 87-88; or functional sequence variants thereof having at least 70%, at least 75%, at least 80%, at least 85%, at least 88%, at least 90%, at least 92%, at least 95%, at least 96%, at least 97%, at least 98% or at least 99% sequence identity.

In addition, it is also preferred that the antibody, or the antigen binding fragment thereof, according to the present invention comprises a heavy chain variable region (VH) and, optionally, a light chain variable region (VL), wherein the heavy chain variable region (VH) comprises or consists of an amino acid sequence according to any of SEQ ID NOs: 71, 89, 143, 161, 213, 231, 265, 283, and 301; or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

Moreover, it is also preferred that the antibody, or the antigen binding fragment thereof, according to the present invention comprises (i) a heavy chain variable region (VH) amino acid sequence according to SEQ ID NO: 71 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 72 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; (ii) a heavy chain variable region (VH) amino acid sequence according to SEQ ID NO: 89 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 90 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; (iii) a heavy chain variable region (VH) amino acid sequence according to SEQ ID NO: 143 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 144 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; (iv) a heavy chain variable region (VH) amino acid sequence according to SEQ ID NO: 161 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 162 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; or (v) a heavy chain variable region (VH) amino acid sequence according to SEQ ID NO: 213 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 214 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; (vi) a heavy chain variable region (VH) amino acid sequence according to SEQ ID NO: 231 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 232 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; (vii) a heavy chain variable region (VH) amino acid sequence according to SEQ ID NO: 265 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 266 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; (viii) a heavy chain variable region (VH) amino acid sequence according to SEQ ID NO: 283 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 284 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; or (ix) a heavy chain variable region (VH) amino acid sequence according to SEQ ID NO: 301 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 302 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

More preferably, the antibody, or the antigen binding fragment thereof, according to the present invention comprises a heavy chain variable region (VH) amino acid sequence according to SEQ ID NO: 71 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 72 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

More preferably, the antibody, or the antigen binding fragment thereof, according to the present invention comprises a heavy chain variable region (VH) amino acid sequence according to SEQ ID NO: 231 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 232 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

Even more preferably, the antibody, or the antigen binding fragment thereof, according to the present invention comprises a heavy chain variable region (VH) amino acid sequence according to SEQ ID NO: 283 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 284 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

Still more preferably, the antibody, or the antigen binding fragment thereof, according to the present invention comprises a heavy chain variable region (VH) amino acid sequence according to SEQ ID NO: 213 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 214 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

Particularly preferably, the antibody, or the antigen binding fragment thereof, according to the present invention comprises a heavy chain variable region (VH) amino acid sequence according to SEQ ID NO: 143 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 144 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

Most preferably, the antibody, or the antigen binding fragment thereof, according to the present invention comprises a heavy chain variable region (VH) amino acid sequence according to SEQ ID NO: 89 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 90 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

Preferably, the antibody, or the antigen binding fragment thereof, according to the present invention is gMGG3, gMGG4, gMGH2, gMGH3, gMGU5, gMGU8, gMGU11, gMGU12 or gMGV3, preferably the antibody, or the antigen binding fragment thereof, is gMGG3, gMGG4, gMGH2, gMGU5, gMGU8 or gMGU12, more preferably the antibody, or the antigen binding fragment thereof, is gMGG4 or gMGH2.

The present inventors have isolated monoclonal antibody (mAb) according to the present invention, which are referred to herein as MGG3, MGG4, MGH2, MGH3, MGU5, MGU8, MGU11, MGU12 and MGV3 (cf. Tables 1 and 2, Example 1). Based on those antibodies, in particular on the VH and VL genes of those antibodies, the terms "gMGG3", "gMGG4", "gMGH2", "gMGH3", "gMGU5", "gMGU8", "gMGU11", "gMGU12", and "gMGV3", as used herein, refer to the respective "generic" antibodies, or antigen binding fragments thereof.

Namely, "gMGG3" refers to an antibody, or antigen binding fragment thereof, having a CDRH1 amino acid sequence according to SEQ ID NO: 64, a CDRH2 amino acid sequence according to SEQ ID NO: 65, a CDRH3 amino acid sequence according to SEQ ID NO: 66, a CDRL1 amino acid sequence according to SEQ ID NO: 67, a CDRL2 amino acid sequence according to SEQ ID NO: 68 or 69, and a CDRL3 amino acid sequence according to SEQ ID NO: 70. The heavy chain variable region ($V_H$) has preferably an amino acid sequence according to SEQ ID NO: 71 and the light chain variable region ($V_L$) has preferably an amino acid sequence according to SEQ ID NO: 72.

"gMGG4" refers to an antibody, or antigen binding fragment thereof, having a CDRH1 amino acid sequence according to SEQ ID NO: 82, a CDRH2 amino acid sequence according to SEQ ID NO: 83, a CDRH3 amino acid sequence according to SEQ ID NO: 84, a CDRL1 amino acid sequence according to SEQ ID NO: 85, a CDRL2 amino acid sequence according to SEQ ID NO: 86 or 87, and a CDRL3 amino acid sequence according to SEQ ID NO: 88. The heavy chain variable region ($V_H$) has preferably an amino acid sequence according to SEQ ID NO: 89 and the light chain variable region ($V_L$) has preferably an amino acid sequence according to SEQ ID NO: 90.

"gMGH2" refers to an antibody, or antigen binding fragment thereof, having a CDRH1 amino acid sequence according to SEQ ID NO: 136, a CDRH2 amino acid sequence according to SEQ ID NO: 137, a CDRH3 amino acid sequence according to SEQ ID NO: 138, a CDRL1 amino acid sequence according to SEQ ID NO: 139, a CDRL2 amino acid sequence according to SEQ ID NO: 140 or 141, and a CDRL3 amino acid sequence according to SEQ ID NO: 142. The heavy chain variable region ($V_H$) has preferably an amino acid sequence according to SEQ ID NO: 143 and the light chain variable region ($V_L$) has preferably an amino acid sequence according to SEQ ID NO: 144.

"gMGH3" refers to an antibody, or antigen binding fragment thereof, having a CDRH1 amino acid sequence according to SEQ ID NO: 154, a CDRH2 amino acid sequence according to SEQ ID NO: 155, a CDRH3 amino acid sequence according to SEQ ID NO: 156, a CDRL1 amino acid sequence according to SEQ ID NO: 157, a CDRL2 amino acid sequence according to SEQ ID NO: 158 or 159, and a CDRL3 amino acid sequence according to SEQ ID NO: 160. The heavy chain variable region ($V_H$) has preferably an amino acid sequence according to SEQ ID NO: 161 and the light chain variable region ($V_L$) has preferably an amino acid sequence according to SEQ ID NO: 162.

"gMGU5" refers to an antibody, or antigen binding fragment thereof, having a CDRH1 amino acid sequence according to SEQ ID NO: 206, a CDRH2 amino acid sequence according to SEQ ID NO: 207, a CDRH3 amino acid sequence according to SEQ ID NO: 208, a CDRL1 amino acid sequence according to SEQ ID NO: 209, a CDRL2 amino acid sequence according to SEQ ID NO: 210 or 211, and a CDRL3 amino acid sequence according to SEQ ID NO: 212. The heavy chain variable region (V$_H$) has preferably an amino acid sequence according to SEQ ID NO: 213 and the light chain variable region (V$_L$) has preferably an amino acid sequence according to SEQ ID NO: 214.

"gMGU8" refers to an antibody, or antigen binding fragment thereof, having a CDRH1 amino acid sequence according to SEQ ID NO: 224, a CDRH2 amino acid sequence according to SEQ ID NO: 225, a CDRH3 amino acid sequence according to SEQ ID NO: 226, a CDRL1 amino acid sequence according to SEQ ID NO: 227, a CDRL2 amino acid sequence according to SEQ ID NO: 228 or 229, and a CDRL3 amino acid sequence according to SEQ ID NO: 230. The heavy chain variable region (V$_H$) has preferably an amino acid sequence according to SEQ ID NO: 231 and the light chain variable region (V$_L$) has preferably an amino acid sequence according to SEQ ID NO: 232.

"gMGU11" refers to an antibody, or antigen binding fragment thereof, having a CDRH1 amino acid sequence according to SEQ ID NO: 258, a CDRH2 amino acid sequence according to SEQ ID NO: 259, a CDRH3 amino acid sequence according to SEQ ID NO: 260, a CDRL1 amino acid sequence according to SEQ ID NO: 261, a CDRL2 amino acid sequence according to SEQ ID NO: 262 or 263, and a CDRL3 amino acid sequence according to SEQ ID NO: 264. The heavy chain variable region (V$_H$) has preferably an amino acid sequence according to SEQ ID NO: 265 and the light chain variable region (V$_L$) has preferably an amino acid sequence according to SEQ ID NO: 266.

"gMGU12" refers to an antibody, or antigen binding fragment thereof, having a CDRH1 amino acid sequence according to SEQ ID NO: 276, a CDRH2 amino acid sequence according to SEQ ID NO: 277, a CDRH3 amino acid sequence according to SEQ ID NO: 278, a CDRL1 amino acid sequence according to SEQ ID NO: 279, a CDRL2 amino acid sequence according to SEQ ID NO: 280 or 281, and a CDRL3 amino acid sequence according to SEQ ID NO: 282. The heavy chain variable region (V$_H$) has preferably an amino acid sequence according to SEQ ID NO: 283 and the light chain variable region (V$_L$) has preferably an amino acid sequence according to SEQ ID NO: 284.

"gMGV3" refers to an antibody, or antigen binding fragment thereof, having a CDRH1 amino acid sequence according to SEQ ID NO: 294, a CDRH2 amino acid sequence according to SEQ ID NO: 295, a CDRH3 amino acid sequence according to SEQ ID NO: 296, a CDRL1 amino acid sequence according to SEQ ID NO: 297, a CDRL2 amino acid sequence according to SEQ ID NO: 298 or 299, and a CDRL3 amino acid sequence according to SEQ ID NO: 300. The heavy chain variable region (V$_H$) has preferably an amino acid sequence according to SEQ ID NO: 301 and the light chain variable region (V$_L$) has preferably an amino acid sequence according to SEQ ID NO: 302.

Antibody Binding to *P. falciparum* Sporozoites

In a further aspect the present invention provides an antibody, or an antigen-binding fragment thereof, that (specifically) binds to *P. falciparum* sporozoites. More preferably, the antibody according to the present invention, or the antigen-binding fragment thereof, (specifically) binds to *Plasmodium* circumsporozoite protein, most preferably to *Plasmodium* circumsporozoite protein according to SEQ ID NO: 24. In other words, the antibody according to the present invention, or the antigen-binding fragment thereof, is able to recognize an epitope, in particular a CSP epitope.

Preferably, the antibody, or an antigen binding fragment thereof, according to the present invention is a human antibody. It is also preferred that the antibody, or an antigen binding fragment thereof, according to the present invention is a monoclonal antibody, preferably a human monoclonal antibody. Furthermore, it is also preferred that the antibody, or an antigen binding fragment thereof, according to the present invention is a recombinant antibody.

Preferably, the antibody according to the present invention, or an antigen binding fragment thereof, comprises an Fc moiety as described above. It is understood that preferred embodiments of the Fc moiety of the antibody according to the present invention binding to the peptide according to the present invention correspond to preferred embodiments of the Fc moiety of the antibody according to the present invention binding to *P. falciparum* sporozoites. For example, the Fc moiety is preferably derived from human origin, e.g. from human IgG1, IgG2, IgG3, and/or IgG4, whereby human IgG1 is particularly preferred.

For all antibodies according to the present invention, i.e. antibodies binding to the peptide according to the present invention and antibodies binding to *P. falciparum* sporozoites, it is also preferred that the antibody, or an antigen binding fragment thereof, does not comprise an Fc moiety. In particular it is preferred that the antibody according to the present invention, or an antigen binding fragment thereof, is a purified antibody, a single chain antibody, Fab, Fab', F(ab')2, Fv or scFv.

As described above, the antibody according to the present invention, or the antigen binding fragment thereof, preferably comprises (at least) three complementarity determining regions (CDRs) on a heavy chain and (at least) three CDRs on a light chain. In general, complementarity determining regions (CDRs) are the hypervariable regions present in heavy chain variable domains and light chain variable domains. Typically, the CDRs of a heavy chain and the connected light chain of an antibody together form the antigen receptor. Usually, the three CDRs (CDR1, CDR2, and CDR3) are arranged non-consecutively in the variable domain. Since antigen receptors are typically composed of two variable domains (on two different polypeptide chains, i.e. heavy and light chain), there are six CDRs for each antigen receptor (heavy chain: CDRH1, CDRH2, and CDRH3; light chain: CDRL1, CDRL2, and CDRL3). A single antibody molecule usually has two antigen receptors and therefore contains twelve CDRs. The CDRs on the heavy and/or light chain may be separated by framework regions, whereby a framework region (FR) is a region in the variable domain which is less "variable" than the CDR. For example, a chain (or each chain, respectively) may be composed of four framework regions, separated by three CDR's.

The sequences of the heavy chains and light chains of exemplary antibodies of the invention, comprising three different CDRs on the heavy chain and three different CDRs on the light chain were determined. The position of the CDR amino acids are defined according to the IMGT numbering system (IMGT: http://www.imgt.org/; cf. Lefranc, M.-P. et al. (2009) Nucleic Acids Res. 37, D1006-D1012).

Table 1 below shows the SEQ ID NOs of the amino acid sequences of the heavy chain CDR's (CDRH1, CDRH2, and CDRH3) and of the heavy chain variable region (referred to as "VH") of exemplary antibodies according to the present invention:

TABLE 1

| Antibody name | CDRH1 | CDRH2 | CDRH3 | VH |
|---|---|---|---|---|
| MGG1 | 28 | 29 | 30 | 35 |
| MGG2 | 46 | 47 | 48 | 53 |
| MGG3 | 64 | 65 | 66 | 71 |
| MGG4 | 82 | 83 | 84 | 89 |
| MGG8 | 100 | 101 | 102 | 107 |
| MGH1 | 118 | 119 | 120 | 125 |
| MGH2 | 136 | 137 | 138 | 143 |
| MGH3 | 154 | 155 | 156 | 161 |
| MGU1 | 172 | 173 | 174 | 178 |
| MGU3 | 188 | 189 | 190 | 195 |
| MGU5 | 206 | 207 | 208 | 213 |
| MGU8 | 224 | 225 | 226 | 231 |
| MGU10 | 242 | 243 | 244 | 248 |
| MGU11 | 258 | 259 | 260 | 265 |
| MGU12 | 276 | 277 | 278 | 283 |
| MGV3 | 294 | 295 | 296 | 301 |

Table 2 below shows the SEQ ID NOs of the amino acid sequences of the light chain CDR's (CDRL1, CDRL2, and CDRL3) and of the light chain variable region (referred to as "VL") of exemplary antibodies according to the present invention:

TABLE 2

| Antibody name | CDRL1 | CDRL2 | CDRL2 long | CDRL3 | VL |
|---|---|---|---|---|---|
| MGG1 | 31 | 32 | 33 | 34 | 36 |
| MGG2 | 49 | 50 | 51 | 52 | 54 |
| MGG3 | 67 | 68 | 69 | 70 | 72 |
| MGG4 | 85 | 86 | 87 | 88 | 90 |
| MGG8 | 103 | 104 | 105 | 106 | 108 |
| MGH1 | 121 | 122 | 123 | 124 | 126 |
| MGH2 | 139 | 140 | 141 | 142 | 144 |
| MGH3 | 157 | 158 | 159 | 160 | 162 |
| MGU1 | 175 | 176 | — | 177 | 179 |
| MGU3 | 191 | 192 | 193 | 194 | 196 |
| MGU5 | 209 | 210 | 211 | 212 | 214 |
| MGU8 | 227 | 228 | 229 | 230 | 232 |
| MGU10 | 245 | 246 | — | 247 | 249 |
| MGU11 | 261 | 262 | 263 | 264 | 266 |
| MGU12 | 279 | 280 | 281 | 282 | 284 |
| MGV3 | 297 | 298 | 299 | 300 | 302 |

It is thus preferred that the antibody, or the antigen binding fragment thereof, according to the present invention comprises amino acid sequences having at least 70%, at least 75%, at least 80%, at least 85%, at least 88%, at least 90%, at least 92%, at least 95%, at least 96%, at least 97%, at least 98% or at least 99% identity to at least one of the CDR sequences, the VH sequence and/or the VL sequence shown in Table 1 and/or in Table 2.

Preferably, the antibody, or the antigen binding fragment thereof, according to the present invention comprises a heavy chain comprising at least one CDRH1, at least one CDRH2 and at least one CDRH3 and a light chain comprising at least one CDRL1, at least one CDRL2 and at least one CDRL3, wherein at least one CDR, preferably the at least one heavy chain CDRH3, comprises or consists of an amino acid sequence according to any of SEQ ID NOs: 30, 48, 66, 84, 102, 120, 138, 156, 174, 190, 208, 226, 260, 244, 278 and 296, or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

More preferably, the antibody, or the antigen binding fragment thereof, according to the present invention comprises a heavy chain comprising at least one CDRH1, at least one CDRH2 and at least one CDRH3 and a light chain comprising at least one CDRL1, at least one CDRL2 and at least one CDRL3, wherein (i) the at least one heavy chain CDRH1 comprises an amino acid sequence according to any of SEQ ID NOs: 28, 46, 64, 82, 100, 118, 136, 154, 172, 188, 206, 224, 242, 258, 276, and 294, or a functional sequence variant thereof having at least 70%, at least 75%, at least 80%, at least 85%, at least 88%, at least 90%, at least 92%, at least 95%, at least 96%, at least 97%, at least 98% or at least 99% sequence identity;

(ii) the at least one CDRH2 comprises an amino acid sequence according to any of SEQ ID NOs: 29, 47, 65, 83, 101, 119, 137, 155, 173, 189, 207, 225, 243, 259, 277, and 295, or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; and/or (iii) the at least one heavy chain CDRH3 comprises an amino acid sequence according to any of SEQ ID NOs: 30, 48, 66, 84, 102, 120, 138, 156, 174, 190, 208, 226, 260, 244, 278 and 296, or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

It is also preferred that the antibody, or the antigen binding fragment thereof, according to the present invention comprises a heavy chain comprising at least one CDRH1, at least one CDRH2 and at least one CDRH3 and a light chain comprising at least one CDRL1, at least one CDRL2 and at least one CDRL3, wherein (i) the at least one CDRL1 comprises an amino acid sequence according to any of SEQ ID NOs: 31, 49, 67, 85, 103, 121, 139, 157, 175, 191, 209, 227, 245, 261, 279, and 297, or a functional sequence variant thereof having at least 70%, at least 75%, at least 80%, at least 85%, at least 88%, at least 90%, at least 92%, at least 95%, at least 96%, at least 97%, at least 98% or at least 99% sequence identity;

(ii) the at least one CDRL2 comprises an amino acid sequence according to any of SEQ ID NOs: 32, 33, 50, 51, 68, 69, 86, 87, 104, 105, 122, 123, 140, 141, 158, 159, 176, 192, 193, 210, 211, 228, 229, 246, 262, 263, 280, 281, 298 and 299, or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; and/or (iii) the at least one CDRL3 amino comprises an amino acid sequence according to any of SEQ ID NOs: 34, 52, 70, 88, 106, 124, 142, 160, 177, 194, 212, 230, 247, 264, 282, and 300 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

Preferably, the antibody, or the antigen binding fragment thereof, according to the present invention comprises CDRH1, CDRH2, and CDRH3 amino acid sequences (i) according to SEQ ID NOs: 64-66; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (ii) according to SEQ ID NOs: 82-84; or functional sequence variants thereof having at least 70%, at least 75%, at least 80%, at least 85%, at least 88%, at least 90%, at least 92%, at least 95%, at least 96%, at least 97%, at least 98% or at least 99% sequence identity;

(iii) according to SEQ ID NOs: 136-138; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (iv) according to SEQ ID NOs: 154-156; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (v) according to SEQ ID NOs: 206-208; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (vi) according to SEQ ID NOs: 224-226; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (vii) according to SEQ ID NOs: 258-260; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (viii) according to SEQ ID NOs: 276-278; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (ix) according to SEQ ID NOs: 294-296; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (x) according to SEQ ID NOs: 28-30; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xi) according to SEQ ID NOs: 46-48; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xii) according to SEQ ID NOs: 100-102; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xiii) according to SEQ ID NOs: 118-120; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xiv) according to SEQ ID NOs: 172-174; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xv) according to SEQ ID NOs: 188-190; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; or (xvi) according to SEQ ID NOs: 242-244; or functional sequence variants thereof having at least 70%, at least 75%, at least 80%, at least 85%, at least 88%, at least 90%, at least 92%, at least 95%, at least 96%, at least 97%, at least 98% or at least 99% sequence identity.

Preferably, the antibody, or the antigen binding fragment thereof, according to the present invention comprises CDRH1, CDRH2, and CDRH3 amino acid sequences and CDRL1, CDRL2, and CDRL3 amino acid sequences (i) according to SEQ ID NOs: 64-68 and 70; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (ii) according to SEQ ID NOs: 64-67 and 69-70; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (iii) according to SEQ ID NOs: 82-86 and 88; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (iv) according to SEQ ID NOs: 82-85 and 87-88; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (v) according to SEQ ID NOs: 136-140 and 142; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (vi) according to SEQ ID NOs: 136-139 and 141-142; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (vii) according to SEQ ID NOs: 154-158 and 160; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (viii) according to SEQ ID NOs: 154-157 and 159-160; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (ix) according to SEQ ID NOs: 206-210 and 212; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; or (x) according to SEQ ID NOs: 206-209 and 211-212; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; or (xi) according to SEQ ID NOs: 224-228 and 230; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; or (xii) according to SEQ ID NOs: 224-227 and 229-230; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; or (xiii) according to SEQ ID NOs: 258-262 and 264; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; or (xiv) according to SEQ ID NOs: 258-261 and 263-264; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; or (xv) according to SEQ ID NOs: 276-280 and 282; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; or (xvi) according to SEQ ID NOs: 276-279 and 281-282; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; or (xvii) according to SEQ ID NOs: 294-298 and 300; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; or (xviii) according to SEQ ID NOs: 294-297 and 299-300; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; or (xix) according to SEQ ID NOs: 28-32 and 34; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; or (xx) according to SEQ ID NOs: 28-31 and 33-34; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; or (xxi) according to SEQ ID NOs: 46-50 and 52; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; or (xxii) according to SEQ ID NOs: 46-49 and 51-52; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; or (xxiii) according to SEQ ID NOs: 100-104 and 106; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; or (xxiv) according to SEQ ID NOs: 100-103 and 105-106; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; or (xxv) according to SEQ ID NOs: 118-122 and 124; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; or (xxvi) according to SEQ ID NOs: 118-121 and 123-124; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; or (xxvii) according to SEQ ID NOs: 172-176 and 178; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; or (xxviii) according to SEQ ID NOs: 172-177; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; or (xxix) according to SEQ ID NOs: 188-192 and 194; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; or (xxx) according to SEQ ID NOs: 188-191 and 193-194; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; or (xxxi) according to SEQ ID NOs: 242-247; or functional sequence variants thereof having at least 70%, at least 75%, at least 80%, at least 85%, at least 88%, at least 90%, at least 92%, at least 95%, at least 96%, at least 97%, at least 98% or at least 99% sequence identity.

More preferably, the antibody, or the antigen binding fragment thereof, according to the present invention comprises CDRH1, CDRH2, and CDRH3 amino acid sequences and CDRL1, CDRL2, and CDRL3 amino acid sequences (i) according to SEQ ID NOs: 64-68 and 70, respectively; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; or (ii) according to SEQ ID NOs: 64-67 and 69-70; or functional sequence variants thereof having at least 70%, at least 75%, at least 80%, at least 85%, at least 88%, at least 90%, at least 92%, at least 95%, at least 96%, at least 97%, at least 98% or at least 99% sequence identity.

More preferably, the antibody, or the antigen binding fragment thereof, according to the present invention comprises CDRH1, CDRH2, and CDRH3 amino acid sequences and CDRL1, CDRL2, and CDRL3 amino acid sequences (i) according to SEQ ID NOs: 224-228 and 230; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; or (ii) according to SEQ ID NOs: 224-227 and 229-230; or functional sequence variants thereof having at least 70%, at least 75%, at least 80%, at least 85%, at least 88%, at least 90%, at least 92%, at least 95%, at least 96%, at least 97%, at least 98% or at least 99% sequence identity.

Even more preferably, the antibody, or the antigen binding fragment thereof, according to the present invention comprises CDRH1, CDRH2, and CDRH3 amino acid sequences and CDRL1, CDRL2, and CDRL3 amino acid sequences (i) according to SEQ ID NOs: 276-280 and 282; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; or (ii) according to SEQ ID NOs: 276-279 and 281-282; or functional sequence variants thereof having at least 70%, at least 75%, at least 80%, at least 85%, at least 88%, at least 90%, at least 92%, at least 95%, at least 96%, at least 97%, at least 98% or at least 99% sequence identity.

Still more preferably, the antibody, or the antigen binding fragment thereof, according to the present invention comprises CDRH1, CDRH2, and CDRH3 amino acid sequences and CDRL1, CDRL2, and CDRL3 amino acid sequences (i) according to SEQ ID NOs: 206-210 and 212; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; or (ii) according to SEQ ID NOs: 206-209 and 211-212; or functional sequence variants thereof having at least 70%, at least 75%, at least 80%, at least 85%, at least 88%, at least 90%, at least 92%, at least 95%, at least 96%, at least 97%, at least 98% or at least 99% sequence identity.

Particularly preferably, the antibody, or the antigen binding fragment thereof, according to the present invention comprises CDRH1, CDRH2, and CDRH3 amino acid sequences and CDRL1, CDRL2, and CDRL3 amino acid sequences (i) according to SEQ ID NOs: 136-140 and 142; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (ii) according to SEQ ID NOs: 136-139 and 141-142; or functional sequence variants thereof having at least 70%, at least 75%, at least 80%, at least 85%, at least 88%, at least 90%, at least 92%, at least 95%, at least 96%, at least 97%, at least 98% or at least 99% sequence identity.

Most preferably, the antibody, or the antigen binding fragment thereof, according to the present invention comprises CDRH1, CDRH2, and CDRH3 amino acid sequences and CDRL1, CDRL2, and CDRL3 amino acid sequences (i) according to SEQ ID NOs: 82-86 and 88; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (ii) according to SEQ ID NOs: 82-85 and 87-88; or functional sequence variants thereof having at least 70%, at least 75%, at least 80%, at least 85%, at least 88%, at least 90%, at least 92%, at least 95%, at least 96%, at least 97%, at least 98% or at least 99% sequence identity.

In addition, it is also preferred that the antibody, or the antigen binding fragment thereof, according to the present invention comprises a heavy chain variable region (VH) and, optionally, a light chain variable region (VL), wherein the heavy chain variable region (VH) comprises or consists of an amino acid sequence according to any of SEQ ID NOs: 35, 53, 71, 89, 107, 125, 143, 161, 178, 195, 213, 231, 248, 265, 283, and 301; or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

Preferably, the antibody, or the antigen binding fragment thereof, according to the present invention comprises (i) a heavy chain variable region (VH) amino acid sequence according to SEQ ID NO: 71 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 72 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; (ii) a heavy chain variable region (VH) amino acid sequence according to SEQ ID NO: 89 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 90 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; (iii) a heavy chain variable region (VH) amino acid sequence according to SEQ ID NO: 143 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 144 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; (iv) a heavy chain variable region (VH) amino acid sequence according to SEQ ID NO: 161 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 162 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; or (v) a heavy chain variable region (VH) amino acid sequence according to SEQ ID NO: 213 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 214 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; (vi) a heavy chain variable region (VH) amino acid sequence according to SEQ ID NO: 231 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 232 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; (vii) a heavy chain variable region (VH) amino acid sequence according to SEQ ID NO: 265 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 266 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; (viii) a heavy chain variable region (VH) amino acid sequence according to SEQ ID NO: 283 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 284 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; or (ix) a heavy chain variable region (VH) amino acid sequence according to SEQ ID NO: 301 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 302 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; or (x) a heavy chain variable region (VH) amino acid sequence according to SEQ ID NO: 35 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 36 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; or (xi) a heavy chain variable region (VH) amino acid sequence according to SEQ ID NO: 53 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 54 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; or (xii) a heavy chain variable region (VH) amino acid sequence according to SEQ ID NO: 107 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 108 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; or (xiii) a heavy chain variable region (VH) amino acid sequence according to SEQ ID NO: 125 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 126 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; or (xiv) a heavy chain variable region (VH) amino acid sequence according to SEQ ID NO: 178 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 179 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; or (xv) a heavy chain variable region (VH) amino acid sequence according to SEQ ID NO: 195 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 196 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; or (xvi) a heavy chain variable region (VH) amino acid sequence according to SEQ ID NO: 248 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 249 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

More preferably, the antibody, or the antigen binding fragment thereof, according to the present invention comprises a heavy chain variable region (VH) amino acid sequence according to SEQ ID NO: 71 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 72 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

More preferably, the antibody, or the antigen binding fragment thereof, according to the present invention comprises a heavy chain variable region (VH) amino acid sequence according to SEQ ID NO: 231 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 232 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

Even more preferably, the antibody, or the antigen binding fragment thereof, according to the present invention comprises a heavy chain variable region (VH) amino acid sequence according to SEQ ID NO: 283 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 284 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

Still more preferably, the antibody, or the antigen binding fragment thereof, according to the present invention comprises a heavy chain variable region (VH) amino acid sequence according to SEQ ID NO: 213 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 214 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

Particularly preferably, the antibody, or the antigen binding fragment thereof, according to the present invention comprises a heavy chain variable region (VH) amino acid sequence according to SEQ ID NO: 143 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 144 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

Most preferably, the antibody, or the antigen binding fragment thereof, according to the present invention comprises a heavy chain variable region (VH) amino acid sequence according to SEQ ID NO: 89 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 90 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

Preferably, the antibody, or the antigen binding fragment thereof, according to the present invention is gMGG1, gMGG2, gMGG3, gMGG4, gMGG8, gMGH1, gMGH2, gMGH3, gMGU1, gMGU3, gMGU5, gMGU8, gMGU10, gMGU11, gMGU12 or gMGV3, preferably the antibody, or the antigen binding fragment thereof, is gMGG3, gMGG4, gMGH2, gMGU5, gMGU8 or gMGU12, more preferably the antibody, or the antigen binding fragment thereof, is gMGG4 or gMGH2.

The present inventors have isolated monoclonal antibody (mAb) according to the present invention, which are referred to herein as MGG1, MGG2, MGG3, MGG4, MGG8, MGH1, MGH2, MGH3, MGU1, MGU3, MGU5, MGU8, MGU10, MGU11, MGU12 and MGV3 (cf. Tables 1 and 2, Example 1). Based on those antibodies, in particular on the VH and VL genes of those antibodies, the terms "gMGG1", "gMGG2", "gMGG3", "gMGG4", "gMGG8", "gMGH1", "gMGH2", "gMGH3", "gMGU1", "gMGU3", "gMGU5", "gMGU8", "gMGU10", "gMGU11", "gMGU12", and "gMGV3", as used herein, refer to the respective "generic" antibodies, or antigen binding fragments thereof.

Namely, "gMGG1" refers to an antibody, or antigen binding fragment thereof, having a CDRH1 amino acid sequence according to SEQ ID NO: 28, a CDRH2 amino acid sequence according to SEQ ID NO: 29, a CDRH3 amino acid sequence according to SEQ ID NO: 30, a CDRL1 amino acid sequence according to SEQ ID NO: 31, a CDRL2 amino acid sequence according to SEQ ID NO: 32 or 33, and a CDRL3 amino acid sequence according to SEQ ID NO: 34. The heavy chain variable region ($V_H$) has preferably an amino acid sequence according to SEQ ID NO: 35 and the light chain variable region ($V_L$) has preferably an amino acid sequence according to SEQ ID NO: 36.

"gMGG2" refers to an antibody, or antigen binding fragment thereof, having a CDRH1 amino acid sequence according to SEQ ID NO: 46, a CDRH2 amino acid sequence according to SEQ ID NO: 47, a CDRH3 amino acid sequence according to SEQ ID NO: 48, a CDRL1 amino acid sequence according to SEQ ID NO: 49, a CDRL2 amino acid sequence according to SEQ ID NO: 50 or 51, and a CDRL3 amino acid sequence according to SEQ ID NO: 52. The heavy chain variable region ($V_H$) has preferably an amino acid sequence according to SEQ ID NO: 53 and the light chain variable region ($V_L$) has preferably an amino acid sequence according to SEQ ID NO: 54.

"gMGG3" refers to an antibody, or antigen binding fragment thereof, having a CDRH1 amino acid sequence according to SEQ ID NO: 64, a CDRH2 amino acid sequence according to SEQ ID NO: 65, a CDRH3 amino acid sequence according to SEQ ID NO: 66, a CDRL1 amino acid sequence according to SEQ ID NO: 67, a CDRL2 amino acid sequence according to SEQ ID NO: 68 or 69, and a CDRL3 amino acid sequence according to SEQ ID NO: 70. The heavy chain variable region ($V_1$) has preferably an amino acid sequence according to SEQ ID NO: 71 and the light chain variable region ($V_1$) has preferably an amino acid sequence according to SEQ ID NO: 72.

"gMGG4" refers to an antibody, or antigen binding fragment thereof, having a CDRH1 amino acid sequence according to SEQ ID NO: 82, a CDRH2 amino acid sequence according to SEQ ID NO: 83, a CDRH3 amino acid sequence according to SEQ ID NO: 84, a CDRL1 amino acid sequence according to SEQ ID NO: 85, a CDRL2 amino acid sequence according to SEQ ID NO: 86 or 87, and a CDRL3 amino acid sequence according to SEQ ID NO: 88.

The heavy chain variable region ($V_H$) has preferably an amino acid sequence according to SEQ ID NO: 89 and the light chain variable region ($V_L$) has preferably an amino acid sequence according to SEQ ID NO: 90.

"gMGG8" refers to an antibody, or antigen binding fragment thereof, having a CDRH1 amino acid sequence according to SEQ ID NO: 100, a CDRH2 amino acid sequence according to SEQ ID NO: 101, a CDRH3 amino acid sequence according to SEQ ID NO: 102, a CDRL1 amino acid sequence according to SEQ ID NO: 103, a CDRL2 amino acid sequence according to SEQ ID NO: 104 or 105, and a CDRL3 amino acid sequence according to SEQ ID NO: 106. The heavy chain variable region ($V_H$) has preferably an amino acid sequence according to SEQ ID NO: 107 and the light chain variable region (V) has preferably an amino acid sequence according to SEQ ID NO: 108.

"gMGH1" refers to an antibody, or antigen binding fragment thereof, having a CDRH1 amino acid sequence according to SEQ ID NO: 118, a CDRH2 amino acid sequence according to SEQ ID NO: 119, a CDRH3 amino acid sequence according to SEQ ID NO: 120, a CDRL1 amino acid sequence according to SEQ ID NO: 121, a CDRL2 amino acid sequence according to SEQ ID NO: 122 or 123, and a CDRL3 amino acid sequence according to SEQ ID NO: 124. The heavy chain variable region ($V_H$) has preferably an amino acid sequence according to SEQ ID NO: 125 and the light chain variable region ($V_L$) has preferably an amino acid sequence according to SEQ ID NO: 126.

"gMGH2" refers to an antibody, or antigen binding fragment thereof, having a CDRH1 amino acid sequence according to SEQ ID NO: 136, a CDRH2 amino acid sequence according to SEQ ID NO: 137, a CDRH3 amino acid sequence according to SEQ ID NO: 138, a CDRL1 amino acid sequence according to SEQ ID NO: 139, a CDRL2 amino acid sequence according to SEQ ID NO: 140 or 141, and a CDRL3 amino acid sequence according to SEQ ID NO: 142. The heavy chain variable region ($V_H$) has preferably an amino acid sequence according to SEQ ID NO: 143 and the light chain variable region (V) has preferably an amino acid sequence according to SEQ ID NO: 144.

"gMGH3" refers to an antibody, or antigen binding fragment thereof, having a CDRH1 amino acid sequence according to SEQ ID NO: 154, a CDRH2 amino acid sequence according to SEQ ID NO: 155, a CDRH3 amino acid sequence according to SEQ ID NO: 156, a CDRL1 amino acid sequence according to SEQ ID NO: 157, a CDRL2 amino acid sequence according to SEQ ID NO: 158 or 159, and a CDRL3 amino acid sequence according to SEQ ID NO: 160. The heavy chain variable region ($V_H$) has preferably an amino acid sequence according to SEQ ID NO: 161 and the light chain variable region (V) has preferably an amino acid sequence according to SEQ ID NO: 162.

"gMGU1" refers to an antibody, or antigen binding fragment thereof, having a CDRH1 amino acid sequence according to SEQ ID NO: 172, a CDRH2 amino acid sequence according to SEQ ID NO: 173, a CDRH3 amino acid sequence according to SEQ ID NO: 174, a CDRL1 amino acid sequence according to SEQ ID NO: 175, a CDRL2 amino acid sequence according to SEQ ID NO: 176, and a CDRL3 amino acid sequence according to SEQ ID NO: 177. The heavy chain variable region ($V_H$) has preferably an amino acid sequence according to SEQ ID NO: 178 and the light chain variable region (VL) has preferably an amino acid sequence according to SEQ ID NO: 179.

"gMGU3" refers to an antibody, or antigen binding fragment thereof, having a CDRH1 amino acid sequence according to SEQ ID NO: 188, a CDRH2 amino acid sequence according to SEQ ID NO: 189, a CDRH3 amino acid sequence according to SEQ ID NO: 190, a CDRL1 amino acid sequence according to SEQ ID NO: 191, a CDRL2 amino acid sequence according to SEQ ID NO: 192 or 193, and a CDRL3 amino acid sequence according to SEQ ID NO: 194. The heavy chain variable region ($V_H$) has preferably an amino acid sequence according to SEQ ID NO: 195 and the light chain variable region ($V_L$) has preferably an amino acid sequence according to SEQ ID NO: 196.

"gMGU5" refers to an antibody, or antigen binding fragment thereof, having a CDRH1 amino acid sequence according to SEQ ID NO: 206, a CDRH2 amino acid sequence according to SEQ ID NO: 207, a CDRH3 amino acid sequence according to SEQ ID NO: 208, a CDRL1 amino acid sequence according to SEQ ID NO: 209, a CDRL2 amino acid sequence according to SEQ ID NO: 210 or 211, and a CDRL3 amino acid sequence according to SEQ ID NO: 212. The heavy chain variable region ($V_H$) has preferably an amino acid sequence according to SEQ ID NO: 213 and the light chain variable region ($V_1$) has preferably an amino acid sequence according to SEQ ID NO: 214.

"gMGU8" refers to an antibody, or antigen binding fragment thereof, having a CDRH1 amino acid sequence according to SEQ ID NO: 224, a CDRH2 amino acid sequence according to SEQ ID NO: 225, a CDRH3 amino acid sequence according to SEQ ID NO: 226, a CDRL1 amino acid sequence according to SEQ ID NO: 227, a CDRL2 amino acid sequence according to SEQ ID NO: 228 or 229, and a CDRL3 amino acid sequence according to SEQ ID NO: 230. The heavy chain variable region ($V_H$) has preferably an amino acid sequence according to SEQ ID NO: 231 and the light chain variable region (V) has preferably an amino acid sequence according to SEQ ID NO: 232.

"gMGU10" refers to an antibody, or antigen binding fragment thereof, having a CDRH1 amino acid sequence according to SEQ ID NO: 242, a CDRH2 amino acid sequence according to SEQ ID NO: 243, a CDRH3 amino acid sequence according to SEQ ID NO: 244, a CDRL1 amino acid sequence according to SEQ ID NO: 245, a CDRL2 amino acid sequence according to SEQ ID NO: 246, and a CDRL3 amino acid sequence according to SEQ ID NO: 247. The heavy chain variable region ($V_H$) has preferably an amino acid sequence according to SEQ ID NO: 248 and the light chain variable region ($V_1$) has preferably an amino acid sequence according to SEQ ID NO: 249.

"gMGU11" refers to an antibody, or antigen binding fragment thereof, having a CDRH1 amino acid sequence according to SEQ ID NO: 258, a CDRH2 amino acid sequence according to SEQ ID NO: 259, a CDRH3 amino acid sequence according to SEQ ID NO: 260, a CDRL1 amino acid sequence according to SEQ ID NO: 261, a CDRL2 amino acid sequence according to SEQ ID NO: 262 or 263, and a CDRL3 amino acid sequence according to SEQ ID NO: 264. The heavy chain variable region ($V_H$) has preferably an amino acid sequence according to SEQ ID NO: 265 and the light chain variable region (VL) has preferably an amino acid sequence according to SEQ ID NO: 266.

"gMGU12" refers to an antibody, or antigen binding fragment thereof, having a CDRH1 amino acid sequence according to SEQ ID NO: 276, a CDRH2 amino acid sequence according to SEQ ID NO: 277, a CDRH3 amino acid sequence according to SEQ ID NO: 278, a CDRL1 amino acid sequence according to SEQ ID NO: 279, a CDRL2 amino acid sequence according to SEQ ID NO: 280 or 281, and a CDRL3 amino acid sequence according to SEQ ID NO: 282. The heavy chain variable region (VH) has preferably an amino acid sequence according to SEQ ID NO: 283 and the light chain variable region (V) has preferably an amino acid sequence according to SEQ ID NO: 284.

"gMGV3" refers to an antibody, or antigen binding fragment thereof, having a CDRH1 amino acid sequence according to SEQ ID NO: 294, a CDRH2 amino acid sequence according to SEQ ID NO: 295, a CDRH3 amino acid sequence according to SEQ ID NO: 296, a CDRL1 amino acid sequence according to SEQ ID NO: 297, a CDRL2 amino acid sequence according to SEQ ID NO: 298 or 299, and a CDRL3 amino acid sequence according to SEQ ID NO: 300. The heavy chain variable region ($V_H$) has preferably an amino acid sequence according to SEQ ID NO: 301 and the light chain variable region (V) has preferably an amino acid sequence according to SEQ ID NO: 302.

Optional Additional Features of the Antibodies

Antibodies of the invention (i.e. antibodies binding to *P. falciparum* sporozoites and antibodies binding to the peptide of the invention), and antigen-binding fragments thereof, may be coupled, for example, to a drug for delivery to a treatment site or coupled to a detectable label to facilitate imaging of a site comprising cells of interest. Methods for coupling antibodies to drugs and detectable labels are well known in the art, as are methods for imaging using detectable labels. Labeled antibodies may be employed in a wide variety of assays, employing a wide variety of labels. Detection of the formation of an antibody-antigen complex, for example between an antibody of the invention and an epitope of interest or between the peptide or protein according to the invention and an antibody, can be facilitated by attaching a detectable substance to the antibody. Suitable detection means include the use of labels such as radionuclides, enzymes, coenzymes, fluorescers, chemiluminescers, chromogens, enzyme substrates or co-factors, enzyme inhibitors, prosthetic group complexes, free radicals, particles, dyes, and the like. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material is luminol; examples of bioluminescent materials include luciferase, luciferin, and aequorin; and examples of suitable radioactive material include 125I, 131I, 35S, or 3H. Such labeled reagents may be used in a variety of well-known assays, such as radioimmunoassays, enzyme immunoassays, e.g., ELISA, fluorescent immunoassays, and the like. Labeled antibodies according to the present invention may be thus be used in such assays for example as described in U.S. Pat. Nos. 3,766,162; 3,791,932; 3,817,837; and 4,233,402.

An antibody according to the invention may be conjugated to a therapeutic moiety such as a cytotoxin, a therapeutic agent, or a radioactive metal ion or radioisotope. Examples of radioisotopes include, but are not limited to, I-131, I-123, I-125, Y-90, Re-188, Re-186, At-211, Cu-67, Bi-212, Bi-213, Pd-109, Tc-99, In-111, and the like. Such antibody conjugates can be used for modifying a given biological response; the drug moiety is not to be construed as limited to classical chemical therapeutic agents. For example, the drug moiety may be a protein or polypeptide possessing a desired biological activity. Such proteins may include, for example, a toxin such as abrin, ricin A, *Pseudomonas* exotoxin, or diphtheria toxin.

Techniques for conjugating such therapeutic moiety to antibodies are well known. See, for example, Arnon et al. (1985) "Monoclonal Antibodies for Immunotargeting of Drugs in Cancer Therapy," in Monoclonal Antibodies and Cancer Therapy, ed. Reisfeld et al. (Alan R. Liss, Inc.), pp. 243-256; ed. Hellstrom et al. (1987) "Antibodies for Drug Delivery," in Controlled Drug Delivery, ed. Robinson et al. (2d ed; Marcel Dekker, Inc.), pp. 623-653; Thorpe (1985) "Antibody Carriers of Cytotoxic Agents in Cancer Therapy: A Review," in Monoclonal Antibodies '84: Biological and Clinical Applications, ed. Pinchera et al. pp. 475-506 (Editrice Kurtis, Milano, Italy, 1985); "Analysis, Results, and Future Prospective of the Therapeutic Use of Radiolabeled Antibody in Cancer Therapy," in Monoclonal Antibodies for Cancer Detection and Therapy, ed. Baldwin et al. (Academic Press, New York, 1985), pp. 303-316; and Thorpe et al. (1982) Immunol. Rev. 62:119-158.

Alternatively, an antibody, or antibody fragment thereof, can be conjugated to a second antibody, or antibody fragment thereof, to form an antibody heteroconjugate as described in U.S. Pat. No. 4,676,980. In addition, linkers may be used between the labels and the antibodies of the invention, e.g., as described in U.S. Pat. No. 4,831,175. Antibodies or, antigen-binding fragments thereof may be directly labeled with radioactive iodine, indium, yttrium, or other radioactive particle known in the art, e.g., as described in U.S. Pat. No. 5,595,721. Treatment may consist of a combination of treatment with conjugated and non-conjugated antibodies administered simultaneously or subsequently e.g., as described in WO00/52031; WO0/52473.

Antibodies of the invention may also be attached to a solid support. Additionally, antibodies of the invention, or functional antibody fragments thereof, can be chemically modified by covalent conjugation to a polymer to, for example, increase their circulating half-life. Examples of polymers, and methods to attach them to peptides, are shown in U.S. Pat. Nos. 4,766,106; 4,179,337; 4,495,285 and 4,609,546. In some embodiments the polymers may be selected from polyoxyethylated polyols and polyethylene glycol (PEG). PEG is soluble in water at room temperature and has the general formula: $R(O-CH_2-CH_2)_nO-R$, wherein R can be hydrogen, or a protective group such as an alkyl or alkanol group. Preferably, the protective group may have between 1 and 8 carbons. For example, the protective group is methyl. The symbol n is a positive integer. In one embodiment n is between 1 and 1,000. In another embodiment n is between 2 and 500. Preferably, the PEG has an average molecular weight between 1,000 and 40,000, more preferably the PEG has a molecular weight between 2,000 and 20,000, even more preferably the PEG has a molecular weight between 3,000 and 12,000. Furthermore, PEG may have at least one hydroxy group, for example the PEG may have a terminal hydroxy group. For example, it is the terminal hydroxy group which is activated to react with a free amino group on the inhibitor. However, it will be understood that the type and amount of the reactive groups may be varied to achieve a covalently conjugated PEG/antibody of the present invention.

Water-soluble polyoxyethylated polyols are also useful in the present invention. They include polyoxyethylated sorbitol, polyoxyethylated glucose, polyoxyethylated glycerol (POG), and the like. In one embodiment, POG is used. Without being bound by any theory, because the glycerol backbone of polyoxyethylated glycerol is the same backbone occurring naturally in, for example, animals and humans in mono-, di-, triglycerides, this branching would not necessarily be seen as a foreign agent in the body. POG may have a molecular weight in the same range as PEG. Another drug delivery system that can be used for increasing circulatory half-life is the liposome. Methods of preparing liposome delivery systems are known to one of skill in the art. Other drug delivery systems are known in the art and are described in, for example, referenced in Poznansky M J and Juliano R L, 1984, Pharmacol. Rev. 36(4): 277-336.

Antibodies of the invention may be provided in purified form. Typically, the antibody will be present in a composition that is substantially free of other polypeptides e.g., where less than 90% (by weight), usually less than 60% and more usually less than 50% of the composition is made up of other polypeptides.

Antibodies of the invention may be immunogenic in non-human (or heterologous) hosts e.g., in mice. In particular, the antibodies may have an idiotope that is immunogenic in non-human hosts, but not in a human host. In particular, antibodies of the invention for human use include those that cannot be easily isolated from hosts such as mice, goats, rabbits, rats, non-primate mammals, etc. and cannot generally be obtained by humanization or from xeno-mice.

Production of Antibodies

Antibodies according to the invention can be made by any method known in the art. For example, the general methodology for making monoclonal antibodies using hybridoma technology is well known (Kohler, G. and Milstein, C., 1975; Kozbar et al. 1983).

Preferably, the EBV immortalization method described in WO2004/076677 is used. In this method B cells producing the antibody of the invention are transformed with EBV and a polyclonal B cell activator. Additional stimulants of cellular growth and differentiation may optionally be added during the transformation step to further enhance the efficiency. These stimulants may be cytokines such as IL-2 and IL-15. In one aspect, IL-2 is added during the immortalization step to further improve the efficiency of immortalization, but its use is not essential. The immortalized B cells produced using these methods can then be cultured using methods known in the art and antibodies isolated therefrom.

Another preferred method is described in WO 2010/046775. In this method plasma cells are cultured in limited numbers, or as single plasma cells in microwell culture plates. Antibodies can be isolated from the plasma cell cultures. Further, from the plasma cell cultures, RNA can be extracted and PCR can be performed using methods known in the art. The VH and VL regions of the antibodies can be amplified by RT-PCR (reverse transcriptase PCR), sequenced and cloned into an expression vector that is then transfected into HEK293T cells or other host cells. The cloning of nucleic acid in expression vectors, the transfection of host cells, the culture of the transfected host cells and the isolation of the produced antibody can be done using any methods known to one of skill in the art.

The antibodies may be further purified, if desired, using filtration, centrifugation and various chromatographic methods such as HPLC or affinity chromatography. Techniques for purification of antibodies, e.g., monoclonal antibodies, including techniques for producing pharmaceutical-grade antibodies, are well known in the art.

Fragments of the antibodies of the invention can be obtained from the antibodies by methods that include digestion with enzymes, such as pepsin or papain, and/or by cleavage of disulfide bonds by chemical reduction. Alternatively, fragments of the antibodies can be obtained by cloning and expression of part of the sequences of the heavy or light chains. Antibody "fragments" include Fab, Fab', F(ab')2 and Fv fragments. The invention also encompasses single-chain Fv fragments (scFv) derived from the heavy and light chains of an antibody of the invention. For example, the invention includes a scFv comprising the CDRs from an antibody of the invention. Also included are heavy or light chain monomers and dimers, single domain heavy chain antibodies, single domain light chain antibodies, as well as single chain antibodies, e.g., single chain Fv in which the heavy and light chain variable domains are joined by a peptide linker.

Antibody fragments of the invention may impart monovalent or multivalent interactions and be contained in a variety of structures as described above. For instance, scFv molecules may be synthesized to create a trivalent "triabody" or a tetravalent "tetrabody." The scFv molecules may include a domain of the Fc region resulting in bivalent minibodies. In addition, the sequences of the invention may be a component of multispecific molecules in which the sequences of the invention target the epitopes of the invention and other regions of the molecule bind to other targets. Exemplary molecules include, but are not limited to, bispecific Fab2, trispecific Fab3, bispecific scFv, and diabodies (Holliger and Hudson, 2005, *Nature Biotechnology* 9: 1126-1136).

Standard techniques of molecular biology may be used to prepare DNA sequences encoding the antibodies or antibody fragments of the present invention. Desired DNA sequences may be synthesized completely or in part using oligonucleotide synthesis techniques. Site-directed mutagenesis and polymerase chain reaction (PCR) techniques may be used as appropriate.

Any suitable host cell/vector system may be used for expression of the DNA sequences encoding the antibody molecules of the present invention or fragments thereof. Bacterial, for example *E. coli*, and other microbial systems may be used, in part, for expression of antibody fragments such as Fab and F(ab')2 fragments, and especially Fv fragments and single chain antibody fragments, for example, single chain Fvs. Eukaryotic, e.g., mammalian, host cell expression systems may be used for production of larger antibody molecules, including complete antibody molecules. Suitable mammalian host cells include, but are not limited to, CHO, HEK293T, PER.C6, NS0, myeloma or hybridoma cells.

The present invention also provides a process for the production of an antibody molecule according to the present invention comprising culturing a host cell comprising a vector encoding a nucleic acid of the present invention under conditions suitable for expression of protein from DNA encoding the antibody molecule of the present invention, and isolating the antibody molecule.

The antibody molecule may comprise only a heavy or light chain polypeptide, in which case only a heavy chain or light chain polypeptide coding sequence needs to be used to transfect the host cells. For production of products comprising both heavy and light chains, the cell line may be transfected with two vectors, a first vector encoding a light chain polypeptide and a second vector encoding a heavy chain polypeptide. Alternatively, a single vector may be used, the vector including sequences encoding light chain and heavy chain polypeptides. Alternatively, antibodies according to the invention may be produced by (i) expressing a nucleic acid sequence according to the invention in a host cell, e.g. by use of a vector according to the present invention, and (ii) isolating the expressed antibody product. Additionally, the method may include (iii) purifying the isolated antibody. Transformed B cells and cultured plasma cells may be screened for those producing antibodies of the desired specificity or function.

The screening step may be carried out by any immunoassay, e.g., ELISA, by staining of tissues or cells (including transfected cells), by neutralization assay or by one of a number of other methods known in the art for identifying desired specificity or function. The assay may select on the basis of simple recognition of one or more antigens, or may select on the additional basis of a desired function e.g., to select neutralizing antibodies rather than just antigen-binding antibodies, to select antibodies that can change characteristics of targeted cells, such as their signaling cascades, their shape, their growth rate, their capability of influencing other cells, their response to the influence by other cells or by other reagents or by a change in conditions, their differentiation status, etc.

Individual transformed B cell clones may then be produced from the positive transformed B cell culture. The cloning step for separating individual clones from the mixture of positive cells may be carried out using limiting dilution, micromanipulation, single cell deposition by cell sorting or another method known in the art.

Nucleic acid from the cultured plasma cells can be isolated, cloned and expressed in HEK293T cells or other known host cells using methods known in the art.

The immortalized B cell clones or the transfected host-cells of the invention can be used in various ways e.g., as a source of monoclonal antibodies, as a source of nucleic acid (DNA or mRNA) encoding a monoclonal antibody of interest, for research, etc.

The invention also provides a composition comprising immortalized B memory cells or transfected host cells that produce antibodies according to the present invention.

The immortalized B cell clone or the cultured plasma cells of the invention may also be used as a source of nucleic acid for the cloning of antibody genes for subsequent recombinant expression. Expression from recombinant sources is more common for pharmaceutical purposes than expression from B cells or hybridomas e.g., for reasons of stability, reproducibility, culture ease, etc.

Thus the invention also provides a method for preparing a recombinant cell, comprising the steps of: (i) obtaining one or more nucleic acids (e.g., heavy and/or light chain mRNAs) from the B cell clone or the cultured plasma cells that encodes the antibody of interest; (ii) inserting the nucleic acid into an expression vector and (iii) transfecting the vector into a host cell in order to permit expression of the antibody of interest in that host cell.

Similarly, the invention provides a method for preparing a recombinant cell, comprising the steps of: (i) sequencing nucleic acid(s) from the B cell clone or the cultured plasma cells that encodes the antibody of interest; and (ii) using the sequence information from step (i) to prepare nucleic acid(s) for insertion into a host cell in order to permit expression of the antibody of interest in that host cell. The nucleic acid may, but need not, be manipulated between steps (i) and (ii) to introduce restriction sites, to change codon usage, and/or to optimize transcription and/or translation regulatory sequences.

Furthermore, the invention also provides a method of preparing a transfected host cell, comprising the step of transfecting a host cell with one or more nucleic acids that encode an antibody of interest, wherein the nucleic acids are nucleic acids that were derived from an immortalized B cell clone or a cultured plasma cell of the invention. Thus the procedures for first preparing the nucleic acid(s) and then using it to transfect a host cell can be performed at different times by different people in different places (e.g., in different countries).

These recombinant cells of the invention can then be used for expression and culture purposes. They are particularly useful for expression of antibodies for large-scale pharmaceutical production. They can also be used as the active ingredient of a pharmaceutical composition. Any suitable culture technique can be used, including but not limited to static culture, roller bottle culture, ascites fluid, hollow-fiber type bioreactor cartridge, modular minifermenter, stirred tank, microcarrier culture, ceramic core perfusion, etc.

Methods for obtaining and sequencing immunoglobulin genes from B cells or plasma cells are well known in the art (e.g., see Chapter 4 of Kuby Immunology, 4th edition, 2000).

The transfected host cell may be a eukaryotic cell, including yeast and animal cells, particularly mammalian cells (e.g., CHO cells, NS0 cells, human cells such as PER.C6 or HKB-11 cells, myeloma cells, or a human liver cell), as well as plant cells, whereby mammalian cells are preferred. Preferred expression hosts can glycosylate the antibody of the invention, particularly with carbohydrate structures that are not themselves immunogenic in humans. In one embodiment the transfected host cell may be able to grow in serum-free media. In a further embodiment the transfected host cell may be able to grow in culture without the presence of animal-derived products. The transfected host cell may also be cultured to give a cell line.

The invention also provides a method for preparing one or more nucleic acid molecules (e.g., heavy and light chain genes) that encode an antibody of interest, comprising the steps of: (i) preparing an immortalized B cell clone or culturing plasma cells according to the invention; (ii) obtaining from the B cell clone or the cultured plasma cells nucleic acid that encodes the antibody of interest. Further, the invention provides a method for obtaining a nucleic acid sequence that encodes an antibody of interest, comprising the steps of: (i) preparing an immortalized B cell clone or culturing plasma cells according to the invention; (ii) sequencing nucleic acid from the B cell clone or the cultured plasma cells that encodes the antibody of interest.

The invention further provides a method of preparing nucleic acid molecule(s) that encode an antibody of interest, comprising the step of obtaining the nucleic acid that was obtained from a transformed B cell clone or cultured plasma cells of the invention. Thus the procedures for first obtaining the B cell clone or the cultured plasma cell, and then obtaining nucleic acid(s) from the B cell clone or the cultured plasma cells can be performed at different times by different people in different places (e.g., in different countries).

The invention also comprises a method for preparing an antibody (e.g., for pharmaceutical use) according to the present invention, comprising the steps of: (i) obtaining and/or sequencing one or more nucleic acids (e.g., heavy and light chain genes) from the selected B cell clone or the cultured plasma cells expressing the antibody of interest; (ii) inserting the nucleic acid(s) into or using the nucleic acid(s) sequence(s) to prepare an expression vector; (iii) transfecting a host cell that can express the antibody of interest; (iv) culturing or sub-culturing the transfected host cells under conditions where the antibody of interest is expressed; and, optionally, (v) purifying the antibody of interest.

The invention also provides a method of preparing an antibody comprising the steps of: culturing or sub-culturing a transfected host cell population, e.g. a stably transfected host cell population, under conditions where the antibody of interest is expressed and, optionally, purifying the antibody of interest, wherein said transfected host cell population has been prepared by (i) providing nucleic acid(s) encoding a selected antibody of interest that is produced by a B cell clone or cultured plasma cells prepared as described above, (ii) inserting the nucleic acid(s) into an expression vector, (iii) transfecting the vector in a host cell that can express the antibody of interest, and (iv) culturing or sub-culturing the transfected host cell comprising the inserted nucleic acids to produce the antibody of interest. Thus the procedures for first preparing the recombinant host cell and then culturing it to express antibody can be performed at very different times by different people in different places (e.g., in different countries).

Nucleic Acid Molecules, Vectors and Cells

In another aspect, the invention also provides a nucleic acid molecule comprising a polynucleotide encoding the antibody, or the antigen binding fragment thereof, according to the present invention as described above. In another aspect, the present invention also provides a nucleic acid molecule comprising a polynucleotide encoding the peptide according to the present invention as described above or the protein according to the present invention as described above.

Examples of nucleic acid molecules and/or polynucleotides include, e.g., a recombinant polynucleotide, a vector, an oligonucleotide, an RNA molecule such as an rRNA, an mRNA, an miRNA, an siRNA, or a tRNA, or a DNA molecule such as a cDNA. The nucleic acid molecule may also be a vector as described below.

A nucleic acid molecule is a molecule comprising, preferably consisting of nucleic acid components. The term nucleic acid molecule preferably refers to DNA or RNA molecules. In particular, it is used synonymous with the term "polynucleotide". Preferably, a nucleic acid molecule is a polymer comprising or consisting of nucleotide monomers which are covalently linked to each other by phosphodiester-bonds of a sugar/phosphate-backbone. The term "nucleic acid molecule" also encompasses modified nucleic acid molecules, such as base-modified, sugar-modified or backbone-modified etc. DNA or RNA molecules.

Regarding nucleic acid molecules comprising a polynucleotide encoding the antibody according to the present invention, such nucleic acid sequences, which encode part or all of the light and heavy chains and CDRs of the antibodies of the present invention are preferred. Preferably provided herein are thus nucleic acid sequences encoding part or all of the light and heavy chains, in particular VH and VL sequences and CDRs of the exemplary antibodies of the invention. Tables 1 and 2 provide the SEQ ID numbers for the amino acid sequences of the CDRs and VH and VL of exemplary antibodies according to the present invention.

Tables 3 and 4 below provides the SEQ ID numbers for exemplary nucleic acid sequences encoding the CDRs and VH and VL of exemplary antibodies according to the present invention. Due to the redundancy of the genetic code, the present invention also comprises sequence variants of these nucleic acid sequences and in particular such sequence variants, which encode the same amino acid sequences.

Table 3 below shows the SEQ ID NOs of the nucleic acid sequences of the heavy chain CDR's (CDRH1, CDRH2, and CDRH3) and of the heavy chain variable region (referred to as "VH") of exemplary antibodies according to the present invention:

TABLE 3

| Antibody name | CDRH1 | CDRH2 | CDRH3 | VH |
| --- | --- | --- | --- | --- |
| MGG1 | 37 | 38 | 39 | 44 |
| MGG2 | 55 | 56 | 57 | 62 |
| MGG3 | 73 | 74 | 75 | 80 |
| MGG4 | 91 | 92 | 93 | 98 |
| MGG8 | 109 | 110 | 111 | 116 |
| MGH1 | 127 | 128 | 129 | 134 |
| MGH2 | 145 | 146 | 147 | 152 |
| MGH3 | 163 | 164 | 165 | 170 |
| MGU1 | 180 | 181 | 182 | 186 |
| MGU3 | 197 | 198 | 199 | 204 |
| MGU5 | 215 | 216 | 217 | 222 |
| MGU8 | 233 | 234 | 235 | 240 |
| MGU10 | 250 | 251 | 252 | 256 |
| MGU11 | 267 | 268 | 269 | 274 |
| MGU12 | 285 | 286 | 287 | 292 |
| MGV3 | 303 | 304 | 305 | 310 |

Table 4 below shows the SEQ ID NOs of the nucleic acid sequences of the light chain CDR's (CDRL1, CDRL2, and CDRL3) and of the light chain variable region (referred to as "VL") of exemplary antibodies according to the present invention:

TABLE 4

| Antibody name | CDRL1 | CDRL2 | CDRL2 long | CDRL3 | VL |
| --- | --- | --- | --- | --- | --- |
| MGG1 | 40 | 41 | 42 | 43 | 45 |
| MGG2 | 58 | 59 | 60 | 61 | 63 |
| MGG3 | 76 | 77 | 78 | 79 | 81 |
| MGG4 | 94 | 95 | 96 | 97 | 99 |
| MGG8 | 112 | 113 | 114 | 115 | 117 |
| MGH1 | 130 | 131 | 132 | 133 | 135 |
| MGH2 | 148 | 149 | 150 | 151 | 153 |
| MGH3 | 166 | 167 | 168 | 169 | 171 |
| MGU1 | 183 | 184 | — | 185 | 187 |
| MGU3 | 200 | 201 | 202 | 203 | 205 |
| MGU5 | 218 | 219 | 220 | 221 | 223 |
| MGU8 | 236 | 237 | 238 | 239 | 241 |
| MGU10 | 253 | 254 | — | 255 | 257 |
| MGU11 | 270 | 271 | 272 | 273 | 275 |
| MGU12 | 288 | 289 | 290 | 291 | 293 |
| MGV3 | 306 | 307 | 308 | 309 | 311 |

Preferably, the sequence of the nucleic acid molecule according to the present invention comprises or consists of a polynucleotide sequence according to any one of SEQ ID NOs: 37-45, 55-63, 73-81, 91-99, 109-117, 127-135, 145-153, 163-171, 180-187, 197-205, 215-223, 233-241, 250-257, 267-275, 285-293, 303-311; or a functional sequence variant thereof. In other words, it is preferred that the nucleic acid molecule according to the present invention comprises a the polynucleotide sequence, which comprises or consists of a nucleic acid sequence according to any one of SEQ ID NOs: 37-45, 55-63, 73-81, 91-99, 109-117, 127-135, 145-153, 163-171, 180-187, 197-205, 215-223, 233-241, 250-257, 267-275, 285-293, 303-311; or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

It is also preferred that nucleic acid sequences according to the invention include nucleic acid sequences having at least 70%, at least 75%, at least 80%, at least 85%, at least 88%, at least 90%, at least 92%, at least 95%, at least 96%, at least 97%, at least 98% or at least 99% identity to the nucleic acid encoding a CDR, a VH sequence and/or a VL sequence used in an (exemplary) antibody according to the present invention, for example to the sequences shown in Tables 3 and 4.

It is also preferred that nucleic acid sequences according to the invention include nucleic acid sequences having at least 70%, at least 75%, at least 80%, at least 85%, at least 88%, at least 90%, at least 92%, at least 95%, at least 96%, at least 97%, at least 98% or at least 99% identity to the nucleic acid encoding a peptide according to the present invention, for example to the sequences according to any of SEQ ID NOs: 1-24. More preferably, the nucleic acid molecule according to the present invention comprises a the polynucleotide encoding any of the amino acid sequences according to any of SEQ ID NOs: 1-24.

In general, the nucleic acid molecule may be manipulated to insert, delete or alter certain nucleic acid sequences. Changes from such manipulation include, but are not limited to, changes to introduce restriction sites, to amend codon usage, to add or optimize transcription and/or translation regulatory sequences, etc. It is also possible to change the nucleic acid to alter the encoded amino acids. For example, it may be useful to introduce one or more (e.g., 1, 2, 3, 4, 5, 6, 7, 8, 9, 10, etc.) amino acid substitutions, deletions and/or insertions into the antibody's amino acid sequence. Such point mutations can modify effector functions, antigen-binding affinity, post-translational modifications, immunogenicity, etc., can introduce amino acids for the attachment of covalent groups (e.g., labels) or can introduce tags (e.g., for purification purposes). Mutations can be introduced in specific sites or can be introduced at random, followed by selection (e.g., molecular evolution). For instance, one or more nucleic acids encoding any of the CDR regions, a VH sequence and/or a VL sequence of an (exemplary) antibody of the invention can be randomly or directionally mutated to introduce different properties in the encoded amino acids. Such changes can be the result of an iterative process wherein initial changes are retained and new changes at other nucleotide positions are introduced. Further, changes achieved in independent steps may be combined. Different properties introduced into the encoded amino acids may include, but are not limited to, enhanced affinity.

In another aspect the present invention also provides a vector, for example an expression vector, comprising a nucleic acid molecule according to the present invention. Preferably, a vector comprises a nucleic acid molecule as described above.

The term "vector" refers to a nucleic acid molecule, preferably to a recombinant nucleic acid molecule, i.e. a nucleic acid molecule which does not occur in nature. A vector in the context of the present invention is suitable for incorporating or harboring a desired nucleic acid sequence. Such vectors may be storage vectors, expression vectors, cloning vectors, transfer vectors etc. A storage vector is a vector which allows the convenient storage of a nucleic acid molecule. Thus, the vector may comprise a sequence corresponding, e.g., to a desired antibody or antibody fragment thereof according to the present invention or to a desired peptide or protein according to the present invention. An expression vector may be used for production of expression products such as RNA, e.g. mRNA, or peptides, polypeptides or proteins. For example, an expression vector may comprise sequences needed for transcription of a sequence stretch of the vector, such as a promoter sequence. A cloning vector is typically a vector that contains a cloning site, which may be used to incorporate nucleic acid sequences into the vector. A cloning vector may be, e.g., a plasmid vector or a bacteriophage vector. A transfer vector may be a vector which is suitable for transferring nucleic acid molecules into cells or organisms, for example, viral vectors. A vector in the context of the present invention may be, e.g., an RNA vector or a DNA vector. Preferably, a vector is a DNA molecule. For example, a vector in the sense of the present application comprises a cloning site, a selection marker, such as an antibiotic resistance factor, and a sequence suitable for multiplication of the vector, such as an origin of replication. Preferably, a vector in the context of the present application is a plasmid vector.

In a further aspect, the present invention also provides cell (a) expressing (i) the antibody, or the antigen binding fragment thereof, according to the present invention or (ii) the peptide or protein according to the present invention; and/or (b) comprising the vector according the present invention.

Examples of such cells include but are not limited to, eukaryotic cells, e.g., yeast cells, animal cells or plant cells. Preferably, the cells are mammalian cells, more preferably a mammalian cell line. Preferred examples include human cells, CHO cells, HEK293T cells, PER.C6 cells, NS0 cells, human liver cells, myeloma cells or hybridoma cells.

In particular, the cell may be transfected with a vector according to the present invention, preferably with an expression vector. The term "transfection" refers to the introduction of nucleic acid molecules, such as DNA or RNA (e.g. mRNA) molecules, into cells, preferably into eukaryotic cells. In the context of the present invention, the term "transfection" encompasses any method known to the skilled person for introducing nucleic acid molecules into cells, preferably into eukaryotic cells, such as into mammalian cells. Such methods encompass, for example, electroporation, lipofection, e.g. based on cationic lipids and/or liposomes, calcium phosphate precipitation, nanoparticle based transfection, virus based transfection, or transfection based on cationic polymers, such as DEAE-dextran or polyethylenimine etc. Preferably, the introduction is non-viral.

Moreover, the cells of the present invention may be transfected stably or transiently with the vector according to the present invention, e.g. for expressing the antibody, or the antigen binding fragment thereof, according to the present invention or for expressing the peptide or protein according to the present invention. Preferably, the cells are stably transfected with the vector according to the present invention, for example encoding the antibody, or the antigen binding fragment thereof, according to the present invention or encoding the peptide or protein according to the present invention. Alternatively, it is also preferred that the cells are transiently transfected with the vector according to the present invention, for example encoding the antibody, or the antigen binding fragment thereof, according to the present invention or encoding the peptide or protein according to the present invention.

Pharmaceutical Composition

In a further aspect the present invention provides a pharmaceutical composition comprising one or more of:
(i) the peptide according to the present invention;
(ii) the protein according to the present invention;
(iii) the nucleic acid encoding the protein or the peptide according to the present invention;
(iv) the virus-like particle according to the present invention;
(v) the protein nanoparticle according to the present invention;
(vi) the antibody, or the antibody fragment thereof, according to the present invention;
(vii) the nucleic acid encoding the antibody, or antibody fragments according to the present invention;
(viii) the vector comprising the nucleic acid according to the present invention; and/or
(ix) the cell expressing the antibody or the peptide according to the present invention, or comprising the vector according to the present invention.

In other words, the present invention also provides a pharmaceutical composition comprising the peptide according to the present invention, the protein according to the present invention, the virus-like particle according to the present invention, the protein nanoparticle according to the present invention, the antibody, or the antigen binding fragment thereof, according to the present invention, the nucleic acid according to the present invention, the vector according to the present invention and/or the cell according to the present invention.

Preferably, the pharmaceutical composition comprises the peptide according to the present invention and/or the protein according to the present invention.

It is also preferred that the pharmaceutical composition comprises the virus-like particle according to the present invention and/or the protein nanoparticle according to the present invention.

In this context, i.e. if the pharmaceutical composition comprises the peptide according to the present invention, the protein according to the present invention, the virus-like particle according to the present invention and/or the protein nanoparticle according to the present invention, the pharmaceutical composition is preferably a vaccine. A "vaccine" is typically understood to be a prophylactic or therapeutic material providing at least one antigen, preferably an immunogen, such as the peptide according to the present invention. An "immunogen" is typically able to elicit an immune response. As used herein an "immunogen" is in particular a protein or a portion thereof that is capable of inducing an immune response in a mammal (such as humans and cattle, preferably cattle), such as a mammal infected or at risk of infection with a pathogen (such as *Plasmodium*). Administration of an immunogen can for example lead to protective immunity and/or proactive immunity against a pathogen of interest. Accordingly, the antigen or immunogen can typically stimulate the body's adaptive immune system to provide an adaptive immune response. In particular, an "antigen" or an "immunogen" refers typically to a substance which may be recognized by the immune system, preferably by the adaptive immune system, and which is capable of triggering an antigen-specific immune response, e.g. by formation of antibodies and/or antigen-specific T cells as part of an adaptive immune response. Typically, an antigen may be or may comprise a peptide or protein which may be presented by the MHC to T-cells.

Preferably, the pharmaceutical composition comprises the antibody, or the antibody fragment thereof, according to the present invention.

It is also preferred that the composition comprises the nucleic acid according to the invention.

Preferably, the pharmaceutical composition comprises the vector according to the present invention and/or the cell according to the present invention.

The pharmaceutical composition may preferably also contain a pharmaceutically acceptable carrier, diluent and/or excipient. Although the carrier or excipient may facilitate administration, it should preferably not itself induce the production of antibodies harmful to the individual receiving the composition. Nor should it be toxic. Suitable carriers may be large, slowly metabolized macromolecules such as proteins, polypeptides, liposomes, polysaccharides, polylactic acids, polyglycolic acids, polymeric amino acids, amino acid copolymers and inactive virus particles. In general, pharmaceutically acceptable carriers in a pharmaceutical composition according to the present invention may be active components or inactive components. Preferably, the pharmaceutically acceptable carrier in a pharmaceutical composition according to the present invention is not an active component in respect to malaria.

Pharmaceutically acceptable salts can be used, for example mineral acid salts, such as hydrochlorides, hydrobromides, phosphates and sulphates, or salts of organic acids, such as acetates, propionates, malonates and benzoates.

Pharmaceutically acceptable carriers in a pharmaceutical composition may additionally contain liquids such as water, saline, glycerol and ethanol. Additionally, auxiliary substances, such as wetting or emulsifying agents or pH buffering substances, may be present in such compositions. Such carriers enable the pharmaceutical compositions to be formulated as tablets, pills, dragees, capsules, liquids, gels, syrups, slurries and suspensions, for ingestion by the subject.

Pharmaceutical compositions of the invention may be prepared in various forms. For example, the compositions may be prepared as injectables, either as liquid solutions or suspensions. Solid forms suitable for solution in, or suspension in, liquid vehicles prior to injection can also be prepared (e.g., a lyophilized composition, similar to Synagis™ and Herceptin™, for reconstitution with sterile water containing a preservative). The composition may be prepared for topical administration e.g., as an ointment, cream or powder.

The composition may be prepared for oral administration e.g., as a tablet or capsule, as a spray, or as a syrup (optionally flavored). The composition may be prepared for pulmonary administration e.g., as an inhaler, using a fine powder or a spray. The composition may be prepared as a suppository or pessary. The composition may be prepared for nasal, aural or ocular administration e.g., as drops. The composition may be in kit form, designed such that a combined composition is reconstituted just prior to administration to a subject. For example, a lyophilized antibody may be provided in kit form with sterile water or a sterile buffer.

It is preferred that the active ingredient in the composition is the antibody, or an antibody fragment thereof, according to the present invention. It is also preferred that the active ingredient in the composition is the peptide according to the present invention, the protein according to the present invention, the protein nanoparticle according to the present invention and/or the virus-like particle according to the present invention. As such, it (the antibody, the peptide, the protein, etc.) may be susceptible to degradation in the gastrointestinal tract. Thus, if the composition is to be administered by a route using the gastrointestinal tract, the composition may contain agents which protect the antibody, the peptide, the protein, the protein nanoparticle or the virus-like particle from degradation but which release it once it has been absorbed from the gastrointestinal tract.

A thorough discussion of pharmaceutically acceptable carriers is available in Gennaro (2000) Remington: The Science and Practice of Pharmacy, 20th edition, ISBN: 0683306472.

Pharmaceutical compositions of the invention generally have a pH between 5.5 and 8.5, in some embodiments this may be between 6 and 8, and in other embodiments about 7. The pH may be maintained by the use of a buffer. The composition may be sterile and/or pyrogen free. The composition may be isotonic with respect to humans. In one embodiment pharmaceutical compositions of the invention are supplied in hermetically-sealed containers.

Within the scope of the invention are compositions present in several forms of administration; the forms include, but are not limited to, those forms suitable for parenteral administration, e.g., by injection or infusion, for example by bolus injection or continuous infusion. Where the product is for injection or infusion, it may take the form of a suspension, solution or emulsion in an oily or aqueous vehicle and it may contain formulatory agents, such as suspending, preservative, stabilizing and/or dispersing agents. Alternatively, the antibody or the peptide/protein may be in dry form, for reconstitution before use with an appropriate sterile liquid. A vehicle is typically understood to be a material that is suitable for storing, transporting, and/or administering a compound, such as a pharmaceutically active compound, in particular the antibody or the peptide/protein according to the present invention. For example, the vehicle may be a physiologically acceptable liquid, which is suitable for storing, transporting, and/or administering a pharmaceutically active compound, in particular the antibody or the peptide/protein according to the present invention. Once formulated, the compositions of the invention can be administered directly to the subject. In one embodiment the compositions are adapted for administration to mammalian, e.g., human subjects.

The pharmaceutical compositions of this invention may be administered by any number of routes including, but not limited to, oral, intravenous, intramuscular, intra-arterial, intramedullary, intraperitoneal, intrathecal, intraventricular, transdermal, transcutaneous, topical, subcutaneous, intranasal, enteral, sublingual, intravaginal or rectal routes. Hyposprays may also be used to administer the pharmaceutical compositions of the invention. Preferably, the pharmaceutical composition may be prepared for oral administration, e.g. as tablets, capsules and the like, for topical administration, or as injectable, e.g. as liquid solutions or suspensions, whereby it is particularly preferred that the pharmaceutical composition is an injectable. Solid forms suitable for solution in, or suspension in, liquid vehicles prior to injection are also be preferred, e.g. that the pharmaceutical composition is in lyophilized form.

For injection, e.g. intravenous, cutaneous or subcutaneous injection, or injection at the site of affliction, the active ingredient will preferably be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives may be included, as required. Whether it is a polypeptide, peptide, or nucleic acid molecule, other pharmaceutically useful compound according to the present invention that is to be given to an individual, administration is preferably in a "prophylactically effective amount" or a "therapeutically effective amount" (as the case may be), this being sufficient to show benefit to the individual. The actual amount administered, and rate and time-course of administration, will depend on the nature and severity of what is being treated. For injection, the pharmaceutical composition according to the present invention may be provided for example in a pre-filled syringe.

The inventive pharmaceutical composition as defined above may also be administered orally in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient, i.e. the inventive transporter cargo conjugate molecule as defined above, is combined with emulsifying and suspending agents. If desired, certain sweetening, flavoring or coloring agents may also be added.

The inventive pharmaceutical composition may also be administered topically, especially when the target of treatment includes areas or organs readily accessible by topical application, e.g. including diseases of the skin or of any other accessible epithelial tissue. Suitable topical formulations are readily prepared for each of these areas or organs. For topical applications, the inventive pharmaceutical composition may be formulated in a suitable ointment, containing the inventive pharmaceutical composition, particularly its components as defined above, suspended or dissolved in one or more carriers. Carriers for topical administration include, but are not limited to, mineral oil, liquid petrolatum, white petrolatum, propylene glycol, polyoxyethylene, polyoxypropylene compound, emulsifying wax and water. Alternatively, the inventive pharmaceutical composition can be formulated in a suitable lotion or cream. In the context of the present invention, suitable carriers include, but are not limited to, mineral oil, sorbitan monostearate, polysorbate 60, cetyl esters wax, cetearyl alcohol, 2-octyldodecanol, benzyl alcohol and water.

Dosage treatment may be a single dose schedule or a multiple dose schedule. In particular, the pharmaceutical composition may be provided as single-dose product. Preferably, the amount of the antibody or of the peptide/protein in the pharmaceutical composition—in particular if provided as single-dose product—does not exceed 200 mg, more preferably does not exceed 100 mg, and even more preferably does not exceed 50 mg.

The pharmaceutical composition according to the present invention may be administered once or repeatedly. For example, the pharmaceutical composition according to the present invention may be administered daily, e.g. once or several times per day, e.g. once, twice, three times or four times per day, preferably once or twice per day, more preferable once per day, for 1, 2, 3, 4, 5, 6, 7, 8, 9, 10, 11, 12, 13, 14, 15, 16, 17, 18, 19, 20 or 21 or more days, e.g. daily for 1, 2, 3, 4, 5, 6 months. Preferably, the pharmaceutical composition according to the present invention may be administered weekly, e.g. once or twice per week, for 1, 2, 3, 4, 5, 6, 7, 8, 9, 10, 11, 12, 13, 14, 15, 16, 17, 18, 19, 20 or 21 or more weeks, e.g. weekly for 1, 2, 3, 4, 5, 6, 7, 8, 9, 10, 11, or 12 months or weekly for 2, 3, 4, or 5 years. Moreover, the pharmaceutical composition according to the present invention may be preferably administered monthly, e.g. once per month or, more preferably, every second month for 1, 2, 3, 4, or 5 or more years. It is also preferred that the administration continues for the lifetime. In addition, one single administration only is also envisaged, in particular in respect to certain indications, e.g. for prevention of malaria in case of accidental exposure, e.g. in non-immunized subjects.

In particular, it is preferred that for a single dose, e.g. a daily, weekly or monthly dose, preferably for a weekly dose, the amount of the antibody or of the peptide/protein in the pharmaceutical composition according to the present invention, does not exceed 1 g, preferably does not exceed 500 mg, more preferably does not exceed 200 mg, even more preferably does not exceed 100 mg, and particularly preferably does not exceed 50 mg.

Pharmaceutical compositions typically include an "effective" amount of the antibody of the invention, or of the peptide/protein of the invention, i.e. an amount that is sufficient to treat, ameliorate, attenuate or prevent a desired disease or condition, or to exhibit a detectable therapeutic effect. Therapeutic effects also include reduction or attenuation in pathogenic potency or physical symptoms. The precise effective amount for any particular subject will depend upon their size, weight, and health, the nature and extent of the condition, and the therapeutics or combination of therapeutics selected for administration. The effective amount for a given situation is determined by routine experimentation and is within the judgment of a clinician. For purposes of the present invention, an effective dose will generally be from about 0.005 to about 100 mg/kg, preferably from about 0.0075 to about 50 mg/kg, more preferably from about 0.01 to about 10 mg/kg, and even more preferably from about 0.02 to about 5 mg/kg, of the antibody of the present invention (e.g. amount of the antibody in the pharmaceutical composition) in relation to the bodyweight (e.g., in kg) of the individual to which it is administered.

Moreover, the pharmaceutical composition according to the present invention may also comprise an additional active component, which may be a further antibody or a component, which is not an antibody. The additional active component is preferably a checkpoint inhibitor.

The antibody, or the antigen binding fragment, according to the present invention and/or the peptide/protein according to the present invention can be present either in the same pharmaceutical composition as the additional active component or, preferably, it can be comprised by a first pharmaceutical composition and the additional active component is comprised by a second pharmaceutical composition different from the first pharmaceutical composition. Accordingly, if more than one additional active component is envisaged, each additional active component and the antibody, or the antigen binding fragment, according to the present invention or the peptide/protein according to the present invention is preferably comprised by a different pharmaceutical composition. Such different pharmaceutical compositions may be administered either combined/simultaneously or at separate times or at separate locations (e.g. separate parts of the body).

Preferably, the antibody (or the peptide/protein) according to the present invention and the additional active component provide an additive therapeutic effect or, preferably, a synergistic therapeutic effect. The term "synergy" is used to describe a combined effect of two or more active agents that is greater than the sum of the individual effects of each respective active agent. Thus, where the combined effect of two or more agents results in "synergistic inhibition" of an activity or process, it is intended that the inhibition of the activity or process is greater than the sum of the inhibitory effects of each respective active agent. The term "synergistic therapeutic effect" refers to a therapeutic effect observed with a combination of two or more therapies wherein the therapeutic effect (as measured by any of a number of parameters) is greater than the sum of the individual therapeutic effects observed with the respective individual therapies.

In one embodiment, a composition of the invention may include an antibody of the invention, wherein the antibodies may make up at least 50% by weight (e.g., 60%, 70%, 75%, 80%, 85%, 90%, 95%, 96%, 97%, 98%, 99% or more) of the total protein in the composition. In such a composition, the antibodies are preferably in purified form.

In another embodiment, a composition of the invention may include a peptide/protein of the invention, wherein the peptide/protein may make up at least 50% by weight (e.g., 60%, 70%, 75%, 80%, 85%, 90%, 95%, 96%, 97%, 98%, 99% or more) of the total protein in the composition. In such a composition, the peptides/proteins are preferably in purified form.

The present invention also provides a method of preparing a pharmaceutical composition comprising the steps of: (i) preparing an antibody or a peptide/protein of the invention; and (ii) admixing the purified antibody or the purified peptide/protein with one or more pharmaceutically-acceptable carriers.

In another embodiment, a method of preparing a pharmaceutical composition comprises the step of: admixing an antibody with one or more pharmaceutically-acceptable carriers, wherein the antibody is a monoclonal antibody that was obtained from a transformed B cell or a cultured plasma cell of the invention.

As an alternative to delivering antibodies or B cells for therapeutic purposes, it is possible to deliver nucleic acid (typically DNA) that encodes the antibody or the peptide/protein to a subject, such that the nucleic acid can be expressed in the subject in situ to provide a desired therapeutic effect. Suitable gene therapy and nucleic acid delivery vectors are known in the art.

Pharmaceutical compositions may include an antimicrobial particularly if packaged in a multiple dose format. They may comprise detergent e.g., a Tween (polysorbate), such as Tween 80. Detergents are generally present at low levels e.g., less than 0.01%. Compositions may also include sodium salts (e.g., sodium chloride) to give tonicity. For example, a concentration of 10±2 mg/ml NaCl is typical.

Further, pharmaceutical compositions may comprise a sugar alcohol (e.g., mannitol) or a disaccharide (e.g., sucrose or trehalose) e.g., at around 15-30 mg/ml (e.g., 25 mg/ml), particularly if they are to be lyophilized or if they include material which has been reconstituted from lyophilized material. The pH of a composition for lyophilization may be adjusted to between 5 and 8, or between 5.5 and 7, or around 6.1 prior to lyophilization.

The compositions of the invention may also comprise one or more immunoregulatory agents. In general, immunoregulatory agents include(s) an adjuvant. Accordingly, it is preferred, in particular for vaccines, that the pharmaceutical composition comprises an adjuvant. Examples of adjuvants include aluminum hydroxide (ALHYDROGEL®, available from Brenntag Biosector, Copenhagen, Denmark and AMPHOGEL®, Wyeth Laboratories, Madison, NJ), Freund's adjuvant, MPL™ (3-0-deacylated monophosphoryl lipid A; Corixa, Hamilton, IN), IL-12 (Genetics Institute, Cambridge, MA), TLR agonists (such as TLR-9 agonists), and QS-21 (a purified plant extract derived from the soap bark tree *Quillaja saponaria*).

As used herein, the term "adjuvant" refers in particular to a vehicle used to enhance antigenicity/immunogenicity. Adjuvants include a suspension of minerals (alum, aluminum hydroxide, or phosphate) on which the antigen is adsorbed; or water-in-oil emulsion, for example, in which antigen solution is emulsified in mineral oil (Freund incomplete adjuvant), sometimes with the inclusion of killed mycobacteria (Freund's complete adjuvant) to further enhance antigenicity (inhibits degradation of antigen and/or causes influx of macrophages). Immunostimulatory oligonucleotides (such as those including a CpG motif) can also be used as adjuvants. Adjuvants include biological molecules (a "biological adjuvant"), such as costimulatory molecules. Exemplary adjuvants include IL-2, RANTES, GM-CSF, TNF-a, IFN-γ, G-CSF, LFA-3, CD72, B7-1, B7-2, OX-40L, 4-IBBL and toll-like receptor (TLR) agonists, such as TLR-9 agonists. The person of ordinary skill in the art is familiar with adjuvants (see, e.g., Singh (ed.) Vaccine Adjuvants and Delivery Systems. Wiley-Interscience, 2007), for example, those that can be included in a pharmaceutical composition. Preferably, the adjuvant is selected to elicit a Th1 immune response in a subject administered the pharmaceutical composition. In other words, the adjuvant comprised by the pharmaceutical composition preferably promotes a Th1 immune response. Preferably, the adjuvant is alum, an oil-in water composition, MF59, ASOI, AS03, AS04, MPL, QS21, a CpG oligonucleotide, a TLR7 agonist, a TLR4 agonist, a TLR3 agonist, or a combination of two or more thereof.

The adjuvant may be selected from the group comprising mineral salts, surface-active agents, microparticles, cytokines, hormones, antigen constructs, polyanions, polyacrylics, or water-in-oil emulsions. Accordingly, the inventive composition may comprise one more adjuvants, e.g. one, two, three, four, five, six, seven, eight, nine, or ten or more adjuvants. For example the inventive composition may comprise one, two, three, four, five, six, seven, eight, nine, or ten or more adjuvants selected from aluminum ("Alum"), aluminum hydroxide, aluminum phosphate, calcium phosphate, nonionic block polymer surfactants, virosomes, saponin (QS-21), meningococcal outer membrane proteins (Proteosomes), immune stimulating complexes (ISCOMs), Cochleates Dimethyl dioctadecyl ammonium bromide (DDA), Avridine (CP20,961), vitamin A, vitamin E, cell wall skeleton of *Mycobacterium phlei* (Detox®), muramyl dipeptides and tripeptides, Threonyl MDP (SAF-1), Butylester MDP (Murabutide®), Dipalmitoyl phosphatidylethanolamine MTP, Monophosphoryl lipid A, *Klebsiella pneumonia* glycoprotein, *Bordetella pertussis*, Bacillus Calmette-Guérin, *Vibrio cholerae* and *Escherichia coli* heat labile enterotoxin, trehalose dimycolate, CpG oligodeoxynucleotides, interleukin-2, interferon-γ, interferon-β, granulocyte-macrophage colony stimulating factor, dehydroepiandrosterone, Flt3 ligand, 1,25-dihydroxy vitamin D3, interleukin-1, interleukin-6, interleukin-12, human growth hormone, 2-microglobulin, lymphotactin, polyanions, e.g. dextran, double-stranded polynucleotides, polyacrylics, e.g. polymethylmethacrylate, acrylic acid crosslinked with allyl sucrose (Carbopol 934P), or e.g. N-acetyl-glucosamine-3yl-acetyl-L-alanyl-D-isoglutamine (CGP-11637), gamma inulin+aluminum hydroxide (Algammulin), human dendritic cells, lysophosphatidyl glycerol, stearyl tyrosine, tripalmitoyl pentapeptide, Carbopol 974P NF polymer, water-in-oil emulsions, mineral oil (Freund's incomplete), vegetable oil (peanut oil), squalene and squalane, oil-in-water emulsions, Squalene+Tween-80+Span 85 (MF59), or e.g. liposomes, or e.g. biodegradable polymer microspheres, lactide and glycolide, polyphosphazenes, beta-glucan, or e.g. proteinoids. A list of typically used vaccine adjuvants may also be found in "Vaccine Adjuvants", edited by D. T. O'Hogan, Humana Press 2000. The adjuvant comprised in the inventive composition may also include e.g. a synthetic derivative of lipid A, some of which are TLR-4 agonists, and include, but are not limited to: OM174 (2-deoxy-6-o-[2-deoxy-2-[(R)-3-dodecanoyloxytetra-decanoylamino]-4-o-phosphono-D-D-glucopyranosyl]-2-[(R)-3-hydroxy-tetradecanoylamino]-p-D-glucopyranosyldihydrogen-phosphate), (WO 95/14026) OM-294-DP (3S,9R)-3-~[(R)-dodecanoyloxytetradecanoylam, [(R)-3-hydroxytetradecanoylamino]decan-1,10-diol, 1,10-bis(dihydrogenophosphate) (WO 99/64301 and WO 00/0462) OM 197 MP-Ac DP(3S-,9R)-3-D(R)-dodecanoyloxytetradecanoylamino]-4-oxo-5-aza-9-[(R)-3-hydroxytetradecanoylamino]decan-1,10-diol, 1-dihydrogenophosphate-10-(6-aminohexanoate) (WO 01/46127). For example the inventive vaccine may comprise only one of the above adjuvants, or e.g. two of the above adjuvants, e.g. combination adjuvants such as e.g. Alum and MPL, or oil-in-water emulsion and MPL and QS-21, or liposomes and MPL and QS21.

It is preferred that the vaccine according to the invention comprises an adjuvant selected from the group comprising Alum, Ribi (Monophosphoryl lipid A, MPL), or MF59. Accordingly, the inventive vaccine composition may comprise Alum, or Ribi (Monophosphoryl lipid A, MPL), or MF59, or e.g. Alum and Ribi, or e.g. Alum and MF59, or e.g. Ribi and MF59.

A particularly preferred adjuvant is a non-toxic bacterial lipopolysaccharide derivative. A preferred example of a suitable nontoxic derivative of lipid A, is monophosphoryl lipid A (MPL), or, more particularly, 3-Deacylated monophosphoryl lipid A (3DMPL). See, for example, U.S. Pat. Nos. 4,436,727; 4,877,611; 4,866,034 and 4,912,094. MPL primarily promotes CD4+ T cell responses with an IFN-γ (Th1) phenotype. In the pharmaceutical composition, for example small particle 3D-MPL can be used. Small particle 3D-MPL has a particle size such that it can be sterile-filtered through a 0.22 µm filter. Such preparations are described in WO 94/21292. Alternatively, the lipopolysaccharide can be a B(1-6) glucosamine disaccharide, as described in U.S. Pat. No. 6,005,099 and EP Patent No. 0 729 473 B1. One of skill in the art would be readily able to produce various lipopolysaccharides, such as 3D-MPL, based on the teachings of these references.

In addition to the aforementioned immunostimulants (that are similar in structure to that of LPS or MPL or 3D-MPL), acylated monosaccharide and disaccharide derivatives that are a sub-portion to the above structure of MPL are also suitable adjuvants.

Another particularly preferred adjuvant that can be used in the pharmaceutical composition is a saponin, such as QS21. QS-21 is a one of the active fractions derived from the soap bark tree *Quillaja saponaria* (Zhu W. and Tuo W., 2016, Nat Prod Chem Res 3(4): e113. QS-21: A potent vaccine adjuvant). QS denotes its source as *Q. saponaria* and the number 21 as the identity of the RP-HPLC peak. QS-21 is an acylated 3, 28-bisdesmodic triterpene glycosides (1,3) or "saponin" with a molecular formula of $C_{92}O_{46}H_{148}$ and molecular weight of 1990 Da. Saponins, such as QS-21, may be preferably used as an adjuvant, e.g., for systemic administration. Use of saponins (e.g., use of Quil A, derived from the bark of the South American tree *Quillaja saponaria* Molina) as adjuvants is familiar to the person of ordinary skill in the art (see, e.g., U.S. Pat. No. 5,057,540 and EP 0 362 279 B1. EP 0 109 942 B1; WO 96/11711; WO 96/33739). The haemolytic saponins QS21 and QS17 (HPLC purified fractions of Quil A) have been described as potent systemic adjuvants, and the method of their production is disclosed in U.S. Pat. No. 5,057,540 and EP 0 362279 B1.

Preferably, the pharmaceutical composition comprises monophosphoryl lipid A (MPL) and/or a saponin, such as QS-21.

It is also preferred that a Toll-like receptor (TLR) agonist is used as an adjuvant. For example, the pharmaceutical composition may comprise a TLR agonist. For example, the TLR agonist can be a TLR-4 agonist such as a synthetic derivative of lipid A (see, e.g., WO 95/14026, and WO 01/46127) an alkyl Glucosaminide phosphate (AGP; see, e.g., WO 98/50399 or U.S. Pat. Nos. 6,303,347; 6,764,840). Other suitable TLR-4 ligands, capable of causing a signaling response through TLR-4 are, for example, lipopolysaccharide from gram-negative bacteria and its derivatives, or fragments thereof, in particular a non-toxic derivative of LPS (such as MPL). Other suitable TLR agonists are: heat shock protein (HSP) 10, 60, 65, 70, 75 or 90; surfactant Protein A, hyaluronan oligosaccharides, heparin sulphate fragments, fibronectin fragments, fibrinogen peptides and B-defensin-2, and muramyl dipeptide (MDP). For example, the TLR agonist may be HSP 60, 70 or 90. Other suitable TLR-4 ligands are as described in WO 2003/011223 and in WO 2003/099195.

Additional TLR agonists (such as an agent that is capable of causing a signaling response through a TLR signaling pathway) are also useful as adjuvants, such as agonists for TLR2, TLR3, TLR7, TLR8 and/or TLR9. Accordingly, the composition may further include an adjuvant which is selected from the group consisting of: a TLR-1 agonist, a TLR-2 agonist, TLR-3 agonist, a TLR-4 agonist, TLR-5 agonist, a TLR-6 agonist, TLR-7 agonist, a TLR-8 agonist, TLR-9 agonist, or a combination thereof. For example, a TLR agonist may be used that is capable of causing a signaling response through TLR-1, for example one or more of from: tri-acylated lipopeptides (LPs); phenol-soluble modulin; *Mycobacterium tuberculosis* LP; S-(2,3-bis(palmitoyloxy)-(2-RS)-propyl)-N-palmitoyl-(R)-Cys-(S)-Ser-(S)-L-ys(4)-OH, trihydrochloride (Pam3Cys) LP which mimics the acetylated amino terminus of a bacterial lipoprotein and OspA LP from *Borrelia burgdorferi*. For example, a TLR agonist may be used that is capable of causing a signaling response through TLR-2, such as one or more of a lipoprotein, a peptidoglycan, a bacterial lipopeptide from *M. tuberculosis, B. burgdorferi* or *T. pallidum*; peptidoglycans from species including *Staphylococcus aureus*; lipoteichoic acids, mannuronic acids, *Neisseria porins*, bacterial fimbriae, *Yersinia virulence* factors, CMV virions, measles haemagluttinin, and zymosan from yeast. Furthermore, a TLR agonist may be used that is capable of causing a signaling response through TLR-3, such as one or more of double stranded RNA (dsRNA), or polyinosinicpolycytidylic acid (Poly IC), a molecular nucleic acid pattern associated with viral infection. Moreover, a TLR agonist may be used that is capable of causing a signaling response through TLR-5, such as bacterial flagellin. Also, a TLR agonist may be used that is capable of causing a signaling response through TLR-6, such as one or more of mycobacterial lipoprotein, di-acylated LP, and phenol-soluble modulin. Additional TLR6 agonists are described in WO 2003/043572. For example, a TLR agonist is used that is capable of causing a signaling response through TLR-7, such as one or more of a single stranded RNA (ssRNA), loxoribine, a guanosine analogue at positions N7 and CS, or an imidazoquinoline compound, or derivative thereof. In one embodiment, the TLR agonist may be imiquimod. Further TLR-7 agonists are described in WO 2002/085905. Moreover, a TLR agonist may be used that is capable of causing a signaling response through TLR-8. Suitably, the TLR agonist capable of causing a signaling response through TLR-8 is a single stranded RNA (ssRNA), an imidazoquinoline molecule with antiviral activity, for example resiquimod (R848); resiquimod is also capable of recognition by TLR-7. Other TLR-8 agonists which can be used include those described in WO 2004/071459. Furthermore, an adjuvant may include a TLR agonist capable of inducing a signaling response through TLR-9. For example, the adjuvant can include HSP90, bacterial or viral DNA, and/or DNA containing unmethylated CpG nucleotides (e.g., a CpG oligonucleotide). For example, CpG-containing oligonucleotides induces a predominantly Th1 response. Such oligonucleotides are well known and are described, for example, in WO 95/26204, WO 96/02555, WO 99/33488 and U.S. Pat. Nos. 5,278,302, 5,666,153, and. 6,008,200 and 5,856,462. Accordingly, oligonucleotides for use as adjuvants in the disclosed compositions include CpG containing oligonucleotides, for example, containing two or more dinucleotide CpG motifs. Also included are oligonucleotides with mixed internucleotide linkages.

The adjuvant can also include mineral salts such as an aluminum or calcium salts, in particular aluminum hydroxide, aluminum phosphate and calcium phosphate.

Combinations of different adjuvants can also be used in the pharmaceutical compositions described herein. For example, as already noted, QS21 can be formulated together with (3D-)MPL. The ratio of QS21:(3D-)MPL will typically be in the order of 1:10 to 10:1; such as 1:5 to 5:1, and often substantially 1:1. Typically, the ratio is in the range of 2.5:1 to 1:1 (3D-)MPL:QS21 (such as AS01 (GlaxoSmithKline)). Another combination adjuvant formulation includes (3D-) MPL and an aluminum salt, such as aluminum hydroxide (such as AS04 (GlaxoSmithKline)). When formulated in combination, this combination can enhance an antigen-specific Th1 immune response. The adjuvant formulation may comprise a mineral salt, such as a calcium or aluminum (alum) salt, for example calcium phosphate, aluminum phosphate or aluminum hydroxide. Moreover, the adjuvant may include an oil and water emulsion, e.g., an oil-in-water emulsion (such as MF59 (Novartis) or AS03 (GlaxoSmithKline)). One example of an oil-in-water emulsion comprises a metabolisable oil, such as squalene, a tocol such as a tocopherol, e.g., alpha-tocopherol, and a surfactant, such as sorbitan trioleate (Span 85) or polyoxyethylene sorbitan monooleate (Tween 80), in an aqueous carrier.

Moreover, the pharmaceutical composition, in particular the vaccine, according to the present invention preferably also comprises further component, such as a peptide or a protein, which may aggregate with the peptide/protein according to the present inventions to form aggregates, such as particles. An example of such a component is HBsAg or a fragment thereof as described herein. Accordingly, HBsAg or a fragment thereof as described herein may be (i) comprised by a (fusion) protein according to the present invention, and/or (ii) present in a pharmaceutical composition according to the present invention ("free" HBsAg), wherein the (fusion) protein may aggregate with the "free" HBsAg to form particles.

Medical Treatments, Kits and Uses
Medical Treatments

In a further aspect, the present invention provides the use of
(i) the peptide according to the present invention;
(ii) the protein according to the present invention;
(iii) the nucleic acid encoding the protein or the peptide according to the present invention;
(iv) the virus-like particle according to the present invention;
(v) the protein nanoparticle according to the present invention;
(vi) the antibody, or the antibody fragment thereof, according to the present invention;
(vii) the nucleic acid encoding the antibody, or antibody fragments according to the present invention;
(viii) the vector comprising the nucleic acid according to the present invention;
(ix) the cell expressing the antibody or the peptide according to the present invention, or comprising the vector according to the present invention; and/or
(x) the pharmaceutical composition according to the present invention as a medicament.

Preferably
(i) the peptide according to the present invention;
(ii) the protein according to the present invention;
(iii) the nucleic acid encoding the protein or the peptide according to the present invention;
(iv) the virus-like particle according to the present invention;
(v) the protein nanoparticle according to the present invention;
(vi) the antibody, or the antibody fragment thereof, according to the present invention;
(vii) the nucleic acid encoding the antibody, or antibody fragments according to the present invention;
(viii) the vector comprising the nucleic acid according to the present invention;
(ix) the cell expressing the antibody or the peptide according to the present invention, or comprising the vector according to the present invention; and/or
(x) the pharmaceutical composition according to the present invention
are for use in the prevention and/or treatment of malaria.

In other words, the antibody, or an antigen binding fragment thereof, according to the present invention is preferably for use in the prevention and/or treatment of malaria. It is also preferred that the peptide and/or the protein according to the present invention is for use in the prevention and/or treatment of malaria. Most preferably, the pharmaceutical composition according to the present invention as described above is for use in the prevention and/or treatment of malaria.

Preferably, the malaria to be prevented and/or treated is caused by *P. falciparum* (infection).

Prevention of malaria refers in particular to prophylactic settings, wherein the subject was not diagnosed with malaria (either no diagnosis was performed or diagnosis results were negative) and/or the subject does not show symptoms of malaria. Preferably, the inventive product is administered before infection, e.g. with *P. falciparum*. However, prevention of malaria also includes "post-exposure prophylaxis" (PEP), i.e. preventive treatment after a possible *P. falciparum* infection, for example after a mosquito bite in a *P. falciparum* affected area. Prevention of malaria is in particular useful in high-risk subjects, such as in subjects staying in malaria areas (such as subjects living in malaria affected areas or travelling to malaria affected areas).

Accordingly, the peptide according to the present invention, the protein according to the present invention, the virus-like particle according to the present invention, the protein nanoparticle according to the present invention, the antibody, or an antigen binding fragment thereof, according to the present invention, the nucleic acid according to the present invention, the vector according to the present invention, the cell according to the present invention or the pharmaceutical composition according to the present invention is preferably used for prevention of malaria in subjects not diagnosed with malaria or in subjects showing no symptoms of malaria.

In therapeutic settings, in contrast, the subject is typically diagnosed with malaria and/or showing symptoms of malaria. Of note, the terms "treatment" and "therapy"/"therapeutic" of malaria include (complete) cure as well as attenuation of malaria.

Accordingly, the peptide according to the present invention, the protein according to the present invention, the virus-like particle according to the present invention, the protein nanoparticle according to the present invention, the antibody, or an antigen binding fragment thereof, according to the present invention, the nucleic acid according to the present invention, the vector according to the present invention, the cell according to the present invention or the pharmaceutical composition according to the present invention is preferably used for treatment of malaria in subjects diagnosed with malaria or in subjects showing symptoms of malaria.

It is also preferred that the peptide according to the present invention, the protein according to the present invention, the virus-like particle according to the present invention, the protein nanoparticle according to the present invention, the antibody, or an antigen binding fragment thereof, according to the present invention, the nucleic acid according to the present invention, the vector according to the present invention, the cell according to the present invention or the pharmaceutical composition according to the present invention is used for prevention and/or treatment of malaria in asymptomatic subjects. Those subjects may be diagnosed or not diagnosed with malaria.

Preferably, the peptide according to the present invention, the protein according to the present invention, the virus-like particle according to the present invention, the protein nanoparticle according to the present invention, the antibody, or an antigen binding fragment thereof, according to the present invention, the nucleic acid according to the present invention, the vector according to the present invention, the cell according to the present invention or the pharmaceutical composition according to the present invention is used for prevention of malaria, wherein the peptide according to the present invention, the protein according to the present invention, the virus-like particle according to the present invention, the protein nanoparticle according to the present invention, the antibody, or an antigen binding fragment thereof, according to the present invention, the nucleic acid according to the present invention, the vector according to the present invention, the cell according to the present invention or the pharmaceutical composition according to the present invention is administered up to three months before (a possible) *Plasmodium* infection, preferably up to one month before (a possible) *Plasmodium* infection, more preferably up to two weeks before (a possible) *Plasmodium* infection, even more preferably up to one week before (a possible) *Plasmodium* infection, and most preferably up to one day before (a possible) *Plasmodium* infection. Such a treatment schedule refers in particular to a prophylactic setting.

In general, the peptide according to the present invention, the protein according to the present invention, the virus-like particle according to the present invention, the protein nanoparticle according to the present invention, the antibody, or an antigen binding fragment thereof, according to the present invention, the nucleic acid according to the present invention, the vector according to the present invention, the cell according to the present invention or the pharmaceutical composition according to the present invention may be administered once or repeatedly. Accordingly, after the first administration of the peptide according to the present invention, the protein according to the present invention, the virus-like particle according to the present invention, the protein nanoparticle according to the present invention, the antibody, or an antigen binding fragment thereof, according to the present invention, the nucleic acid according to the present invention, the vector according to the present invention, the cell according to the present invention or the pharmaceutical composition according to the present invention, one or more subsequent administrations may follow, preferably a single dose per day or per every second day for 1, 2, 3, 4, 5, 6, 7, 8, 9, 10, 11, 12, 13, 1, 15, 16, 17, 18, 19, 20, or 21 days. It is also preferred that after the first administration of the peptide according to the present invention, the protein according to the present invention, the virus-like particle according to the present invention, the protein nanoparticle according to the present invention, the antibody, or an antigen binding fragment thereof, according to the present invention, the nucleic acid according to the present invention, the vector according to the present invention, the cell according to the present invention or the pharmaceutical composition according to the present invention, one or more subsequent administrations may follow, preferably a single dose once or twice per week for 1, 2, 3, 4, 5, 6, 7, 8, 9, 10, 11, 12, 13, 1, 15, 16, 17, 18, 19, 20, or 21 weeks. It is also preferred that after the first administration of the peptide according to the present invention, the protein according to the present invention, the virus-like particle according to the present invention, the protein nanoparticle according to the present invention, the antibody, or an antigen binding fragment thereof, according to the present invention, the nucleic acid according to the present invention, the vector according to the present invention, the cell according to the present invention or the pharmaceutical composition according to the present invention, one or more subsequent administrations may follow, preferably a single dose every 2 or 4 weeks for 1, 2, 3, 4, 5, 6, 7, 8, 9, 10, 11, 12, 13, 1, 15, 16, 17, 18, 19, 20, or 21 weeks. It is also preferred that after the first administration of the peptide according to the present invention, the protein according to the present invention, the virus-like particle according to the present invention, the protein nanoparticle according to the present invention, the antibody, or an antigen binding fragment thereof, according to the present invention, the nucleic acid according to the present invention, the vector according to the present invention, the cell according to the present invention or the pharmaceutical composition according to the present invention, one or more subsequent administrations may follow, preferably a single dose every two or four months for 1, 2, 3, 4, 5, 6, 7, 8, 9, 10, 11, 12, 13, 1, 15, 16, 17, 18, 19, 20, or 21 months. It is also preferred that after the first administration of the peptide according to the present invention, the protein according to the present invention, the virus-like particle according to the present invention, the protein nanoparticle according to the present invention, the antibody, or an antigen binding fragment thereof, according to the present invention, the nucleic acid according to the present invention, the vector according to the present invention, the cell according to the present invention or the pharmaceutical composition according to the present invention, one or more subsequent administrations may follow, preferably a single dose once or twice per year for 1, 2, 3, 4, 5, 6, 7, 8, 9, or 10 years.

Preferably, the peptide according to the present invention, the protein according to the present invention, the virus-like particle according to the present invention, the protein nanoparticle according to the present invention, the antibody, or an antigen binding fragment thereof, according to the present invention, the nucleic acid according to the present invention, the vector according to the present invention, the cell according to the present invention or the pharmaceutical composition according to the present invention is administered at a (single) dose of 0.005 to 100 mg/kg bodyweight, preferably at a (single) dose of 0.0075 to 50 mg/kg bodyweight, more preferably at a (single) dose of 0.01 to 10 mg/kg bodyweight, even more preferably at a (single) dose of 0.05 to 5 mg/kg bodyweight, and particularly preferably at a (single) dose of 0.1 to 1 mg/kg bodyweight.

The peptide according to the present invention, the protein according to the present invention, the virus-like particle according to the present invention, the protein nanoparticle according to the present invention, the antibody, or an antigen binding fragment thereof, according to the present invention, the nucleic acid according to the present invention, the vector according to the present invention, the cell according to the present invention or the pharmaceutical composition according to the present invention may be administered by any number of routes such as oral, intravenous, intramuscular, intra-arterial, intramedullary, intraperitoneal, intrathecal, intraventricular, transdermal, transcutaneous, topical, subcutaneous, intranasal, enteral, sublingual, intravaginal or rectal routes. Intravenous administration, or subcutaneous administration or intramuscular administration are preferred and intravenous administration or subcutaneous administration are more preferred.

Accordingly, the present invention also provides a method of preventing and/or treating malaria in a subject, wherein the method comprises administering to a subject in need thereof (i) the peptide according to the present invention;
(ii) the protein according to the present invention;
(iii) the nucleic acid encoding the protein or the peptide according to the present invention;
(iv) the virus-like particle according to the present invention;
(v) the protein nanoparticle according to the present invention;
(vi) the antibody, or the antibody fragment thereof, according to the present invention;
(vii) the nucleic acid encoding the antibody, or antibody fragments according to the present invention;
(viii) the vector comprising the nucleic acid according to the present invention;
(ix) the cell expressing the antibody or the peptide according to the present invention, or comprising the vector according to the present invention; and/or
(x) the pharmaceutical composition according to the present invention.

Preferred embodiments of this method correspond to preferred embodiments of the medical use as described above.

Further Use and Kits

In a further aspect, the present invention also provides the use of the antibody, or the antibody fragment thereof, according to the present invention or of the pharmaceutical composition according to the present invention for monitoring the quality of an anti-malaria vaccine by checking that the antigen of said vaccine contains the specific epitope in the correct conformation. Preferred antigens comprised by such an anti-malaria vaccine to be checked include the peptide according to the present invention as described above.

Moreover, the present invention also provides the use of
(i) the peptide according to the present invention;
(ii) the protein according to the present invention;
(iii) the nucleic acid encoding the protein or the peptide according to the present invention;
(iv) the virus-like particle according to the present invention;
(v) the protein nanoparticle according to the present invention;
(vi) the antibody, or the antibody fragment thereof, according to the present invention;
(vii) the nucleic acid encoding the antibody, or antibody fragments according to the present invention;
(viii) the vector comprising the nucleic acid according to the present invention;
(ix) the cell expressing the antibody or the peptide according to the present invention, or comprising the vector according to the present invention; and/or
(x) the pharmaceutical composition according to the present invention in diagnosis of malaria infection.

In addition also the use of
(i) the peptide according to the present invention;
(ii) the protein according to the present invention;
(iii) the nucleic acid encoding the protein or the peptide according to the present invention;
(iv) the virus-like particle according to the present invention;
(v) the protein nanoparticle according to the present invention;
(vi) the antibody, or the antibody fragment thereof, according to the present invention;
(vii) the nucleic acid encoding the antibody, or antibody fragments according to the present invention;

(viii) the vector comprising the nucleic acid according to the present invention;

(ix) the cell expressing the antibody or the peptide according to the present invention, or comprising the vector according to the present invention; and/or (x) the pharmaceutical composition according to the present invention in determining whether an isolated blood sample (e.g., whole blood, serum and/or plasma) is infected with *Plasmodium* is provided.

Methods of diagnosis may include contacting the antibody or the peptide/protein according to the present invention with a sample. Such samples may be isolated from a subject, for example an isolated tissue sample taken from, for example, nasal passages, sinus cavities, salivary glands, lung, liver, pancreas, kidney, ear, eye, placenta, alimentary tract, heart, ovaries, pituitary, adrenals, thyroid, brain, skin or blood, preferably plasma or serum. The methods of diagnosis may also include the detection of an antigen/antibody complex, in particular following the contacting of the antibody or the peptide/protein according to the present invention with a sample. Such a detection step is typically performed at the bench, i.e. without any contact to the human or animal body. Examples of detection methods are well-known to the person skilled in the art and include, e.g., ELISA (enzyme-linked immunosorbent assay).

In a further aspect, the present invention also provides a kit of parts comprising at least one peptide according to the present invention, at least one protein according to the present invention, at least one virus-like particle according to the present invention, at least one protein nanoparticle according to the present invention, at least one pharmaceutical composition according to the present invention, at least one antibody, or the antigen binding fragment thereof, according to the present invention, at least one nucleic acid according to the present invention, at least one vector according to the present invention, at least one cell according to the present invention, and/or at least one pharmaceutical composition according to the present invention. In addition, the kit may comprise a leaflet with instructions for administration of the peptide according to the present invention, the protein according to the present invention, the nucleic acid encoding the protein or the peptide according to the present invention, the virus-like particle according to the present invention, the protein nanoparticle according to the present invention, the antibody, or the antibody fragment thereof, according to the present invention, the nucleic acid encoding the antibody, or antibody fragments according to the present invention, the vector comprising the nucleic acid according to the present invention, the cell expressing the antibody or the peptide according to the present invention, or comprising the vector according to the present invention, and/or the pharmaceutical composition according to the present invention and/or means for administration of the peptide according to the present invention, the protein according to the present invention, the nucleic acid encoding the protein or the peptide according to the present invention, the virus-like particle according to the present invention, the protein nanoparticle according to the present invention, the antibody, or the antibody fragment thereof, according to the present invention, the nucleic acid encoding the antibody, or antibody fragments according to the present invention, the vector comprising the nucleic acid according to the present invention, the cell expressing the antibody or the peptide according to the present invention, or comprising the vector according to the present invention, and/or the pharmaceutical composition according to the present invention, such as a syringe or a vessel.

BRIEF DESCRIPTION OF THE FIGURES

In the following a brief description of the appended figures will be given. The figures are intended to illustrate the present invention in more detail. However, they are not intended to limit the subject matter of the invention in any way.

FIGS. 4A-4C show for Example 3 (4A) a schematic overview over *P. falciparum* circumsporozoite protein. SP, signal peptide; R1, region I. (4B) Sequence of PfCSP (isolate NF54, Uniprot accession number PI 9597; SEQ ID NO: 24). The functionally important region I is shown in bold. (4C) Sequence of CSP peptides that were tested for binding by antibodies: 22-110-peptide (SEQ ID NO: 27), NPDP-peptide (SEQ ID NO: 23), and NANP-peptide (SEQ ID NO: 26). Amino acids belonging to region I are shown in bold.

FIG. 6 shows for Example 4 the binding of monoclonal antibodies MGV3, MGG4, MGU5 and MGG1 to overlapping peptides from CSP. Only the region of CSP that showed binding by the monoclonal antibodies are shown.

EXAMPLES

In the following, particular examples illustrating various embodiments and aspects of the invention are presented. However, the present invention shall not to be limited in scope by the specific embodiments described herein. The following preparations and examples are given to enable those skilled in the art to more clearly understand and to practice the present invention. The present invention, however, is not limited in scope by the exemplified embodiments, which are intended as illustrations of single aspects of the invention only, and methods which are functionally equivalent are within the scope of the invention. Indeed, various modifications of the invention in addition to those described herein will become readily apparent to those skilled in the art from the foregoing description, accompanying figures and the examples below. All such modifications fall within the scope of the appended claims.

Example 1: Isolation of Human Monoclonal Antibodies that Bind to P. falciparum Sporozoites Four Tanzanian donors (identified as donors G, H, U and V) who were protected from malaria challenge were selected for isolation of human monoclonal antibodies. To this end, peripheral blood mononuclear cells (PBMCs) were isolated from blood samples of the four donors. IgG memory B cells were isolated from frozen peripheral blood mononuclear cells (PBMCs) by magnetic cell sorting. The B cells were incubated with 0.5 µg/mL of anti-CD19-PECy7 antibodies for 20 min on ice and then incubated with mouse anti-PE microbeads for 30 min on ice. The cells were then stained with 3.75 µg/mL goat Alexa Fluor 647-conjugated anti-human IgG for 20 min on ice and sorted by FACS. As previously described in Traggiai et al. (2004) Nat Med. 10, 871-875, sorted B cells were immortalized with Epstein-Barr virus (EBV) and plated in single cell cultures in the presence of CpG and irradiated PBMC-feeder cells. After 14 days, culture supernatants were screened using a high-throughput flow cytometer for their capacity to stain sporozoites. In this assay, the sporozoites were labelled with 6.25×SYBR Green I and incubated with the B cell culture supernatants at a 1/2 dilution for 30 min at room temperature. Without any washing step, the sporozoites were then incubated with 1 µg/mL of goat Alexa Fluor 647-conjugated anti-human IgG for 1 h at 4° C. and analyzed by flow cytometry.

For sporozoite staining using recombinant monoclonal antibodies, the sporozoites were stained with 6.25×SYBR Green I and incubated with the monoclonal antibodies for 30 min at room temperature. The sporozoites were then washed once and stained with 2.5 µg/mL of goat Alexa Fluor 647-conjugated anti-human IgG for 30 min at room temperature and analyzed by flow cytometry.

Figure 1:
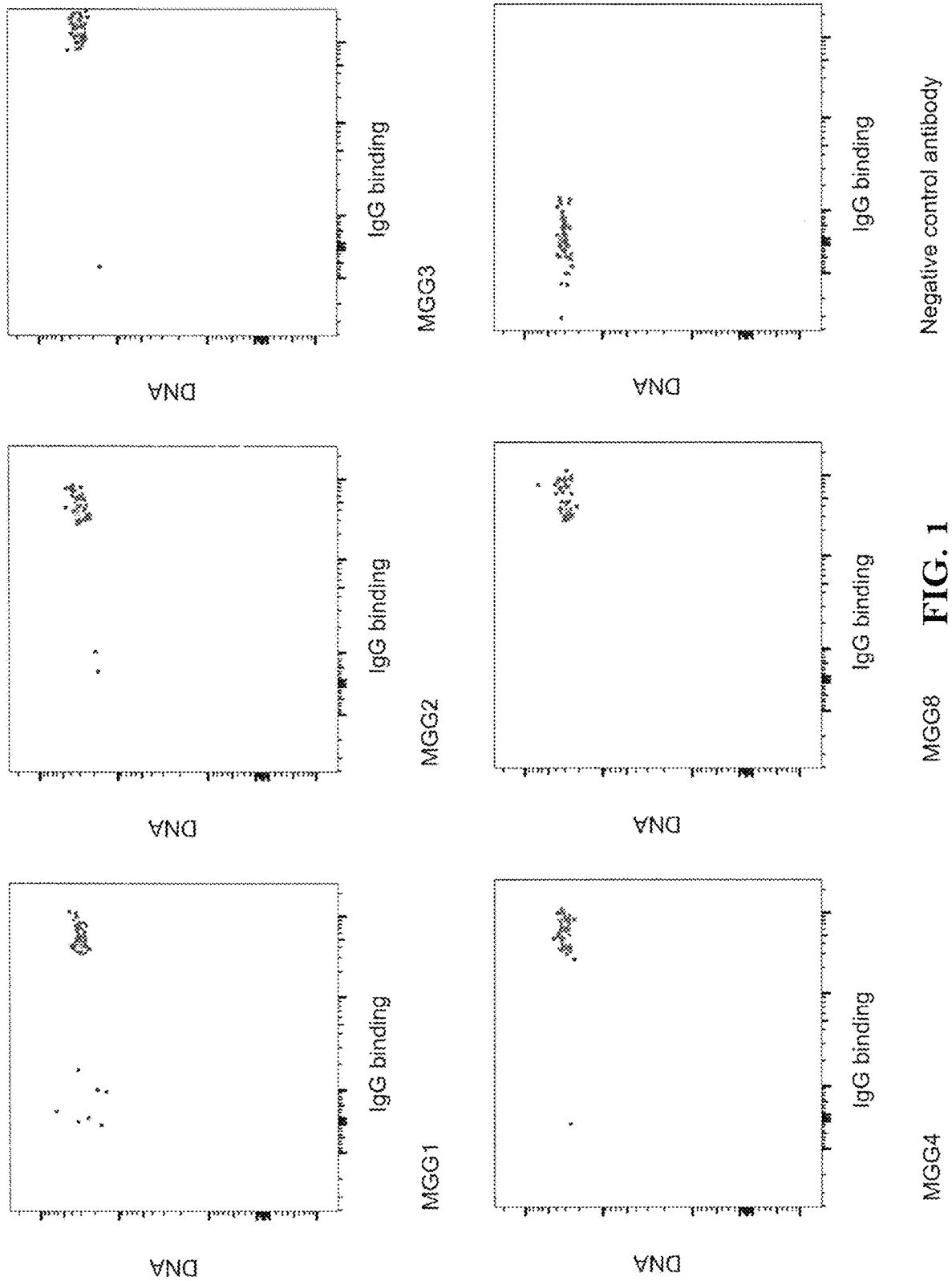
FIG. 1 shows for Example 1 exemplary staining of *P. falciparum* sporozoites by monoclonal antibodies MGG1, MGG2, MGG3, MGG4 and MGG8 (each of them based on VH/VL genes of antibodies isolated from Donor G) and by control antibody BKC3. The sporozoites were labeled with SYBR Green I and incubated with the monoclonal antibodies. Antibody detection was conducted with anti-human IgG conjugated to a fluorophore.

An example of sporozoite staining is shown in FIG. 1. FIG. 1 shows exemplary staining of P. falciparum sporozoites by monoclonal antibodies MGG1, MGG2, MGG3, MGG4 and MGG5 (each of them based on VH/VL genes of antibodies isolated from Donor G) and by a negative control antibody.

Positive cultures were expanded and the VH and VL genes from individual clones were sequenced and cloned into human IgG1, Igκ and Igλ expression vectors (kindly provided by Michel Nussenzweig, Rockefeller University, New York, US) essentially as described (Tiller T, Meffre E, Yurasov S, Tsuiji M, Nussenzweig M C, Wardemann H (2008) Efficient generation of monoclonal antibodies from single human B cells by single cell RT-PCR and expression vector cloning. J Immunol Methods 329: 112-124) and expressed by transient transfection of Expi293F Cells using polyethylenimine (PEI).

Table 5 below shows exemplary human monoclonal antibodies that were found to bind to P. falciparum sporozoites, along with their VH and VL usage (see Tables 1 and 2 for SEQ ID NOs):

|  |  | Heavy chain | | Light chain | |
| --- | --- | --- | --- | --- | --- |
|  |  | VH | JH | VL | JL |
| Donor G | MGG1 | VH3-20 | JH6 | VL1-51 | JL3 |
|  | MGG2 | VH3-74 | JH5 | VL7-46 | JL2/JL3 |
|  | MGG3 | VH3-30 | JH2 | VK2-29 | JK1 |
|  | MGG4 | VH3-30 | JH3 | VK4-1 | JK4 |
|  | MGG8 | VH3-73 | JH5 | VK2D-29 | JK1 |
| Donor H | MGH1 | VH1-2 | JH4 | VK2-30 | JK2 |
|  | MGH2 | VH3-30 | JH4 | VK2-30 | JK1 |
|  | MGH3 | VH3-21 | JH4 | VK1-47 | JK3 |
| Donor U | MGU1 | VH3-30 | JH3 | VL4-69 | JL3 |
|  | MGU3 | VH3-48 | JH4 | VK1-33 | JK4 |
|  | MGU5 | VH3-30 | JH3 | VK1-33 | JK4 |
|  | MGU8 | VH3-30 | JH3 | VK1-33 | JK1/JK4 |
|  | MGU10 | VH3-30 | JH3 | VL4-69 | JL3 |
|  | MGU11 | VH3-33 | JH3 | VK2-30 | JK3 |
|  | MGU12 | VH3-30 | JH3 | VK1-5 | JK1 |
| Donor V | MGV3 | VH3-66 | JH6 | VK3-20 | JK2 |

Figure 2A:
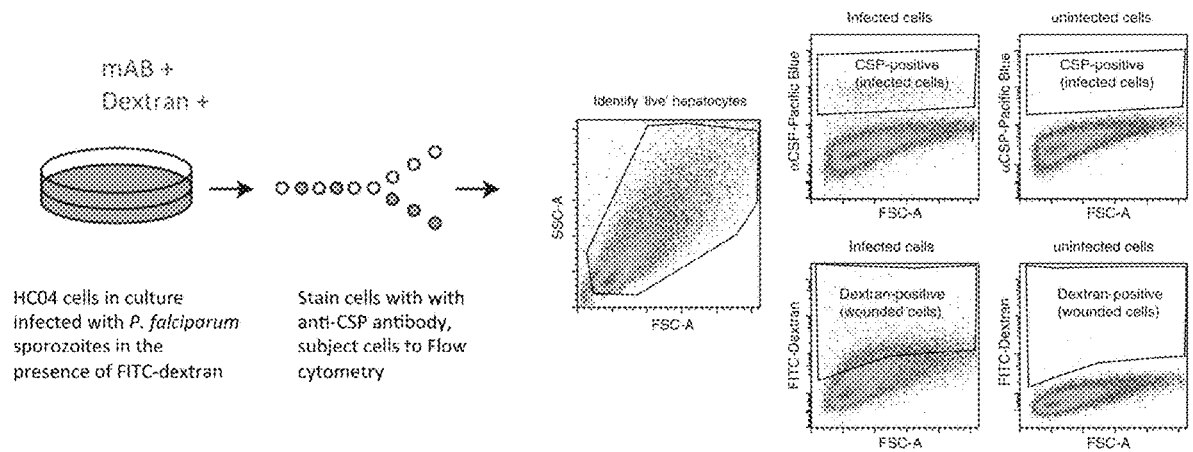
FIGS. 2A and 2B show for Example 2 (2A) a schematic overview of the assay used and (2B) the inhibition of sporozoite traversal and invasion (ISTQ of hepatocytes by human monoclonal antibodies MGG1, MGG2, MGG3, MGG4, MGG8, MGH1, MGH2, MGH3 and for control antibody 2A10.

Example 2: Several Monoclonal Antibodies Show Potent In Vitro and In Vivo Anti-Sporozoite Function During the liver stage of the Plasmodium life cycle, sporozoites often traverse hepatocytes before productive invasion of target hepatocytes. Exemplary monoclonal antibodies MGG1, MGG2, MGG3, MGG4, MGG8, MGH1, MGH2 and MGH3 (see Tables 1 and 2 for SEQ ID NOs) were tested in vitro for their ability to inhibit sporozoite traversal and invasion of hepatocytes. To this end, a quantitative flow-cytometry-based assay was used, which is described in Kaushansky A, Rezakhani N, Mann H, Kappe S H, 2012: Development of a quantitative flow cytometry-based assay to assess infection by Plasmodium falciparum sporozoites. Mol Biochem Parasitol. 183(1):100-3. A schematic overview over this assay is shown in FIG. 2A. Briefly, in this assay, the hepatocyte HC04 cell line was infected with P. falciparum sporozoites in the presence of FITC-dextran. Sporozoite traversal was measured by the uptake of FITC-dextran, which can enter hepatocytes with membranes injured during traversal. Sporozoite invasion was measured by staining of sporozoites in hepatocytes with an anti-circumsporozoite protein (anti-CSP) antibody. As a control, murine monoclonal antibody 2A10, which targets the NANP repeat region of the circumsporozoite protein (Zavala F. et al., 1983, J. Exp. Med. 157: 1947-1957; Wirtz R. A. et al, 1987, Bulletin of the World Health Organization 65(1): 39-45), was used.

Figure 2B:
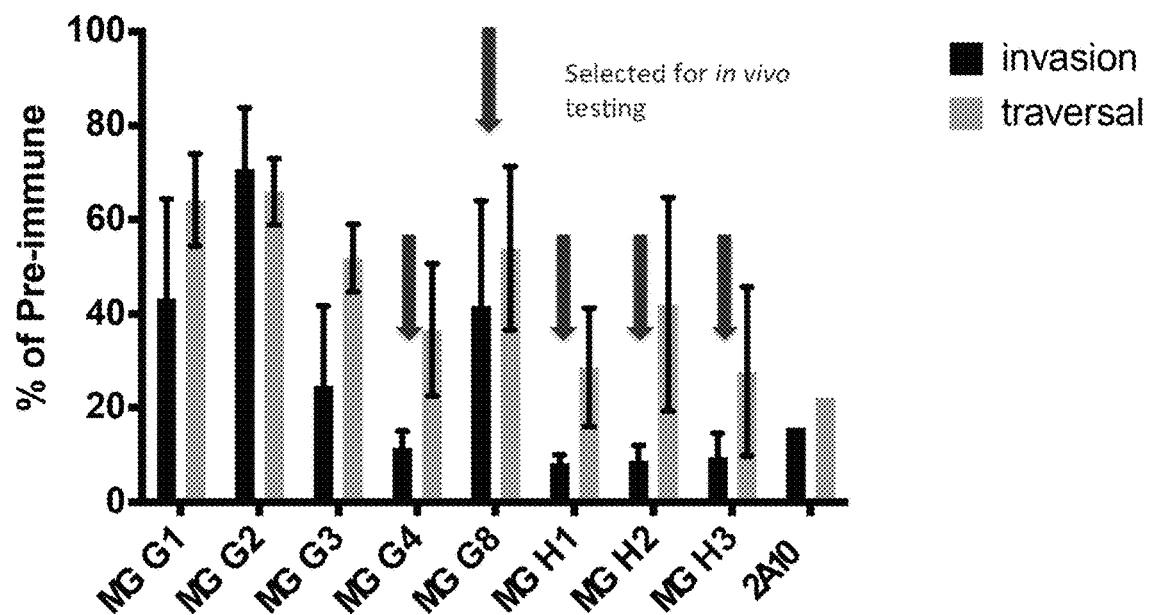

Results are shown in FIG. 2B. Here, the percentage of sporozoite invasion or traversal in the presence of a monoclonal antibody of interest relative to when irrelevant IgG is added is measured. A low percentage signifies good inhibition by the monoclonal antibody. In this assay, MGG4, MGH1, MGH2 and MGH3 showed the highest inhibition of sporozoite invasion. Hence, these antibodies, along with MGG8, were selected for further testing.

Figure 3A:
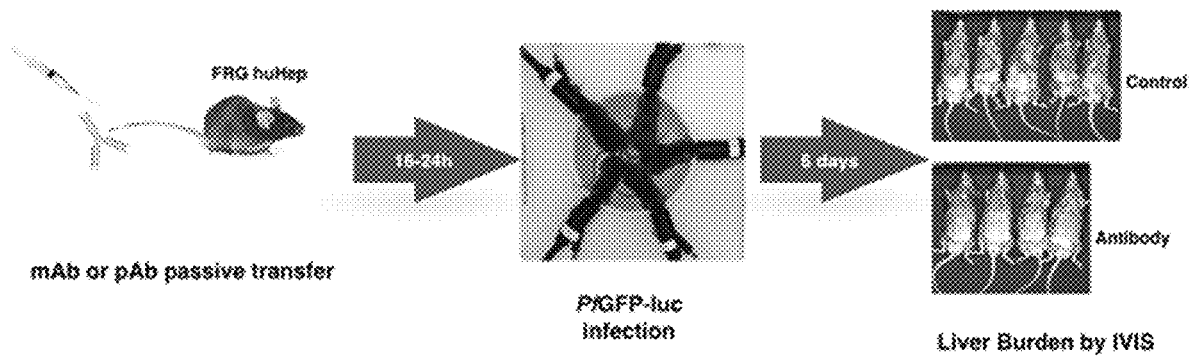
FIG. 3 shows for Example 2 (A) a schematic overview over the experimental design of the in vivo humanized mouse model of sporozoite invasion and (B) the in vivo reduction of sporozoites by the selected antibodies MGG4, MGG8, MGH1, MGH2 and MGH3.

Selected monoclonal antibodies were then tested in the FRG huHEP liver-chimeric mouse model, essentially as described in Sack et al. (Sack et al., 2014, Infection and Immunity 82(2): 808-817. Model for in vivo assessment of humoral protection against malaria sporozoite challenge by passive transfer of monoclonal antibodies and immune serum) and, in particular, also in Vaughan et al. (Vaughan et al., 2012, *J Clin Invest* 122, 3618-3628. The FRG huHEP liver-chimeric mouse model measures sporozoite invasion and liver-stage parasite multiplication in mice with humanized livers). A schematic overview over the experimental design is shown in FIG. 3A. In this model, the antibodies were first injected into mice, which were then infected by *P. falciparum* sporozoites by mosquito bite 16-24 h later. Liver parasite burden was then detected by imaging six days after infection.

Figure 3B:
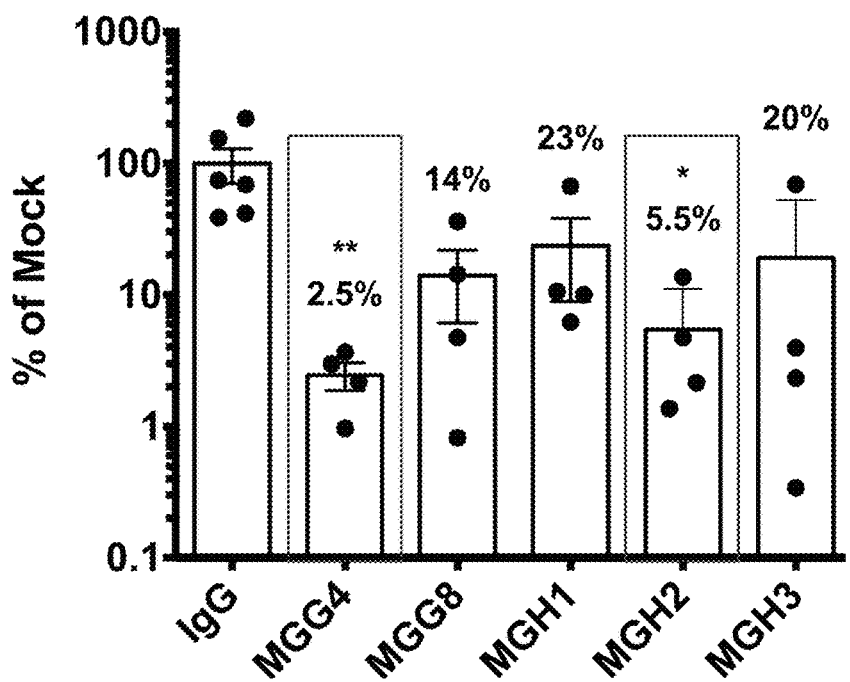

Results are shown in FIG. 3B. The liver burden in mice injected with a monoclonal antibody of interest was measured and calculated as a percentage of the liver burden in mice injected with non-specific IgG. The largest reduction of liver burden was observed in mice injected with antibody MGG4 or MGH2 (showing only 2.5% and 5.5% liver burden as compared to negative control mice, respectively).

Example 3: Potent Monoclonal Antibodies Show Distinct Patterns of Binding to CSP and Use VH3-30

*Plasmodium* circumsporozoite protein (CSP) is an immunodominant protein that coats the entire sporozoite surface and that plays an important role in sporozoite function. As shown in FIG. 4A, this protein contains an N-terminal segment starting with a signal peptide (SP) and ending with Region I (RI). Region I is a pentapeptide (KLKQP; SEQ ID NO: 25) that is involved in binding to hepatocytes and mosquito salivary glands. In CSP, region I is followed by an NANP repeat region that is the immunodominant site for antibodies and a C-terminal thrombospondin-like domain that contains T cell epitopes (FIG. 4A). FIG. 48 shows an exemplary sequence of the circumsporozoite protein of *P. falciparum* isolate NF54 (SEQ ID NO: 24).

An antigen-agnostic approach as described in Example 1 was used to identify any antibody that can bind to the sporozoite surface. In that approach, it was found that all of the antibodies shown in Table 5 bound to CSP, confirming the immunodominance of this protein (data not shown).

Next, the binding of the antibodies to peptides from different parts of CSP as shown in FIG. 4C was tested. In this assay, half-area 96-well ELISA plates were coated with whole recombinant CSP (SEQ ID NO: 24; 1 µg/mL), NANP-peptide (SEQ ID NO: 26; 2 µg/mL), NPDP-peptide (SEQ ID NO: 23; 5 µg/mL) or 22-110-peptide (SEQ ID NO: 27; 1 µg/mL) overnight at 4° C. The plates were blocked with 1% bovine serum albumin in PBS and incubated with titrated antibodies, followed by AP-conjugated goat anti-human IgG. The plates were then washed, substrate (p-NPP) is added and the plates were read at 405 nm.

Figure 5:
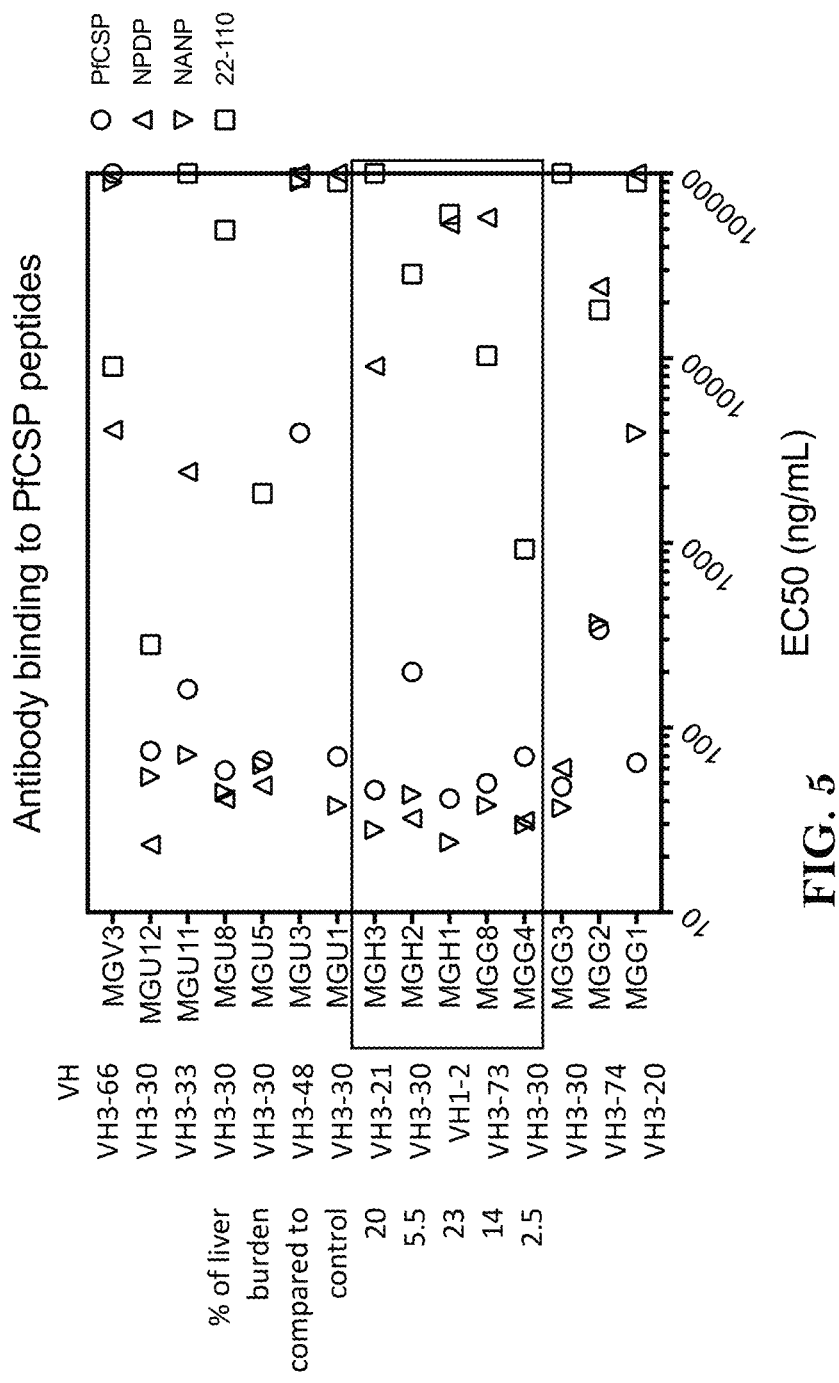
FIG. 5 shows for Example 3 the binding of monoclonal antibodies to different peptides by ELISA. Different dilutions of the antibodies were tested for binding to the CSP peptides (sequences are shown in FIG. 4) and EC50 values were calculated for each antibody. The antibodies that were tested in the in vivo mouse model are boxed. The two antibodies that showed the best protection in this model (MGG4 and MGH2) showed good binding to the NPDP peptide and used VH3-30. All of the other antibodies that bound strongly to NPDP (with an EC50<100 ng/mL) also used VH3-30. One antibody, MGV3, bound relatively weakly to NPDP and 22-110 but not to the NANP repeat region.

Results are shown in FIG. 5 with the antibodies that were tested in the in vivo mouse model shown in a box. Interestingly, out of the five antibodies tested in the in vivo assay (MGG4, MGG8, MGH1, MGH2, MGH3), the two antibodies that showed the best function in the in vivo assay (MGG4, MGH2, see Example 2) bound well to the NPDP-peptide (SEQ ID NO: 23), i.e. in CSP at the junction between the N-terminus and the NANP repeat region. The other three antibodies tested in the in vivo assay (MGG8, MGH1, MGH3) showed only poor or negligible binding to this region. In contrast, the affinity of binding to a peptide containing only the repeat region or to whole CSP did not distinguish between the antibodies with different functional capacity in the in vivo assay.

Interestingly, the CSP region to which the most potent antibodies MGG4 and MGH2 bind to, i.e. the junction between the N-terminus and the NANP repeat region, is not included in the leading malaria vaccine RTS,S. Rather, RTS,S incorporates the C-terminal half of the NANP repeat region and the C-terminal domain. The present data suggest that the junction between the N-terminus and the NANP repeat region is an important target of antibodies from protected individuals that show the most potent function in an in vivo model. Without being bound to any theory, the inventors assume that this region may be important due to its proximity to Region I, which is thought to be a target of parasite proteases that cleave the N-terminus of CSP during invasion of hepatocytes (Coppi et al. (2011) *J Exp Med* 208, 341-356; Coppi et al. (2005) *J Exp Med* 201, 27-33).

Further antibodies, which bound well to the NPDP-peptide (SEQ ID NO: 23) include MGG3, MGU5, MGU8 and MGU12.

Furthermore, all of the antibodies that bound well to the NPDP-peptide (MGG4, MGH2, MGG3, MGU5, MGU8 and MGU12) used VH3-30, suggesting that the usage of this VH is preferential for binding to this key region.

One antibody, MGV3, was found to bind relatively weakly to the NPDP-peptide and to the 22-110-peptide, but not to the NANP-peptide. This indicates that antibody MGV3 recognizes the N-terminus of CSP and the NPDP-region, but not to the NANP repeat region. Accordingly, MGV3 appears to bind slightly N-terminal as compared to the binding site of MGG4, MGH2, MGG3, MGU5, MGU8 and MGU12.

Other antibodies were found to bind well to the NANP-peptide, but weakly, if at all, to the NPDP-peptide and the 22-110-peptide, thereby indicating a binding site in the (middle of the) NANP-repeat region. Such antibodies include MGU11, MGU1, MGH3, MGH1, MGG8 and, to a lesser extent, MGG2 and MGG1.

Only antibody MGU3 showed no binding to any of the CSP-peptides used (22-110, NPDP-peptide, NANP-peptide), although it showed binding to the entire PfCSP. This may indicate a binding site for MGU3, which is located C-terminal of the NANP-repeat in CSP.

Example 4: Fine Epitope Mapping of Monoclonal Antibodies

To identify the precise region of CSP targeted by the monoclonal antibodies, linear epitope mappings of selected antibodies were performed against CSP (PEPperMAP® by PEPperPRINT GmbH, Heidelberg, Germany). To this end, antibodies MGV3, MGG4, MGU5 and MGG1 were tested for binding to an array of 15-aa CSP peptides (shifted by a single amino acid) covering the entire protein (FIG. 6). Briefly, the sequence of circumsporozoite protein (CSP) was elongated by neutral GSGSGSG linkers (SEQ ID NO: 28) at the C- and N-terminus to avoid truncated peptides. The elongated antigen sequence was translated into linear 15 amino acid peptides with a peptide-peptide overlap of 14 amino acids (FIG. 6). The resulting CSP peptide microarrays contained 457 different peptides printed in duplicate (914 peptide spots), additional custom control peptides (2 spots each control), c-Myc controls (2 spots) and a frame of HA control peptides (82 spots). The CSP peptide microarrays were incubated with the antibody samples at concentrations 1 µg/ml, 10 µg/ml and 100 µg/ml in incubation buffer followed by staining with secondary and control antibodies as well as read-out with a LI-COR Odyssey Imaging System. Quantification of spot intensities and peptide annotation were done with PepSlide® Analyzer.

Results are shown in FIG. 6. It was found that MGV3, a peptide that recognizes the N-terminus and the NPDP peptide (FIG. 5) but not the NANP repeat region, appears to bind to a NPDP motif, whereas MGG4 and MGU5 are able to bind to the first NANP repeat close to this region.

Example 5: Inhibition of Binding of MGV3 to Intact Sporozoites

Next, it was tested whether monoclonal antibodies MGG1, MGG4, MGU5 and MGU3 could inhibit the binding of MGV3 to intact sporozoites in a blocking-of-binding (BOB) assay. In this assay, sporozoites were stained with 3.3×SYBR Green I and incubated with titrated monoclonal antibodies (from 0.1 to 100 µg/mL) for 20 min at room temperature. Without washing, the sporozoites were subsequently incubated with 10 µg/mL of biotin-labeled MGV3 for 20 min at room temperature. The sporozoites were washed twice, incubated with streptavidin conjugated to Alexa Fluor 647 for 20 min at room temperature, and analyzed by flow cytometry. The decrease in median fluorescence intensity (median FI) in the Alexa Fluor 647 channel was used to measure the degree of inhibition of binding of biotinylated MGV3.

Figure 7:
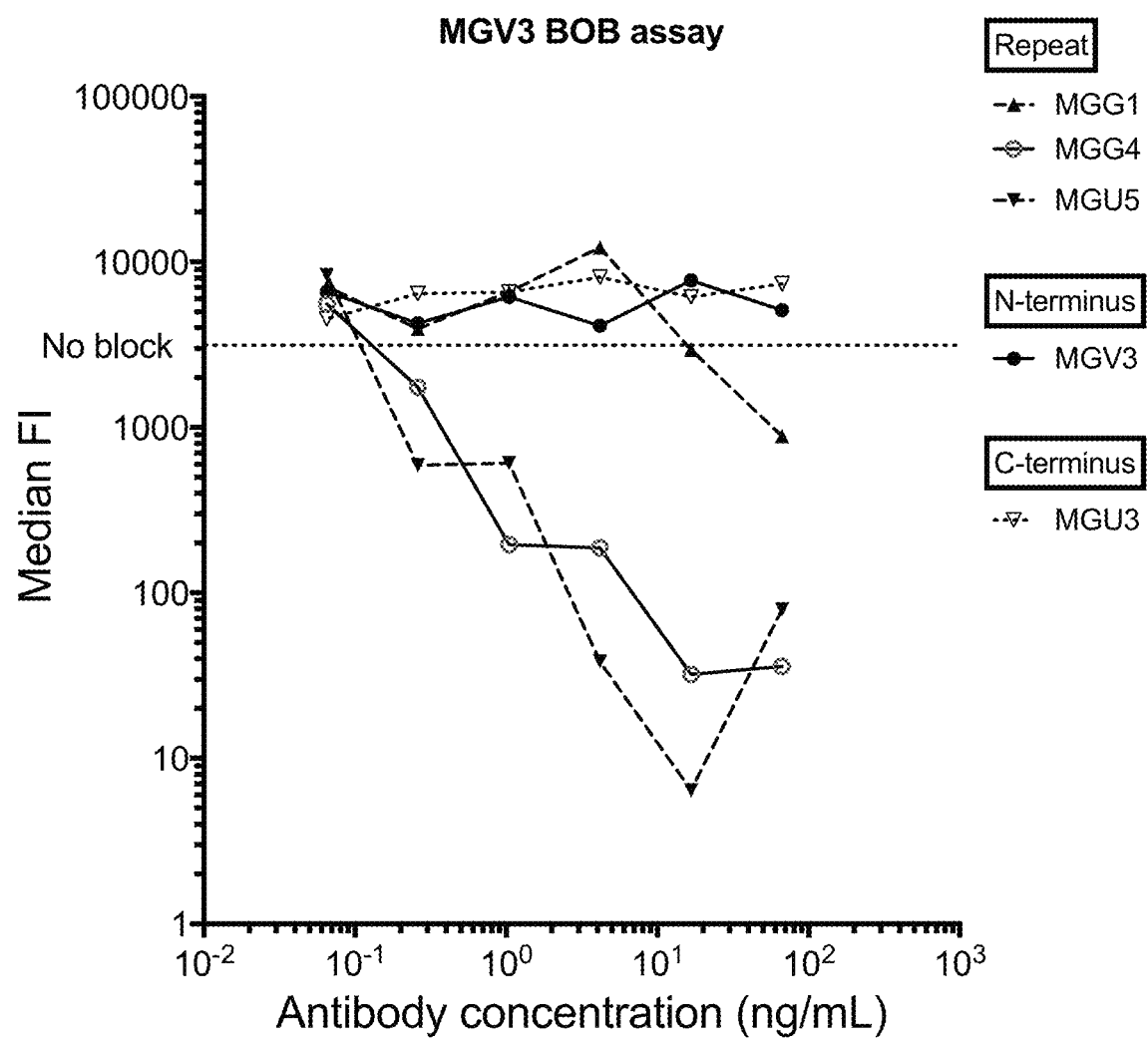
FIG. 7 shows for Example 5 the inhibition of binding of MGV3 by different monoclonal antibodies. Inhibition of binding is calculated by the median fluorescence intensity (FI) of IgG binding to sporozoites. MGU3 is an antibody that binds to the C-terminus of CSP, MGV3 binds to the NPDP region at the N-terminus, and the remaining antibodies bind to the repeat region of CSP.

Results are shown in FIG. 7. It was found that MGG4 and MGU5, which bind well to the NPDP peptide and could bind to the first NANP repeat based on the peptide array results (FIG. 6), could inhibit binding by MGV3, while MGG1, which bound further away from the N-terminus, could not efficiently inhibit binding. This confirms the results of Examples 3 and 4 that antibodies binding to the NDPD-peptide, such as MGG4 and MGU5, bind to a more N-terminal region of CSP than those antibodies, which do not bind to the NDPD-peptide, such as MGG1 or MGU3. In summary, the data suggest that antibodies binding to the NDPD-peptide, such as MGG4 and MGU5, have potent functional activity due to their ability to bind closer to the N-terminus.

As a note, unlabelled MGV3 could not inhibit binding as overall this antibody bound with low affinity to sporozoites and the concentration of biotinylated MGV3 used was much below its saturation point.

Example 6: Identification of Antibodies Binding to a C-Terminal Binding Site in CSP Since the data of Example 3 (FIG. 5) suggest that of all antibodies tested only antibody MGU3 binds to a C-terminal binding site in CSP, different antibodies were tested for their ability to bind to the C-terminus of CSP.

To this end, essentially the same experiment as described in Example 3 was performed with the antibodies shown in Table 1. However, instead of the CSP-test-peptides described in Example 3 (i.e., 22-110-peptide, NPDP-peptide, NANP-peptide) in the present experiment C-terminal peptide 282-383 (SEQ ID NO: 312) was used. Briefly, the C-terminal peptide 282-383 was coated at a concentration of 1 µg/ml, and the B cell supernatants were tested from a 1/3 dilution to a 1/648 dilution.

Figure 8:
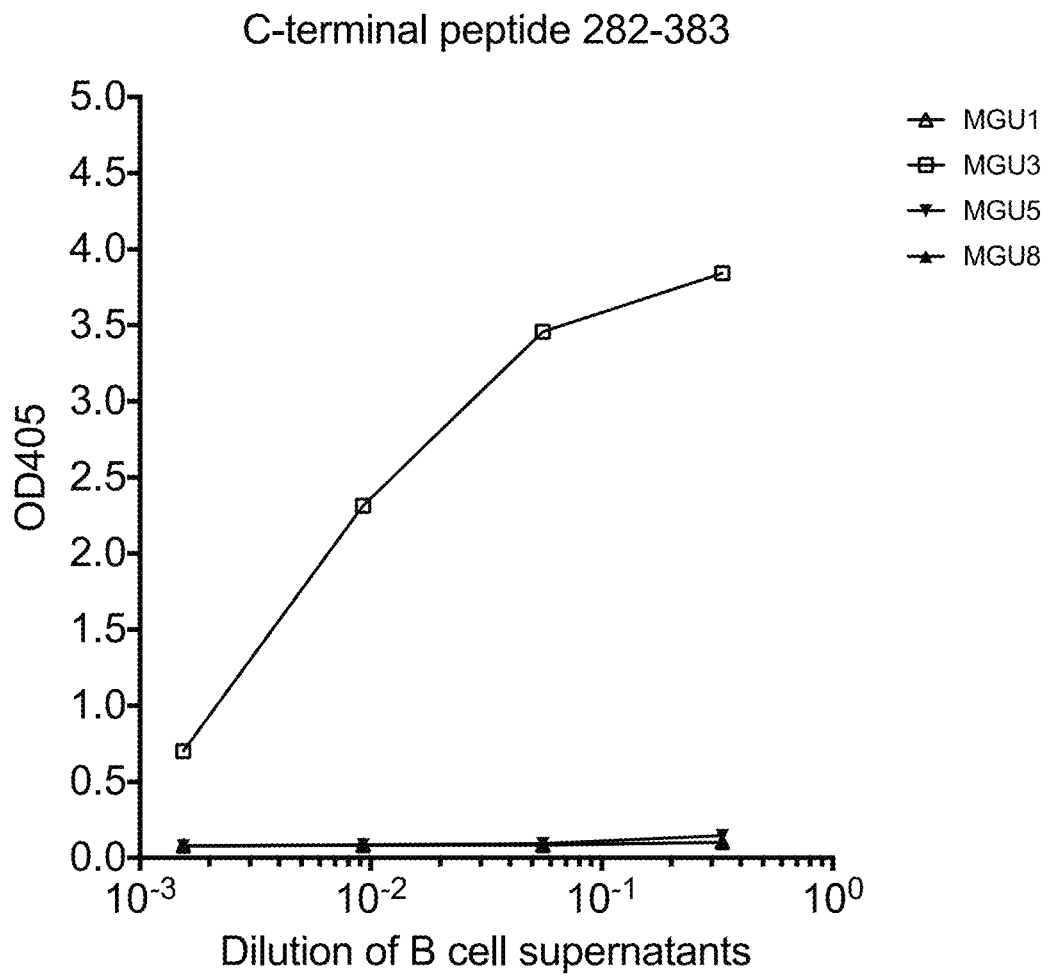
FIG. 8 shows for Example 6 the identification of antibodies binding to a C-terminal binding site in CSP. Briefly, C-terminal peptide 282-383 was coated at a concentration of 1 µg/ml, and the B cell supernatants were tested from a 1/3 dilution to a 1/648 dilution. MGU3 can bind to the peptide, while MGU1, MGU5 and MGU8 are shown as examples of antibodies that cannot bind to the peptide.

Results for selected antibodies MGU1, MGU3, MGU5 and MGU8 are shown in FIG. 8 (data of the other antibodies of Table 1 not shown). As expected from the results of Examples 3 and 5, only antibody MGU3 bound to C-terminal peptide 282-383, whereas all other antibodies tested did not bind to the C-terminus of CSP. These results confirm that antibody MGU3 binds to the C-terminus of CSP, whereas the other antibodies do not bind to that region of CSP.

TABLE OF SEQUENCES AND SEQ ID NUMBERS (SEQUENCE LISTING):

| SEQ ID NO | Sequence | Remarks |
|---|---|---|
| SEQ ID NO: 1 | NPDP | CSP epitope |
| SEQ ID NO: 2 | NPDPN | CSP epitope |
| SEQ ID NO: 3 | NPDPNA | CSP epitope |
| SEQ ID NO: 4 | NPDPNAN | CSP epitope |
| SEQ ID NO: 5 | NPDPNANP | CSP epitope |
| SEQ ID NO: 6 | NPDPNANPN | CSP epitope |
| SEQ ID NO: 7 | GNPDPNANP | CSP epitope |
| SEQ ID NO: 8 | GNPDPNANPN | CSP epitope |
| SEQ ID NO: 9 | DGNPDPNANP | CSP epitope |
| SEQ ID NO: 10 | NPDPNANPNK | CSP epitope |
| SEQ ID NO: 11 | DGNPDPNANPN | CSP epitope |
| SEQ ID NO: 12 | GNPDPNANPNK | CSP epitope |
| SEQ ID NO: 13 | DGNPDPNANPNK | CSP epitope |
| SEQ ID NO: 14 | ADGNPDPNANPN | CSP epitope |
| SEQ ID NO: 15 | QPADGNPDPNANPNK | CSP epitope |

TABLE OF SEQUENCES AND SEQ ID NUMBERS (SEQUENCE LISTING):

| SEQ ID NO | Sequence | Remarks |
| --- | --- | --- |
| SEQ ID NO: 16 | ADGNPDPNANPNK | CSP epitope |
| SEQ ID NO: 17 | PADGNPDPNANPNK | CSP epitope |
| SEQ ID NO: 18 | ADGNPDPNANPNKN | CSP epitope |
| SEQ ID NO: 19 | PADGNPDPNANPNKN | CSP epitope |
| SEQ ID NO: 20 | QPADGNPDPNANPNKN | CSP epitope |
| SEQ ID NO: 21 | PADGNPDPNANPNKNN | CSP epitope |
| SEQ ID NO: 22 | QPADGNPDPNANPNKNN | CSP epitope |
| SEQ ID NO: 23 | KQPADGNPDPNANPNKNN | NPDP-peptide |
| SEQ ID NO: 24 | MMRKLAILSVSSFLFVEALFQEYQCYGSSSNTRVL NELNYDNAGTNLYNELEMNYYGKQENWYSLK KNSRSLGENDDGNNEDNEKLRKPKHKKLKQPA DGNPDPNANPNVDPNANPNVDPNANPNVDP NANPNANPNANPNANPNANPNANPNANPNA NPNANPNANPNANPNANPNANPNANPNANP NANPNANPNVDPNANPNANPNANPNANPNA NPNANPNANPNANPNANPNANPNANPNANP NANPNANPNANPNANPNANPNANPNKNNQ GNGQGHNMPNDPNRNVDENANANSAVKNN NNEEPSDKHIKEYLNKIQNSLSTEWSPCSVTCGN GIQVRIKPGSANKPKDELDYANDIEKKICKMEKC SSVFNVVNSSIGLIMVLSFLFLN | PfCSP |
| SEQ ID NO: 25 | KLKQP | CSP region I |
| SEQ ID NO: 26 | NANPNANPNANPNANPNANPNANPNANPNA NPNANPNANP | NANP-peptide |
| SEQ ID NO: 27 | EYQCYGSSSNTRVLNELNYDNAGTNLYNELEM NYYGKQENWYSLKKNSRSLGENDDGNNEDNE KLRKPKHKKLKQPADGNPDPNANPNV | 22-110-peptide |
| MGG1 | | |
| SEQ ID NO: 28 | GFTFDDYA | CDRH1 aa |
| SEQ ID NO: 29 | INWNGGST | CDRH2 aa |
| SEQ ID NO: 30 | ARLGRAAREYYYYYMDV | CDRH3 aa |
| SEQ ID NO: 31 | SSNIGNNY | CDRL1 aa |
| SEQ ID NO: 32 | DNN | CDRL2 aa |
| SEQ ID NO: 33 | LIYDNNKRP | CDRL2 long aa |
| SEQ ID NO: 34 | GTWDSSLSAGV | CDRL3 aa |
| SEQ ID NO: 35 | EVQLVESGGGVVRPGGSLRLSCAASGFTFDDYA MSWVRQAPGKGLEWVSGINWNGGSTGYADS VKGRFTISRDNAKNSLYLQMNSLRAEDTALYHC ARLGRAAREYYYYYMDVWGKGTTVTVSS | VH aa |
| SEQ ID NO: 36 | QSVLTQPPSVSAAPGQKVTISCSGSSSNIGNNYV SWYQQLPGTAPKLLIYDNNKRPSGIPDRFSGSKS GTSATLGITGLQTGDEADYYCGTWDSSLSAGVF GGGTKLTVLGQ | VL aa |
| SEQ ID NO: 37 | ggattcacctttgatgattatgcc | CDRH1 nuc |
| SEQ ID NO: 38 | attaattggaatggtggtagcaca | CDRH2 nuc |
| SEQ ID NO: 39 | gcgagacttgggagagcagcccgtgagtactactactactacatg gacgtc | CDRH3 nuc |
| SEQ ID NO: 40 | agctccaacattgggaataattat | CDRL1 nuc |

TABLE OF SEQUENCES AND SEQ ID NUMBERS (SEQUENCE LISTING):

| SEQ ID NO | Sequence | Remarks |
|---|---|---|
| SEQ ID NO: 41 | gacaataat | CDRL2 nuc |
| SEQ ID NO: 42 | ctcatttatgacaataataagcgaccc | CDRL2 long nuc |
| SEQ ID NO: 43 | ggcacatgggatagcagcctgagtgctggagtg | CDRL3 nuc |
| SEQ ID NO: 44 | gaggtgcagctggtggagtctgggggaggtgtggtacggcctgggg<br>ggtccctgagactctcctgtgcagcctctggattcacctttgatgatta<br>tgccatgagctgggtccgccaagctccagggaaggggctggagtg<br>ggtctctggtattaattggaatggtggtagcacaggttatgcagactct<br>gtgaagggccgattcaccatctccagagacaacgccaagaactc<br>cctgtatctgcaaatgaacagtctgagagccgaggacacggccttg<br>tatcactgtgcgagacttgggagagcagcccgtgagtactacta<br>ctacatggacgtctggggcaaagggaccacggtcaccgtctcctca | VH nuc |
| SEQ ID NO: 45 | cagtctgtgttgacgcagccgccctcagtgtctgcggccccaggac<br>agaaggtcaccatctcctgctctggaagcagctccaacattgggaa<br>taattatgtatcctggtaccagcagctcccaggaacagcccccaaa<br>ctccctcatttatgacaataataagcgaccctcagggattcctgaccg<br>attctctggctccaagtctggcacgtcagccaccctgggcatcacc<br>ggactccagactggggacgaggccgattattactgcggcacatgg<br>gatagcagcctgagtgctggagtgttcggcggagggaccaagctg<br>accgtcctaggtcag | VL nuc |

MGG2

| SEQ ID NO | Sequence | Remarks |
|---|---|---|
| SEQ ID NO: 46 | GFTLNNYW | CDRH1 aa |
| SEQ ID NO: 47 | INIDGSTT | CDRH2 aa |
| SEQ ID NO: 48 | AKGSIKAGGFWSGYSNWFDP | CDRH3 aa |
| SEQ ID NO: 49 | PGPVTSGHY | CDRL1 aa |
| SEQ ID NO: 50 | DTS | CDRL2 aa |
| SEQ ID NO: 51 | LIYDTSNKH | CDRL2 long aa |
| SEQ ID NO: 52 | LLSYGGAPV | CDRL3 aa |
| SEQ ID NO: 53 | EVQLVESGGGLVQPGGSLRLSCAASGFTLNNY<br>WMHWVRQAPGKGLVWVAHINIDGSTTTYADS<br>VKGRFTISRDNAKNTLYLQMNSLRAEDTAVYYC<br>AKGSIKAGGFWSGYSNWFDPWGQGTLVTVSS | VH aa |
| SEQ ID NO: 54 | QAVVTQEPSLTVSPGGTVTLTCDSDPGPVTSGH<br>YPYWFQQKPGQVPRTLIYDTSNKHSWTPARFS<br>GSLLGGKAALTLSGAQPEDEADYYCLLSYGGAP<br>VFGGGTKLTVL | VL aa |
| SEQ ID NO: 55 | ggattcaccctcaataactactgg | CDRH1 nuc |
| SEQ ID NO: 56 | attaatatcgatggcagtactaca | CDRH2 nuc |
| SEQ ID NO: 57 | gcaaagggaagtattaaggccggaggttttggagtggttactccaa<br>ctggttcgacccc | CDRH3 nuc |
| SEQ ID NO: 58 | cctggacctgtcaccagtggtcattat | CDRL1 nuc |
| SEQ ID NO: 59 | gataccagc | CDRL2 nuc |
| SEQ ID NO: 60 | ctgatttatgataccagcaacaaacac | CDRL2 long nuc |
| SEQ ID NO: 61 | ctgctctcgtatggtggtgcccctgta | CDRL3 nuc |
| SEQ ID NO: 62 | gaggtgcagctggtggagtccggggaggcttagttcagccgggg<br>gggtccctgagactctcctgtgcagcctctggattcaccctcaataa<br>ctactggatgcactgggtccgccaagctccagggaaggggctggt<br>ctgggtcgcacatattaatatcgatggcagtactacaacctacgcgg<br>actccgtgaagggccgattcaccatctccagagacaacgccaag<br>aacacgctgtatctgcaaatgaacagtctgagagccgaggacacg<br>gctgtctattactgtgcaaagggaagtattaaggccggaggttttgg<br>agtggttactccaactggttcgacccctggggccagggaaccctgg<br>tcaccgtctcctcag | VH nuc |

TABLE OF SEQUENCES AND SEQ ID NUMBERS (SEQUENCE LISTING):

| SEQ ID NO | Sequence | Remarks |
|---|---|---|
| SEQ ID NO: 63 | caggctgtggtgactcaggagccctcactgactgtgtcccccaggag ggacagtcactctcacctgtgactccgaccctggacctgtcaccag tggtcattatccctactggttccagcagaagcctggccaagtcccc aggacactgatttatgataccagcaacaaacactcctggacacctg cccggttttcaggctccctccttgggggcaaagctgccctgacctt tcgggtgcgcagcctgaggatgaggctgactattactgcctgctctc gtatggtggtgcccctgtattcggcggagggaccaaactgaccgtc ctaa | VL nuc |

MGG3

| SEQ ID NO | Sequence | Remarks |
|---|---|---|
| SEQ ID NO: 64 | GFTFSTFG | CDRH1 aa |
| SEQ ID NO: 65 | IWYDGSSK | CDRH2 aa |
| SEQ ID NO: 66 | VKVGANWGWRYFDL | CDRH3 aa |
| SEQ ID NO: 67 | QSLLHSDGNTY | CDRL1 aa |
| SEQ ID NO: 68 | EVS | CDRL2 aa |
| SEQ ID NO: 69 | LIYEVSSRF | CDRL2 long aa |
| SEQ ID NO: 70 | MQGIHSWT | CDRL3 aa |
| SEQ ID NO: 71 | QEQLVESGGGVVQPGKSLRLSCAASGFTFSTFG MHWVRQAPGKGLEWVAVIWYDGSSKYHADS VKGRFTISRDNSKSTLYLQMNSLRAEDTAMYYC VKVGANWGWRYFDLWGRGTLVTVSS | VH aa |
| SEQ ID NO: 72 | DIVMTQTPLSLSVTPGQPASISCKSSQSLLHSDG NTYLSWYLQKPGQSPQLLIYEVSSRFSGVPDRFS GSGSGTDFTLKISRVEADDVGVYYCMQGIHSW TFGQGTKVEIK | VL aa |
| SEQ ID NO: 73 | gattcaccttcagtacctttggc | CDRH1 nuc |
| SEQ ID NO: 74 | atctggtatgatggaagtagtaaa | CDRH2 nuc |
| SEQ ID NO: 75 | gtgaaagtcggagctaactggggatggaggtacttcgatctc | CDRH3 nuc |
| SEQ ID NO: 76 | cagagcctcctacatagtgatggaaacacctat | CDRL1 nuc |
| SEQ ID NO: 77 | gaagtttcc | CDRL2 nuc |
| SEQ ID NO: 78 | ctgatctatgaagtttccagccggttc | CDRL2 long nuc |
| SEQ ID NO: 79 | atgcaaggcatacactcgtggacg | CDRL3 nuc |
| SEQ ID NO: 80 | caggagcaactggtggagtctggggggaggcgtggtccagcctggg aagtccctgagactctcctgtgcagcctctggattcaccttcagtacc tttggcatgcactgggtccgccaggctccaggcaaggggctggagt gggtggcagtcatctggtatgatggaagtagtaaataccatgcagac tccgtgaagggccgattcaccatctccagagacaattccaagagc acgctgtatctgcaaatgaacagcctgagagctgaggacacggct atgtattactgtgtgaaagtcggagctaactggggatggaggtacttc gatctctggggccgtggcaccctggtcaccgtctcctcag | VH nuc |
| SEQ ID NO: 81 | gatattgtgatgacccagactccactctctctgtccgtcacccctgg acagccggcctccatctcctgcaagtctagtcagagcctcctacat agtgatggaaacacctatttgtcttggtacctgcagaagccaggcc agtctccacagctcctgatctatgaagtttccagccggttctctggag tgccagataggttcagcggcagcgggtcagggacagatttcacact gaaaatcagccgggtggaggctgacgatgttggggtttactactgc atgcaaggcatacactcgtggacgttcggccaagggaccaaggtg gaaatcaaac | VL nuc |

MGG4

| SEQ ID NO | Sequence | Remarks |
|---|---|---|
| SEQ ID NO: 82 | GFRFSDYG | CDRH1 aa |
| SEQ ID NO: 83 | IWYDGSNE | CDRH2 aa |
| SEQ ID NO: 84 | AKLLVGITTDVFDV | CDRH3 aa |

-continued

| TABLE OF SEQUENCES AND SEQ ID NUMBERS (SEQUENCE LISTING): | | |
|---|---|---|
| SEQ ID NO | Sequence | Remarks |
| SEQ ID NO: 85 | QSVLSSSNNKNY | CDRL1 aa |
| SEQ ID NO: 86 | WAS | CDRL2 aa |
| SEQ ID NO: 87 | LIYWASTRE | CDRL2 long aa |
| SEQ ID NO: 88 | QQYYTASPF | CDRL3 aa |
| SEQ ID NO: 89 | QVQLVESGGGVVQPGRSLRLSCAASGFRFSDYG<br>MHWVRQAPGKGLEWVALIWYDGSNESYLDSV<br>KGRFTISRDNSKNTLYLQMNNLRTEDTAVYYCA<br>KLLVGITTDVFDVWGQGTVVTVSS | VH aa |
| SEQ ID NO: 90 | DIVMTQSPDSLAVSLGERATINCRSSQSVLSSSN<br>NKNYLAWYQHKPRQPPKLLIYWASTRESGVPD<br>RFSGSGSGTDFTLTISSLQAEDVAVYYCQQYYTA<br>SPFFGGGTKVEIK | VL aa |
| SEQ ID NO: 91 | ggattcaggttcagtgactatggc | CDRH1 nuc |
| SEQ ID NO: 92 | atatggtatgatggaagtaatgaa | CDRH2 nuc |
| SEQ ID NO: 93 | gcgaaactactagtgggaattactactgatgtttttgatgtc | CDRH3 nuc |
| SEQ ID NO: 94 | cagagtgttttatccagctccaacaataagaactac | CDRL1 nuc |
| SEQ ID NO: 95 | tgggcatct | CDRL2 nuc |
| SEQ ID NO: 96 | ctcatttactgggcatctacccgggaa | CDRL2 long nuc |
| SEQ ID NO: 97 | cagcaatattatactgcttccccatt | CDRL3 nuc |
| SEQ ID NO: 98 | caggtgcagctggtggagtctggggggaggcgtggtccagcctggg<br>aggtccctgagactctcctgtgcagcctctggattcaggttcagtgac<br>tatggcatgcactgggtccgccaggctccgggcaaggggctggag<br>tgggtggcacttatatggtatgatggaagtaatgaatcctatttagact<br>ccgtgaagggccgattcaccatctccagagacaattccaagaaca<br>cactgtatctgcaaatgaacaacctgagaactgaggacacggctgt<br>gtattactgtgcgaaactactagtgggaattactactgatgtttttgatgt<br>ctggggccaagggacagtggtcaccgtctcttcag | VH nuc |
| SEQ ID NO: 99 | gacatcgtgatgacccagtctccagactccctggctgtgtctctggg<br>cgagagggccaccatcaactgcaggtccagccagagtgttttatcc<br>agctccaacaataagaactacttagcttggtaccagcacaaacca<br>cgacagcctcctaaactgctcatttactgggcatctacccgggaatc<br>cggggtccctgaccgattcagtggcagcgggtctgggacagatttc<br>actctcaccatcagcagcctgcaggctgaagatgtggcagtttatta<br>ctgtcagcaatattatactgcttccccattttttcggcggagggaccaa<br>ggtagagatcaaac | VL nuc |
| MGG8 | | |
| SEQ ID NO: 100 | GFMISGSV | CDRH1 aa |
| SEQ ID NO: 101 | IRDKANNEAT | CDRH2 aa |
| SEQ ID NO: 102 | TRGIIVGDTWHFDP | CDRH3 aa |
| SEQ ID NO: 103 | ESLLRSDGKTY | CDRL1 aa |
| SEQ ID NO: 104 | EVS | CDRL2 aa |
| SEQ ID NO: 105 | LMYEVSKRF | CDRL2 long aa |
| SEQ ID NO: 106 | MQSIQLVT | CDRL3 aa |
| SEQ ID NO: 107 | EVQLVESGGGLVQPGGSLKLSCAASGFMISGSVL<br>HWVRQASGKGLEWLGRIRDKANNEATAYAASV<br>KGRFTISRDDSKDTTYLQMNSLRIEDTAVYYCTR<br>GIIVGDTWHFDPWGQGTLVTVSS | VH aa |
| SEQ ID NO: 108 | DIVMTQTPLSLSVTPGQTASISCKSSESLLRSDGK<br>TYLYWYLQKPGQSPQLLMYEVSKRFSGVPDRFS<br>GSGSGTDFTLKISRVETDDVGIYYCMQSIQLVTF<br>GQGTKVEIK | VL aa |

| TABLE OF SEQUENCES AND SEQ ID NUMBERS (SEQUENCE LISTING): | | |
|---|---|---|
| SEQ ID NO | Sequence | Remarks |
| SEQ ID NO: 109 | gggttcatgatcagtggctctgtt | CDRH1 nuc |
| SEQ ID NO: 110 | attagagacaaagctaacaatgaggcgaca | CDRH2 nuc |
| SEQ ID NO: 111 | acgaggggtatcatagtaggtgacacctggcacttcgacccc | CDRH3 nuc |
| SEQ ID NO: 112 | gagagcctcctgagaagcgatggaaagaccta | CDRL1 nuc |
| SEQ ID NO: 113 | gaagtttcc | CDRL2 nuc |
| SEQ ID NO: 114 | ctgatgtatgaagtttccaagcgcttc | CDRL2 long nuc |
| SEQ ID NO: 115 | atgcaaagtatacagcttgtgact | CDRL3 nuc |
| SEQ ID NO: 116 | gaagtgcagctggtggagtccggggggaggcctggtccagcctggg gggtccctgaaactctcctgtgcagcctctgggttcatgatcagtggc tctgttctacactgggtccgccaggcctccgggaaagggctggagt ggctggccgtattagagacaaagctaacaatgaggcgacagcat atgcagcgtcggtgaaaggcaggttcaccatctccagagatgattc aaaggacacgacatatctgcaaatgaacagcctgagaatcgagg acacggccgtgtattactgtacgagggggtatcatagtaggtgacacc tggcacttcgacccctggggccagggaaccctggtcaccgtctcct cag | VH nuc |
| SEQ ID NO: 117 | gatattgtgatgacccagactccactctctctgtccgtcaccccctgg acagacggcctccatctcctgcaagtctagtgagagcctcctgaga agcgatggaaagacctacttgtattggtatctgcagaagccaggcc agtctccacagctcctgatgtatgaagtttccaagcgcttctctggag tgccagataggttcagtggcagcgggtcaggaacagattttacact gaaaatcagccgggtggagactgatgatgttggcatttattactgcat gcaaagtatacagcttgtgactttcggccaagggaccaaggtggaa atcaaac | VL nuc |
| MGH1 | | |
| SEQ ID NO: 118 | GYTFTDYY | CDRH1 aa |
| SEQ ID NO: 119 | INPYIGVS | CDRH2 aa |
| SEQ ID NO: 120 | AACSNVGCYVY | CDRH3 aa |
| SEQ ID NO: 121 | QSLVYSDGNTY | CDRL1 aa |
| SEQ ID NO: 122 | KVS | CDRL2 aa |
| SEQ ID NO: 123 | LIYKVSNRD | CDRL2 long aa |
| SEQ ID NO: 124 | MQGTHWPDT | CDRL3 aa |
| SEQ ID NO: 125 | QVQLVQSGAEVKKPGASVRVSCKTSGYTFTDYY VHWVRQAPGHGLECMGWINPYIGVSKYAQKF QGRVTLTRDTSISTAYMEISRLTSDDTAVYYCAA CSNVGCYVYWGQGSLVTVSS | VH aa |
| SEQ ID NO: 126 | DVVMTQSPLSLPVTLGQPASISCRSSQSLVYSDG NTYLNWFQQRPGQSPRRLIYKVSNRDSGVPDR FSGSGSGTDFTLKISRVEAEDVAIYFCMQGTHW PDTFGQGTKLEIK | VL aa |
| SEQ ID NO: 127 | ggatacacgttcaccgactactat | CDRH1 nuc |
| SEQ ID NO: 128 | atcaatccttacattggtgtctca | CDRH2 nuc |
| SEQ ID NO: 129 | gcggcttgtagtaacgttggctgctacgtctat | CDRH3 nuc |
| SEQ ID NO: 130 | caaagtctcgtgtacagtgatggaaacacctac | CDRL1 nuc |
| SEQ ID NO: 131 | aaggtttct | CDRL2 nuc |
| SEQ ID NO: 132 | ctaatttataaggtttctaatcgggac | CDRL2 long nuc |
| SEQ ID NO: 133 | atgcaaggtacacactggcctgacact | CDRL3 nuc |

| TABLE OF SEQUENCES AND SEQ ID NUMBERS (SEQUENCE LISTING): | | |
|---|---|---|
| SEQ ID NO | Sequence | Remarks |
| SEQ ID NO: 134 | caggtgcagctggtgcagtctggggctgaggtgaagaagcctggg gcctcagtgagagtctcctgcaagacatctggatacacgttcaccg actactatgtccactgggtgcgacaggccccaggacacgggcttg agtgcatgggctggatcaatccttacattggtgtctcaaagtatgcac agaagtttcagggcagggtcaccttgaccagggacacgtccatca gcacagcctacatggaaattagcaggctaacatctgacgacacgg ccgtctattactgtgcggcttgtagtaacgttggctgctacgtctattgg ggccagggatcgctggtcaccgtctcctcag | VH nuc |
| SEQ ID NO: 135 | gatgttgtgatgactcagtctccactctcctgcccgtcaccttgga cagccggcctccatctcctgcaggtctagtcaaagtctcgtgtaca gtgatggaaacacctacttgaattggtttcagcagaggccaggcca atctccaaggcgcctaatttataaggtttctaatcgggactctgggt cccagacagattcagcggcagtgggtcaggcactgatttcacactg aaaatcagcagggtggaggctgaggatgttgcgatttatttctgcatg caaggtacacactggcctgacacttttggccaggggaccaaactg gagatcaaac | VL nuc |
| MGH2 | | |
| SEQ ID NO: 136 | GFSFSSYA | CDRH1 aa |
| SEQ ID NO: 137 | TRYDGSNK | CDRH2 aa |
| SEQ ID NO: 138 | AKVGDGTVAGTIDY | CDRH3 aa |
| SEQ ID NO: 139 | QSLVYSDGNTY | CDRL1 aa |
| SEQ ID NO: 140 | KVS | CDRL2 aa |
| SEQ ID NO: 141 | LIYKVSNRD | CDRL2 long aa |
| SEQ ID NO: 142 | MQGTHWWT | CDRL3 aa |
| SEQ ID NO: 143 | QVQLVESGGGVVQPGGSLRLSCTASGFSFSSYA MHWVRQAPGKGLEWVAYTRYDGSNKFYLDSV QGRFTISRDNSKNTLYLEMDSLRLEDTAVYFCAK VGDGTVAGTIDYWGQGTLVTVSS | VH aa |
| SEQ ID NO: 144 | YIVMTQSPLSLPVTLGQPASISCRSSQSLVYSDGN TYLNWYQQRPGQSPRRLIYKVSNRDSGVPDRFS GSGSGTDFTLKISRVEAEDVGVYYCMQGTHW WTFGQGTKVEIK | VL aa |
| SEQ ID NO: 145 | ggtttcagcttcagtagttatgcc | CDRH1 nuc |
| SEQ ID NO: 146 | acacggtatgatggaagtaataag | CDRH2 nuc |
| SEQ ID NO: 147 | gcgaaagtgggggacgggacagtggctggtactattgacta | CDRH3 nuc |
| SEQ ID NO: 148 | caaagcctcgtatatagtgatggaaacacctac | CDRL1 nuc |
| SEQ ID NO: 149 | aaggtttct | CDRL2 nuc |
| SEQ ID NO: 150 | ctaatttataaggtttctaatcgggac | CDRL2 long nuc |
| SEQ ID NO: 151 | atgcaaggtacacactggtggacg | CDRL3 nuc |
| SEQ ID NO: 152 | caggtgcagctggtggagtctgggggaggcgtggtccagcctggg gggtccctgagactctcctgtacagcgtctggtttcagcttcagtagtt atgccatgcactgggtccgccaggctccaggcaagggactggagt gggtggcatatacacggtatgatggaagtaataagttctacctagact ccgtgcagggccgattcaccatctccagagacaattccaagaaca cgctgtatctggaaatggacagcctgagacttgaggacacggctgt ctatttctgtgcgaaagtgggggacgggacagtggctggtactattga ctactggggccagggaacgctggtcaccgtctcctcag | VH nuc |
| SEQ ID NO: 153 | tatattgtgatgactcagtctccactctcctgcccgtcaccttgga cagccggcctccatctcctgcaggtctagtcaaagcctcgtatata gtgatggaaacacctacttgaattggtatcagcagaggccaggcca atctccaaggcgcctaatttataaggtttctaatcgggactctgggt | VL nuc |

| TABLE OF SEQUENCES AND SEQ ID NUMBERS (SEQUENCE LISTING): | | |
|---|---|---|
| SEQ ID NO | Sequence | Remarks |
| | cccagacagatttagcggcagtgggtcaggcactgatttcacactg<br>aaaatcagcagggtggaggctgaggatgttggggtttattactgcat<br>gcaaggtacacactggtggacgttcggccaagggaccaaggtgg<br>aaatcaaac | |
| MGH3 | | |
| SEQ ID NO: 154 | GFTFSSYT | CDRH1 aa |
| SEQ ID NO: 155 | ISSSGSYI | CDRH2 aa |
| SEQ ID NO: 156 | ARNVLDSSGYPTYFDY | CDRH3 aa |
| SEQ ID NO: 157 | QSLLYSNGYNY | CDRL1 aa |
| SEQ ID NO: 158 | LGS | CDRL2 aa |
| SEQ ID NO: 159 | LIYLGSNRA | CDRL2 long aa |
| SEQ ID NO: 160 | MQAVQTPLT | CDRL3 aa |
| SEQ ID NO: 161 | EVQLVESGGGLVKPGGSLRLSCAASGFTFSSYTM<br>NWVRQAPGKGLEWVSSISSSGSYIYYADSVKGR<br>CTISRDNAKNSLDLQMNSLRAEDAAVYYCARN<br>VLDSSGYPTYFDYWGQGTLVTVSS | VH aa |
| SEQ ID NO: 162 | DIVMTQSPLSLPVTPGEPASISCRSSQSLLYSNGY<br>NYLDWYVQKPGQSPRLLIYLGSNRASGVPDRFS<br>GSGSGTDFTLRISRVEAEDVGFYYCMQAVQTPL<br>TFGGGTKVEIK | VL aa |
| SEQ ID NO: 163 | ggattcaccttcagtagttatacc | CDRH1 nuc |
| SEQ ID NO: 164 | attagtagtagtggtagttacata | CDRH2 nuc |
| SEQ ID NO: 165 | gcaagaaatgtcttggacagtagtggttaccccacgtactttgactat | CDRH3 nuc |
| SEQ ID NO: 166 | agagcctcctatatagtaatggatacaactat | CDRL1 nuc |
| SEQ ID NO: 167 | ttgggttct | CDRL2 nuc |
| SEQ ID NO: 168 | ctgatctatttgggttctaatcgggcc | CDRL2 long nuc |
| SEQ ID NO: 169 | atgcaagctgtacaaactcccctcact | CDRL3 nuc |
| SEQ ID NO: 170 | gaggtgcagctggtggagtctgggggaggcctggtcaagcctggg<br>gggtccctgagactctcctgtgcagcctctggattcaccttcagtagt<br>tataccatgaactgggtccgccaggctccagggaaggggctggag<br>tgggtctcatccattagtagtagtggtagttacatatattacgcagact<br>cagtgaagggccgatgcaccatctccagagacaacgccaagaac<br>tcactggatctgcaaatgaacagcctgagagccgaggacggcgct<br>gtgtattactgtgcaagaaatgtcttggacagtagtggttaccccacg<br>tactttgactattggggccagggaacgctggtcaccgtctcctcag | VH nuc |
| SEQ ID NO: 171 | gatattgtgatgactcagtctccactctccctgcccgtcacccctgg<br>agagccggcctccatctcctgcaggtctagtcagagcctcctatat<br>agtaatggatacaactatctggattggtacgtgcagaagccagggc<br>agtctccacgcctcctgatctatttgggttctaatcgggcctccgggg<br>tccctgacaggttcagtggcagtggatcaggcacagattttacactg<br>agaatcagcagagtggaggctgaggatgttggttttattactgcatg<br>caagctgtacaaactcccctcactttcggcggagggaccaaggtg<br>gagatcaaac | VL nuc |
| MGU1 | | |
| SEQ ID NO: 172 | GFAFSSYG | CDRH1 aa |
| SEQ ID NO: 173 | IWHDGTNK | CDRH2 aa |
| SEQ ID NO: 174 | AIWYLDSPDHGFDI | CDRH3 aa |
| SEQ ID NO: 175 | NGHSSNA | CDRL1 aa |
| SEQ ID NO: 176 | VNSDGSH | CDRL2 aa |

| SEQ ID NO | Sequence | Remarks |
|---|---|---|
| SEQ ID NO: 177 | QAWDSGIWV | CDRL3 aa |
| SEQ ID NO: 178 | QVQLVESGGGVVQPGRSLRLSCAASGFAFSSYG<br>MNWVRQAPGKGLEWVAVIWHDGTNKYYRDS<br>VKGRFIISRDNAKNTLYLQMDSLSAEDTAMYYC<br>AIWYLDSPDHGFDIWGRGTMVTVSS | VH aa |
| SEQ ID NO: 179 | QLVLTQSPSASASLGVSVTLTCTLNNGHSSNAIA<br>WHQQQPGKGPRYLMKVNSDGSHNKGAAVP<br>DRFSGSSSGTERHLTISSLQSDDEADYYCQAWD<br>SGIWVFGGGTKLTVL | VL aa |
| SEQ ID NO: 180 | ggattcgctttcagtagttatggc | CDRH1 nuc |
| SEQ ID NO: 181 | atttggcatgatggcaccaataaa | CDRH2 nuc |
| SEQ ID NO: 182 | gccatttggtatcttgatagtcctgatcatggtttcgatatc | CDRH3 nuc |
| SEQ ID NO: 183 | aatggccacagttccaatgcc | CDRL1 nuc |
| SEQ ID NO: 184 | gttaatagtgatggcagcca | CDRL2 nuc |
| SEQ ID NO: 185 | caggcctgggacagtggcatttgggtt | CDRL3 nuc |
| SEQ ID NO: 186 | caggtgcagctggtggagtctgggggaggcgtggtccagcctggg<br>aggtccctgagactctcatgtgcagcctccggattcgctttcagtagt<br>tatggcatgaactgggtccgccaggctccaggcaagggactggag<br>tgggtggcagttatttggcatgatggcaccaataaatactatagagac<br>tccgtgaagggccgattcatcatctccagagacaatgccaagaac<br>accttgtatctgcaaatggacagcctgagcgctgaggacacggcta<br>tgtattactgtgccatttggtatcttgatagtcctgatcatggtttcgatat<br>ctggggccagggacaatggtcaccgtctcttcag | VH nuc |
| SEQ ID NO: 187 | cagcttgtcctgactcaatcgccctctgcctctgcctcccctgggagt<br>ctcggtcaccctcacctgtactctgaacaatggccacagttccaat<br>gccatcgcatggcatcaacagcagccaggaagggccctcgttat<br>ttgatgaaggttaatagtgatggcagccacaataaggggccgctg<br>tccctgatcgcttctcaggctctagttctgggactgagcgccacctc<br>accatctccagcctccagtctgacgatgaggctgactattattgtca<br>ggcctgggacagtggcatttgggttttcggcggagggaccaagttg<br>accgtcctag | VL nuc |
| MGU3 |  |  |
| SEQ ID NO: 188 | GFTFSDYN | CDRH1 aa |
| SEQ ID NO: 189 | ISHSSSTT | CDRH2 aa |
| SEQ ID NO: 190 | ARLRPLSYSGRYRDY | CDRH3 aa |
| SEQ ID NO: 191 | QDVSNY | CDRL1 aa |
| SEQ ID NO: 192 | DAS | CDRL2 aa |
| SEQ ID NO: 193 | LIYDASTLQ | CDRL2 long aa |
| SEQ ID NO: 194 | QQYDSLPLT | CDRL3 aa |
| SEQ ID NO: 195 | EVLLVESGGGLVQPGGSLRLSCAASGFTFSDYN<br>MHWVRQAPGKGLEWLSYISHSSSTTYYADSVR<br>GRFTISRDNAKNSLYLQMNSLRAEDTAVYYCAR<br>LRPLSYSGRYRDYWGQGTLVTVSS | VH aa |
| SEQ ID NO: 196 | DIQMTQSPSSLSASVGDRVTITCQASQDVSNYV<br>NWYQQKPGKAPKVLIYDASTLQTGVPSRFSGSG<br>SGTDFTFSISSLQPEDIATYYCQQYDSLPLTFGGG<br>TKVEIK | VL aa |
| SEQ ID NO: 197 | ggattcaccttcagtgactataac | CDRH1 nuc |
| SEQ ID NO: 198 | attagtcatagtagtagtaccaca | CDRH2 nuc |
| SEQ ID NO: 199 | gcgagacttcgtcccttatcgtatagtggcaggtaccgcgactac | CDRH3 nuc |
| SEQ ID NO: 200 | caggacgttagtaattat | CDRL1 nuc |

| SEQ ID NO | Sequence | Remarks |
|---|---|---|
| SEQ ID NO: 201 | gatgcatcc | CDRL2 nuc |
| SEQ ID NO: 202 | ctgatctacgatgcatccactttgcaa | CDRL2 long nuc |
| SEQ ID NO: 203 | cagcagtatgatagcctcccactcact | CDRL3 nuc |
| SEQ ID NO: 204 | gaggtgctactagtggagtctgggggaggcttggtacaacctgggg<br>ggtccctgagactctcctgtgcagcctctggattcaccttcagtgact<br>ataacatgcactgggtccgccaggctccagggaaggggctggagt<br>ggctttcatacattagtcatagtagtagtaccacatactacgcagact<br>ctgtgaggggccgattcaccatctccagagacaatgccaagaact<br>cactgtatctgcaaatgaacagcctgagagccgaggacacggctg<br>tgtattactgtgcgagacttcgtcccttatcgtatagtggcaggtaccg<br>cgactactggggccagggaacgctggtcaccgtctcctcag | VH nuc |
| SEQ ID NO: 205 | gacatccagatgacccagtctccatcctccctgtctgcatctgtagg<br>agacagagtcaccatcacttgccaggcgagtcaggacgttagtaat<br>tatgtaaattggtatcagcagaaaccagggaaagcccctaaggtcc<br>tgatctacgatgcatccactttgcaaacaggggtcccatcaaggttc<br>agtggaagtggatcgggacagattttactttcagcatcagcagcct<br>gcagcctgaagatattgcaacatattactgtcagcagtatgatagcc<br>tcccactcactttcggcggagggaccaaggtggagatcaaac | VL nuc |
| MGU5 | | |
| SEQ ID NO: 206 | GFSFSSYG | CDRH1 aa |
| SEQ ID NO: 207 | IWHDGTNK | CDRH2 aa |
| SEQ ID NO: 208 | TKRAGWGDALDI | CDRH3 aa |
| SEQ ID NO: 209 | QDISNY | CDRL1 aa |
| SEQ ID NO: 210 | DAS | CDRL2 aa |
| SEQ ID NO: 211 | LIYDASNLE | CDRL2 long aa |
| SEQ ID NO: 212 | QQQRI | CDRL3 aa |
| SEQ ID NO: 213 | QVQLVESGGGVVQPGRSLRLSCAASGFSFSSYG<br>MHWVRQAPGKGLDWVALIWHDGTNKFYTDS<br>VKGRFTISRDNSKDTLFLQMNSLRVEDTAVYYCT<br>KRAGWGDALDIWGQGTMVTVSS | VH aa |
| SEQ ID NO: 214 | DIQMTQSPSSLSASVGDRVTITCQASQDISNYLN<br>WYQQKPGKAPKLLIYDASNLETGVPSRFSGSGS<br>ATDFTLTISSLQSEDIATYYCQQQRIFGGGTKVEIK | VL aa |
| SEQ ID NO: 215 | ggattcagcttcagtagttatggc | CDRH1 nuc |
| SEQ ID NO: 216 | atatggcatgatggaactaataaa | CDRH2 nuc |
| SEQ ID NO: 217 | acgaagcgggctggctggggtgatgctcttgatatc | CDRH3 nuc |
| SEQ ID NO: 218 | caggacattagcaactat | CDRL1 nuc |
| SEQ ID NO: 219 | gatgcatcc | CDRL2 nuc |
| SEQ ID NO: 220 | ctgatctacgatgcatccaatttggaa | CDRL2 long nuc |
| SEQ ID NO: 221 | caacaacaaaggatt | CDRL3 nuc |
| SEQ ID NO: 222 | caggtgcagttggtggagtctgggggaggcgtggtccagcctggga<br>ggtccctgagactctcctgtgcagcctctggattcagcttcagtagtt<br>atggcatgcactgggtccgccaggctccaggcaaggggctggatt<br>gggtggctcttatatggcatgatggaactaataaattttacacagact<br>ccgtgaagggccgattcaccatctccagagacaattccaaggaca<br>cactgtttctgcaaatgaacagtctgagagttgaggacacggctgtgt<br>attactgtacgaagcgggctggctggggtgatgctcttgatatctggg<br>gccaagggacaatggtcaccgtctcttcag | VH nuc |
| SEQ ID NO: 223 | gacatccagatgacccagtctccatcctccctgtctgcatctgtagg<br>agacagagtcaccatcacttgccaggcgagtcaggacattagcaa<br>ctatttaaattggtatcagcagaaaccagggaaagcccctaaactc | VL nuc |

| TABLE OF SEQUENCES AND SEQ ID NUMBERS (SEQUENCE LISTING): | | |
|---|---|---|
| SEQ ID NO | Sequence | Remarks |
| | ctgatctacgatgcatccaatttggaaacaggggtcccatcaaggtt<br>cagtggaagtggatctgcgacagattttactctcaccatcagcagc<br>ctgcagtctgaagacattgcaacatattactgtcaacaacaaagga<br>ttttcggcggagggaccaaggtggagatcaaac | |
| MGU8 | | |
| SEQ ID NO: 224 | GFTFSNYG | CDRH1 aa |
| SEQ ID NO: 225 | IWHDGTNK | CDRH2 aa |
| SEQ ID NO: 226 | TKRGGWGDGSDI | CDRH3 aa |
| SEQ ID NO: 227 | QDVDNY | CDRL1 aa |
| SEQ ID NO: 228 | DAS | CDRL2 aa |
| SEQ ID NO: 229 | LIYDASNLA | CDRL2 long aa |
| SEQ ID NO: 230 | QQQRI | CDRL3 aa |
| SEQ ID NO: 231 | QVQLVESGGGVVQPGRSLRLSCAAGGFTFSNY<br>GMHWVRQAPGKGLEWVALIWHDGTNKFYAD<br>SVKGRFTISRDNSKNTLSLQMDSLTTEDTAIYFCT<br>KRGGWGDGSDIWGQGTMVTVSS | VH aa |
| SEQ ID NO: 232 | DIQMTQSPSSLSASVGDRVTITCQASQDVDNYL<br>NWYQHKPGKAPKLLIYDASNLATGVPSRFSGSG<br>SSTDFTLTISSLQSDDFATYYCQQQRIFGGGTRV<br>EIK | VL aa |
| SEQ ID NO: 233 | ggatttaccttcagtaactatggc | CDRH1 nuc |
| SEQ ID NO: 234 | atatggcatgatggaactaataaa | CDRH2 nuc |
| SEQ ID NO: 235 | acgaagcgaggtggctggggtgatggttctgatatc | CDRH3 nuc |
| SEQ ID NO: 236 | caggacgttgacaactat | CDRL1 nuc |
| SEQ ID NO: 237 | gatgcatcc | CDRL2 nuc |
| SEQ ID NO: 238 | ctgatctacgatgcatccaatttggcg | CDRL2 long nuc |
| SEQ ID NO: 239 | caacaacaaaggatt | CDRL3 nuc |
| SEQ ID NO: 240 | caggtgcagctggtggagtctggggggaggcgtggtccagcctggg<br>aggtccctaagactctcctgtgcagccggtggatttaccttcagtaac<br>tatggcatgcactgggtccgccaggctccaggcaaggggctggag<br>tgggtggcacttatatggcatgatggaactaataaattctatgcagac<br>tccgtgaagggccgattcaccatctccagagacaattccaagaac<br>acgctgtctctgcaaatggacagcctgacaactgaggacacggct<br>atatatttctgtacgaagcgaggtggctggggtgatggttctgatatct<br>ggggccaagggacaatggtcaccgtctcttcag | VH nuc |
| SEQ ID NO: 241 | gacatccagatgacccagtctccatcctccctgtctgcatctgtagg<br>agacagagtcaccatcacttgccaggcgagtcaggacgttgacaa<br>ctatttaaattggtatcagcataaaccagggaaagcccctaagctcc<br>tgatctacgatgcatccaatttggcgacaggggtcccatcaaggttc<br>agtggaagtggatcttcgacagattttactctcaccatcagcagcctg<br>cagtctgatgactttgcaacatattactgtcaacaacaaaggattttc<br>ggcggagggaccagggtggaaatcaaac | VL nuc |
| MGU10 | | |
| SEQ ID NO: 242 | GFAFSNYG | CDRH1 aa |
| SEQ ID NO: 243 | IWHDGSLK | CDRH2 aa |
| SEQ ID NO: 244 | TVWYLETPDDGFDI | CDRH3 aa |
| SEQ ID NO: 245 | HGHTSKA | CDRL1 aa |
| SEQ ID NO: 246 | VNSDGSH | CDRL2 aa |
| SEQ ID NO: 247 | QAWDSGIWV | CDRL3 aa |

TABLE OF SEQUENCES AND SEQ ID NUMBERS (SEQUENCE LISTING):

| SEQ ID NO | Sequence | Remarks |
|---|---|---|
| SEQ ID NO: 248 | QVQLVESGGGVVQPGRSLRLSCAASGFAFSNY GMNWVRQAPGKGLEWVAVIWHDGSLKYYTQ SVKGRFTISRDNAKNTLFLQMDSLSADDTAMYY CTVWYLETPDDGFDIWGRGTMVTVSS | VH aa |
| SEQ ID NO: 249 | QLVLTQPPSASASLGVSVTLTCTLSHGHTSKAIA WHQQQPGKGPRYLMKVNSDGSHTKGAAVPD RFSGSTSGAERHFTISNLQSDDEADYYCQAWDS GIWVFGGGTKLTVL | VL aa |
| SEQ ID NO: 250 | ggattcgctttcagcaattatggc | CDRH1 nuc |
| SEQ ID NO: 251 | atttggcatgacggcagtcttaaa | CDRH2 nuc |
| SEQ ID NO: 252 | accgtttggtaccttgaaactcctgatgatggtttcgatatt | CDRH3 nuc |
| SEQ ID NO: 253 | catggccacacctccaaagcc | CDRL1 nuc |
| SEQ ID NO: 254 | gttaatagtgatggcagccac | CDRL2 nuc |
| SEQ ID NO: 255 | caggcctgggacagtggcatttgggtt | CDRL3 nuc |
| SEQ ID NO: 256 | caggtgcagctggtggagtctggggaggcgtggtccagcctggg aggtccctgagactctcatgtgcagcctccggattcgctttcagcaat tatggcatgaactgggtccgccaggctccaggcaagggactggaa tgggtggcagttatttggcatgacggcagtcttaaatattatacacagt ccgtgaagggccgattcaccatctccagagacaatgccaagaac acgttgtttctccaaatggacagcctgagcgctgacgacacggctat gtattattgtaccgtttggtaccttgaaactcctgatgatggtttcgatatt tggggccgagggacaatggtcaccgtctcgtcag | VH nuc |
| SEQ ID NO: 257 | cagcttgtcctgactcaaccgccctctgcctctgcctccctgggagt ctcggtcaccctcacctgtactctgagtcatggccacacctccaaa gccatcgcgtggcatcaacagcagccagggaagggccctcgttat ttgatgaaagttaatagtgatggcagccacactaaggggccgctg tccctgatcgcttctcaggctctacttctggggctgagcgccacttca ccatctccaacctcagtctgacgatgaggctgattattattgtcagg cctgggacagtggcatttgggttttcggcggagggaccaagttgac cgtcctag | VL nuc |

MGU11

| SEQ ID NO | Sequence | Remarks |
|---|---|---|
| SEQ ID NO: 258 | GFSFSSYG | CDRH1 aa |
| SEQ ID NO: 259 | IWYDGTNK | CDRH2 aa |
| SEQ ID NO: 260 | ANDIAGWGYDGSNA | CDRH3 aa |
| SEQ ID NO: 261 | QSLVYSDGNTY | CDRL1 aa |
| SEQ ID NO: 262 | KVS | CDRL2 aa |
| SEQ ID NO: 263 | LIYKVSNRD | CDRL2 long aa |
| SEQ ID NO: 264 | MQGTVGFT | CDRL3 aa |
| SEQ ID NO: 265 | QVQLVESGGGVVQPGRSLRLSCVASGFSFSSYG MHWVRQAPGKGLEWVAVIVVYDGTNKYYADS VKGRFTISRDNTKNTLYLQMNSLRADDTAMYYC ANDIAGWGYDGSNAWGQGTLVTVSS | VH aa |
| SEQ ID NO: 266 | LSLPVTPGQPASISCKSSQSLVYSDGNTYLNWFQ QRPGQSPRRLIYKVSNRDSGVPDRFSGSGSGTD FTLKISRVEAEDVGVYYCMQGTVGFTFGPGTTV DIK | VL aa |
| SEQ ID NO: 267 | ggattcagcttcagtagctatggc | CDRH1 nuc |
| SEQ ID NO: 268 | atatggtatgatggaaccaataaa | CDRH2 nuc |
| SEQ ID NO: 269 | gcgaatgatattgcggggtggggctatgatggtagtaatgcc | CDRH3 nuc |
| SEQ ID NO: 270 | caaagcctcgtatatagtgatggaaacacctac | CDRL1 nuc |

TABLE OF SEQUENCES AND SEQ ID NUMBERS (SEQUENCE LISTING):

| SEQ ID NO | Sequence | Remarks |
|---|---|---|
| SEQ ID NO: 271 | aaggtttct | CDRL2 nuc |
| SEQ ID NO: 272 | ctaatttataaggtttctaaccgggac | CDRL2 long nuc |
| SEQ ID NO: 273 | atgcaaggtacagtggggttcact | CDRL3 nuc |
| SEQ ID NO: 274 | caggtgcagctggtggagtctgggggaggcgtagtccagcctggg aggtccctgagactctcctgcgtagcctctggattcagcttcagtagc tatggcatgcactgggtccgccaggctccaggcaaggggctggag tgggtggcagttatatggtatgatggaaccaataaatactatgcagat tccgtgaagggccgattcaccatctccagagacaataccaagaac acgttgtacctgcaaatgaacagcctgagagcggacgacacggct atgtattactgtgcgaatgatattgcggggtgggctatgatggtagta atgcctggggccagggaaccctggtcaccgtctcctcag | VH nuc |
| SEQ ID NO: 275 | ctctcccctgcccgtcacccctggacagccggcctccatctcctgca agtctagtcaaagcctcgtatatagtgatggaaacacctacttgaatt ggtttcagcagaggccaggccaatctccaaggcgcctaatttataa ggtttctaaccgggactctggggtcccagacagattcagcggcagt gggtcaggcactgatttcacactgaaaatcagcagggtggaggctg aggatgttggggtttattactgcatgcaaggtacagtggggttcacttt cggccctgggaccacagtggatatcaaac | VL nuc |

MGU12

| SEQ ID NO | Sequence | Remarks |
|---|---|---|
| SEQ ID NO: 276 | GFSFSSYG | CDRH1 aa |
| SEQ ID NO: 277 | IWHDGSYS | CDRH2 aa |
| SEQ ID NO: 278 | VKVEDYVRGSSHGGAFHI | CDRH3 aa |
| SEQ ID NO: 279 | QTINNW | CDRL1 aa |
| SEQ ID NO: 280 | KAS | CDRL2 aa |
| SEQ ID NO: 281 | LIYKASSLE | CDRL2 long aa |
| SEQ ID NO: 282 | QQYSSYWT | CDRL3 aa |
| SEQ ID NO: 283 | QVQLVESGGGVVQPGRSLRLSCAASGFSFSSYG MHWVRQAPGKGPEWVAVIWHDGSYSYYADS VRGRFTISRDNSKNTLYLQMNSLRPEDTGMYHC VKVEDYVRGSSHGGAFHIWGQGTMVTVSS | VH aa |
| SEQ ID NO: 284 | DIQMTQSPSTLSASVGDRVTITCRASQTINNWL AWYQWKPGKAPELLIYKASSLESGVPSRFSGSGS GTEFTLTISSLQPDDFATYYCQQYSSYWTFGQG TKVDIK | VL aa |
| SEQ ID NO: 285 | ggattcagcttcagtagttatggc | CDRH1 nuc |
| SEQ ID NO: 286 | atttggcatgatggaagttacagt | CDRH2 nuc |
| SEQ ID NO: 287 | gtgaaagttgaggattacgttagggggagttcacatgggggtgcttttcatatc | CDRH3 nuc |
| SEQ ID NO: 288 | cagactattaataactgg | CDRL1 nuc |
| SEQ ID NO: 289 | taaggcgtct | CDRL2 nuc |
| SEQ ID NO: 290 | ctgatctataaggcgtctagtttagaa | CDRL2 long nuc |
| SEQ ID NO: 291 | caacagtatagtagttattggacg | CDRL3 nuc |
| SEQ ID NO: 292 | caggtacaactggtggaatctgggggaggcgtggtccagcctggg aggtccctgagactctcctgtgcagcctccggattcagcttcagtagt tatggcatgcactgggtccgccaggctccaggcaaggggccgga gtgggtggcagttgatttggcatgatggaagttacagttactatgcaga ctccgtgaggggccgattcaccatctccagagacaattccaagaa cacgctgtatctgcaaatgaacagcctgagacctgaggacacggg gatgtatcactgtgtgaaagttgaggattacgttagggggagttcaca tggggggtgcttttcatatctggggccaagggacaatggtcaccgtctc ttcag | VH nuc |

121
122

-continued

TABLE OF SEQUENCES AND SEQ ID NUMBERS (SEQUENCE LISTING):

| SEQ ID NO | Sequence | Remarks |
|---|---|---|
| SEQ ID NO: 293 | gacatccagatgacccagtctccttccacccgtctgcatctgtagg ggacagagtcaccatcacttgccgggccagtcagactattaataac tggttggcctggtatcagtggaaaccggggaaagcccctgagctcc tgatctataaggcgtctagtttagaaagtggggtcccatcaaggttca gcggcagtggatctgggacagaattcactctcaccatcagcagcct gcagcctgatgattttgcaacttattactgccaacagtatagtagttatt ggacgttcggccaagggaccaaggtggacatcaaac | VL nuc |
| | MGV3 | |
| SEQ ID NO: 294 | GFTVSDSY | CDRH1 aa |
| SEQ ID NO: 295 | IYSGSST | CDRH2 aa |
| SEQ ID NO: 296 | ARGPNDYRNRKYYYYMDV | CDRH3 aa |
| SEQ ID NO: 297 | QSVDSPY | CDRL1 aa |
| SEQ ID NO: 298 | GAS | CDRL2 aa |
| SEQ ID NO: 299 | LIFGASIRA | CDRL2 long aa |
| SEQ ID NO: 300 | HQYGNAPYI | CDRL3 aa |
| SEQ ID NO: 301 | EVQVVESGGDLVQPGGSLRLSCAVYGFTVSDSY MSWVRQAPGKGLEWVSVIYSGSSTYYIDSVKGR FTISRDRSKNTLYLQMNTLRVEDTALYYCARGPN DYRNRKYYYYMDVWGKGTAVTVSS | VH aa |
| SEQ ID NO: 302 | EIVLTQSPDTLSLSAGERVTLSCRASQSVDSPYLA WYQQRPGQTPRLLIFGASIRATDIPDRFSGGGS GTDFTLTISRLEPEDSGVYYCHQYGNAPYIFGQG TKLEIK | VL aa |
| SEQ ID NO: 303 | ggattcaccgtcagtgacagctac | CDRH1 nuc |
| SEQ ID NO: 304 | atctatagtggtagtagtaca | CDRH2 nuc |
| SEQ ID NO: 305 | gcgagaggccctaatgactacagaaatcgcaaatattactactac atggacgtc | CDRH3 nuc |
| SEQ ID NO: 306 | cagagtgttgacagtccctac | CDRL1 nuc |
| SEQ ID NO: 307 | ggtgcctct | CDRL2 nuc |
| SEQ ID NO: 308 | ctcattttggtgcctctattagggcc | CDRL2 long nuc |
| SEQ ID NO: 309 | caccagtatggtaacgcaccctacatt | CDRL3 nuc |
| SEQ ID NO: 310 | gaggtgcaggtggtggagtctggggggagacttggtccagccgggg gggtccctgagactctcctgtgcagtctatggattcaccgtcagtgac agctacatgagctgggtccgccaggctccggggaaggggctgga gtgggtctcagttatctatagtggtagtagtacatactacatagactcc gtgaagggccgattcaccatctccagagacaggtccaagaacac cttgtatcttcaaatgaacaccctgagagttgaggacacggctcttta ttactgcgcgagaggccctaatgactacagaaatcgcaaatattact actacatggacgtctggggcaaagggaccgcggtcaccgtctcct cag | VH nuc |
| SEQ ID NO: 311 | gaaattgtgttgacacagtctccagacacccgtccttgtctgcagg ggaaagagtcaccctctcttgcagggccagtcagagtgttgacagt ccctacttagcctggtatcagcaaagacctggccagactcccagg ctcctcattttggtgcctctattagggccactgacatcccagacagg ttcagtggcggtgggtctgggacagacttcactctcaccatcagca gactggaacctgaagattctggagtgtattactgtcaccagtatggta acgcaccctacattttggccaggggaccaagctggagatcaaac | VL nuc |
| SEQ ID NO: 312 | KNNQGNGQGHNMPNDPNRNVDENANANSA VKNNNNEEPSDKHIKEYLNKIQNSLSTEWSPCSV TCGNGIQVRIKPGSANKPKDELDYANDIEKKICK MEKCS | CSP C-terminal peptide 282-383 |

TABLE OF SEQUENCES AND SEQ ID NUMBERS (SEQUENCE LISTING):

| SEQ ID NO | Sequence | Remarks |
| --- | --- | --- |
| SEQ ID NO: 313 | ASTKGPSVFPLAPSSKSTSGGTAALGCLVKDYFPE PVTVSWNSGALTSGVHTFPAVLQSSGLYSLSSVV TVPSSSLGTQTYICNVNHKPSNTKVDKRVEPKSC DKTHTCPPCPAPELLGGPSVFLFPPKPKDTLMISR TPEVTCVVVDVSHEDPEVKFNWYVDGVEVHNA KTKPREEQYNSTYRVVSVLTVLHQDWLNGKEYK CKVSNKALPAPIEKTISKAKGQPREPQVYTLPPSR EEMTKNQVSLTCLVKGFYPSDIAVEWESNGQPE NNYKTTPPVLDSDGSFFLYSKLTVDKSRWQQG NVFSCSVMHEALHNHYTQKSLSLSPGK | IgG1 CH1—CH2—CH3 aa |
| SEQ ID NO: 314 | RTVAAPSVFIFPPSDEQLKSGTASVVCLLNNFYPR EAKVQWKVDNALQSGNSQESVTEQDSKDSTYS LSSTLTLSKADYEKHKVYACEVTHQGLSSPVTKSF NRGEC | IgG CK aa |
| SEQ ID NO: 315 | GQPKAAPSVTLFPPSSEELQANKATLVCLISDFYP GAVTVAWKADSSPVKAGVETTTPSKQSNNKYA ASSYLSLTPEQWKSHRSYSCQVTHEGSTVEKTVA PTECS | IgG CL aa |
| SEQ ID NO: 316 | gcgtcgaccaagggcccatcggtcttccccctggcaccctcctcc aagagcacctctggggcacagcggccctgggctgcctggtcaa ggactacttccccgaacctgtgacggtctcgtggaactcaggcgcc ctgaccagcggcgtgcacaccttcccggctgtcctacagtcctcag gactctactccctcagcagcgtggtgaccgtgccctccagcagctt gggcacccagacctacatctgcaacgtgaatcacaagcccagca acaccaaggtggacaagagagttgagcccaaatcttgtgacaaaa ctcacacatgcccaccgtgcccagcacctgaactcctgggggga ccgtcagtcttcctcttccccccaaaacccaaggacaccctcatga tctcccggacccctgaggtcacatgcgtggtggtggacgtgagcca cgaAgaCcctgaggtcaagttcaactggtacgtggacggcgtgga ggtgcataatgccaagacaaagccgcgggaggagcagtacaaca gcacgtaccgtgtggtcagcgtcctcaccgtcctgcaccaggactg gctgaatggcaaggagtacaagtgcaaggtctccaacaaagccct cccagccccatcgagaaaaccatctccaaagccaaagggcag ccccgagaaccacaggtgtacaccctgcccccatcccgggagga tgaccaagaaccaggtcagcctgacctgcctggtcaaaggcttc ctatcccagcgacatcgccgtggagtgggagagcaatgggcagc cggagaacaactacaagaccacgcctcccgtgctggactccgac ggctccttcttcctctatagcaagctcaccgtggacaagagcaggtg gcagcaggggaacgtcttctcatgctccgtgatgcatgaggctctgc acaaccactacacgcagaagagcctctccctgtccccgggtaaa | IgG1 CH1—CH2—CH3 nuc |
| SEQ ID NO: 317 | cgTacGgtggctgcaccatctgtcttcatcttcccgccatctgatga gcagttgaaatctggaactgcctctgttgtgtgcctgctgaataacttc tatcccagagaggccaaagtacagtggaaggtggataacgccctc caatcgggtaactcccaggagagtgtcacagagcaggacagcaa ggacagcacctacagcctcagcagcaccctgacgctgagcaaag cagactacgagaaacacaaagtctacgcctgcgaagtcacccat cagggcctgagctcgcccgtcacaaagagcttcaacaggggaga gtgt | IgG CK nuc |
| SEQ ID NO: 318 | ggtcagcccaaggctgccccctcggtcactctgttcccgccctcct ctgaggagcttcaagccaacaaggccacactggtgtgtctcataag tgacttctacccgggagccgtgacagtggcttggaaagcagatagc agccccgtcaaggcgggagtggagaccaccacacccctccaaac aaagcaacaacaagtacgcggccagcagctatctgagcctgacg cctgagcagtggaagtcccacagaagctacagctgccaggtcac gcatgaagggagcaccgtggagaagacagtggcccctacagaat gttca | IgG CL nuc |
| SEQ ID NO: 319 | MENITSGFLGPLLVLQAGFFLLTRILTIPQSLDSW WTSLNFLGGTTVCLGQNSQSPTSNHSPTSCPPT CPGYRWMCLRRFIIFLFILLLCLIFLLVLLDYQGML PVCPLIPGSSTTSTGPCRTCMTTAQGTSMYPSCC CTKPSDGNCTCIPIPSSWAFGKFLWEWASARFS WLSLLVPFVQWFVGLSPTVWLSVIWMMWYWG PSLYSILSPFLPLLPIFFCLWVYI | HBsAg S domain |
| SEQ ID NO: 320 | MMRKLAILSVSSFLF

TABLE OF SEQUENCES AND SEQ ID NUMBERS (SEQUENCE LISTING):

| SEQ ID NO | Sequence | Remarks |
|---|---|---|
| SEQ ID NO: 321 | KKLKQPA | N-terminal region of CSP |
| SEQ ID NO: 322 | HKKLKQPAD | N-terminal region of CSP |
| SEQ ID NO: 323 | KHKKLKQPADG | N-terminal region of CSP |
| SEQ ID NO: 324 | KHKKLKQP | N-terminal region of CSP |
| SEQ ID NO: 325 | RKPKHKKLKQP | N-terminal region of CSP |
| SEQ ID NO: 326 | PKHKKLKQPADGN | N-terminal region of CSP |
| SEQ ID NO: 327 | KPKHKKLKQPADGNP | N-terminal region of CSP |
| SEQ ID NO: 328 | RKPKHKKLKQPADGNPD | N-terminal region of CSP |
| SEQ ID NO: 329 | NEKLRKPKHKKLKQP | N-terminal region of CSP |
| SEQ ID NO: 330 | NEKLRKPKHKKLKQPADG | N-terminal region of CSP |
| SEQ ID NO: 331 | MLSKDIIKLLNEQVNKEMNSSNLYMSMSSWCYT HSLDGAGLFLFDHAAEEYEHAKKLIVFLNENNVP VQLTSISAPEHKFEGLTQIFQKAYEHEQHISESINN IVDHAIKGKDHATFNFLQWYVAEQHEEEVLFKD ILDKIELIGNENHGLYLADQYVKGIAKSRKS | ferritin polypeptide |
| SEQ ID NO: 332 | MEFLKRSFAPLTEKQWQEIDNRAREIFKTQLYGR KFVDVEGPYGWEYAAHPLGEVEVLSDENEVVK WGLRKSLPLIELRATFTLDLWELDNLERGKPNVD LSSLEETVRKVAEFEDEVIFRGCEKSGVKGLLSFEER KIECGSTPKDLLEAIVRALSIFSKDGIEGPYTLVINT DRWINFLKEEAGHYPLEKRVEECLRGGKIITTPRIE DALVVSERGGDFKLILGQDLSIGYEDREKDAVRL FITETFTFQVVNPEALILLKF | encapsulin polypeptide: |

In the VH/VL sequences the three sequences in bold show the CDR1, CDR2 and CDR3 in this order.

The invention claimed is:

1. A recombinant nucleic acid molecule comprising:
   (i) a polynucleotide encoding an antibody, or an antigen-binding fragment thereof, that is capable of binding to a *Plasmodium falciparum* sporozoite, wherein the antibody, or the antigen-binding fragment thereof, comprises:
      a heavy chain variable region (VH) comprising a CDRH1, a CDRH2, and a CDRH3, the heavy chain variable region (VH) having an amino acid sequence, the amino acid sequence consisting of SEQ ID NO: 248;
      a light chain variable region (VL) comprising a CDRL1, a CDRL2, and a CDRL3, the light chain variable region (VL) having an amino acid sequence, the amino acid sequence consisting of SEQ ID NO: 249;
      an IgG1 Fc moiety comprising:
      a heavy chain amino acid sequence, wherein the heavy chain amino acid sequence is according to SEQ ID NO: 313; and
      a light chain amino acid sequence, wherein the light chain amino acid sequence is according to SEQ ID NO: 314 or 315; and
   (ii) a promoter sequence.

2. A vector comprising the recombinant nucleic acid molecule according to claim 1.

3. The vector of claim 2, which is an expression vector, a cloning vector, or a transfer vector.

4. A cell comprising a vector according to claim 2.

5. The cell according to claim 4, wherein the cell comprises a eukaryotic cell.

6. The cell according to claim 5, wherein the cell comprises a CHO cell, a NS0 cell, a PER.C6 cell, a HEK293T cell, a HKB-11 cell, a myeloma cell, a hybridoma cell, a yeast cell, a plant cell, a human liver cell, a human B cell, or a human plasma cell.

7. A pharmaceutical composition comprising:
   a recombinant nucleic acid molecule according to claim 1, and a pharmaceutically acceptable excipient, diluent, or carrier.

8. The recombinant nucleic acid molecule according to claim 1, comprising mRNA.

9. The recombinant nucleic acid molecule of claim 1, in which the recombinant nucleic acid molecule is codon-optimized for expression in a CHO cell, a NS0 cell, a PER.C6 cell, a HEK293T cell, a HKB-11 cell, a myeloma cell, a hybridoma cell, a yeast cell, a plant cell, a human liver cell, a human B cell, or a human plasma cell.

10. The recombinant nucleic acid of claim 1, wherein the light chain amino acid sequence of the IgG1 Fc moiety is according to SEQ ID NO: 314.

11. The recombinant nucleic acid of claim 1, wherein the light chain amino acid sequence of the IgG1 Fc moiety is according to SEQ ID NO: 315.

12. The recombinant nucleic acid molecule according to claim 1, wherein the polynucleotide comprises a sequence consisting of SEQ ID NO: 256.

13. The recombinant nucleic acid molecule according to claim 1, wherein the polynucleotide comprises a sequence consisting of SEQ ID NO: 257.

14. The recombinant nucleic acid molecule according to claim 1, wherein polynucleotide comprises a sequence consisting of SEQ ID NO: 256 and a sequence consisting of SEQ ID NO: 257.

15. The recombinant nucleic acid molecule according to claim 1, wherein the polynucleotide comprises a sequence consisting of SEQ ID NO: 316.

16. The recombinant nucleic acid molecule according to claim 1, wherein the polynucleotide comprises a sequence consisting of SEQ ID NO: 318 that encodes the light chain amino acid sequence of the IgG1 Fc moiety.

17. The recombinant nucleic acid molecule according to claim 1, wherein the polynucleotide comprises a sequence consisting of SEQ ID NO: 316 and a sequence consisting of SEQ ID NO: 318.

18. The recombinant nucleic acid molecule according to claim 1, wherein the polynucleotide comprises a sequence consisting of SEQ ID NO: 256 and a sequence consisting of SEQ ID NO: 316.

19. The recombinant nucleic acid molecule according to claim 1, wherein the polynucleotide comprises a sequence consisting of SEQ ID NO: 257 and a sequence consisting of SEQ ID NO: 318.

20. The recombinant nucleic acid molecule according to claim 1, wherein the polynucleotide comprises a sequence consisting of SEQ ID NO: 256, a sequence consisting of SEQ ID NO: 257, and a sequence consisting of SEQ ID NO: 316.

21. The recombinant nucleic acid molecule according to claim 1, wherein the polynucleotide comprises a sequence consisting of SEQ ID NO: 256, a sequence consisting of SEQ ID NO: 257, a sequence consisting of SEQ ID NO: 316, and a sequence consisting of SEQ ID NO: 318.

* * * * *

```
                    SEQUENCE LISTING

<160> NUMBER OF SEQ ID NOS: 385

<210> SEQ ID NO 1
<211> LENGTH: 4
<212> TYPE: PRT
<213> ORGANISM: Artificial Sequence
<220> FEATURE:
<223> OTHER INFORMATION: CSP epitope

<400> SEQUENCE: 1

Asn Pro Asp Pro
1

<210> SEQ ID NO 2
<211> LENGTH: 5
<212> TYPE: PRT
<213> ORGANISM: Artificial Sequence
<220> FEATURE:
```

```
<223> OTHER INFORMATION: CSP epitope

<400> SEQUENCE: 2

Asn Pro Asp Pro Asn
1               5

<210> SEQ ID NO 3
<211> LENGTH: 6
<212> TYPE: PRT
<213> ORGANISM: Artificial Sequence
<220> FEATURE:
<223> OTHER INFORMATION: CSP epitope

<400> SEQUENCE: 3

Asn Pro Asp Pro Asn Ala
1               5

<210> SEQ ID NO 4
<211> LENGTH: 7
<212> TYPE: PRT
<213> ORGANISM: Artificial Sequence
<220> FEATURE:
<223> OTHER INFORMATION: CSP epitope

<400> SEQUENCE: 4

Asn Pro Asp Pro Asn Ala Asn
1               5

<210> SEQ ID NO 5
<211> LENGTH: 8
<212> TYPE: PRT
<213> ORGANISM: Artificial Sequence
<220> FEATURE:
<223> OTHER INFORMATION: CSP epitope

<400> SEQUENCE: 5

Asn Pro Asp Pro Asn Ala Asn Pro
1               5

<210> SEQ ID NO 6
<211> LENGTH: 9
<212> TYPE: PRT
<213> ORGANISM: Artificial Sequence
<220> FEATURE:
<223> OTHER INFORMATION: CSP epitope

<400> SEQUENCE: 6

Asn Pro Asp Pro Asn Ala Asn Pro Asn
1               5

<210> SEQ ID NO 7
<211> LENGTH: 9
<212> TYPE: PRT
<213> ORGANISM: Artificial Sequence
<220> FEATURE:
<223> OTHER INFORMATION: CSP epitope

<400> SEQUENCE: 7

Gly Asn Pro Asp Pro Asn Ala Asn Pro
1               5

<210> SEQ ID NO 8
<211> LENGTH: 10
<212> TYPE: PRT
<213> ORGANISM: Artificial Sequence
<220> FEATURE:
<223> OTHER INFORMATION: CSP epitope
```

```
<400> SEQUENCE: 8

Gly Asn Pro Asp Pro Asn Ala Asn Pro Asn
1               5                   10

<210> SEQ ID NO 9
<211> LENGTH: 10
<212> TYPE: PRT
<213> ORGANISM: Artificial Sequence
<220> FEATURE:
<223> OTHER INFORMATION: CSP epitope

<400> SEQUENCE: 9

Asp Gly Asn Pro Asp Pro Asn Ala Asn Pro
1               5                   10

<210> SEQ ID NO 10
<211> LENGTH: 10
<212> TYPE: PRT
<213> ORGANISM: Artificial Sequence
<220> FEATURE:
<223> OTHER INFORMATION: CSP epitope

<400> SEQUENCE: 10

Asn Pro Asp Pro Asn Ala Asn Pro Asn Lys
1               5                   10

<210> SEQ ID NO 11
<211> LENGTH: 11
<212> TYPE: PRT
<213> ORGANISM: Artificial Sequence
<220> FEATURE:
<223> OTHER INFORMATION: CSP epitope

<400> SEQUENCE: 11

Asp Gly Asn Pro Asp Pro Asn Ala Asn Pro Asn
1               5                   10

<210> SEQ ID NO 12
<211> LENGTH: 11
<212> TYPE: PRT
<213> ORGANISM: Artificial Sequence
<220> FEATURE:
<223> OTHER INFORMATION: CSP epitope

<400> SEQUENCE: 12

Gly Asn Pro Asp Pro Asn Ala Asn Pro Asn Lys
1               5                   10

<210> SEQ ID NO 13
<211> LENGTH: 12
<212> TYPE: PRT
<213> ORGANISM: Artificial Sequence
<220> FEATURE:
<223> OTHER INFORMATION: CSP epitope

<400> SEQUENCE: 13

Asp Gly Asn Pro Asp Pro Asn Ala Asn Pro Asn Lys
1               5                   10

<210> SEQ ID NO 14
<211> LENGTH: 12
<212> TYPE: PRT
<213> ORGANISM: Artificial Sequence
<220> FEATURE:
<223> OTHER INFORMATION: CSP epitope
```

```
<400> SEQUENCE: 14

Ala Asp Gly Asn Pro Asp Pro Asn Ala Asn Pro Asn
1               5                   10

<210> SEQ ID NO 15
<211> LENGTH: 15
<212> TYPE: PRT
<213> ORGANISM: Artificial Sequence
<220> FEATURE:
<223> OTHER INFORMATION: CSP epitope

<400> SEQUENCE: 15

Gln Pro Ala Asp Gly Asn Pro Asp Pro Asn Ala Asn Pro Asn Lys
1               5                   10                  15

<210> SEQ ID NO 16
<211> LENGTH: 13
<212> TYPE: PRT
<213> ORGANISM: Artificial Sequence
<220> FEATURE:
<223> OTHER INFORMATION: CSP epitope

<400> SEQUENCE: 16

Ala Asp Gly Asn Pro Asp Pro Asn Ala Asn Pro Asn Lys
1               5                   10

<210> SEQ ID NO 17
<211> LENGTH: 14
<212> TYPE: PRT
<213> ORGANISM: Artificial Sequence
<220> FEATURE:
<223> OTHER INFORMATION: CSP epitope

<400> SEQUENCE: 17

Pro Ala Asp Gly Asn Pro Asp Pro Asn Ala Asn Pro Asn Lys
1               5                   10

<210> SEQ ID NO 18
<211> LENGTH: 14
<212> TYPE: PRT
<213> ORGANISM: Artificial Sequence
<220> FEATURE:
<223> OTHER INFORMATION: CSP epitope

<400> SEQUENCE: 18

Ala Asp Gly Asn Pro Asp Pro Asn Ala Asn Pro Asn Lys Asn
1               5                   10

<210> SEQ ID NO 19
<211> LENGTH: 15
<212> TYPE: PRT
<213> ORGANISM: Artificial Sequence
<220> FEATURE:
<223> OTHER INFORMATION: CSP epitope

<400> SEQUENCE: 19

Pro Ala Asp Gly Asn Pro Asp Pro Asn Ala Asn Pro Asn Lys Asn
1               5                   10                  15

<210> SEQ ID NO 20
<211> LENGTH: 16
<212> TYPE: PRT
<213> ORGANISM: Artificial Sequence
<220> FEATURE:
<223> OTHER INFORMATION: CSP epitope

<400> SEQUENCE: 20
```

```
Gln Pro Ala Asp Gly Asn Pro Asp Pro Asn Ala Asn Pro Asn Lys Asn
1               5                   10                  15

<210> SEQ ID NO 21
<211> LENGTH: 16
<212> TYPE: PRT
<213> ORGANISM: Artificial Sequence
<220> FEATURE:
<223> OTHER INFORMATION: CSP epitope

<400> SEQUENCE: 21

Pro Ala Asp Gly Asn Pro Asp Pro Asn Ala Asn Pro Asn Lys Asn Asn
1               5                   10                  15

<210> SEQ ID NO 22
<211> LENGTH: 17
<212> TYPE: PRT
<213> ORGANISM: Artificial Sequence
<220> FEATURE:
<223> OTHER INFORMATION: CSP epitope

<400> SEQUENCE: 22

Gln Pro Ala Asp Gly Asn Pro Asp Pro Asn Ala Asn Pro Asn Lys Asn
1               5                   10                  15

Asn

<210> SEQ ID NO 23
<211> LENGTH: 18
<212> TYPE: PRT
<213> ORGANISM: Artificial Sequence
<220> FEATURE:
<223> OTHER INFORMATION: NPDP-peptide

<400> SEQUENCE: 23

Lys Gln Pro Ala Asp Gly Asn Pro Asp Pro Asn Ala Asn Pro Asn Lys
1               5                   10                  15

Asn Asn

<210> SEQ ID NO 24
<211> LENGTH: 397
<212> TYPE: PRT
<213> ORGANISM: Artificial Sequence
<220> FEATURE:
<223> OTHER INFORMATION: PfCSP

<400> SEQUENCE: 24

Met Met Arg Lys Leu Ala Ile Leu Ser Val Ser Ser Phe Leu Phe Val
1               5                   10                  15

Glu Ala Leu Phe Gln Glu Tyr Gln Cys Tyr Gly Ser Ser Ser Asn Thr
            20                  25                  30

Arg Val Leu Asn Glu Leu Asn Tyr Asp Asn Ala Gly Thr Asn Leu Tyr
        35                  40                  45

Asn Glu Leu Glu Met Asn Tyr Tyr Gly Lys Gln Glu Asn Trp Tyr Ser
    50                  55                  60

Leu Lys Lys Asn Ser Arg Ser Leu Gly Glu Asn Asp Asp Gly Asn Asn
65                  70                  75                  80

Glu Asp Asn Glu Lys Leu Arg Lys Pro Lys His Lys Lys Leu Lys Gln
                85                  90                  95

Pro Ala Asp Gly Asn Pro Asp Pro Asn Ala Asn Pro Asn Val Asp Pro
            100                 105                 110

Asn Ala Asn Pro Asn Val Asp Pro Asn Ala Asn Pro Asn Val Asp Pro
```

-continued

```
                    115                 120                 125
Asn Ala Asn Pro Asn Ala Asn Pro Asn Ala Asn Pro Asn Ala Asn Pro
            130                 135                 140
Asn Ala Asn Pro Asn Ala Asn Pro Asn Ala Asn Pro Asn Ala Asn Pro
145                 150                 155                 160
Asn Ala Asn Pro Asn Ala Asn Pro Asn Ala Asn Pro Asn Ala Asn Pro
                165                 170                 175
Asn Ala Asn Pro Asn Ala Asn Pro Asn Ala Asn Pro Asn Ala Asn Pro
            180                 185                 190
Asn Ala Asn Pro Asn Val Asp Pro Asn Ala Asn Pro Asn Ala Asn Pro
        195                 200                 205
Asn Ala Asn Pro Asn Ala Asn Pro Asn Ala Asn Pro Asn Ala Asn Pro
            210                 215                 220
Asn Ala Asn Pro Asn Ala Asn Pro Asn Ala Asn Pro Asn Ala Asn Pro
225                 230                 235                 240
Asn Ala Asn Pro Asn Ala Asn Pro Asn Ala Asn Pro Asn Ala Asn Pro
                245                 250                 255
Asn Ala Asn Pro Asn Ala Asn Pro Asn Ala Asn Pro Asn Ala Asn Pro
            260                 265                 270
Asn Lys Asn Asn Gln Gly Asn Gly Gln Gly His Asn Met Pro Asn Asp
        275                 280                 285
Pro Asn Arg Asn Val Asp Glu Asn Ala Asn Ala Asn Ser Ala Val Lys
            290                 295                 300
Asn Asn Asn Asn Glu Glu Pro Ser Asp Lys His Ile Lys Glu Tyr Leu
305                 310                 315                 320
Asn Lys Ile Gln Asn Ser Leu Ser Thr Glu Trp Ser Pro Cys Ser Val
                325                 330                 335
Thr Cys Gly Asn Gly Ile Gln Val Arg Ile Lys Pro Gly Ser Ala Asn
            340                 345                 350
Lys Pro Lys Asp Glu Leu Asp Tyr Ala Asn Asp Ile Glu Lys Lys Ile
        355                 360                 365
Cys Lys Met Glu Lys Cys Ser Ser Val Phe Asn Val Val Asn Ser Ser
            370                 375                 380
Ile Gly Leu Ile Met Val Leu Ser Phe Leu Phe Leu Asn
385                 390                 395

<210> SEQ ID NO 25
<211> LENGTH: 5
<212> TYPE: PRT
<213> ORGANISM: Artificial Sequence
<220> FEATURE:
<223> OTHER INFORMATION: CSP region I

<400> SEQUENCE: 25

Lys Leu Lys Gln Pro
1               5

<210> SEQ ID NO 26
<211> LENGTH: 40
<212> TYPE: PRT
<213> ORGANISM: Artificial Sequence
<220> FEATURE:
<223> OTHER INFORMATION: NANP-peptide

<400> SEQUENCE: 26

Asn Ala Asn Pro Asn Ala Asn Pro Asn Ala Asn Pro Asn Ala Asn Pro
1               5                   10                  15
```

```
Asn Ala Asn Pro Asn Ala Asn Pro Ala Asn Pro Asn Ala Asn Pro
        20                  25                  30

Asn Ala Asn Pro Asn Ala Asn Pro
        35                  40
```

<210> SEQ ID NO 27
<211> LENGTH: 89
<212> TYPE: PRT
<213> ORGANISM: Artificial Sequence
<220> FEATURE:
<223> OTHER INFORMATION: 22-110-peptide

<400> SEQUENCE: 27

```
Glu Tyr Gln Cys Tyr Gly Ser Ser Ser Asn Thr Arg Val Leu Asn Glu
1               5                   10                  15

Leu Asn Tyr Asp Asn Ala Gly Thr Asn Leu Tyr Asn Glu Leu Glu Met
            20                  25                  30

Asn Tyr Tyr Gly Lys Gln Glu Asn Trp Tyr Ser Leu Lys Lys Asn Ser
        35                  40                  45

Arg Ser Leu Gly Glu Asn Asp Asp Gly Asn Asn Glu Asp Asn Glu Lys
    50                  55                  60

Leu Arg Lys Pro Lys His Lys Lys Leu Lys Gln Pro Ala Asp Gly Asn
65                  70                  75                  80

Pro Asp Pro Asn Ala Asn Pro Asn Val
                85
```

<210> SEQ ID NO 28
<211> LENGTH: 8
<212> TYPE: PRT
<213> ORGANISM: Artificial Sequence
<220> FEATURE:
<223> OTHER INFORMATION: MGG1 CDRH1 aa

<400> SEQUENCE: 28

```
Gly Phe Thr Phe Asp Asp Tyr Ala
1               5
```

<210> SEQ ID NO 29
<211> LENGTH: 8
<212> TYPE: PRT
<213> ORGANISM: Artificial Sequence
<220> FEATURE:
<223> OTHER INFORMATION: MGG1 CDRH2 aa

<400> SEQUENCE: 29

```
Ile Asn Trp Asn Gly Gly Ser Thr
1               5
```

<210> SEQ ID NO 30
<211> LENGTH: 17
<212> TYPE: PRT
<213> ORGANISM: Artificial Sequence
<220> FEATURE:
<223> OTHER INFORMATION: MGG1 CDRH3 aa

<400> SEQUENCE: 30

```
Ala Arg Leu Gly Arg Ala Ala Arg Glu Tyr Tyr Tyr Tyr Met Asp
1               5                   10                  15

Val
```

<210> SEQ ID NO 31
<211> LENGTH: 8
<212> TYPE: PRT

<213> ORGANISM: Artificial Sequence
<220> FEATURE:
<223> OTHER INFORMATION: MGG1 CDRL1 aa

<400> SEQUENCE: 31

Ser Ser Asn Ile Gly Asn Asn Tyr
1               5

<210> SEQ ID NO 32

<400> SEQUENCE: 32

000

<210> SEQ ID NO 33
<211> LENGTH: 9
<212> TYPE: PRT
<213> ORGANISM: Artificial Sequence
<220> FEATURE:
<223> OTHER INFORMATION: MGG1 CDRL2 long aa

<400> SEQUENCE: 33

Leu Ile Tyr Asp Asn Asn Lys Arg Pro
1               5

<210> SEQ ID NO 34
<211> LENGTH: 11
<212> TYPE: PRT
<213> ORGANISM: Artificial Sequence
<220> FEATURE:
<223> OTHER INFORMATION: MGG1 CDRL3 aa

<400> SEQUENCE: 34

Gly Thr Trp Asp Ser Ser Leu Ser Ala Gly Val
1               5                   10

<210> SEQ ID NO 35
<211> LENGTH: 124
<212> TYPE: PRT
<213> ORGANISM: Artificial Sequence
<220> FEATURE:
<223> OTHER INFORMATION: MGG1 VH aa

<400> SEQUENCE: 35

Glu Val Gln Leu Val Glu Ser Gly Gly Val Val Arg Pro Gly Gly
1               5                   10                  15

Ser Leu Arg Leu Ser Cys Ala Ala Ser Gly Phe Thr Phe Asp Asp Tyr
                20                  25                  30

Ala Met Ser Trp Val Arg Gln Ala Pro Gly Lys Gly Leu Glu Trp Val
            35                  40                  45

Ser Gly Ile Asn Trp Asn Gly Gly Ser Thr Gly Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr His Cys
                85                  90                  95

Ala Arg Leu Gly Arg Ala Ala Arg Glu Tyr Tyr Tyr Tyr Tyr Met Asp
            100                 105                 110

Val Trp Gly Lys Gly Thr Thr Val Thr Val Ser Ser
        115                 120

<210> SEQ ID NO 36
<211> LENGTH: 112

```
<212> TYPE: PRT
<213> ORGANISM: Artificial Sequence
<220> FEATURE:
<223> OTHER INFORMATION: MGG1 VL aa

<400> SEQUENCE: 36

Gln Ser Val Leu Thr Gln Pro Pro Ser Val Ser Ala Ala Pro Gly Gln
1               5                  10                  15

Lys Val Thr Ile Ser Cys Ser Gly Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Gly Val Phe Gly Gly Gly Thr Lys Leu Thr Val Leu Gly Gln
            100                 105                 110

<210> SEQ ID NO 37
<211> LENGTH: 24
<212> TYPE: DNA
<213> ORGANISM: Artificial Sequence
<220> FEATURE:
<223> OTHER INFORMATION: MGG1 CDRH1 nuc

<400> SEQUENCE: 37
ggattcacct ttgatgatta tgcc                                          24

<210> SEQ ID NO 38
<211> LENGTH: 24
<212> TYPE: DNA
<213> ORGANISM: Artificial Sequence
<220> FEATURE:
<223> OTHER INFORMATION: MGG1 CDRH2 nuc

<400> SEQUENCE: 38
attaattgga atggtggtag caca                                          24

<210> SEQ ID NO 39
<211> LENGTH: 51
<212> TYPE: DNA
<213> ORGANISM: Artificial Sequence
<220> FEATURE:
<223> OTHER INFORMATION: MGG1 CDRH3 nuc

<400> SEQUENCE: 39
gcgagacttg ggagagcagc ccgtgagtac tactactact acatggacgt c            51

<210> SEQ ID NO 40
<211> LENGTH: 24
<212> TYPE: DNA
<213> ORGANISM: Artificial Sequence
<220> FEATURE:
<223> OTHER INFORMATION: MGG1 CDRL1 nuc

<400> SEQUENCE: 40
agctccaaca ttgggaataa ttat                                          24

<210> SEQ ID NO 41
```

<400> SEQUENCE: 41

000

<210> SEQ ID NO 42
<211> LENGTH: 27
<212> TYPE: DNA
<213> ORGANISM: Artificial Sequence
<220> FEATURE:
<223> OTHER INFORMATION: MGG1 CDRL2 long nuc

<400> SEQUENCE: 42
ctcatttatg acaataataa gcgaccc                                          27

<210> SEQ ID NO 43
<211> LENGTH: 33
<212> TYPE: DNA
<213> ORGANISM: Artificial Sequence
<220> FEATURE:
<223> OTHER INFORMATION: MGG1 CDRL3 nuc

<400> SEQUENCE: 43
ggcacatggg atagcagcct gagtgctgga gtg                                   33

<210> SEQ ID NO 44
<211> LENGTH: 372
<212> TYPE: DNA
<213> ORGANISM: Artificial Sequence
<220> FEATURE:
<223> OTHER INFORMATION: MGG1 VH nuc

<400> SEQUENCE: 44
gaggtgcagc tggtggagtc tgggggaggt gtggtacggc ctgggggtc cctgagactc        60 tcctgtgcag cctctggatt caccttttgat gattatgcca tgagctgggt ccgccaagct     120
ccagggaagg gctggagtg gtctctggt attaattgga atggtggtag cacaggttat        180
gcagactctg tgaagggccg attcaccatc tccagagaca cgccaagaa ctccctgtat       240 ctgcaaatga acagtctgag agccgaggac acggccttgt atcactgtgc gagacttggg     300
agagcagccc gtgagtacta ctactactac atggacgtct ggggcaaagg gaccacggtc     360
accgtctcct ca                                                         372

<210> SEQ ID NO 45
<211> LENGTH: 336
<212> TYPE: DNA
<213> ORGANISM: Artificial Sequence
<220> FEATURE:
<223> OTHER INFORMATION: MGG1 VL nuc

<400> SEQUENCE: 45
cagtctgtgt tgacgcagcc gccctcagtg tctgcggccc caggacagaa ggtcaccatc       60
tcctgctctg gaagcagctc caacattggg aataattatg tatcctggta ccagcagctc     120
ccaggaacag cccccaaact cctcatttat gacaataata gcgaccctc agggattcct       180 gaccgattct ctggctccaa gtctggcacg tcagccaccc tgggcatcac cggactccag     240
actggggacg aggccgatta ttactgcggc acatgggata gcagcctgag tgctggagtg     300
ttcggcggag ggaccaagct gaccgtccta ggtcag                                336

<210> SEQ ID NO 46
<211> LENGTH: 8
<212> TYPE: PRT
<213> ORGANISM: Artificial Sequence

```
<220> FEATURE:
<223> OTHER INFORMATION: MGG2 CDRH1 aa

<400> SEQUENCE: 46

Gly Phe Thr Leu Asn Asn Tyr Trp
1               5

<210> SEQ ID NO 47
<211> LENGTH: 8
<212> TYPE: PRT
<213> ORGANISM: Artificial Sequence
<220> FEATURE:
<223> OTHER INFORMATION: MGG2 CDRH2 aa

<400> SEQUENCE: 47

Ile Asn Ile Asp Gly Ser Thr Thr
1               5

<210> SEQ ID NO 48
<211> LENGTH: 20
<212> TYPE: PRT
<213> ORGANISM: Artificial Sequence
<220> FEATURE:
<223> OTHER INFORMATION: MGG2 CDRH3 aa

<400> SEQUENCE: 48

Ala Lys Gly Ser Ile Lys Ala Gly Gly Phe Trp Ser Gly Tyr Ser Asn
1               5                   10                  15

Trp Phe Asp Pro
            20

<210> SEQ ID NO 49
<211> LENGTH: 9
<212> TYPE: PRT
<213> ORGANISM: Artificial Sequence
<220> FEATURE:
<223> OTHER INFORMATION: MGG2 CDRL1 aa

<400> SEQUENCE: 49

Pro Gly Pro Val Thr Ser Gly His Tyr
1               5

<210> SEQ ID NO 50

<400> SEQUENCE: 50

000

<210> SEQ ID NO 51
<211> LENGTH: 9
<212> TYPE: PRT
<213> ORGANISM: Artificial Sequence
<220> FEATURE:
<223> OTHER INFORMATION: MGG2 CDRL2 long aa

<400> SEQUENCE: 51

Leu Ile Tyr Asp Thr Ser Asn Lys His
1               5

<210> SEQ ID NO 52
<211> LENGTH: 9
<212> TYPE: PRT
<213> ORGANISM: Artificial Sequence
<220> FEATURE:
<223> OTHER INFORMATION: MGG2 CDRL3 aa

<400> SEQUENCE: 52
```

```
Leu Leu Ser Tyr Gly Gly Ala Pro Val
1               5

<210> SEQ ID NO 53
<211> LENGTH: 127
<212> TYPE: PRT
<213> ORGANISM: Artificial Sequence
<220> FEATURE:
<223> OTHER INFORMATION: MGG2 VH aa

<400> SEQUENCE: 53

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Asn Asn Tyr
            20                  25                  30

Trp Met His Trp Val Arg Gln Ala Pro Gly Lys Gly Leu Val Trp Val
        35                  40                  45

Ala His Ile Asn Ile Asp Gly Ser Thr Thr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Ile Lys Ala Gly Gly Phe Trp Ser Gly Tyr Ser Asn
            100                 105                 110

Trp Phe Asp Pro Trp Gly Gln Gly Thr Leu Val Thr Val Ser Ser
        115                 120                 125

<210> SEQ ID NO 54
<211> LENGTH: 109
<212> TYPE: PRT
<213> ORGANISM: Artificial Sequence
<220> FEATURE:
<223> OTHER INFORMATION: MGG2 VL aa

<400> SEQUENCE: 54

Gln Ala Val Val Thr Gln Glu Pro Ser Leu Thr Val Ser Pro Gly Gly
1               5                   10                  15

Thr Val Thr Leu Thr Cys Asp Ser Asp Pro Gly Pro Val Thr Ser Gly
            20                  25                  30

His Tyr Pro Tyr Trp Phe Gln Gln Lys Pro Gly Gln Val Pro Arg Thr
        35                  40                  45

Leu Ile Tyr Asp Thr Ser Asn Lys His Ser Trp Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Asp Tyr Tyr Cys Leu Leu Ser Tyr Gly Gly
                85                  90                  95

Ala Pro Val Phe Gly Gly Gly Thr Lys Leu Thr Val Leu
            100                 105

<210> SEQ ID NO 55
<211> LENGTH: 24
<212> TYPE: DNA
<213> ORGANISM: Artificial Sequence
<220> FEATURE:
<223> OTHER INFORMATION: MGG2 CDRH1 nuc

<400> SEQUENCE: 55
```
ggattcaccc tcaataacta ctgg                                         24

<210> SEQ ID NO 56
<211> LENGTH: 24
<212> TYPE: DNA
<213> ORGANISM: Artificial Sequence
<220> FEATURE:
<223> OTHER INFORMATION: MGG2 CDRH2 nuc

<400> SEQUENCE: 56
attaatatcg atggcagtac taca                                         24

<210> SEQ ID NO 57
<211> LENGTH: 60
<212> TYPE: DNA
<213> ORGANISM: Artificial Sequence
<220> FEATURE:
<223> OTHER INFORMATION: MGG2 CDRH3 nuc

<400> SEQUENCE: 57
gcaaagggaa gtattaaggc cggaggtttt tggagtggtt actccaactg gttcgacccc    60

<210> SEQ ID NO 58
<211> LENGTH: 27
<212> TYPE: DNA
<213> ORGANISM: Artificial Sequence
<220> FEATURE:
<223> OTHER INFORMATION: MGG2 CDRL1 nuc

<400> SEQUENCE: 58
cctggacctg tcaccagtgg tcattat                                      27

<210> SEQ ID NO 59

<400> SEQUENCE: 59

000

<210> SEQ ID NO 60
<211> LENGTH: 27
<212> TYPE: DNA
<213> ORGANISM: Artificial Sequence
<220> FEATURE:
<223> OTHER INFORMATION: MGG2 CDRL2 long nuc

<400> SEQUENCE: 60
ctgatttatg ataccagcaa caaacac                                      27

<210> SEQ ID NO 61
<211> LENGTH: 27
<212> TYPE: DNA
<213> ORGANISM: Artificial Sequence
<220> FEATURE:
<223> OTHER INFORMATION: MGG2 CDRL3 nuc

<400> SEQUENCE: 61
ctgctctcgt atggtggtgc ccctgta                                      27

<210> SEQ ID NO 62
<211> LENGTH: 382
<212> TYPE: DNA
<213> ORGANISM: Artificial Sequence
<220> FEATURE:
<223> OTHER INFORMATION: MGG2 VH nuc

<400> SEQUENCE: 62

```
gaggtgcagc tggtggagtc cggggggaggc ttagttcagc cggggggggtc cctgagactc    60 tcctgtgcag cctctggatt caccctcaat aactactgga tgcactgggt ccgccaagct    120
ccagggaagg ggctggtctg ggtcgcacat attaatatcg atggcagtac tacaacctac    180
gcggactccg tgaagggccg attcaccatc tccagagaca cgccaagaa cacgctgtat    240 ctgcaaatga acagtctgag agccgaggac acggctgtct attactgtgc aaagggaagt    300
attaaggccg gaggttttg gagtggttac tccaactggt tcgacccctg ggccaggga    360 accctggtca ccgtctcctc ag                                            382
```

<210> SEQ ID NO 63
<211> LENGTH: 328
<212> TYPE: DNA
<213> ORGANISM: Artificial Sequence
<220> FEATURE:
<223> OTHER INFORMATION: MGG2 VL nuc

<400> SEQUENCE: 63

```
caggctgtgg tgactcagga gccctcactg actgtgtccc caggagggac agtcactctc    60
acctgtgact ccgaccctgg acctgtcacc agtggtcatt atcccactg gttccagcag    120 aagcctggcc aagtccccag gacactgatt tatgatacca gcaacaaaca ctcctggaca    180
cctgcccggt tttcaggctc cctccttggg ggcaaagctg ccctgaccct ttcgggtgcg    240
cagcctgagg atgaggctga ctattactgc ctgctctcgt atggtggtgc ccctgtattc    300
ggcggaggga ccaaactgac cgtcctaa                                      328
```

<210> SEQ ID NO 64
<211> LENGTH: 8
<212> TYPE: PRT
<213> ORGANISM: Artificial Sequence
<220> FEATURE:
<223> OTHER INFORMATION: MGG3 CDRH1 aa

<400> SEQUENCE: 64

Gly Phe Thr Phe Ser Thr Phe Gly
1               5

<210> SEQ ID NO 65
<211> LENGTH: 8
<212> TYPE: PRT
<213> ORGANISM: Artificial Sequence
<220> FEATURE:
<223> OTHER INFORMATION: MGG3 CDRH2 aa

<400> SEQUENCE: 65

Ile Trp Tyr Asp Gly Ser Ser Lys
1               5

<210> SEQ ID NO 66
<211> LENGTH: 14
<212> TYPE: PRT
<213> ORGANISM: Artificial Sequence
<220> FEATURE:
<223> OTHER INFORMATION: MGG3 CDRH3 aa

<400> SEQUENCE: 66

Val Lys Val Gly Ala Asn Trp Gly Trp Arg Tyr Phe Asp Leu
1               5                   10

<210> SEQ ID NO 67
<211> LENGTH: 11
<212> TYPE: PRT

```
<213> ORGANISM: Artificial Sequence
<220> FEATURE:
<223> OTHER INFORMATION: MGG3 CDRL1 aa

<400> SEQUENCE: 67

Gln Ser Leu Leu His Ser Asp Gly Asn Thr Tyr
1               5                   10

<210> SEQ ID NO 68

<400> SEQUENCE: 68

000

<210> SEQ ID NO 69
<211> LENGTH: 9
<212> TYPE: PRT
<213> ORGANISM: Artificial Sequence
<220> FEATURE:
<223> OTHER INFORMATION: MGG3 CDRL2 long aa

<400> SEQUENCE: 69

Leu Ile Tyr Glu Val Ser Ser Arg Phe
1               5

<210> SEQ ID NO 70
<211> LENGTH: 8
<212> TYPE: PRT
<213> ORGANISM: Artificial Sequence
<220> FEATURE:
<223> OTHER INFORMATION: MGG3 CDRL3 aa

<400> SEQUENCE: 70

Met Gln Gly Ile His Ser Trp Thr
1               5

<210> SEQ ID NO 71
<211> LENGTH: 121
<212> TYPE: PRT
<213> ORGANISM: Artificial Sequence
<220> FEATURE:
<223> OTHER INFORMATION: MGG3 VH aa

<400> SEQUENCE: 71

Gln Glu Gln Leu Val Glu Ser Gly Gly Val Val Gln Pro Gly Lys
1               5                   10                  15

Ser Leu Arg Leu Ser Cys Ala Ala Ser Gly Phe Thr Phe Ser Thr Phe
                20                  25                  30

Gly Met His Trp Val Arg Gln Ala Pro Gly Lys Gly Leu Glu Trp Val
            35                  40                  45

Ala Val Ile Trp Tyr Asp Gly Ser Ser Lys Tyr His Ala Asp Ser Val
        50                  55                  60

Lys Gly Arg Phe Thr Ile Ser Arg Asp Asn Ser Lys Ser Thr Leu Tyr
65                  70                  75                  80

Leu Gln Met Asn Ser Leu Arg Ala Glu Asp Thr Ala Met Tyr Tyr Cys
                85                  90                  95

Val Lys Val Gly Ala Asn Trp Gly Trp Arg Tyr Phe Asp Leu Trp Gly
            100                 105                 110

Arg Gly Thr Leu Val Thr Val Ser Ser
        115                 120

<210> SEQ ID NO 72
<211> LENGTH: 111
```

```
<212> TYPE: PRT
<213> ORGANISM: Artificial Sequence
<220> FEATURE:
<223> OTHER INFORMATION: MGG3 VL aa

<400> SEQUENCE: 72

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Asn Thr Tyr Leu Ser Trp Tyr Leu Gln Lys Pro Gly Gln Ser
        35                  40                  45

Pro Gln Leu Leu Ile Tyr Glu Val Ser Ser Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Asp Asp Val Gly Val Tyr Tyr Cys Met Gln Gly
                85                  90                  95

Ile His Ser Trp Thr Phe Gly Gln Gly Thr Lys Val Glu Ile Lys
            100                 105                 110

<210> SEQ ID NO 73
<211> LENGTH: 23
<212> TYPE: DNA
<213> ORGANISM: Artificial Sequence
<220> FEATURE:
<223> OTHER INFORMATION: MGG3 CDRH1 nuc

<400> SEQUENCE: 73
gattcacctt cagtaccttt ggc                                           23

<210> SEQ ID NO 74
<211> LENGTH: 24
<212> TYPE: DNA
<213> ORGANISM: Artificial Sequence
<220> FEATURE:
<223> OTHER INFORMATION: MGG3 CDRH2 nuc

<400> SEQUENCE: 74
atctggtatg atggaagtag taaa                                          24

<210> SEQ ID NO 75
<211> LENGTH: 42
<212> TYPE: DNA
<213> ORGANISM: Artificial Sequence
<220> FEATURE:
<223> OTHER INFORMATION: MGG3 CDRH3 nuc

<400> SEQUENCE: 75
gtgaaagtcg gagctaactg gggatggagg tacttcgatc tc                      42

<210> SEQ ID NO 76
<211> LENGTH: 33
<212> TYPE: DNA
<213> ORGANISM: Artificial Sequence
<220> FEATURE:
<223> OTHER INFORMATION: MGG3 CDRL1 nuc

<400> SEQUENCE: 76
cagagcctcc tacatagtga tggaaacacc tat                                33

<210> SEQ ID NO 77
```

<400> SEQUENCE: 77

000

<210> SEQ ID NO 78
<211> LENGTH: 27
<212> TYPE: DNA
<213> ORGANISM: Artificial Sequence
<220> FEATURE:
<223> OTHER INFORMATION: MGG3 CDRL2 long nuc

<400> SEQUENCE: 78
ctgatctatg aagtttccag ccggttc                                        27

<210> SEQ ID NO 79
<211> LENGTH: 24
<212> TYPE: DNA
<213> ORGANISM: Artificial Sequence
<220> FEATURE:
<223> OTHER INFORMATION: MGG3 CDRL3 nuc

<400> SEQUENCE: 79
atgcaaggca tacactcgtg gacg                                           24

<210> SEQ ID NO 80
<211> LENGTH: 364
<212> TYPE: DNA
<213> ORGANISM: Artificial Sequence
<220> FEATURE:
<223> OTHER INFORMATION: MGG3 VH nuc

<400> SEQUENCE: 80
caggagcaac tggtggagtc tgggggaggc gtggtccagc ctgggaagtc cctgagactc    60
tcctgtgcag cctctggatt caccttcagt acctttggca tgcactgggt ccgccaggct  120
ccaggcaagg ggctggagtg ggtggcagtc atctggtatg atggaagtag taaataccat  180
gcagactccg tgaagggccg attcaccatc tccagagaca attccaagag cacgctgtat  240
ctgcaaatga acagcctgag agctgaggac acggctatgt attactgtgt gaaagtcgga  300
gctaactggg gatggaggta cttcgatctc tggggccgtg gcaccctggt caccgtctcc  360
tcag                                                                364

<210> SEQ ID NO 81
<211> LENGTH: 334
<212> TYPE: DNA
<213> ORGANISM: Artificial Sequence
<220> FEATURE:
<223> OTHER INFORMATION: MGG3 VL nuc

<400> SEQUENCE: 81
gatattgtga tgacccagac tccactctct ctgtccgtca cccctggaca gccggcctcc    60
atctcctgca gtctagtca gagcctccta catagtgatg aaacaccta tttgtcttgg   120 tacctgcaga agccaggcca gtctccacag ctcctgatct atgaagtttc agccggttc   180 tctggagtgc cagataggtt cagcggcagc gggtcaggga cagatttcac actgaaaatc  240
agccgggtgg aggctgacga tgttggggtt tactactgca tgcaaggcat acactcgtgg  300
acgttcggcc aagggaccaa ggtggaaatc aaac                               334

<210> SEQ ID NO 82
<211> LENGTH: 8
<212> TYPE: PRT
<213> ORGANISM: Artificial Sequence

```
<220> FEATURE:
<223> OTHER INFORMATION: MGG4 CDRH1 aa

<400> SEQUENCE: 82

Gly Phe Arg Phe Ser Asp Tyr Gly
1               5

<210> SEQ ID NO 83
<211> LENGTH: 8
<212> TYPE: PRT
<213> ORGANISM: Artificial Sequence
<220> FEATURE:
<223> OTHER INFORMATION: MGG4 CDRH2 aa

<400> SEQUENCE: 83

Ile Trp Tyr Asp Gly Ser Asn Glu
1               5

<210> SEQ ID NO 84
<211> LENGTH: 14
<212> TYPE: PRT
<213> ORGANISM: Artificial Sequence
<220> FEATURE:
<223> OTHER INFORMATION: MGG4 CDRH3 aa

<400> SEQUENCE: 84

Ala Lys Leu Leu Val Gly Ile Thr Thr Asp Val Phe Asp Val
1               5                   10

<210> SEQ ID NO 85
<211> LENGTH: 12
<212> TYPE: PRT
<213> ORGANISM: Artificial Sequence
<220> FEATURE:
<223> OTHER INFORMATION: MGG4 CDRL1 aa

<400> SEQUENCE: 85

Gln Ser Val Leu Ser Ser Ser Asn Asn Lys Asn Tyr
1               5                   10

<210> SEQ ID NO 86

<400> SEQUENCE: 86

000

<210> SEQ ID NO 87
<211> LENGTH: 9
<212> TYPE: PRT
<213> ORGANISM: Artificial Sequence
<220> FEATURE:
<223> OTHER INFORMATION: MGG4 CDRL2 long aa

<400> SEQUENCE: 87

Leu Ile Tyr Trp Ala Ser Thr Arg Glu
1               5

<210> SEQ ID NO 88
<211> LENGTH: 9
<212> TYPE: PRT
<213> ORGANISM: Artificial Sequence
<220> FEATURE:
<223> OTHER INFORMATION: MGG4 CDRL3 aa

<400> SEQUENCE: 88

Gln Gln Tyr Tyr Thr Ala Ser Pro Phe
1               5
```

<210> SEQ ID NO 89
<211> LENGTH: 121
<212> TYPE: PRT
<213> ORGANISM: Artificial Sequence
<220> FEATURE:
<223> OTHER INFORMATION: MGG4 VH aa

<400> SEQUENCE: 89

```
Gln Val Gln Leu Val Glu Ser Gly Gly Val Val Gln Pro Gly Arg
1               5                   10                  15

Ser Leu Arg Leu Ser Cys Ala Ala Ser Gly Phe Arg Phe Ser Asp Tyr
            20                  25                  30

Gly Met His Trp Val Arg Gln Ala Pro Gly Lys Gly Leu Glu Trp Val
        35                  40                  45

Ala Leu Ile Trp Tyr Asp Gly Ser Asn Glu Ser Tyr Leu Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Asn Leu Arg Thr Glu Asp Thr Ala Val Tyr Tyr Cys
                85                  90                  95

Ala Lys Leu Leu Val Gly Ile Thr Thr Asp Val Phe Asp Val Trp Gly
            100                 105                 110

Gln Gly Thr Val Val Thr Val Ser Ser
        115                 120
```

<210> SEQ ID NO 90
<211> LENGTH: 113
<212> TYPE: PRT
<213> ORGANISM: Artificial Sequence
<220> FEATURE:
<223> OTHER INFORMATION: MGG4 VL aa

<400> SEQUENCE: 90

```
Asp Ile Val Met Thr Gln Ser Pro Asp Ser Leu Ala Val Ser Leu Gly
1               5                   10                  15

Glu Arg Ala Thr Ile Asn Cys Arg Ser Ser Gln Ser Val Leu Ser Ser
            20                  25                  30

Ser Asn Asn Lys Asn Tyr Leu Ala Trp Tyr Gln His Lys Pro Arg Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Thr Ala Ser Pro Phe Phe Gly Gly Thr Lys Val Glu Ile
            100                 105                 110

Lys
```

<210> SEQ ID NO 91
<211> LENGTH: 24
<212> TYPE: DNA
<213> ORGANISM: Artificial Sequence
<220> FEATURE:
<223> OTHER INFORMATION: MGG4 CDRH1 nuc

<400> SEQUENCE: 91
ggattcaggt tcagtgacta tggc                                    24

<210> SEQ ID NO 92
<211> LENGTH: 24
<212> TYPE: DNA
<213> ORGANISM: Artificial Sequence
<220> FEATURE:
<223> OTHER INFORMATION: MGG4 CDRH2 nuc

<400> SEQUENCE: 92
atatggtatg atggaagtaa tgaa                                           24

<210> SEQ ID NO 93
<211> LENGTH: 42
<212> TYPE: DNA
<213> ORGANISM: Artificial Sequence
<220> FEATURE:
<223> OTHER INFORMATION: MGG4 CDRH3 nuc

<400> SEQUENCE: 93
gcgaaactac tagtgggaat tactactgat gttttttgatg tc                      42

<210> SEQ ID NO 94
<211> LENGTH: 36
<212> TYPE: DNA
<213> ORGANISM: Artificial Sequence
<220> FEATURE:
<223> OTHER INFORMATION: MGG4 CDRL1 nuc

<400> SEQUENCE: 94
cagagtgttt tatccagctc caacaataag aactac                              36

<210> SEQ ID NO 95

<400> SEQUENCE: 95

000

<210> SEQ ID NO 96
<211> LENGTH: 27
<212> TYPE: DNA
<213> ORGANISM: Artificial Sequence
<220> FEATURE:
<223> OTHER INFORMATION: MGG4 CDRL2 long nuc

<400> SEQUENCE: 96
ctcatttact gggcatctac ccgggaa                                        27

<210> SEQ ID NO 97
<211> LENGTH: 26
<212> TYPE: DNA
<213> ORGANISM: Artificial Sequence
<220> FEATURE:
<223> OTHER INFORMATION: MGG4 CDRL3 nuc

<400> SEQUENCE: 97
cagcaatatt atactgcttc cccatt                                         26

<210> SEQ ID NO 98
<211> LENGTH: 364
<212> TYPE: DNA
<213> ORGANISM: Artificial Sequence
<220> FEATURE:
<223> OTHER INFORMATION: MGG4 VH nuc

<400> SEQUENCE: 98
caggtgcagc tggtggagtc tgggggaggc gtggtccagc ctggagggtc cctgagactc    60

```
tcctgtgcag cctctggatt caggttcagt gactatggca tgcactgggt ccgccaggct    120
ccgggcaagg ggctggagtg ggtggcactt atatggtatg atggaagtaa tgaatcctat    180
ttagactccg tgaagggccg attcaccatc tccagagaca attccaagaa cacactgtat    240
ctgcaaatga caacctgag aactgaggac acggctgtgt attactgtgc gaaactacta    300
gtgggaatta ctactgatgt ttttgatgtc tggggccaag ggacagtggt caccgtctct    360
tcag                                                                 364
```

<210> SEQ ID NO 99
<211> LENGTH: 340
<212> TYPE: DNA
<213> ORGANISM: Artificial Sequence
<220> FEATURE:
<223> OTHER INFORMATION: MGG4 VL nuc

<400> SEQUENCE: 99

```
gacatcgtga tgacccagtc tccagactcc ctggctgtgt ctctgggcga gagggccacc     60
atcaactgca ggtccagcca gagtgtttta tccagctcca acaataagaa ctacttagct    120
tggtaccagc acaaaccacg acagcctcct aaactgctca tttactgggc atctacccgg    180
gaatccgggg tccctgaccg attcagtggc agcgggtctg ggacagattt cactctcacc    240
atcagcagcc tgcaggctga agatgtggca gtttattact gtcagcaata ttatactgct    300
tccccatttt tcggcggagg gaccaaggta gagatcaaac                          340
```

<210> SEQ ID NO 100
<211> LENGTH: 8
<212> TYPE: PRT
<213> ORGANISM: Artificial Sequence
<220> FEATURE:
<223> OTHER INFORMATION: MGG8 CDRH1 aa

<400> SEQUENCE: 100

Gly Phe Met Ile Ser Gly Ser Val
1               5

<210> SEQ ID NO 101
<211> LENGTH: 10
<212> TYPE: PRT
<213> ORGANISM: Artificial Sequence
<220> FEATURE:
<223> OTHER INFORMATION: MGG8 CDRH2 aa

<400> SEQUENCE: 101

Ile Arg Asp Lys Ala Asn Asn Glu Ala Thr
1               5                   10

<210> SEQ ID NO 102
<211> LENGTH: 14
<212> TYPE: PRT
<213> ORGANISM: Artificial Sequence
<220> FEATURE:
<223> OTHER INFORMATION: MGG8 CDRH3 aa

<400> SEQUENCE: 102

Thr Arg Gly Ile Ile Val Gly Asp Thr Trp His Phe Asp Pro
1               5                   10

<210> SEQ ID NO 103
<211> LENGTH: 11
<212> TYPE: PRT
<213> ORGANISM: Artificial Sequence

```
<220> FEATURE:
<223> OTHER INFORMATION: MGG8 CDRL1 aa

<400> SEQUENCE: 103

Glu Ser Leu Leu Arg Ser Asp Gly Lys Thr Tyr
1               5                   10

<210> SEQ ID NO 104

<400> SEQUENCE: 104

000

<210> SEQ ID NO 105
<211> LENGTH: 9
<212> TYPE: PRT
<213> ORGANISM: Artificial Sequence
<220> FEATURE:
<223> OTHER INFORMATION: MGG8 CDRL2 long aa

<400> SEQUENCE: 105

Leu Met Tyr Glu Val Ser Lys Arg Phe
1               5

<210> SEQ ID NO 106
<211> LENGTH: 8
<212> TYPE: PRT
<213> ORGANISM: Artificial Sequence
<220> FEATURE:
<223> OTHER INFORMATION: MGG8 CDRL3 aa

<400> SEQUENCE: 106

Met Gln Ser Ile Gln Leu Val Thr
1               5

<210> SEQ ID NO 107
<211> LENGTH: 123
<212> TYPE: PRT
<213> ORGANISM: Artificial Sequence
<220> FEATURE:
<223> OTHER INFORMATION: MGG8 VH aa

<400> SEQUENCE: 107

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Met Ile Ser Gly Ser
                20                  25                  30

Val Leu His Trp Val Arg Gln Ala Ser Gly Lys Gly Leu Glu Trp Leu
            35                  40                  45

Gly Arg Ile Arg Asp Lys Ala Asn Asn Glu Ala Thr Ala Tyr Ala Ala
        50                  55                  60

Ser Val Lys Gly Arg Phe Thr Ile Ser Arg Asp Asp Ser Lys Asp Thr
65                  70                  75                  80

Thr Tyr Leu Gln Met Asn Ser Leu Arg Ile Glu Asp Thr Ala Val Tyr
                85                  90                  95

Tyr Cys Thr Arg Gly Ile Ile Val Gly Asp Thr Trp His Phe Asp Pro
            100                 105                 110

Trp Gly Gln Gly Thr Leu Val Thr Val Ser Ser
        115                 120

<210> SEQ ID NO 108
<211> LENGTH: 111
<212> TYPE: PRT
```

<213> ORGANISM: Artificial Sequence
<220> FEATURE:
<223> OTHER INFORMATION: MGG8 VL aa

<400> SEQUENCE: 108

Asp Ile Val Met Thr Gln Thr Pro Leu Ser Leu Ser Val Thr Pro Gly
1               5                   10                  15

Gln Thr Ala Ser Ile Ser Cys Lys Ser Ser Glu Ser Leu Leu Arg Ser
            20                  25                  30

Asp Gly Lys Thr Tyr Leu Tyr Trp Tyr Leu Gln Lys Pro Gly Gln Ser
        35                  40                  45

Pro Gln Leu Leu Met Tyr Glu Val Ser Lys Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Thr Asp Asp Val Gly Ile Tyr Tyr Cys Met Gln Ser
                85                  90                  95

Ile Gln Leu Val Thr Phe Gly Gln Gly Thr Lys Val Glu Ile Lys
            100                 105                 110

<210> SEQ ID NO 109
<211> LENGTH: 24
<212> TYPE: DNA
<213> ORGANISM: Artificial Sequence
<220> FEATURE:
<223> OTHER INFORMATION: MGG8 CDRH1 nuc

<400> SEQUENCE: 109
gggttcatga tcagtggctc tgtt                                          24

<210> SEQ ID NO 110
<211> LENGTH: 30
<212> TYPE: DNA
<213> ORGANISM: Artificial Sequence
<220> FEATURE:
<223> OTHER INFORMATION: MGG8 CDRH2 nuc

<400> SEQUENCE: 110
attagagaca agctaacaa tgaggcgaca                                     30

<210> SEQ ID NO 111
<211> LENGTH: 42
<212> TYPE: DNA
<213> ORGANISM: Artificial Sequence
<220> FEATURE:
<223> OTHER INFORMATION: MGG8 CDRH3 nuc

<400> SEQUENCE: 111
acgaggggta tcatagtagg tgacacctgg cacttcgacc cc                      42

<210> SEQ ID NO 112
<211> LENGTH: 32
<212> TYPE: DNA
<213> ORGANISM: Artificial Sequence
<220> FEATURE:
<223> OTHER INFORMATION: MGG8 CDRL1 nuc

<400> SEQUENCE: 112
gagagcctcc tgagaagcga tggaaagacc ta                                 32

<210> SEQ ID NO 113

<400> SEQUENCE: 113

000

<210> SEQ ID NO 114
<211> LENGTH: 27
<212> TYPE: DNA
<213> ORGANISM: Artificial Sequence
<220> FEATURE:
<223> OTHER INFORMATION: MGG8 CDRL2 long nuc

<400> SEQUENCE: 114
ctgatgtatg aagtttccaa gcgcttc                                27

<210> SEQ ID NO 115
<211> LENGTH: 24
<212> TYPE: DNA
<213> ORGANISM: Artificial Sequence
<220> FEATURE:
<223> OTHER INFORMATION: MGG8 CDRL3 nuc

<400> SEQUENCE: 115
atgcaaagta tacagcttgt gact                                   24

<210> SEQ ID NO 116
<211> LENGTH: 370
<212> TYPE: DNA
<213> ORGANISM: Artificial Sequence
<220> FEATURE:
<223> OTHER INFORMATION: MGG8 VH nuc

<400> SEQUENCE: 116
gaagtgcagc tggtggagtc cggggaggc ctggtccagc ctgggggtc cctgaaactc         60 tcctgtgcag cctctgggtt catgatcagt ggctctgttc tacactgggt ccgccaggcc      120
tccgggaaag gctggagtg gcttggccgt attagagaca agctaacaa tgaggcgaca        180 gcatatgcag cgtcggtgaa aggcaggttc accatctcca gagatgattc aaaggacacg     240
acatatctgc aaatgaacag cctgagaatc gaggacacgg ccgtgtatta ctgtacgagg     300
ggtatcatag taggtgacac ctggcacttc gaccccctggg gccagggaac cctggtcacc   360
gtctcctcag                                                           370

<210> SEQ ID NO 117
<211> LENGTH: 334
<212> TYPE: DNA
<213> ORGANISM: Artificial Sequence
<220> FEATURE:
<223> OTHER INFORMATION: MGG8 VL nuc

<400> SEQUENCE: 117
gatattgtga tgacccagac tccactctct ctgtccgtca cccctggaca gacggcctcc      60
atctcctgca agtctagtga gagcctcctg agaagcgatg gaaagaccta cttgtattgg    120
tatctgcaga agccaggcca gtctccacag ctcctgatgt atgaagtttc caagcgcttc    180
tctggagtgc cagataggtt cagtggcagc gggtcaggaa cagattttac actgaaaatc   240
agccgggtgg agactgatga tgttggcatt tattactgca tgcaaagtat acagcttgtg   300
actttcggcc aagggaccaa ggtggaaatc aaac                               334

<210> SEQ ID NO 118
<211> LENGTH: 8
<212> TYPE: PRT
<213> ORGANISM: Artificial Sequence
<220> FEATURE:

<223> OTHER INFORMATION: MGH1 CDRH1 aa

<400> SEQUENCE: 118

Gly Tyr Thr Phe Thr Asp Tyr Tyr
1               5

<210> SEQ ID NO 119
<211> LENGTH: 8
<212> TYPE: PRT
<213> ORGANISM: Artificial Sequence
<220> FEATURE:
<223> OTHER INFORMATION: MGH1 CDRH2 aa

<400> SEQUENCE: 119

Ile Asn Pro Tyr Ile Gly Val Ser
1               5

<210> SEQ ID NO 120
<211> LENGTH: 11
<212> TYPE: PRT
<213> ORGANISM: Artificial Sequence
<220> FEATURE:
<223> OTHER INFORMATION: MGH1 CDRH3 aa

<400> SEQUENCE: 120

Ala Ala Cys Ser Asn Val Gly Cys Tyr Val Tyr
1               5                   10

<210> SEQ ID NO 121
<211> LENGTH: 11
<212> TYPE: PRT
<213> ORGANISM: Artificial Sequence
<220> FEATURE:
<223> OTHER INFORMATION: MGH1 CDRL1 aa

<400> SEQUENCE: 121

Gln Ser Leu Val Tyr Ser Asp Gly Asn Thr Tyr
1               5                   10

<210> SEQ ID NO 122

<400> SEQUENCE: 122

000

<210> SEQ ID NO 123
<211> LENGTH: 9
<212> TYPE: PRT
<213> ORGANISM: Artificial Sequence
<220> FEATURE:
<223> OTHER INFORMATION: MGH1 CDRL2 long aa

<400> SEQUENCE: 123

Leu Ile Tyr Lys Val Ser Asn Arg Asp
1               5

<210> SEQ ID NO 124
<211> LENGTH: 9
<212> TYPE: PRT
<213> ORGANISM: Artificial Sequence
<220> FEATURE:
<223> OTHER INFORMATION: MGH1 CDRL3 aa

<400> SEQUENCE: 124

Met Gln Gly Thr His Trp Pro Asp Thr
1               5

```
<210> SEQ ID NO 125
<211> LENGTH: 118
<212> TYPE: PRT
<213> ORGANISM: Artificial Sequence
<220> FEATURE:
<223> OTHER INFORMATION: MGH1 VH aa

<400> SEQUENCE: 125
```

| | | | | | | | | | | | | | | |
|---|---|---|---|---|---|---|---|---|---|---|---|---|---|---|
| Gln | Val | Gln | Leu | Val | Gln | Ser | Gly | Ala | Glu | Val | Lys | Lys | Pro | Gly | Ala |
| 1 | | | | 5 | | | | | 10 | | | | | 15 | |

Ser Val Arg Val Ser Cys Lys Thr Ser Gly Tyr Thr Phe Thr Asp Tyr
            20                  25                  30

Tyr Val His Trp Val Arg Gln Ala Pro Gly His Gly Leu Glu Cys Met
          35                  40                  45

Gly Trp Ile Asn Pro Tyr Ile Gly Val Ser Lys Tyr Ala Gln Lys Phe
  50                    55                  60

Gln Gly Arg Val Thr Leu Thr Arg Asp Thr Ser Ile Ser Thr Ala Tyr
65              70                  75                  80

Met Glu Ile Ser Arg Leu Thr Ser Asp Asp Thr Ala Val Tyr Tyr Cys
              85                  90              95

Ala Ala Cys Ser Asn Val Gly Cys Tyr Val Tyr Trp Gly Gln Gly Ser
          100                 105              110

Leu Val Thr Val Ser Ser
       115

```
<210> SEQ ID NO 126
<211> LENGTH: 112
<212> TYPE: PRT
<213> ORGANISM: Artificial Sequence
<220> FEATURE:
<223> OTHER INFORMATION: MGH1 VL aa

<400> SEQUENCE: 126
```

Asp Val Val Met Thr Gln Ser Pro Leu Ser Leu Pro Val Thr Leu Gly
1              5                  10                  15

Gln Pro Ala Ser Ile Ser Cys Arg Ser Ser Gln Ser Leu Val Tyr Ser
          20                  25                  30

Asp Gly Asn Thr Tyr Leu Asn Trp Phe Gln Gln Arg Pro Gly Gln Ser
          35                  40                  45

Pro Arg Arg Leu Ile Tyr Lys Val Ser Asn Arg Asp Ser Gly Val Pro
  50                    55                  60

Asp Arg Phe Ser Gly Ser Gly Ser Gly Thr Asp Phe Thr Leu Lys Ile
65              70                  75                  80

Ser Arg Val Glu Ala Glu Asp Val Ala Ile Tyr Phe Cys Met Gln Gly
              85                  90              95

Thr His Trp Pro Asp Thr Phe Gly Gln Gly Thr Lys Leu Glu Ile Lys
          100                 105              110

```
<210> SEQ ID NO 127
<211> LENGTH: 24
<212> TYPE: DNA
<213> ORGANISM: Artificial Sequence
<220> FEATURE:
<223> OTHER INFORMATION: MGH1 CDRH1 nuc

<400> SEQUENCE: 127
ggatacacgt tcaccgacta ctat                                        24

<210> SEQ ID NO 128
```

```
<211> LENGTH: 24
<212> TYPE: DNA
<213> ORGANISM: Artificial Sequence
<220> FEATURE:
<223> OTHER INFORMATION: MGH1 CDRH2 nuc

<400> SEQUENCE: 128
atcaatcctt acattggtgt ctca                                              24

<210> SEQ ID NO 129
<211> LENGTH: 33
<212> TYPE: DNA
<213> ORGANISM: Artificial Sequence
<220> FEATURE:
<223> OTHER INFORMATION: MGH1 CDRH3 nuc

<400> SEQUENCE: 129
gcggcttgta gtaacgttgg ctgctacgtc tat                                    33

<210> SEQ ID NO 130
<211> LENGTH: 33
<212> TYPE: DNA
<213> ORGANISM: Artificial Sequence
<220> FEATURE:
<223> OTHER INFORMATION: MGH1 CDRL1 nuc

<400> SEQUENCE: 130
caaagtctcg tgtacagtga tggaaacacc tac                                    33

<210> SEQ ID NO 131

<400> SEQUENCE: 131

000

<210> SEQ ID NO 132
<211> LENGTH: 27
<212> TYPE: DNA
<213> ORGANISM: Artificial Sequence
<220> FEATURE:
<223> OTHER INFORMATION: MGH1 CDRL2 long nuc

<400> SEQUENCE: 132
ctaatttata aggtttctaa tcgggac                                           27

<210> SEQ ID NO 133
<211> LENGTH: 27
<212> TYPE: DNA
<213> ORGANISM: Artificial Sequence
<220> FEATURE:
<223> OTHER INFORMATION: MGH1 CDRL3 nuc

<400> SEQUENCE: 133
atgcaaggta cacactggcc tgacact                                           27

<210> SEQ ID NO 134
<211> LENGTH: 355
<212> TYPE: DNA
<213> ORGANISM: Artificial Sequence
<220> FEATURE:
<223> OTHER INFORMATION: MGH1 VH nuc

<400> SEQUENCE: 134
caggtgcagc tggtgcagtc tggggctgag gtgaagaagc ctggggcctc agtgagagtc       60
tcctgcaaga catctggata cacgttcacc gactactatg tccactgggt gcgacaggcc     120
```

```
ccaggacacg ggcttgagtg catgggctgg atcaatcctt acattggtgt ctcaaagtat    180
gcacagaagt tcagggcag ggtcaccttg accagggaca cgtccatcag cacagcctac    240
atggaaatta gcaggctaac atctgacgac acggccgtct attactgtgc ggcttgtagt    300
aacgttggct gctacgtcta ttggggccag ggatcgctgg tcaccgtctc ctcag         355
```

```
<210> SEQ ID NO 135
<211> LENGTH: 337
<212> TYPE: DNA
<213> ORGANISM: Artificial Sequence
<220> FEATURE:
<223> OTHER INFORMATION: MGH1 VL nuc

<400> SEQUENCE: 135
gatgttgtga tgactcagtc tccactctcc ctgcccgtca cccttggaca gccggcctcc    60
atctcctgca ggtctagtca agtctcgtg tacagtgatg gaaacaccta cttgaattgg    120
tttcagcaga ggccaggcca atctccaagg cgcctaattt ataaggtttc taatcgggac    180
tctggggtcc cagacagatt cagcggcagt gggtcaggca ctgatttcac actgaaaatc    240
agcagggtgg aggctgagga tgttgcgatt tatttctgca tgcaaggtac acactggcct    300 gacactttg gccaggggac caaactggag atcaaac                              337
```

```
<210> SEQ ID NO 136
<211> LENGTH: 8
<212> TYPE: PRT
<213> ORGANISM: Artificial Sequence
<220> FEATURE:
<223> OTHER INFORMATION: MGH2 CDRH1 aa

<400> SEQUENCE: 136

Gly Phe Ser Phe Ser Ser Tyr Ala
1               5
```

```
<210> SEQ ID NO 137
<211> LENGTH: 8
<212> TYPE: PRT
<213> ORGANISM: Artificial Sequence
<220> FEATURE:
<223> OTHER INFORMATION: MGH2 CDRH2 aa

<400> SEQUENCE: 137

Thr Arg Tyr Asp Gly Ser Asn Lys
1               5
```

```
<210> SEQ ID NO 138
<211> LENGTH: 14
<212> TYPE: PRT
<213> ORGANISM: Artificial Sequence
<220> FEATURE:
<223> OTHER INFORMATION: MGH2 CDRH3 aa

<400> SEQUENCE: 138

Ala Lys Val Gly Asp Gly Thr Val Ala Gly Thr Ile Asp Tyr
1               5                   10
```

```
<210> SEQ ID NO 139
<211> LENGTH: 11
<212> TYPE: PRT
<213> ORGANISM: Artificial Sequence
<220> FEATURE:
<223> OTHER INFORMATION: MGH2 CDRL1 aa

<400> SEQUENCE: 139
```

Gln Ser Leu Val Tyr Ser Asp Gly Asn Thr Tyr
1               5                   10

<210> SEQ ID NO 140

<400> SEQUENCE: 140

000

<210> SEQ ID NO 141
<211> LENGTH: 9
<212> TYPE: PRT
<213> ORGANISM: Artificial Sequence
<220> FEATURE:
<223> OTHER INFORMATION: MGH2 CDRL2 long aa

<400> SEQUENCE: 141

Leu Ile Tyr Lys Val Ser Asn Arg Asp
1               5

<210> SEQ ID NO 142
<211> LENGTH: 8
<212> TYPE: PRT
<213> ORGANISM: Artificial Sequence
<220> FEATURE:
<223> OTHER INFORMATION: MGH2 CDRL3 aa

<400> SEQUENCE: 142

Met Gln Gly Thr His Trp Trp Thr
1               5

<210> SEQ ID NO 143
<211> LENGTH: 121
<212> TYPE: PRT
<213> ORGANISM: Artificial Sequence
<220> FEATURE:
<223> OTHER INFORMATION: MGH2 VH aa

<400> SEQUENCE: 143

Gln Val Gln Leu Val Glu Ser Gly Gly Gly Val Val Gln Pro Gly Gly
1               5                   10                  15

Ser Leu Arg Leu Ser Cys Thr Ala Ser Gly Phe Ser Phe Ser Ser Tyr
            20                  25                  30

Ala Met His Trp Val Arg Gln Ala Pro Gly Lys Gly Leu Glu Trp Val
        35                  40                  45

Ala Tyr Thr Arg Tyr Asp Gly Ser Asn Lys Phe Tyr Leu Asp Ser Val
    50                  55                  60

Gln Gly Arg Phe Thr Ile Ser Arg Asp Asn Ser Lys Asn Thr Leu Tyr
65                  70                  75                  80

Leu Glu Met Asp Ser Leu Arg Leu Glu Asp Thr Ala Val Tyr Phe Cys
                85                  90                  95

Ala Lys Val Gly Asp Gly Thr Val Ala Gly Thr Ile Asp Tyr Trp Gly
            100                 105                 110

Gln Gly Thr Leu Val Thr Val Ser Ser
        115                 120

<210> SEQ ID NO 144
<211> LENGTH: 111
<212> TYPE: PRT
<213> ORGANISM: Artificial Sequence
<220> FEATURE:
<223> OTHER INFORMATION: MGH2 VL aa

<400> SEQUENCE: 144

```
Tyr Ile Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Tyr Gln Gln Arg Pro Gly Gln Ser
            35                  40                  45

Pro Arg Arg Leu Ile Tyr Lys Val Ser Asn Arg Asp Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Trp Thr Phe Gly Gln Gly Thr Lys Val Glu Ile Lys
            100                 105                 110
```

<210> SEQ ID NO 145
<211> LENGTH: 24
<212> TYPE: DNA
<213> ORGANISM: Artificial Sequence
<220> FEATURE:
<223> OTHER INFORMATION: MGH2 CDRH1 nuc

<400> SEQUENCE: 145
ggtttcagct tcagtagtta tgcc                                    24

<210> SEQ ID NO 146
<211> LENGTH: 24
<212> TYPE: DNA
<213> ORGANISM: Artificial Sequence
<220> FEATURE:
<223> OTHER INFORMATION: MGH2 CDRH2 nuc

<400> SEQUENCE: 146
acacggtatg atggaagtaa taag                                    24

<210> SEQ ID NO 147
<211> LENGTH: 41
<212> TYPE: DNA
<213> ORGANISM: Artificial Sequence
<220> FEATURE:
<223> OTHER INFORMATION: MGH2 CDRH3 nuc

<400> SEQUENCE: 147
gcgaaagtgg gggacgggac agtggctggt actattgact a                 41

<210> SEQ ID NO 148
<211> LENGTH: 33
<212> TYPE: DNA
<213> ORGANISM: Artificial Sequence
<220> FEATURE:
<223> OTHER INFORMATION: MGH2 CDRL1 nuc

<400> SEQUENCE: 148
caaagcctcg tatatagtga tggaaacacc tac                          33

<210> SEQ ID NO 149

<400> SEQUENCE: 149

000

<210> SEQ ID NO 150

```
<211> LENGTH: 27
<212> TYPE: DNA
<213> ORGANISM: Artificial Sequence
<220> FEATURE:
<223> OTHER INFORMATION: MGH2 CDRL2 long nuc

<400> SEQUENCE: 150
ctaatttata aggtttctaa tcgggac                                           27

<210> SEQ ID NO 151
<211> LENGTH: 24
<212> TYPE: DNA
<213> ORGANISM: Artificial Sequence
<220> FEATURE:
<223> OTHER INFORMATION: MGH2 CDRL3 nuc

<400> SEQUENCE: 151
atgcaaggta cacactggtg gacg                                              24

<210> SEQ ID NO 152
<211> LENGTH: 364
<212> TYPE: DNA
<213> ORGANISM: Artificial Sequence
<220> FEATURE:
<223> OTHER INFORMATION: MGH2 VH nuc

<400> SEQUENCE: 152
caggtgcagc tggtggagtc tgggggaggc gtggtccagc ctggggggtc cctgagactc        60
tcctgtacag cgtctggttt cagcttcagt agttatgcca tgcactgggt ccgccaggct       120
ccaggcaagg gactggagtg ggtggcatat acacggtatg atggaagtaa taagttctac       180
ctagactccg tgcagggccg attcaccatc tccagagaca attccaagaa cacgctgtat       240
ctggaaatgg acagcctgag acttgaggac acggctgtct atttctgtgc gaaagtgggg       300
gacgggacag tggctggtac tattgactac tggggccagg aacgctggt caccgtctcc       360 tcag                                                                   364

<210> SEQ ID NO 153
<211> LENGTH: 334
<212> TYPE: DNA
<213> ORGANISM: Artificial Sequence
<220> FEATURE:
<223> OTHER INFORMATION: MGH2 VL nuc

<400> SEQUENCE: 153
tatattgtga tgactcagtc tccactctcc ctgcccgtca cccttggaca gccggcctcc        60
atctcctgca ggtctagtca agcctcgta tatagtgatg aaacaccta cttgaattgg        120 tatcagcaga ggccaggcca atctccaagg cgcctaattt ataaggtttc taatcgggac       180
tctggggtcc cagacagatt tagcggcagt gggtcaggca ctgatttcac actgaaaatc       240
agcagggtgg aggctgagga tgttggggtt tattactgca tgcaaggtac acactggtgg       300
acgttcggcc aagggaccaa ggtggaaatc aaac                                   334

<210> SEQ ID NO 154
<211> LENGTH: 8
<212> TYPE: PRT
<213> ORGANISM: Artificial Sequence
<220> FEATURE:
<223> OTHER INFORMATION: MGH3 CDRH1 aa

<400> SEQUENCE: 154

Gly Phe Thr Phe Ser Ser Tyr Thr
```

<210> SEQ ID NO 155
<211> LENGTH: 8
<212> TYPE: PRT
<213> ORGANISM: Artificial Sequence
<220> FEATURE:
<223> OTHER INFORMATION: MGH3 CDRH2 aa

<400> SEQUENCE: 155

Ile Ser Ser Ser Gly Ser Tyr Ile
1               5

<210> SEQ ID NO 156
<211> LENGTH: 16
<212> TYPE: PRT
<213> ORGANISM: Artificial Sequence
<220> FEATURE:
<223> OTHER INFORMATION: MGH3 CDRH3 aa

<400> SEQUENCE: 156

Ala Arg Asn Val Leu Asp Ser Ser Gly Tyr Pro Thr Tyr Phe Asp Tyr
1               5                   10                  15

<210> SEQ ID NO 157
<211> LENGTH: 11
<212> TYPE: PRT
<213> ORGANISM: Artificial Sequence
<220> FEATURE:
<223> OTHER INFORMATION: MGH3 CDRL1 aa

<400> SEQUENCE: 157

Gln Ser Leu Leu Tyr Ser Asn Gly Tyr Asn Tyr
1               5                   10

<210> SEQ ID NO 158

<400> SEQUENCE: 158

000

<210> SEQ ID NO 159
<211> LENGTH: 9
<212> TYPE: PRT
<213> ORGANISM: Artificial Sequence
<220> FEATURE:
<223> OTHER INFORMATION: MGH3 CDRL2 long aa

<400> SEQUENCE: 159

Leu Ile Tyr Leu Gly Ser Asn Arg Ala
1               5

<210> SEQ ID NO 160
<211> LENGTH: 9
<212> TYPE: PRT
<213> ORGANISM: Artificial Sequence
<220> FEATURE:
<223> OTHER INFORMATION: MGH3 CDRL3 aa

<400> SEQUENCE: 160

Met Gln Ala Val Gln Thr Pro Leu Thr
1               5

<210> SEQ ID NO 161
<211> LENGTH: 123
<212> TYPE: PRT
<213> ORGANISM: Artificial Sequence
<220> FEATURE:
<223> OTHER INFORMATION: MGH3 VH aa

<400> SEQUENCE: 161

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Thr Met Asn Trp Val Arg Gln Ala Pro Gly Lys Gly Leu Glu Trp Val
        35                  40                  45

Ser Ser Ile Ser Ser Ser Gly Ser Tyr Ile Tyr Tyr Ala Asp Ser Val
    50                  55                  60

Lys Gly Arg Cys Thr Ile Ser Arg Asp Asn Ala Lys Asn Ser Leu Asp
65                  70                  75                  80

Leu Gln Met Asn Ser Leu Arg Ala Glu Asp Ala Ala Val Tyr Tyr Cys
                85                  90                  95

Ala Arg Asn Val Leu Asp Ser Ser Gly Tyr Pro Thr Tyr Phe Asp Tyr
            100                 105                 110

Trp Gly Gln Gly Thr Leu Val Thr Val Ser Ser
        115                 120

<210> SEQ ID NO 162
<211> LENGTH: 112
<212> TYPE: PRT
<213> ORGANISM: Artificial Sequence
<220> FEATURE:
<223> OTHER INFORMATION: MGH3 VL aa

<400> SEQUENCE: 162

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Ser
            20                  25                  30

Asn Gly Tyr Asn Tyr Leu Asp Trp Tyr Val Gln Lys Pro Gly Gln Ser
        35                  40                  45

Pro Arg Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Val Gly Phe Tyr Tyr Cys Met Gln Ala
                85                  90                  95

Val Gln Thr Pro Leu Thr Phe Gly Gly Gly Thr Lys Val Glu Ile Lys
            100                 105                 110

<210> SEQ ID NO 163
<211> LENGTH: 24
<212> TYPE: DNA
<213> ORGANISM: Artificial Sequence
<220> FEATURE:
<223> OTHER INFORMATION: MGH3 CDRH1 nuc

<400> SEQUENCE: 163
ggattcacct tcagtagtta tacc                                    24

<210> SEQ ID NO 164
<211> LENGTH: 24
<212> TYPE: DNA
<213> ORGANISM: Artificial Sequence
<220> FEATURE:
<223> OTHER INFORMATION: MGH3 CDRH2 nuc

```
<400> SEQUENCE: 164
attagtagta gtggtagtta cata                                           24

<210> SEQ ID NO 165
<211> LENGTH: 48
<212> TYPE: DNA
<213> ORGANISM: Artificial Sequence
<220> FEATURE:
<223> OTHER INFORMATION: MGH3 CDRH3 nuc

<400> SEQUENCE: 165
gcaagaaatg tcttggacag tagtggttac cccacgtact ttgactat                 48

<210> SEQ ID NO 166
<211> LENGTH: 32
<212> TYPE: DNA
<213> ORGANISM: Artificial Sequence
<220> FEATURE:
<223> OTHER INFORMATION: MGH3 CDRL1 nuc

<400> SEQUENCE: 166
agagcctcct atatagtaat ggatacaact at                                  32

<210> SEQ ID NO 167

<400> SEQUENCE: 167

000

<210> SEQ ID NO 168
<211> LENGTH: 27
<212> TYPE: DNA
<213> ORGANISM: Artificial Sequence
<220> FEATURE:
<223> OTHER INFORMATION: MGH3 CDRL2 long nuc

<400> SEQUENCE: 168
ctgatctatt tgggttctaa tcgggcc                                        27

<210> SEQ ID NO 169
<211> LENGTH: 27
<212> TYPE: DNA
<213> ORGANISM: Artificial Sequence
<220> FEATURE:
<223> OTHER INFORMATION: MGH3 CDRL3 nuc

<400> SEQUENCE: 169
atgcaagctg tacaaactcc cctcact                                        27

<210> SEQ ID NO 170
<211> LENGTH: 370
<212> TYPE: DNA
<213> ORGANISM: Artificial Sequence
<220> FEATURE:
<223> OTHER INFORMATION: MGH3 VH nuc

<400> SEQUENCE: 170
gaggtgcagc tggtggagtc tgggggaggc ctggtcaagc ctggggggtc cctgagactc    60
tcctgtgcag cctctggatt caccttcagt agttatacca tgaactgggt ccgccaggct   120
ccagggaagg ggctggagtg ggtctcatcc attagtagta gtggtagtta catatattac   180
gcagactcag tgaagggccg atgcaccatc tccagagaca cgccaagaa ctcactggat    240 ctgcaaatga acagcctgag agccgaggac gcggctgtgt attactgtgc aagaaatgtc   300
```

```
ttggacagta gtggttaccc cacgtactt  gactattggg gccagggaac gctggtcacc    360
gtctcctcag                                                          370

<210> SEQ ID NO 171
<211> LENGTH: 337
<212> TYPE: DNA
<213> ORGANISM: Artificial Sequence
<220> FEATURE:
<223> OTHER INFORMATION: MGH3 VL nuc

<400> SEQUENCE: 171
gatattgtga tgactcagtc tccactctcc ctgcccgtca cccctggaga gccggcctcc    60
atctcctgca ggtctagtca gagcctccta tatagtaatg gatacaacta tctggattgg   120
tacgtgcaga agccagggca gtctccacgc ctcctgatct atttgggttc taatcgggcc   180
tccggggtcc ctgacaggtt cagtggcagt ggatcaggca cagatttac  actgagaatc   240 agcagagtgg aggctgagga tgttggggtt tattactgca tgcaagctgt acaaactccc   300
ctcactttcg gcggagggac caaggtggag atcaaac                            337

<210> SEQ ID NO 172
<211> LENGTH: 8
<212> TYPE: PRT
<213> ORGANISM: Artificial Sequence
<220> FEATURE:
<223> OTHER INFORMATION: MGU1 CDRH1 aa

<400> SEQUENCE: 172

Gly Phe Ala Phe Ser Ser Tyr Gly
1               5

<210> SEQ ID NO 173
<211> LENGTH: 8
<212> TYPE: PRT
<213> ORGANISM: Artificial Sequence
<220> FEATURE:
<223> OTHER INFORMATION: MGU1 CDRH2 aa

<400> SEQUENCE: 173

Ile Trp His Asp Gly Thr Asn Lys
1               5

<210> SEQ ID NO 174
<211> LENGTH: 14
<212> TYPE: PRT
<213> ORGANISM: Artificial Sequence
<220> FEATURE:
<223> OTHER INFORMATION: MGU1 CDRH3 aa

<400> SEQUENCE: 174

Ala Ile Trp Tyr Leu Asp Ser Pro Asp His Gly Phe Asp Ile
1               5                   10

<210> SEQ ID NO 175
<211> LENGTH: 7
<212> TYPE: PRT
<213> ORGANISM: Artificial Sequence
<220> FEATURE:
<223> OTHER INFORMATION: MGU1 CDRL1 aa

<400> SEQUENCE: 175

Asn Gly His Ser Ser Asn Ala
1               5
```

<210> SEQ ID NO 176
<211> LENGTH: 7
<212> TYPE: PRT
<213> ORGANISM: Artificial Sequence
<220> FEATURE:
<223> OTHER INFORMATION: MGU1 CDRL2 aa

<400> SEQUENCE: 176

Val Asn Ser Asp Gly Ser His
1               5

<210> SEQ ID NO 177
<211> LENGTH: 9
<212> TYPE: PRT
<213> ORGANISM: Artificial Sequence
<220> FEATURE:
<223> OTHER INFORMATION: MGU1 CDRL3 aa

<400> SEQUENCE: 177

Gln Ala Trp Asp Ser Gly Ile Trp Val
1               5

<210> SEQ ID NO 178
<211> LENGTH: 121
<212> TYPE: PRT
<213> ORGANISM: Artificial Sequence
<220> FEATURE:
<223> OTHER INFORMATION: MGU1 VH aa

<400> SEQUENCE: 178

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ala Phe Ser Ser Tyr
            20                  25                  30

Gly Met Asn Trp Val Arg Gln Ala Pro Gly Lys Gly Leu Glu Trp Val
        35                  40                  45

Ala Val Ile Trp His Asp Gly Thr Asn Lys Tyr Tyr Arg Asp Ser Val
    50                  55                  60

Lys Gly Arg Phe Ile Ile Ser Arg Asp Asn Ala Lys Asn Thr Leu Tyr
65                  70                  75                  80

Leu Gln Met Asp Ser Leu Ser Ala Glu Asp Thr Ala Met Tyr Tyr Cys
                85                  90                  95

Ala Ile Trp Tyr Leu Asp Ser Pro Asp His Gly Phe Asp Ile Trp Gly
            100                 105                 110

Arg Gly Thr Met Val Thr Val Ser Ser
        115                 120

<210> SEQ ID NO 179
<211> LENGTH: 111
<212> TYPE: PRT
<213> ORGANISM: Artificial Sequence
<220> FEATURE:
<223> OTHER INFORMATION: MGU1 VL aa

<400> SEQUENCE: 179

Gln Leu Val Leu Thr Gln Ser Pro Ser Ala Ser Ala Ser Leu Gly Val
1               5                   10                  15

Ser Val Thr Leu Thr Cys Thr Leu Asn Asn Gly His Ser Ser Asn Ala
            20                  25                  30

Ile Ala Trp His Gln Gln Pro Gly Lys Gly Pro Arg Tyr Leu Met
        35                  40                  45

-continued

```
Lys Val Asn Ser Asp Gly Ser His Asn Lys Gly Ala Ala Val Pro Asp
 50                  55                  60

Arg Phe Ser Gly Ser Ser Ser Gly Thr Glu Arg His Leu Thr Ile Ser
 65                  70                  75                  80

Ser Leu Gln Ser Asp Asp Glu Ala Asp Tyr Tyr Cys Gln Ala Trp Asp
                 85                  90                  95

Ser Gly Ile Trp Val Phe Gly Gly Gly Thr Lys Leu Thr Val Leu
                100                 105                 110

<210> SEQ ID NO 180
<211> LENGTH: 24
<212> TYPE: DNA
<213> ORGANISM: Artificial Sequence
<220> FEATURE:
<223> OTHER INFORMATION: MGU1 CDRH1 nuc

<400> SEQUENCE: 180
ggattcgctt tcagtagtta tggc                                           24

<210> SEQ ID NO 181
<211> LENGTH: 24
<212> TYPE: DNA
<213> ORGANISM: Artificial Sequence
<220> FEATURE:
<223> OTHER INFORMATION: MGU1 CDRH2 nuc

<400> SEQUENCE: 181
atttggcatg atggcaccaa taaa                                           24

<210> SEQ ID NO 182
<211> LENGTH: 42
<212> TYPE: DNA
<213> ORGANISM: Artificial Sequence
<220> FEATURE:
<223> OTHER INFORMATION: MGU1 CDRH3 nuc

<400> SEQUENCE: 182
gccatttggt atcttgatag tcctgatcat ggtttcgata tc                       42

<210> SEQ ID NO 183
<211> LENGTH: 21
<212> TYPE: DNA
<213> ORGANISM: Artificial Sequence
<220> FEATURE:
<223> OTHER INFORMATION: MGU1 CDRL1 nuc

<400> SEQUENCE: 183
aatggccaca gttccaatgc c                                              21

<210> SEQ ID NO 184
<211> LENGTH: 20
<212> TYPE: DNA
<213> ORGANISM: Artificial Sequence
<220> FEATURE:
<223> OTHER INFORMATION: MGU1 CDRL2 nuc

<400> SEQUENCE: 184
gttaatagtg atggcagcca                                                20

<210> SEQ ID NO 185
<211> LENGTH: 27
<212> TYPE: DNA
<213> ORGANISM: Artificial Sequence
<220> FEATURE:
<223> OTHER INFORMATION: MGU1 CDRL3 nuc
```

<400> SEQUENCE: 185
caggcctggg acagtggcat ttgggtt                                          27

<210> SEQ ID NO 186
<211> LENGTH: 364
<212> TYPE: DNA
<213> ORGANISM: Artificial Sequence
<220> FEATURE:
<223> OTHER INFORMATION: MGU1 VH nuc

<400> SEQUENCE: 186
caggtgcagc tggtggagtc tgggggaggc gtggtccagc ctggggaggtc cctgagactc      60 tcatgtgcag cctccggatt cgctttcagt agttatggca tgaactgggt ccgccaggct     120
ccaggcaagg gactggagtg ggtggcagtt atttggcatg atggcaccaa taaatactat     180
agagactccg tgaagggccg attcatcatc tccagagaca atgccaagaa caccttgtat     240
ctgcaaatgg acagcctgag cgctgaggac acggctatgt attactgtgc catttggtat     300
cttgatagtc ctgatcatgg tttcgatatc tggggccgag ggacaatggt caccgtctct     360
tcag                                                                 364

<210> SEQ ID NO 187
<211> LENGTH: 334
<212> TYPE: DNA
<213> ORGANISM: Artificial Sequence
<220> FEATURE:
<223> OTHER INFORMATION: MGU1 VL nuc

<400> SEQUENCE: 187
cagcttgtcc tgactcaatc gccctctgcc tctgcctccc tgggagtctc ggtcaccctc      60
acctgtactc tgaacaatgg ccacagttcc aatgccatcg catggcatca acagcagcca     120
gggaagggcc ctcgttattt gatgaaggtt aatagtgatg cagccacaa taaggggcc      180 gctgtccctg atcgcttctc aggctctagt tctgggactg agcgccacct caccatctcc     240
agcctccagt ctgacgatga ggctgactat tattgtcagg cctgggacag tggcatttgg     300
gttttcggcg agggaccaa gttgaccgtc ctag                                  334

<210> SEQ ID NO 188
<211> LENGTH: 8
<212> TYPE: PRT
<213> ORGANISM: Artificial Sequence
<220> FEATURE:
<223> OTHER INFORMATION: MGU3 CDRH1 aa

<400> SEQUENCE: 188

Gly Phe Thr Phe Ser Asp Tyr Asn
1               5

<210> SEQ ID NO 189
<211> LENGTH: 8
<212> TYPE: PRT
<213> ORGANISM: Artificial Sequence
<220> FEATURE:
<223> OTHER INFORMATION: MGU3 CDRH2 aa

<400> SEQUENCE: 189

Ile Ser His Ser Ser Ser Thr Thr
1               5

<210> SEQ ID NO 190

```
<211> LENGTH: 15
<212> TYPE: PRT
<213> ORGANISM: Artificial Sequence
<220> FEATURE:
<223> OTHER INFORMATION: MGU3 CDRH3 aa

<400> SEQUENCE: 190

Ala Arg Leu Arg Pro Leu Ser Tyr Ser Gly Arg Tyr Arg Asp Tyr
1               5                   10                  15

<210> SEQ ID NO 191
<211> LENGTH: 6
<212> TYPE: PRT
<213> ORGANISM: Artificial Sequence
<220> FEATURE:
<223> OTHER INFORMATION: MGU3 CDRL1 aa

<400> SEQUENCE: 191

Gln Asp Val Ser Asn Tyr
1               5

<210> SEQ ID NO 192

<400> SEQUENCE: 192

000

<210> SEQ ID NO 193
<211> LENGTH: 9
<212> TYPE: PRT
<213> ORGANISM: Artificial Sequence
<220> FEATURE:
<223> OTHER INFORMATION: MGU3 CDRL2 long aa

<400> SEQUENCE: 193

Leu Ile Tyr Asp Ala Ser Thr Leu Gln
1               5

<210> SEQ ID NO 194
<211> LENGTH: 9
<212> TYPE: PRT
<213> ORGANISM: Artificial Sequence
<220> FEATURE:
<223> OTHER INFORMATION: MGU3 CDRL3 aa

<400> SEQUENCE: 194

Gln Gln Tyr Asp Ser Leu Pro Leu Thr
1               5

<210> SEQ ID NO 195
<211> LENGTH: 122
<212> TYPE: PRT
<213> ORGANISM: Artificial Sequence
<220> FEATURE:
<223> OTHER INFORMATION: MGU3 VH aa

<400> SEQUENCE: 195

Glu Val Leu Leu Val Glu Ser Gly Gly Gly Leu Val Gln Pro Gly
1               5                   10                  15

Ser Leu Arg Leu Ser Cys Ala Ala Ser Gly Phe Thr Phe Ser Asp Tyr
                20                  25                  30

Asn Met His Trp Val Arg Gln Ala Pro Gly Lys Gly Leu Glu Trp Leu
            35                  40                  45

Ser Tyr Ile Ser His Ser Ser Thr Thr Tyr Tyr Ala Asp Ser Val
        50                  55                  60
```

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Leu Arg Pro Leu Ser Tyr Ser Gly Tyr Arg Asp Tyr Trp
            100                 105                 110

Gly Gln Gly Thr Leu Val Thr Val Ser Ser
            115                 120

<210> SEQ ID NO 196
<211> LENGTH: 107
<212> TYPE: PRT
<213> ORGANISM: Artificial Sequence
<220> FEATURE:
<223> OTHER INFORMATION: MGU3 VL aa

<400> SEQUENCE: 196

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Val Ser Asn Tyr
            20                  25                  30

Val Asn Trp Tyr Gln Gln Lys Pro Gly Lys Ala Pro Lys Val Leu Ile
        35                  40                  45

Tyr Asp Ala Ser Thr Leu Gln Thr Gly Val Pro Ser Arg Phe Ser Gly
50                  55                  60

Ser Gly Ser Gly Thr Asp Phe Thr Phe Ser Ile Ser Ser Leu Gln Pro
65                  70                  75                  80

Glu Asp Ile Ala Thr Tyr Tyr Cys Gln Gln Tyr Asp Ser Leu Pro Leu
                85                  90                  95

Thr Phe Gly Gly Gly Thr Lys Val Glu Ile Lys
            100                 105

<210> SEQ ID NO 197
<211> LENGTH: 24
<212> TYPE: DNA
<213> ORGANISM: Artificial Sequence
<220> FEATURE:
<223> OTHER INFORMATION: MGU3 CDRH1 nuc

<400> SEQUENCE: 197
ggattcacct tcagtgacta taac                                          24

<210> SEQ ID NO 198
<211> LENGTH: 24
<212> TYPE: DNA
<213> ORGANISM: Artificial Sequence
<220> FEATURE:
<223> OTHER INFORMATION: MGU3 CDRH2 nuc

<400> SEQUENCE: 198
attagtcata gtagtagtac caca                                          24

<210> SEQ ID NO 199
<211> LENGTH: 45
<212> TYPE: DNA
<213> ORGANISM: Artificial Sequence
<220> FEATURE:
<223> OTHER INFORMATION: MGU3 CDRH3 nuc

<400> SEQUENCE: 199
gcgagacttc gtcccttatc gtatagtggc aggtaccgcg actac                   45

<210> SEQ ID NO 200
<211> LENGTH: 18
<212> TYPE: DNA
<213> ORGANISM: Artificial Sequence
<220> FEATURE:
<223> OTHER INFORMATION: MGU3 CDRL1 nuc

<400> SEQUENCE: 200
caggacgtta gtaattat                                                    18

<210> SEQ ID NO 201

<400> SEQUENCE: 201

000

<210> SEQ ID NO 202
<211> LENGTH: 27
<212> TYPE: DNA
<213> ORGANISM: Artificial Sequence
<220> FEATURE:
<223> OTHER INFORMATION: MGU3 CDRL2 long nuc

<400> SEQUENCE: 202
ctgatctacg atgcatccac tttgcaa                                          27

<210> SEQ ID NO 203
<211> LENGTH: 27
<212> TYPE: DNA
<213> ORGANISM: Artificial Sequence
<220> FEATURE:
<223> OTHER INFORMATION: MGU3 CDRL3 nuc

<400> SEQUENCE: 203
cagcagtatg atagcctccc actcact                                          27

<210> SEQ ID NO 204
<211> LENGTH: 367
<212> TYPE: DNA
<213> ORGANISM: Artificial Sequence
<220> FEATURE:
<223> OTHER INFORMATION: MGU3 VH nuc

<400> SEQUENCE: 204
gaggtgctac tagtggagtc tgggggaggc ttggtacaac ctggggggtc cctgagactc      60
tcctgtgcag cctctggatt caccttcagt gactataaca tgcactgggt ccgccaggct     120
ccagggaagg ggctggagtg gctttcatac attagtcata gtagtagtac cacatactac     180
gcagactctg tgaggggccg attcaccatc tccagagaca atgccaagaa ctcactgtat     240
ctgcaaatga acagcctgag agccgaggac acggctgtgt attactgtgc gagacttcgt     300
cccttatcgt atagtggcag gtaccgcgac tactggggcc agggaacgct ggtcaccgtc     360
tcctcag                                                               367

<210> SEQ ID NO 205
<211> LENGTH: 322
<212> TYPE: DNA
<213> ORGANISM: Artificial Sequence
<220> FEATURE:
<223> OTHER INFORMATION: MGU3 VL nuc

<400> SEQUENCE: 205
gacatccaga tgacccagtc tccatcctcc ctgtctgcat ctgtaggaga cagagtcacc      60

```
atcacttgcc aggcgagtca ggacgttagt aattatgtaa attggtatca gcagaaacca    120
gggaaagccc ctaaggtcct gatctacgat gcatccactt tgcaaacagg ggtcccatca    180
aggttcagtg gaagtggatc ggggacagat tttactttca gcatcagcag cctgcagcct    240
gaagatattg caacatatta ctgtcagcag tatgatagcc tcccactcac tttcggcgga    300
gggaccaagg tggagatcaa ac                                             322
```

<210> SEQ ID NO 206
<211> LENGTH: 8
<212> TYPE: PRT
<213> ORGANISM: Artificial Sequence
<220> FEATURE:
<223> OTHER INFORMATION: MGU5 CDRH1 aa

<400> SEQUENCE: 206

Gly Phe Ser Phe Ser Ser Tyr Gly
1               5

<210> SEQ ID NO 207
<211> LENGTH: 8
<212> TYPE: PRT
<213> ORGANISM: Artificial Sequence
<220> FEATURE:
<223> OTHER INFORMATION: MGU5 CDRH2 aa

<400> SEQUENCE: 207

Ile Trp His Asp Gly Thr Asn Lys
1               5

<210> SEQ ID NO 208
<211> LENGTH: 12
<212> TYPE: PRT
<213> ORGANISM: Artificial Sequence
<220> FEATURE:
<223> OTHER INFORMATION: MGU5 CDRH3 aa

<400> SEQUENCE: 208

Thr Lys Arg Ala Gly Trp Gly Asp Ala Leu Asp Ile
1               5                   10

<210> SEQ ID NO 209
<211> LENGTH: 6
<212> TYPE: PRT
<213> ORGANISM: Artificial Sequence
<220> FEATURE:
<223> OTHER INFORMATION: MGU5 CDRL1 aa

<400> SEQUENCE: 209

Gln Asp Ile Ser Asn Tyr
1               5

<210> SEQ ID NO 210

<400> SEQUENCE: 210

000

<210> SEQ ID NO 211
<211> LENGTH: 9
<212> TYPE: PRT
<213> ORGANISM: Artificial Sequence
<220> FEATURE:
<223> OTHER INFORMATION: MGU5 CDRL2 long aa

<400> SEQUENCE: 211

```
Leu Ile Tyr Asp Ala Ser Asn Leu Glu
1               5
```

<210> SEQ ID NO 212
<211> LENGTH: 5
<212> TYPE: PRT
<213> ORGANISM: Artificial Sequence
<220> FEATURE:
<223> OTHER INFORMATION: MGU5 CDRL3 aa

<400> SEQUENCE: 212

```
Gln Gln Gln Arg Ile
1               5
```

<210> SEQ ID NO 213
<211> LENGTH: 119
<212> TYPE: PRT
<213> ORGANISM: Artificial Sequence
<220> FEATURE:
<223> OTHER INFORMATION: MGU5 VH aa

<400> SEQUENCE: 213

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Ser Tyr
                20                  25                  30

Gly Met His Trp Val Arg Gln Ala Pro Gly Lys Gly Leu Asp Trp Val
            35                  40                  45

Ala Leu Ile Trp His Asp Gly Thr Asn Lys Phe Tyr Thr Asp Ser Val
    50                  55                  60

Lys Gly Arg Phe Thr Ile Ser Arg Asp Asn Ser Lys Asp Thr Leu Phe
65                  70                  75                  80

Leu Gln Met Asn Ser Leu Arg Val Glu Asp Thr Ala Val Tyr Tyr Cys
                85                  90                  95

Thr Lys Arg Ala Gly Trp Gly Asp Ala Leu Asp Ile Trp Gly Gln Gly
            100                 105                 110

Thr Met Val Thr Val Ser Ser
        115
```

<210> SEQ ID NO 214
<211> LENGTH: 103
<212> TYPE: PRT
<213> ORGANISM: Artificial Sequence
<220> FEATURE:
<223> OTHER INFORMATION: MGU5 VL aa

<400> SEQUENCE: 214

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
                20                  25                  30

Leu Asn Trp Tyr Gln Gln Lys Pro Gly Lys Ala Pro Lys Leu Leu Ile
            35                  40                  45

Tyr Asp Ala Ser Asn Leu Glu Thr Gly Val Pro Ser Arg Phe Ser Gly
    50                  55                  60

Ser Gly Ser Ala Thr Asp Phe Thr Leu Thr Ile Ser Ser Leu Gln Ser
65                  70                  75                  80

Glu Asp Ile Ala Thr Tyr Tyr Cys Gln Gln Gln Arg Ile Phe Gly Gly
                85                  90                  95

Gly Thr Lys Val Glu Ile Lys
```

<210> SEQ ID NO 215
<211> LENGTH: 24
<212> TYPE: DNA
<213> ORGANISM: Artificial Sequence
<220> FEATURE:
<223> OTHER INFORMATION: MGU5 CDRH1 nuc

<400> SEQUENCE: 215
ggattcagct tcagtagtta tggc                                            24

<210> SEQ ID NO 216
<211> LENGTH: 24
<212> TYPE: DNA
<213> ORGANISM: Artificial Sequence
<220> FEATURE:
<223> OTHER INFORMATION: MGU5 CDRH2 nuc

<400> SEQUENCE: 216
atatggcatg atggaactaa taaa                                            24

<210> SEQ ID NO 217
<211> LENGTH: 36
<212> TYPE: DNA
<213> ORGANISM: Artificial Sequence
<220> FEATURE:
<223> OTHER INFORMATION: MGU5 CDRH3 nuc

<400> SEQUENCE: 217
acgaagcggg ctggctgggg tgatgctctt gatatc                               36

<210> SEQ ID NO 218
<211> LENGTH: 18
<212> TYPE: DNA
<213> ORGANISM: Artificial Sequence
<220> FEATURE:
<223> OTHER INFORMATION: MGU5 CDRL1 nuc

<400> SEQUENCE: 218
caggacatta gcaactat                                                   18

<210> SEQ ID NO 219

<400> SEQUENCE: 219

000

<210> SEQ ID NO 220
<211> LENGTH: 27
<212> TYPE: DNA
<213> ORGANISM: Artificial Sequence
<220> FEATURE:
<223> OTHER INFORMATION: MGU5 CDRL2 long nuc

<400> SEQUENCE: 220
ctgatctacg atgcatccaa tttggaa                                         27

<210> SEQ ID NO 221
<211> LENGTH: 15
<212> TYPE: DNA
<213> ORGANISM: Artificial Sequence
<220> FEATURE:
<223> OTHER INFORMATION: MGU5 CDRL3 nuc

<400> SEQUENCE: 221

```
caacaacaaa ggatt                                                    15
```

<210> SEQ ID NO 222
<211> LENGTH: 358
<212> TYPE: DNA
<213> ORGANISM: Artificial Sequence
<220> FEATURE:
<223> OTHER INFORMATION: MGU5 VH nuc

<400> SEQUENCE: 222

```
caggtgcagt tggtggagtc tgggggaggc gtggtccagc ctggagggtc cctgagactc    60
tcctgtgcag cctctggatt cagcttcagt agttatggca tgcactgggt ccgccaggct   120
ccaggcaagg ggctggattg ggtggctctt atatggcatg atggaactaa taaattttac   180
acagactccg tgaagggccg attcaccatc tccagagaca attccaagga cacactgttt   240
ctgcaaatga acagtctgag agttgaggac acggctgtgt attactgtac gaagcgggct   300
ggctggggtg atgctcttga tatctggggc caagggacaa tggtcaccgt ctcttcag    358
```

<210> SEQ ID NO 223
<211> LENGTH: 310
<212> TYPE: DNA
<213> ORGANISM: Artificial Sequence
<220> FEATURE:
<223> OTHER INFORMATION: MGU5 VL nuc

<400> SEQUENCE: 223

```
gacatccaga tgacccagtc tccatcctcc ctgtctgcat ctgtaggaga cagagtcacc    60
atcacttgcc aggcgagtca ggacattagc aactatttaa attggtatca gcagaaacca   120
gggaaagccc ctaaactcct gatctacgat gcatccaatt tggaaacagg ggtcccatca   180
aggttcagtg gaagtggatc tgcgacagat tttactctca ccatcagcag cctgcagtct   240
gaagacattg caacatatta ctgtcaacaa caaaggattt tcggcggagg gaccaaggtg   300
gagatcaaac                                                          310
```

<210> SEQ ID NO 224
<211> LENGTH: 8
<212> TYPE: PRT
<213> ORGANISM: Artificial Sequence
<220> FEATURE:
<223> OTHER INFORMATION: MGU8 CDRH1 aa

<400> SEQUENCE: 224

```
Gly Phe Thr Phe Ser Asn Tyr Gly
1               5
```

<210> SEQ ID NO 225
<211> LENGTH: 8
<212> TYPE: PRT
<213> ORGANISM: Artificial Sequence
<220> FEATURE:
<223> OTHER INFORMATION: MGU8 CDRH2 aa

<400> SEQUENCE: 225

```
Ile Trp His Asp Gly Thr Asn Lys
1               5
```

<210> SEQ ID NO 226
<211> LENGTH: 12
<212> TYPE: PRT
<213> ORGANISM: Artificial Sequence
<220> FEATURE:
<223> OTHER INFORMATION: MGU8 CDRH3 aa

```
<400> SEQUENCE: 226

Thr Lys Arg Gly Gly Trp Gly Asp Gly Ser Asp Ile
1               5                   10

<210> SEQ ID NO 227
<211> LENGTH: 6
<212> TYPE: PRT
<213> ORGANISM: Artificial Sequence
<220> FEATURE:
<223> OTHER INFORMATION: MGU8 CDRL1 aa

<400> SEQUENCE: 227

Gln Asp Val Asp Asn Tyr
1               5

<210> SEQ ID NO 228

<400> SEQUENCE: 228

000

<210> SEQ ID NO 229
<211> LENGTH: 9
<212> TYPE: PRT
<213> ORGANISM: Artificial Sequence
<220> FEATURE:
<223> OTHER INFORMATION: MGU8 CDRL2 long aa

<400> SEQUENCE: 229

Leu Ile Tyr Asp Ala Ser Asn Leu Ala
1               5

<210> SEQ ID NO 230
<211> LENGTH: 5
<212> TYPE: PRT
<213> ORGANISM: Artificial Sequence
<220> FEATURE:
<223> OTHER INFORMATION: MGU8 CDRL3 aa

<400> SEQUENCE: 230

Gln Gln Gln Arg Ile
1               5

<210> SEQ ID NO 231
<211> LENGTH: 119
<212> TYPE: PRT
<213> ORGANISM: Artificial Sequence
<220> FEATURE:
<223> OTHER INFORMATION: MGU8 VH aa

<400> SEQUENCE: 231

Gln Val Gln Leu Val Glu Ser Gly Gly Gly Val Val Gln Pro Gly Arg
1               5                   10                  15

Ser Leu Arg Leu Ser Cys Ala Ala Gly Gly Phe Thr Phe Ser Asn Tyr
            20                  25                  30

Gly Met His Trp Val Arg Gln Ala Pro Gly Lys Gly Leu Glu Trp Val
        35                  40                  45

Ala Leu Ile Trp His Asp Gly Thr Asn Lys Phe Tyr Ala Asp Ser Val
    50                  55                  60

Lys Gly Arg Phe Thr Ile Ser Arg Asp Asn Ser Lys Asn Thr Leu Ser
65                  70                  75                  80

Leu Gln Met Asp Ser Leu Thr Thr Glu Asp Thr Ala Ile Tyr Phe Cys
                85                  90                  95
```

-continued

Thr Lys Arg Gly Gly Trp Gly Asp Gly Ser Asp Ile Trp Gly Gln Gly
              100                 105                 110

Thr Met Val Thr Val Ser Ser
        115

<210> SEQ ID NO 232
<211> LENGTH: 103
<212> TYPE: PRT
<213> ORGANISM: Artificial Sequence
<220> FEATURE:
<223> OTHER INFORMATION: MGU8 VL aa

<400> SEQUENCE: 232

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Val Asp Asn Tyr
            20                  25                  30

Leu Asn Trp Tyr Gln His Lys Pro Gly Lys Ala Pro Lys Leu Leu Ile
        35                  40                  45

Tyr Asp Ala Ser Asn Leu Ala Thr Gly Val Pro Ser Arg Phe Ser Gly
    50                  55                  60

Ser Gly Ser Ser Thr Asp Phe Thr Leu Thr Ile Ser Ser Leu Gln Ser
65                  70                  75                  80

Asp Asp Phe Ala Thr Tyr Tyr Cys Gln Gln Gln Arg Ile Phe Gly Gly
                85                  90                  95

Gly Thr Arg Val Glu Ile Lys
        100

<210> SEQ ID NO 233
<211> LENGTH: 24
<212> TYPE: DNA
<213> ORGANISM: Artificial Sequence
<220> FEATURE:
<223> OTHER INFORMATION: MGU8 CDRH1 nuc

<400> SEQUENCE: 233
ggatttacct tcagtaacta tggc                                          24

<210> SEQ ID NO 234
<211> LENGTH: 24
<212> TYPE: DNA
<213> ORGANISM: Artificial Sequence
<220> FEATURE:
<223> OTHER INFORMATION: MGU8 CDRH2 nuc

<400> SEQUENCE: 234
atatggcatg atggaactaa taaa                                          24

<210> SEQ ID NO 235
<211> LENGTH: 36
<212> TYPE: DNA
<213> ORGANISM: Artificial Sequence
<220> FEATURE:
<223> OTHER INFORMATION: MGU8 CDRH3 nuc

<400> SEQUENCE: 235
acgaagcgag gtggctgggg tgatggttct gatatc                             36

<210> SEQ ID NO 236
<211> LENGTH: 18
<212> TYPE: DNA
<213> ORGANISM: Artificial Sequence

```
<220> FEATURE:
<223> OTHER INFORMATION: MGU8 CDRL1 nuc

<400> SEQUENCE: 236
caggacgttg acaactat                                               18

<210> SEQ ID NO 237

<400> SEQUENCE: 237

000

<210> SEQ ID NO 238
<211> LENGTH: 27
<212> TYPE: DNA
<213> ORGANISM: Artificial Sequence
<220> FEATURE:
<223> OTHER INFORMATION: MGU8 CDRL2 long nuc

<400> SEQUENCE: 238
ctgatctacg atgcatccaa tttggcg                                     27

<210> SEQ ID NO 239
<211> LENGTH: 15
<212> TYPE: DNA
<213> ORGANISM: Artificial Sequence
<220> FEATURE:
<223> OTHER INFORMATION: MGU8 CDRL3 nuc

<400> SEQUENCE: 239
caacaacaaa ggatt                                                  15

<210> SEQ ID NO 240
<211> LENGTH: 358
<212> TYPE: DNA
<213> ORGANISM: Artificial Sequence
<220> FEATURE:
<223> OTHER INFORMATION: MGU8 VH nuc

<400> SEQUENCE: 240
caggtgcagc tggtggagtc tgggggaggc gtggtccagc ctggggaggtc cctaagactc    60 tcctgtgcag ccgtggatt taccttcagt aactatggca tgcactgggt ccgccaggct   120
ccaggcaagg ggctggagtg ggtggcactt atatggcatg atggaactaa taaattctat   180
gcagactccg tgaagggccg attcaccatc tccagagaca attccaagaa cacgctgtct   240
ctgcaaatgg acagcctgac aactgaggac acggctatat attctgtac gaagcgaggt   300 ggctggggtg atggttctga tatctggggc caagggacaa tggtcaccgt ctcttcag     358

<210> SEQ ID NO 241
<211> LENGTH: 310
<212> TYPE: DNA
<213> ORGANISM: Artificial Sequence
<220> FEATURE:
<223> OTHER INFORMATION: MGU8 VL nuc

<400> SEQUENCE: 241
gacatccaga tgacccagtc tccatcctcc ctgtctgcat ctgtaggaga cagagtcacc    60
atcacttgcc aggcgagtca ggacgttgac aactatttaa attggtatca gcataaacca   120
gggaaagccc ctaagctcct gatctacgat gcatccaatt tggcgacagg ggtcccatca   180
aggttcagtg aagtggatc ttcgacagat tttactctca ccatcagcag cctgcagtct   240
gatgactttg caacatatta ctgtcaacaa caaaggattt cggcggagg gaccagggtg   300
```

```
gaaatcaaac                                                             310
```

<210> SEQ ID NO 242
<211> LENGTH: 8
<212> TYPE: PRT
<213> ORGANISM: Artificial Sequence
<220> FEATURE:
<223> OTHER INFORMATION: MGU10 CDRH1 aa

<400> SEQUENCE: 242

Gly Phe Ala Phe Ser Asn Tyr Gly
1               5

<210> SEQ ID NO 243
<211> LENGTH: 8
<212> TYPE: PRT
<213> ORGANISM: Artificial Sequence
<220> FEATURE:
<223> OTHER INFORMATION: MGU10 CDRH2 aa

<400> SEQUENCE: 243

Ile Trp His Asp Gly Ser Leu Lys
1               5

<210> SEQ ID NO 244
<211> LENGTH: 14
<212> TYPE: PRT
<213> ORGANISM: Artificial Sequence
<220> FEATURE:
<223> OTHER INFORMATION: MGU10 CDRH3 aa

<400> SEQUENCE: 244

Thr Val Trp Tyr Leu Glu Thr Pro Asp Asp Gly Phe Asp Ile
1               5                   10

<210> SEQ ID NO 245
<211> LENGTH: 7
<212> TYPE: PRT
<213> ORGANISM: Artificial Sequence
<220> FEATURE:
<223> OTHER INFORMATION: MGU10 CDRL1 aa

<400> SEQUENCE: 245

His Gly His Thr Ser Lys Ala
1               5

<210> SEQ ID NO 246
<211> LENGTH: 7
<212> TYPE: PRT
<213> ORGANISM: Artificial Sequence
<220> FEATURE:
<223> OTHER INFORMATION: MGU10 CDRL2 aa

<400> SEQUENCE: 246

Val Asn Ser Asp Gly Ser His
1               5

<210> SEQ ID NO 247
<211> LENGTH: 9
<212> TYPE: PRT
<213> ORGANISM: Artificial Sequence
<220> FEATURE:
<223> OTHER INFORMATION: MGU10 CDRL3 aa

<400> SEQUENCE: 247

Gln Ala Trp Asp Ser Gly Ile Trp Val

<210> SEQ ID NO 248
<211> LENGTH: 121
<212> TYPE: PRT
<213> ORGANISM: Artificial Sequence
<220> FEATURE:
<223> OTHER INFORMATION: MGU10 VH aa

<400> SEQUENCE: 248

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ala Phe Ser Asn Tyr
            20                  25                  30

Gly Met Asn Trp Val Arg Gln Ala Pro Gly Lys Gly Leu Glu Trp Val
        35                  40                  45

Ala Val Ile Trp His Asp Gly Ser Leu Lys Tyr Tyr Thr Gln Ser Val
    50                  55                  60

Lys Gly Arg Phe Thr Ile Ser Arg Asp Asn Ala Lys Asn Thr Leu Phe
65                  70                  75                  80

Leu Gln Met Asp Ser Leu Ser Ala Asp Thr Ala Met Tyr Tyr Cys
                85                  90                  95

Thr Val Trp Tyr Leu Glu Thr Pro Asp Asp Gly Phe Asp Ile Trp Gly
            100                 105                 110

Arg Gly Thr Met Val Thr Val Ser Ser
        115                 120

<210> SEQ ID NO 249
<211> LENGTH: 111
<212> TYPE: PRT
<213> ORGANISM: Artificial Sequence
<220> FEATURE:
<223> OTHER INFORMATION: MGU10 VL aa

<400> SEQUENCE: 249

Gln Leu Val Leu Thr Gln Pro Pro Ser Ala Ser Ala Ser Leu Gly Val
1               5                   10                  15

Ser Val Thr Leu Thr Cys Thr Leu Ser His Gly His Thr Ser Lys Ala
            20                  25                  30

Ile Ala Trp His Gln Gln Gln Pro Gly Lys Gly Pro Arg Tyr Leu Met
            35                  40                  45

Lys Val Asn Ser Asp Gly Ser His Thr Lys Gly Ala Ala Val Pro Asp
    50                  55                  60

Arg Phe Ser Gly Ser Thr Ser Gly Ala Glu Arg His Phe Thr Ile Ser
65                  70                  75                  80

Asn Leu Gln Ser Asp Asp Glu Ala Asp Tyr Tyr Cys Gln Ala Trp Asp
                85                  90                  95

Ser Gly Ile Trp Val Phe Gly Gly Gly Thr Lys Leu Thr Val Leu
            100                 105                 110

<210> SEQ ID NO 250
<211> LENGTH: 24
<212> TYPE: DNA
<213> ORGANISM: Artificial Sequence
<220> FEATURE:
<223> OTHER INFORMATION: MGU10 CDRH1 nuc

<400> SEQUENCE: 250
ggattcgctt tcagcaatta tggc                                  24

```
<210> SEQ ID NO 251
<211> LENGTH: 24
<212> TYPE: DNA
<213> ORGANISM: Artificial Sequence
<220> FEATURE:
<223> OTHER INFORMATION: MGU10 CDRH2 nuc

<400> SEQUENCE: 251
atttggcatg acggcagtct taaa                                              24

<210> SEQ ID NO 252
<211> LENGTH: 42
<212> TYPE: DNA
<213> ORGANISM: Artificial Sequence
<220> FEATURE:
<223> OTHER INFORMATION: MGU10 CDRH3 nuc

<400> SEQUENCE: 252
accgtttggt accttgaaac tcctgatgat ggtttcgata tt                          42

<210> SEQ ID NO 253
<211> LENGTH: 21
<212> TYPE: DNA
<213> ORGANISM: Artificial Sequence
<220> FEATURE:
<223> OTHER INFORMATION: MGU10 CDRL1 nuc

<400> SEQUENCE: 253
catggccaca cctccaaagc c                                                 21

<210> SEQ ID NO 254
<211> LENGTH: 21
<212> TYPE: DNA
<213> ORGANISM: Artificial Sequence
<220> FEATURE:
<223> OTHER INFORMATION: MGU10 CDRL2 nuc

<400> SEQUENCE: 254
gttaatagtg atggcagcca c                                                 21

<210> SEQ ID NO 255
<211> LENGTH: 27
<212> TYPE: DNA
<213> ORGANISM: Artificial Sequence
<220> FEATURE:
<223> OTHER INFORMATION: MGU10 CDRL3 nuc

<400> SEQUENCE: 255
caggcctggg acagtggcat ttgggtt                                           27

<210> SEQ ID NO 256
<211> LENGTH: 364
<212> TYPE: DNA
<213> ORGANISM: Artificial Sequence
<220> FEATURE:
<223> OTHER INFORMATION: MGU10 VH nuc

<400> SEQUENCE: 256
caggtgcagc tggtggagtc tgggggaggc gtggtccagc ctggggaggtc cctgagactc       60 tcatgtgcag cctccggatt cgctttcagc aattatggca tgaactgggt ccgccaggct      120
ccaggcaagg gactggaatg ggtggcagtt atttggcatg acggcagtct taaatattat      180
acacagtccg tgaagggccg attcaccatc tccagagaca tgccaagaa cacgttgttt       240 ctccaaatgg acagcctgag cgctgacgac acggctatgt attattgtac cgtttggtac      300
```

```
cttgaaactc ctgatgatgg tttcgatatt tggggccgag ggacaatggt caccgtctcg    360
tcag                                                                 364
```

<210> SEQ ID NO 257
<211> LENGTH: 334
<212> TYPE: DNA
<213> ORGANISM: Artificial Sequence
<220> FEATURE:
<223> OTHER INFORMATION: MGU10 VL nuc

<400> SEQUENCE: 257

```
cagcttgtcc tgactcaacc gccctctgcc tctgcctccc tgggagtctc ggtcaccctc     60
acctgtactc tgagtcatgg ccacacctcc aaagccatcg cgtggcatca acagcagcca    120
gggaagggcc ctcgttattt gatgaaagtt aatagtgatg cagccacac taaggggggcc    180 gctgtccctg atcgcttctc aggctctact tctggggctg agcgccactt caccatctcc    240
aacctccagt ctgacgatga ggctgattat tattgtcagg cctgggacag tggcatttgg    300
gttttcggcg agggaccaa gttgaccgtc ctag                                 334
```

<210> SEQ ID NO 258
<211> LENGTH: 8
<212> TYPE: PRT
<213> ORGANISM: Artificial Sequence
<220> FEATURE:
<223> OTHER INFORMATION: MGU11 CDRH1 aa

<400> SEQUENCE: 258

```
Gly Phe Ser Phe Ser Ser Tyr Gly
1               5
```

<210> SEQ ID NO 259
<211> LENGTH: 8
<212> TYPE: PRT
<213> ORGANISM: Artificial Sequence
<220> FEATURE:
<223> OTHER INFORMATION: MGU11 CDRH2 aa

<400> SEQUENCE: 259

```
Ile Trp Tyr Asp Gly Thr Asn Lys
1               5
```

<210> SEQ ID NO 260
<211> LENGTH: 14
<212> TYPE: PRT
<213> ORGANISM: Artificial Sequence
<220> FEATURE:
<223> OTHER INFORMATION: MGU11 CDRH3 aa

<400> SEQUENCE: 260

```
Ala Asn Asp Ile Ala Gly Trp Gly Tyr Asp Gly Ser Asn Ala
1               5                   10
```

<210> SEQ ID NO 261
<211> LENGTH: 11
<212> TYPE: PRT
<213> ORGANISM: Artificial Sequence
<220> FEATURE:
<223> OTHER INFORMATION: MGU11 CDRL1 aa

<400> SEQUENCE: 261

```
Gln Ser Leu Val Tyr Ser Asp Gly Asn Thr Tyr
1               5                   10
```

<210> SEQ ID NO 262

<400> SEQUENCE: 262

000

<210> SEQ ID NO 263
<211> LENGTH: 9
<212> TYPE: PRT
<213> ORGANISM: Artificial Sequence
<220> FEATURE:
<223> OTHER INFORMATION: MGU11 CDRL2 long aa

<400> SEQUENCE: 263

Leu Ile Tyr Lys Val Ser Asn Arg Asp
1               5

<210> SEQ ID NO 264
<211> LENGTH: 8
<212> TYPE: PRT
<213> ORGANISM: Artificial Sequence
<220> FEATURE:
<223> OTHER INFORMATION: MGU11 CDRL3 aa

<400> SEQUENCE: 264

Met Gln Gly Thr Val Gly Phe Thr
1               5

<210> SEQ ID NO 265
<211> LENGTH: 121
<212> TYPE: PRT
<213> ORGANISM: Artificial Sequence
<220> FEATURE:
<223> OTHER INFORMATION: MGU11 VH aa

<400> SEQUENCE: 265

Gln Val Gln Leu Val Glu Ser Gly Gly Gly Val Val Gln Pro Gly Arg
1               5                   10                  15

Ser Leu Arg Leu Ser Cys Val Ala Ser Gly Phe Ser Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Asp Gly Thr Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Asp Asp Thr Ala Met Tyr Tyr Cys
                85                  90                  95

Ala Asn Asp Ile Ala Gly Trp Gly Tyr Asp Gly Ser Asn Ala Trp Gly
            100                 105                 110

Gln Gly Thr Leu Val Thr Val Ser Ser
        115                 120

<210> SEQ ID NO 266
<211> LENGTH: 103
<212> TYPE: PRT
<213> ORGANISM: Artificial Sequence
<220> FEATURE:
<223> OTHER INFORMATION: MGU11 VL aa

<400> SEQUENCE: 266

Leu Ser Leu Pro Val Thr Pro Gly Gln Pro Ala Ser Ile Ser Cys Lys
1               5                   10                  15

Ser Ser Gln Ser Leu Val Tyr Ser Asp Gly Asn Thr Tyr Leu Asn Trp
                20                  25                  30

Phe Gln Gln Arg Pro Gly Gln Ser Pro Arg Arg Leu Ile Tyr Lys Val
                35                  40                  45

Ser Asn Arg Asp Ser Gly Val Pro Asp Arg Phe Ser Gly Ser Gly Ser
50                  55                  60

Gly Thr Asp Phe Thr Leu Lys Ile Ser Arg Val Glu Ala Glu Asp Val
65                  70                  75                  80

Gly Val Tyr Tyr Cys Met Gln Gly Thr Val Gly Phe Thr Phe Gly Pro
                85                  90                  95

Gly Thr Thr Val Asp Ile Lys
            100

<210> SEQ ID NO 267
<211> LENGTH: 24
<212> TYPE: DNA
<213> ORGANISM: Artificial Sequence
<220> FEATURE:
<223> OTHER INFORMATION: MGU11 CDRH1 nuc

<400> SEQUENCE: 267
ggattcagct tcagtagcta tggc                                      24

<210> SEQ ID NO 268
<211> LENGTH: 24
<212> TYPE: DNA
<213> ORGANISM: Artificial Sequence
<220> FEATURE:
<223> OTHER INFORMATION: MGU11 CDRH2 nuc

<400> SEQUENCE: 268
atatggtatg atggaaccaa taaa                                      24

<210> SEQ ID NO 269
<211> LENGTH: 42
<212> TYPE: DNA
<213> ORGANISM: Artificial Sequence
<220> FEATURE:
<223> OTHER INFORMATION: MGU11 CDRH3 nuc

<400> SEQUENCE: 269
gcgaatgata ttgcggggtg gggctatgat ggtagtaatg cc                  42

<210> SEQ ID NO 270
<211> LENGTH: 33
<212> TYPE: DNA
<213> ORGANISM: Artificial Sequence
<220> FEATURE:
<223> OTHER INFORMATION: MGU11 CDRL1 nuc

<400> SEQUENCE: 270
caaagcctcg tatatagtga tggaaacacc tac                            33

<210> SEQ ID NO 271

<400> SEQUENCE: 271

000

<210> SEQ ID NO 272
<211> LENGTH: 27
<212> TYPE: DNA
<213> ORGANISM: Artificial Sequence
<220> FEATURE:
<223> OTHER INFORMATION: MGU11 CDRL2 long nuc

<400> SEQUENCE: 272
ctaatttata aggtttctaa ccgggac					27

<210> SEQ ID NO 273
<211> LENGTH: 24
<212> TYPE: DNA
<213> ORGANISM: Artificial Sequence
<220> FEATURE:
<223> OTHER INFORMATION: MGU11 CDRL3 nuc

<400> SEQUENCE: 273
atgcaaggta cagtggggtt cact					24

<210> SEQ ID NO 274
<211> LENGTH: 364
<212> TYPE: DNA
<213> ORGANISM: Artificial Sequence
<220> FEATURE:
<223> OTHER INFORMATION: MGU11 VH nuc

<400> SEQUENCE: 274
caggtgcagc tggtggagtc tggggggaggc gtagtccagc tggggaggtc cctgagactc		60 tcctgcgtag cctctggatt cagcttcagt agctatggca tgcactgggt ccgccaggct		120 ccaggcaagg ggctggagtg ggtggcagtt atatggtatg atggaaccaa taaatactat		180 gcagattccg tgaagggccg attcaccatc tccagagaca ataccaagaa cacgttgtac		240 ctgcaaatga acagcctgag agcggacgac acggctatgt attactgtgc gaatgatatt		300 gcggggtggg gctatgatgg tagtaatgcc tggggccagg gaaccctggt caccgtctcc		360 tcag								364

<210> SEQ ID NO 275
<211> LENGTH: 310
<212> TYPE: DNA
<213> ORGANISM: Artificial Sequence
<220> FEATURE:
<223> OTHER INFORMATION: MGU11 VL nuc

<400> SEQUENCE: 275
ctctccctgc ccgtcacccc tggacagccg gcctccatct cctgcaagtc tagtcaaagc		60 ctcgtatata gtgatggaaa cacctacttg aattggtttc agcagaggcc aggccaatct		120 ccaaggcgcc taatttataa ggtttctaac cgggactctg ggtcccaga cagattcagc		180 ggcagtgggt caggcactga tttcacactg aaaatcagca gggtggaggc tgaggatgtt		240 ggggtttatt actgcatgca aggtacagtg gggttcactt tcggccctgg gaccacagtg		300 gatatcaaac								310

<210> SEQ ID NO 276
<211> LENGTH: 8
<212> TYPE: PRT
<213> ORGANISM: Artificial Sequence
<220> FEATURE:
<223> OTHER INFORMATION: MGU12 CDRH1 aa

<400> SEQUENCE: 276

Gly Phe Ser Phe Ser Ser Tyr Gly
1               5

```
<210> SEQ ID NO 277
<211> LENGTH: 8
<212> TYPE: PRT
<213> ORGANISM: Artificial Sequence
<220> FEATURE:
<223> OTHER INFORMATION: MGU12 CDRH2 aa

<400> SEQUENCE: 277

Ile Trp His Asp Gly Ser Tyr Ser
1               5

<210> SEQ ID NO 278
<211> LENGTH: 18
<212> TYPE: PRT
<213> ORGANISM: Artificial Sequence
<220> FEATURE:
<223> OTHER INFORMATION: MGU12 CDRH3 aa

<400> SEQUENCE: 278

Val Lys Val Glu Asp Tyr Val Arg Gly Ser Ser His Gly Gly Ala Phe
1               5                   10                  15

His Ile

<210> SEQ ID NO 279
<211> LENGTH: 6
<212> TYPE: PRT
<213> ORGANISM: Artificial Sequence
<220> FEATURE:
<223> OTHER INFORMATION: MGU12 CDRL1 aa

<400> SEQUENCE: 279

Gln Thr Ile Asn Asn Trp
1               5

<210> SEQ ID NO 280

<400> SEQUENCE: 280

000

<210> SEQ ID NO 281
<211> LENGTH: 9
<212> TYPE: PRT
<213> ORGANISM: Artificial Sequence
<220> FEATURE:
<223> OTHER INFORMATION: MGU12 CDRL2 long aa

<400> SEQUENCE: 281

Leu Ile Tyr Lys Ala Ser Ser Leu Glu
1               5

<210> SEQ ID NO 282
<211> LENGTH: 8
<212> TYPE: PRT
<213> ORGANISM: Artificial Sequence
<220> FEATURE:
<223> OTHER INFORMATION: MGU12 CDRL3 aa

<400> SEQUENCE: 282

Gln Gln Tyr Ser Ser Tyr Trp Thr
1               5

<210> SEQ ID NO 283
<211> LENGTH: 125
<212> TYPE: PRT
<213> ORGANISM: Artificial Sequence
<220> FEATURE:
```

<223> OTHER INFORMATION: MGU12 VH aa

<400> SEQUENCE: 283

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Ser Tyr
                20                  25                  30

Gly Met His Trp Val Arg Gln Ala Pro Gly Lys Gly Pro Glu Trp Val
            35                  40                  45

Ala Val Ile Trp His Asp Gly Ser Tyr Ser Tyr Tyr Ala Asp Ser Val
        50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Gly Met Tyr His Cys
                85                  90                  95

Val Lys Val Glu Asp Tyr Val Arg Gly Ser Ser His Gly Gly Ala Phe
            100                 105                 110

His Ile Trp Gly Gln Gly Thr Met Val Thr Val Ser Ser
        115                 120                 125

<210> SEQ ID NO 284
<211> LENGTH: 106
<212> TYPE: PRT
<213> ORGANISM: Artificial Sequence
<220> FEATURE:
<223> OTHER INFORMATION: MGU12 VL aa

<400> SEQUENCE: 284

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Thr Ile Asn Asn Trp
                20                  25                  30

Leu Ala Trp Tyr Gln Trp Lys Pro Gly Lys Ala Pro Glu Leu Leu Ile
            35                  40                  45

Tyr Lys Ala Ser Ser Leu Glu Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Ser Ser Tyr Trp Thr
                85                  90                  95

Phe Gly Gln Gly Thr Lys Val Asp Ile Lys
            100                 105

<210> SEQ ID NO 285
<211> LENGTH: 24
<212> TYPE: DNA
<213> ORGANISM: Artificial Sequence
<220> FEATURE:
<223> OTHER INFORMATION: MGU12 CDRH1 nuc

<400> SEQUENCE: 285
ggattcagct tcagtagtta tggc                                      24

<210> SEQ ID NO 286
<211> LENGTH: 24
<212> TYPE: DNA
<213> ORGANISM: Artificial Sequence
<220> FEATURE:
<223> OTHER INFORMATION: MGU12 CDRH2 nuc

```
<400> SEQUENCE: 286
atttggcatg atggaagtta cagt                                            24

<210> SEQ ID NO 287
<211> LENGTH: 54
<212> TYPE: DNA
<213> ORGANISM: Artificial Sequence
<220> FEATURE:
<223> OTHER INFORMATION: MGU12 CDRH3 nuc

<400> SEQUENCE: 287
gtgaaagttg aggattacgt tagggggagt tcacatgggg gtgcttttca tatc           54

<210> SEQ ID NO 288
<211> LENGTH: 18
<212> TYPE: DNA
<213> ORGANISM: Artificial Sequence
<220> FEATURE:
<223> OTHER INFORMATION: MGU12 CDRL1 nuc

<400> SEQUENCE: 288
cagactatta ataactgg                                                   18

<210> SEQ ID NO 289
<211> LENGTH: 10
<212> TYPE: DNA
<213> ORGANISM: Artificial Sequence
<220> FEATURE:
<223> OTHER INFORMATION: MGU12 CDRL2 nuc

<400> SEQUENCE: 289
taaggcgtct                                                            10

<210> SEQ ID NO 290
<211> LENGTH: 27
<212> TYPE: DNA
<213> ORGANISM: Artificial Sequence
<220> FEATURE:
<223> OTHER INFORMATION: MGU12 CDRL2 long nuc

<400> SEQUENCE: 290
ctgatctata aggcgtctag tttagaa                                         27

<210> SEQ ID NO 291
<211> LENGTH: 24
<212> TYPE: DNA
<213> ORGANISM: Artificial Sequence
<220> FEATURE:
<223> OTHER INFORMATION: MGU12 CDRL3 nuc

<400> SEQUENCE: 291
caacagtata gtagttattg gacg                                            24

<210> SEQ ID NO 292
<211> LENGTH: 376
<212> TYPE: DNA
<213> ORGANISM: Artificial Sequence
<220> FEATURE:
<223> OTHER INFORMATION: MGU12 VH nuc

<400> SEQUENCE: 292
caggtacaac tggtggaatc tgggggaggc gtggtccagc ctggagggtc cctgagactc     60
tcctgtgcag cctccggatt cagcttcagt agttatggca tgcactgggt ccgccaggct    120
ccaggcaagg ggccggagtg ggtggcagtg atttggcatg atggaagtta cagttactat    180
```

```
gcagactccg tgaggggccg attcaccatc tccagagaca attccaagaa cacgctgtat    240
ctgcaaatga acagcctgag acctgaggac acggggatgt atcactgtgt gaaagttgag    300
gattacgtta gggggagttc acatgggggt gcttttcata tctggggcca agggacaatg    360
gtcaccgtct cttcag                                                    376
```

```
<210> SEQ ID NO 293
<211> LENGTH: 319
<212> TYPE: DNA
<213> ORGANISM: Artificial Sequence
<220> FEATURE:
<223> OTHER INFORMATION: MGU12 VL nuc

<400> SEQUENCE: 293
```

```
gacatccaga tgacccagtc tccttccacc ctgtctgcat ctgtagggga cagagtcacc     60
atcacttgcc gggccagtca gactattaat aactggttgg cctggtatca gtggaaaccg    120
gggaaagccc ctgagctcct gatctataag gcgtctagtt tagaaagtgg ggtcccatca    180
aggttcagcg gcagtggatc tgggacagaa ttcactctca ccatcagcag cctgcagcct    240
gatgattttg caacttatta ctgccaacag tatagtagtt attggacgtt cggccaaggg    300
accaaggtgg acatcaaac                                                319
```

```
<210> SEQ ID NO 294
<211> LENGTH: 8
<212> TYPE: PRT
<213> ORGANISM: Artificial Sequence
<220> FEATURE:
<223> OTHER INFORMATION: MGV3 CDRH1 aa

<400> SEQUENCE: 294

Gly Phe Thr Val Ser Asp Ser Tyr
1               5
```

```
<210> SEQ ID NO 295
<211> LENGTH: 7
<212> TYPE: PRT
<213> ORGANISM: Artificial Sequence
<220> FEATURE:
<223> OTHER INFORMATION: MGV3 CDRH2 aa

<400> SEQUENCE: 295

Ile Tyr Ser Gly Ser Ser Thr
1               5
```

```
<210> SEQ ID NO 296
<211> LENGTH: 18
<212> TYPE: PRT
<213> ORGANISM: Artificial Sequence
<220> FEATURE:
<223> OTHER INFORMATION: MGV3 CDRH3 aa

<400> SEQUENCE: 296

Ala Arg Gly Pro Asn Asp Tyr Arg Asn Arg Lys Tyr Tyr Tyr Tyr Met
1               5                   10                  15

Asp Val
```

```
<210> SEQ ID NO 297
<211> LENGTH: 7
<212> TYPE: PRT
<213> ORGANISM: Artificial Sequence
<220> FEATURE:
<223> OTHER INFORMATION: MGV3 CDRL1 aa
```

<400> SEQUENCE: 297

Gln Ser Val Asp Ser Pro Tyr
1               5

<210> SEQ ID NO 298

<400> SEQUENCE: 298

000

<210> SEQ ID NO 299
<211> LENGTH: 9
<212> TYPE: PRT
<213> ORGANISM: Artificial Sequence
<220> FEATURE:
<223> OTHER INFORMATION: MGV3 CDRL2 long aa

<400> SEQUENCE: 299

Leu Ile Phe Gly Ala Ser Ile Arg Ala
1               5

<210> SEQ ID NO 300
<211> LENGTH: 9
<212> TYPE: PRT
<213> ORGANISM: Artificial Sequence
<220> FEATURE:
<223> OTHER INFORMATION: MGV3 CDRL3 aa

<400> SEQUENCE: 300

His Gln Tyr Gly Asn Ala Pro Tyr Ile
1               5

<210> SEQ ID NO 301
<211> LENGTH: 124
<212> TYPE: PRT
<213> ORGANISM: Artificial Sequence
<220> FEATURE:
<223> OTHER INFORMATION: MGV3 VH aa

<400> SEQUENCE: 301

Glu Val Gln Val Val Glu Ser Gly Gly Asp Leu Val Gln Pro Gly Gly
1               5                   10                  15

Ser Leu Arg Leu Ser Cys Ala Val Tyr Gly Phe Thr Val Ser Asp Ser
            20                  25                  30

Tyr Met Ser Trp Val Arg Gln Ala Pro Gly Lys Gly Leu Glu Trp Val
        35                  40                  45

Ser Val Ile Tyr Ser Gly Ser Ser Thr Tyr Tyr Ile Asp Ser Val Lys
    50                  55                  60

Gly Arg Phe Thr Ile Ser Arg Asp Arg Ser Lys Asn Thr Leu Tyr Leu
65                  70                  75                  80

Gln Met Asn Thr Leu Arg Val Glu Asp Thr Ala Leu Tyr Tyr Cys Ala
                85                  90                  95

Arg Gly Pro Asn Asp Tyr Arg Asn Arg Lys Tyr Tyr Tyr Met Asp
            100                 105                 110

Val Trp Gly Lys Gly Thr Ala Val Thr Val Ser Ser
        115                 120

<210> SEQ ID NO 302
<211> LENGTH: 108
<212> TYPE: PRT
<213> ORGANISM: Artificial Sequence
<220> FEATURE:

<223> OTHER INFORMATION: MGV3 VL aa

<400> SEQUENCE: 302

Glu Ile Val Leu Thr Gln Ser Pro Asp Thr Leu Ser Leu Ser Ala Gly
1               5                   10                  15

Glu Arg Val Thr Leu Ser Cys Arg Ala Ser Gln Ser Val Asp Ser Pro
            20                  25                  30

Tyr Leu Ala Trp Tyr Gln Gln Arg Pro Gly Gln Thr Pro Arg Leu Leu
        35                  40                  45

Ile Phe Gly Ala Ser Ile Arg Ala Thr Asp Ile Pro Asp Arg Phe Ser
    50                  55                  60

Gly Gly Gly Ser Gly Thr Asp Phe Thr Leu Thr Ile Ser Arg Leu Glu
65                  70                  75                  80

Pro Glu Asp Ser Gly Val Tyr Tyr Cys His Gln Tyr Gly Asn Ala Pro
                85                  90                  95

Tyr Ile Phe Gly Gln Gly Thr Lys Leu Glu Ile Lys
            100                 105

<210> SEQ ID NO 303
<211> LENGTH: 24
<212> TYPE: DNA
<213> ORGANISM: Artificial Sequence
<220> FEATURE:
<223> OTHER INFORMATION: MGV3 CDRH1 nuc

<400> SEQUENCE: 303
ggattcaccg tcagtgacag ctac                                    24

<210> SEQ ID NO 304
<211> LENGTH: 21
<212> TYPE: DNA
<213> ORGANISM: Artificial Sequence
<220> FEATURE:
<223> OTHER INFORMATION: MGV3 CDRH2 nuc

<400> SEQUENCE: 304
atctatagtg gtagtagtac a                                       21

<210> SEQ ID NO 305
<211> LENGTH: 54
<212> TYPE: DNA
<213> ORGANISM: Artificial Sequence
<220> FEATURE:
<223> OTHER INFORMATION: MGV3 CDRH3 nuc

<400> SEQUENCE: 305
gcgagaggcc ctaatgacta cagaaatcgc aaatattact actacatgga cgtc    54

<210> SEQ ID NO 306
<211> LENGTH: 21
<212> TYPE: DNA
<213> ORGANISM: Artificial Sequence
<220> FEATURE:
<223> OTHER INFORMATION: MGV3 CDRL1 nuc

<400> SEQUENCE: 306
cagagtgttg acagtcccta c                                       21

<210> SEQ ID NO 307

<400> SEQUENCE: 307

000

<210> SEQ ID NO 308
<211> LENGTH: 27
<212> TYPE: DNA
<213> ORGANISM: Artificial Sequence
<220> FEATURE:
<223> OTHER INFORMATION: MGV3 CDRL2 long nuc

<400> SEQUENCE: 308 ctcattttg gtgcctctat tagggcc                                          27

<210> SEQ ID NO 309
<211> LENGTH: 27
<212> TYPE: DNA
<213> ORGANISM: Artificial Sequence
<220> FEATURE:
<223> OTHER INFORMATION: MGV3 CDRL3 nuc

<400> SEQUENCE: 309
caccagtatg gtaacgcacc ctacatt                                         27

<210> SEQ ID NO 310
<211> LENGTH: 373
<212> TYPE: DNA
<213> ORGANISM: Artificial Sequence
<220> FEATURE:
<223> OTHER INFORMATION: MGV3 VH nuc

<400> SEQUENCE: 310
gaggtgcagg tggtggagtc tgggggagac ttggtccagc cgggggggtc cctgagactc      60
tcctgtgcag tctatggatt caccgtcagt gacagctaca tgagctgggt ccgccaggct     120
ccggggaagg ggctggagtg ggtctcagtt atctatagtg gtagtagtac atactacata     180
gactccgtga agggccgatt caccatctcc agagacaggt ccaagaacac cttgtatctt     240
caaatgaaca ccctgagagt tgaggacacg gctctttatt actgcgcgag aggccctaat     300
gactacagaa atcgcaaata ttactactac atggacgtct ggggcaaagg gaccgcggtc     360
accgtctcct cag                                                        373

<210> SEQ ID NO 311
<211> LENGTH: 325
<212> TYPE: DNA
<213> ORGANISM: Artificial Sequence
<220> FEATURE:
<223> OTHER INFORMATION: MGV3 VL nuc

<400> SEQUENCE: 311
gaaattgtgt tgacacagtc tccagacacc ctgtccttgt ctgcagggga aagagtcacc      60
ctctcttgca gggccagtca gagtgttgac agtccctact agcctggta tcagcaaaga     120 cctggccaga ctcccaggct cctcattttt ggtgcctcta ttaggccac tgacatccca     180 gacaggttca gtggcggtgg gtctgggaca gacttcactc tcaccatcag cagactggaa     240
cctgaagatt ctggagtgta ttactgtcac cagtatggta acgcacccta cattttggc      300 caggggacca agctggagat caaac                                            325

<210> SEQ ID NO 312
<211> LENGTH: 102
<212> TYPE: PRT
<213> ORGANISM: Artificial Sequence
<220> FEATURE:
<223> OTHER INFORMATION: CSP C-terminal peptide 282 - 383

-continued

<400> SEQUENCE: 312

Lys Asn Asn Gln Gly Asn Gly Gln Gly His Asn Met Pro Asn Asp Pro
1               5                   10                  15

Asn Arg Asn Val Asp Glu Asn Ala Asn Ala Asn Ser Ala Val Lys Asn
            20                  25                  30

Asn Asn Asn Glu Glu Pro Ser Asp Lys His Ile Lys Glu Tyr Leu Asn
        35                  40                  45

Lys Ile Gln Asn Ser Leu Ser Thr Glu Trp Ser Pro Cys Ser Val Thr
50                  55                  60

Cys Gly Asn Gly Ile Gln Val Arg Ile Lys Pro Gly Ser Ala Asn Lys
65                  70                  75                  80

Pro Lys Asp Glu Leu Asp Tyr Ala Asn Asp Ile Glu Lys Lys Ile Cys
                85                  90                  95

Lys Met Glu Lys Cys Ser
            100

<210> SEQ ID NO 313
<211> LENGTH: 330
<212> TYPE: PRT
<213> ORGANISM: Artificial Sequence
<220> FEATURE:
<223> OTHER INFORMATION: IgG1 CH1-CH2-CH3 aa

<400> SEQUENCE: 313

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr

```
                        245                 250                 255
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 314
<211> LENGTH: 107
<212> TYPE: PRT
<213> ORGANISM: Artificial Sequence
<220> FEATURE:
<223> OTHER INFORMATION: IgG CK aa

<400> SEQUENCE: 314

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 315
<211> LENGTH: 106
<212> TYPE: PRT
<213> ORGANISM: Artificial Sequence
<220> FEATURE:
<223> OTHER INFORMATION: IgG CL aa

<400> SEQUENCE: 315

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105
```

<210> SEQ ID NO 316
<211> LENGTH: 990
<212> TYPE: DNA
<213> ORGANISM: Artificial Sequence
<220> FEATURE:
<223> OTHER INFORMATION: IgG1 CH1-CH2-CH3 nuc

<400> SEQUENCE: 316

| | | | | | |
|---|---|---|---|---|---|
| gcgtcgacca | agggcccatc | ggtcttcccc | ctggcaccct | cctccaagag | cacctctggg | 60 |
| ggcacagcgg | ccctgggctg | cctggtcaag | gactacttcc | ccgaacctgt | gacggtctcg | 120 |
| tggaactcag | gcgccctgac | cagcggcgtg | cacaccttcc | cggctgtcct | acagtcctca | 180 |
| ggactctact | ccctcagcag | cgtggtgacc | gtgccctcca | gcagcttggg | cacccagacc | 240 |
| tacatctgca | acgtgaatca | caagcccagc | aacaccaagg | tggacaagag | agttgagccc | 300 |
| aaatcttgtg | acaaaactca | cacatgccca | ccgtgcccag | cacctgaact | cctgggggga | 360 |
| ccgtcagtct | tcctcttccc | cccaaaaccc | aaggacaccc | tcatgatctc | ccggacccct | 420 |
| gaggtcacat | gcgtggtggt | ggacgtgagc | cacgaagacc | ctgaggtcaa | gttcaactgg | 480 |
| tacgtggacg | gcgtggaggt | gcataatgcc | aagacaaagc | cgcgggagga | gcagtacaac | 540 |
| agcacgtacc | gtgtggtcag | cgtcctcacc | gtcctgcacc | aggactggct | gaatggcaag | 600 |
| gagtacaagt | gcaaggtctc | caacaaagcc | ctcccagccc | ccatcgagaa | aaccatctcc | 660 |
| aaagccaaag | gcagccccg | agaaccacag | gtgtacaccc | tgcccccatc | ccgggaggag | 720 |
| atgaccaaga | accaggtcag | cctgacctgc | ctggtcaaag | gcttctatcc | cagcgacatc | 780 |
| gccgtggagt | gggagagcaa | tgggcagccg | gagaacaact | acaagaccac | gcctcccgtg | 840 |
| ctggactccg | acggctcctt | cttcctctat | agcaagctca | ccgtggacaa | gagcaggtgg | 900 |
| cagcagggga | acgtcttctc | atgctccgtg | atgcatgagg | ctctgcacaa | ccactacacg | 960 |
| cagaagagcc | tctccctgtc | cccgggtaaa | | | | 990 |

<210> SEQ ID NO 317
<211> LENGTH: 321
<212> TYPE: DNA
<213> ORGANISM: Artificial Sequence
<220> FEATURE:
<223> OTHER INFORMATION: IgG CK nuc

<400> SEQUENCE: 317

| | | | | | |
|---|---|---|---|---|---|
| cgtacggtgg | ctgcaccatc | tgtcttcatc | ttcccgccat | ctgatgagca | gttgaaatct | 60 |
| ggaactgcct | ctgttgtgtg | cctgctgaat | aacttctatc | ccagagaggc | caaagtacag | 120 |
| tggaaggtgg | ataacgccct | ccaatcgggt | aactcccagg | agagtgtcac | agagcaggac | 180 |
| agcaaggaca | gcacctacag | cctcagcagc | accctgacgc | tgagcaaagc | agactacgag | 240 |
| aaacacaaag | tctacgcctg | cgaagtcacc | catcagggcc | tgagctcgcc | cgtcacaaag | 300 |
| agcttcaaca | ggggagagtg | t | | | | 321 |

<210> SEQ ID NO 318
<211> LENGTH: 318
<212> TYPE: DNA
<213> ORGANISM: Artificial Sequence
<220> FEATURE:
<223> OTHER INFORMATION: IgG CL nuc

<400> SEQUENCE: 318

| | | | | | |
|---|---|---|---|---|---|
| ggtcagccca | aggctgcccc | ctcggtcact | ctgttcccgc | cctcctctga | ggagcttcaa | 60 |
| gccaacaagg | ccacactggt | gtgtctcata | agtgacttct | acccgggagc | cgtgacagtg | 120 |

```
gcttggaaag cagatagcag ccccgtcaag gcgggagtgg agaccaccac accctccaaa    180
caaagcaaca acaagtacgc ggccagcagc tatctgagcc tgacgcctga gcagtggaag    240
tcccacagaa gctacagctg ccaggtcacg catgaaggga gcaccgtgga aagacagtg     300 gccccctacag aatgttca                                                  318
```

```
<210> SEQ ID NO 319
<211> LENGTH: 226
<212> TYPE: PRT
<213> ORGANISM: Artificial Sequence
<220> FEATURE:
<223> OTHER INFORMATION: HBsAg S domain

<400> SEQUENCE: 319
```

| | | | | | | | | | | | | | | |
|---|---|---|---|---|---|---|---|---|---|---|---|---|---|---|
| Met | Glu | Asn | Ile | Thr | Ser | Gly | Phe | Leu | Gly | Pro | Leu | Val | Leu | Gln |
| 1 | | | | 5 | | | | | 10 | | | | | 15 |
| Ala | Gly | Phe | Phe | Leu | Leu | Thr | Arg | Ile | Leu | Thr | Ile | Pro | Gln | Ser | Leu |
| | | | 20 | | | | | 25 | | | | | 30 | | |
| Asp | Ser | Trp | Trp | Thr | Ser | Leu | Asn | Phe | Leu | Gly | Gly | Thr | Thr | Val | Cys |
| | | | 35 | | | | | 40 | | | | | 45 | | |
| Leu | Gly | Gln | Asn | Ser | Gln | Ser | Pro | Thr | Ser | Asn | His | Ser | Pro | Thr | Ser |
| | 50 | | | | | 55 | | | | | 60 | | | | |
| Cys | Pro | Pro | Thr | Cys | Pro | Gly | Tyr | Arg | Trp | Met | Cys | Leu | Arg | Arg | Phe |
| 65 | | | | | 70 | | | | | 75 | | | | | 80 |
| Ile | Ile | Phe | Leu | Phe | Ile | Leu | Leu | Cys | Leu | Ile | Phe | Leu | Leu | Val |
| | | | | 85 | | | | | 90 | | | | | 95 |
| Leu | Leu | Asp | Tyr | Gln | Gly | Met | Leu | Pro | Val | Cys | Pro | Leu | Ile | Pro | Gly |
| | | | 100 | | | | | 105 | | | | | 110 | | |
| Ser | Ser | Thr | Thr | Ser | Thr | Gly | Pro | Cys | Arg | Thr | Cys | Met | Thr | Thr | Ala |
| | | | 115 | | | | | 120 | | | | | 125 | | |
| Gln | Gly | Thr | Ser | Met | Tyr | Pro | Ser | Cys | Cys | Cys | Thr | Lys | Pro | Ser | Asp |
| | | 130 | | | | | 135 | | | | | 140 | | | |
| Gly | Asn | Cys | Thr | Cys | Ile | Pro | Ile | Pro | Ser | Ser | Trp | Ala | Phe | Gly | Lys |
| 145 | | | | | 150 | | | | | 155 | | | | | 160 |
| Phe | Leu | Trp | Glu | Trp | Ala | Ser | Ala | Arg | Phe | Ser | Trp | Leu | Ser | Leu | Leu |
| | | | | 165 | | | | | 170 | | | | | 175 | |
| Val | Pro | Phe | Val | Gln | Trp | Phe | Val | Gly | Leu | Ser | Pro | Thr | Val | Trp | Leu |
| | | | 180 | | | | | 185 | | | | | 190 | | |
| Ser | Val | Ile | Trp | Met | Met | Trp | Tyr | Trp | Gly | Pro | Ser | Leu | Tyr | Ser | Ile |
| | | | 195 | | | | | 200 | | | | | 205 | | |
| Leu | Ser | Pro | Phe | Leu | Pro | Leu | Leu | Pro | Ile | Phe | Phe | Cys | Leu | Trp | Val |
| | | 210 | | | | | 215 | | | | | 220 | | | |
| Tyr | Ile |
| 225 | |

```
<210> SEQ ID NO 320
<211> LENGTH: 104
<212> TYPE: PRT
<213> ORGANISM: Artificial Sequence
<220> FEATURE:
<223> OTHER INFORMATION: N-terminus of CSP

<400> SEQUENCE: 320
```

| | | | | | | | | | | | | | | |
|---|---|---|---|---|---|---|---|---|---|---|---|---|---|---|
| Met | Met | Arg | Lys | Leu | Ala | Ile | Leu | Ser | Val | Ser | Ser | Phe | Leu | Phe | Val |
| 1 | | | | 5 | | | | | 10 | | | | | 15 | |
| Glu | Ala | Leu | Phe | Gln | Glu | Tyr | Gln | Cys | Tyr | Gly | Ser | Ser | Ser | Asn | Thr |
| | | | 20 | | | | | 25 | | | | | 30 | | |

```
Arg Val Leu Asn Glu Leu Asn Tyr Asp Asn Ala Gly Thr Asn Leu Tyr
         35                  40                  45

Asn Glu Leu Glu Met Asn Tyr Tyr Gly Lys Gln Glu Asn Trp Tyr Ser
 50                  55                  60

Leu Lys Lys Asn Ser Arg Ser Leu Gly Glu Asn Asp Asp Gly Asn Asn
 65                  70                  75                  80

Glu Asp Asn Glu Lys Leu Arg Lys Pro Lys His Lys Lys Leu Lys Gln
                 85                  90                  95

Pro Ala Asp Gly Asn Pro Asp Pro
                100

<210> SEQ ID NO 321
<211> LENGTH: 7
<212> TYPE: PRT
<213> ORGANISM: Artificial Sequence
<220> FEATURE:
<223> OTHER INFORMATION: N-terminal region of CSP

<400> SEQUENCE: 321

Lys Lys Leu Lys Gln Pro Ala
1               5

<210> SEQ ID NO 322
<211> LENGTH: 9
<212> TYPE: PRT
<213> ORGANISM: Artificial Sequence
<220> FEATURE:
<223> OTHER INFORMATION: N-terminal region of CSP

<400> SEQUENCE: 322

His Lys Lys Leu Lys Gln Pro Ala Asp
1               5

<210> SEQ ID NO 323
<211> LENGTH: 11
<212> TYPE: PRT
<213> ORGANISM: Artificial Sequence
<220> FEATURE:
<223> OTHER INFORMATION: N-terminal region of CSP

<400> SEQUENCE: 323

Lys His Lys Lys Leu Lys Gln Pro Ala Asp Gly
1               5                   10

<210> SEQ ID NO 324
<211> LENGTH: 8
<212> TYPE: PRT
<213> ORGANISM: Artificial Sequence
<220> FEATURE:
<223> OTHER INFORMATION: N-terminal region of CSP

<400> SEQUENCE: 324

Lys His Lys Lys Leu Lys Gln Pro
1               5

<210> SEQ ID NO 325
<211> LENGTH: 11
<212> TYPE: PRT
<213> ORGANISM: Artificial Sequence
<220> FEATURE:
<223> OTHER INFORMATION: N-terminal region of CSP

<400> SEQUENCE: 325

Arg Lys Pro Lys His Lys Lys Leu Lys Gln Pro
```

```
<210> SEQ ID NO 326
<211> LENGTH: 13
<212> TYPE: PRT
<213> ORGANISM: Artificial Sequence
<220> FEATURE:
<223> OTHER INFORMATION: N-terminal region of CSP

<400> SEQUENCE: 326

Pro Lys His Lys Lys Leu Lys Gln Pro Ala Asp Gly Asn
1               5                   10

<210> SEQ ID NO 327
<211> LENGTH: 15
<212> TYPE: PRT
<213> ORGANISM: Artificial Sequence
<220> FEATURE:
<223> OTHER INFORMATION: N-terminal region of CSP

<400> SEQUENCE: 327

Lys Pro Lys His Lys Lys Leu Lys Gln Pro Ala Asp Gly Asn Pro
1               5                   10                  15

<210> SEQ ID NO 328
<211> LENGTH: 17
<212> TYPE: PRT
<213> ORGANISM: Artificial Sequence
<220> FEATURE:
<223> OTHER INFORMATION: N-terminal region of CSP

<400> SEQUENCE: 328

Arg Lys Pro Lys His Lys Lys Leu Lys Gln Pro Ala Asp Gly Asn Pro
1               5                   10                  15

Asp

<210> SEQ ID NO 329
<211> LENGTH: 15
<212> TYPE: PRT
<213> ORGANISM: Artificial Sequence
<220> FEATURE:
<223> OTHER INFORMATION: N-terminal region of CSP

<400> SEQUENCE: 329

Asn Glu Lys Leu Arg Lys Pro Lys His Lys Lys Leu Lys Gln Pro
1               5                   10                  15

<210> SEQ ID NO 330
<211> LENGTH: 18
<212> TYPE: PRT
<213> ORGANISM: Artificial Sequence
<220> FEATURE:
<223> OTHER INFORMATION: N-terminal region of CSP

<400> SEQUENCE: 330

Asn Glu Lys Leu Arg Lys Pro Lys His Lys Lys Leu Lys Gln Pro Ala
1               5                   10                  15

Asp Gly

<210> SEQ ID NO 331
<211> LENGTH: 167
<212> TYPE: PRT
<213> ORGANISM: Artificial Sequence
<220> FEATURE:
<223> OTHER INFORMATION: ferritin polypeptide
```

<400> SEQUENCE: 331

```
Met Leu Ser Lys Asp Ile Ile Lys Leu Leu Asn Glu Gln Val Asn Lys
1               5                   10                  15

Glu Met Asn Ser Ser Asn Leu Tyr Met Ser Met Ser Ser Trp Cys Tyr
            20                  25                  30

Thr His Ser Leu Asp Gly Ala Gly Leu Phe Leu Phe Asp His Ala Ala
        35                  40                  45

Glu Glu Tyr Glu His Ala Lys Lys Leu Ile Val Phe Leu Asn Glu Asn
    50                  55                  60

Asn Val Pro Val Gln Leu Thr Ser Ile Ser Ala Pro Glu His Lys Phe
65                  70                  75                  80

Glu Gly Leu Thr Gln Ile Phe Gln Lys Ala Tyr Glu His Glu Gln His
                85                  90                  95

Ile Ser Glu Ser Ile Asn Asn Ile Val Asp His Ala Ile Lys Gly Lys
            100                 105                 110

Asp His Ala Thr Phe Asn Phe Leu Gln Trp Tyr Val Ala Glu Gln His
        115                 120                 125

Glu Glu Glu Val Leu Phe Lys Asp Ile Leu Asp Lys Ile Glu Leu Ile
    130                 135                 140

Gly Asn Glu Asn His Gly Leu Tyr Leu Ala Asp Gln Tyr Val Lys Gly
145                 150                 155                 160

Ile Ala Lys Ser Arg Lys Ser
                165
```

<210> SEQ ID NO 332
<211> LENGTH: 265
<212> TYPE: PRT
<213> ORGANISM: Artificial Sequence
<220> FEATURE:
<223> OTHER INFORMATION: encapsulin polypeptide

<400> SEQUENCE: 332

```
Met Glu Phe Leu Lys Arg Ser Phe Ala Pro Leu Thr Glu Lys Gln Trp
1               5                   10                  15

Gln Glu Ile Asp Asn Arg Ala Arg Glu Ile Phe Lys Thr Gln Leu Tyr
            20                  25                  30

Gly Arg Lys Phe Val Asp Val Glu Gly Pro Tyr Gly Trp Glu Tyr Ala
        35                  40                  45

Ala His Pro Leu Gly Glu Val Glu Val Leu Ser Asp Glu Asn Glu Val
    50                  55                  60

Val Lys Trp Gly Leu Arg Lys Ser Leu Pro Leu Ile Glu Leu Arg Ala
65                  70                  75                  80

Thr Phe Thr Leu Asp Leu Trp Glu Leu Asp Asn Leu Glu Arg Gly Lys
                85                  90                  95

Pro Asn Val Asp Leu Ser Ser Leu Glu Glu Thr Val Arg Lys Val Ala
            100                 105                 110

Glu Phe Glu Asp Glu Val Ile Phe Arg Gly Cys Glu Lys Ser Gly Val
        115                 120                 125

Lys Gly Leu Leu Ser Phe Glu Glu Arg Lys Ile Glu Cys Gly Ser Thr
    130                 135                 140

Pro Lys Asp Leu Leu Glu Ala Ile Val Arg Ala Leu Ser Ile Phe Ser
145                 150                 155                 160

Lys Asp Gly Ile Glu Gly Pro Tyr Thr Leu Val Ile Asn Thr Asp Arg
                165                 170                 175

Trp Ile Asn Phe Leu Lys Glu Glu Ala Gly His Tyr Pro Leu Glu Lys
```

-continued

```
                180                 185                 190
Arg Val Glu Glu Cys Leu Arg Gly Gly Lys Ile Ile Thr Thr Pro Arg
            195                 200                 205

Ile Glu Asp Ala Leu Val Val Ser Glu Arg Gly Gly Asp Phe Lys Leu
        210                 215                 220

Ile Leu Gly Gln Asp Leu Ser Ile Gly Tyr Glu Asp Arg Glu Lys Asp
225                 230                 235                 240

Ala Val Arg Leu Phe Ile Thr Glu Thr Phe Thr Phe Gln Val Val Asn
                245                 250                 255

Pro Glu Ala Leu Ile Leu Leu Lys Phe
            260                 265
```

<210> SEQ ID NO 333
<211> LENGTH: 15
<212> TYPE: PRT
<213> ORGANISM: Artificial Sequence
<220> FEATURE:
<223> OTHER INFORMATION: CSP Peptide

<400> SEQUENCE: 333

```
Arg Lys Pro Lys His Lys Lys Leu Lys Gln Pro Ala Asp Gly Asn
1               5                   10                  15
```

<210> SEQ ID NO 334
<211> LENGTH: 15
<212> TYPE: PRT
<213> ORGANISM: Artificial Sequence
<220> FEATURE:
<223> OTHER INFORMATION: CSP Peptide

<400> SEQUENCE: 334

```
Lys Pro Lys His Lys Lys Leu Lys Gln Pro Ala Asp Gly Asn Pro
1               5                   10                  15
```

<210> SEQ ID NO 335
<211> LENGTH: 15
<212> TYPE: PRT
<213> ORGANISM: Artificial Sequence
<220> FEATURE:
<223> OTHER INFORMATION: CSP Peptide

<400> SEQUENCE: 335

```
Pro Lys His Lys Lys Leu Lys Gln Pro Ala Asp Gly Asn Pro Asp
1               5                   10                  15
```

<210> SEQ ID NO 336
<211> LENGTH: 15
<212> TYPE: PRT
<213> ORGANISM: Artificial Sequence
<220> FEATURE:
<223> OTHER INFORMATION: CSP Peptide

<400> SEQUENCE: 336

```
Lys His Lys Lys Leu Lys Gln Pro Ala Asp Gly Asn Pro Asp Pro
1               5                   10                  15
```

<210> SEQ ID NO 337
<211> LENGTH: 15
<212> TYPE: PRT
<213> ORGANISM: Artificial Sequence
<220> FEATURE:
<223> OTHER INFORMATION: CSP Peptide

<400> SEQUENCE: 337

```
His Lys Lys Leu Lys Gln Pro Ala Asp Gly Asn Pro Asp Pro Asn
1               5                   10                  15
```

<210> SEQ ID NO 338
<211> LENGTH: 15
<212> TYPE: PRT
<213> ORGANISM: Artificial Sequence
<220> FEATURE:
<223> OTHER INFORMATION: CSP Peptide

<400> SEQUENCE: 338

```
Lys Lys Leu Lys Gln Pro Ala Asp Gly Asn Pro Asp Pro Asn Ala
1               5                   10                  15
```

<210> SEQ ID NO 339
<211> LENGTH: 15
<212> TYPE: PRT
<213> ORGANISM: Artificial Sequence
<220> FEATURE:
<223> OTHER INFORMATION: CSP Peptide

<400> SEQUENCE: 339

```
Lys Leu Lys Gln Pro Ala Asp Gly Asn Pro Asp Pro Asn Ala Asn
1               5                   10                  15
```

<210> SEQ ID NO 340
<211> LENGTH: 15
<212> TYPE: PRT
<213> ORGANISM: Artificial Sequence
<220> FEATURE:
<223> OTHER INFORMATION: CSP Peptide

<400> SEQUENCE: 340

```
Leu Lys Gln Pro Ala Asp Gly Asn Pro Asp Pro Asn Ala Asn Pro
1               5                   10                  15
```

<210> SEQ ID NO 341
<211> LENGTH: 15
<212> TYPE: PRT
<213> ORGANISM: Artificial Sequence
<220> FEATURE:
<223> OTHER INFORMATION: CSP Peptide

<400> SEQUENCE: 341

```
Lys Gln Pro Ala Asp Gly Asn Pro Asp Pro Asn Ala Asn Pro Asn
1               5                   10                  15
```

<210> SEQ ID NO 342
<211> LENGTH: 15
<212> TYPE: PRT
<213> ORGANISM: Artificial Sequence
<220> FEATURE:
<223> OTHER INFORMATION: CSP Peptide

<400> SEQUENCE: 342

```
Gln Pro Ala Asp Gly Asn Pro Asp Pro Asn Ala Asn Pro Asn Val
1               5                   10                  15
```

<210> SEQ ID NO 343
<211> LENGTH: 15
<212> TYPE: PRT
<213> ORGANISM: Artificial Sequence
<220> FEATURE:
<223> OTHER INFORMATION: CSP Peptide

<400> SEQUENCE: 343

```
Pro Ala Asp Gly Asn Pro Asp Pro Asn Ala Asn Pro Asn Val Asp
```

```
                1               5                  10                 15

<210> SEQ ID NO 344
<211> LENGTH: 15
<212> TYPE: PRT
<213> ORGANISM: Artificial Sequence
<220> FEATURE:
<223> OTHER INFORMATION: CSP Peptide

<400> SEQUENCE: 344

Ala Asp Gly Asn Pro Asp Pro Asn Ala Asn Pro Asn Val Asp Pro
1               5                  10                 15

<210> SEQ ID NO 345
<211> LENGTH: 15
<212> TYPE: PRT
<213> ORGANISM: Artificial Sequence
<220> FEATURE:
<223> OTHER INFORMATION: CSP Peptide

<400> SEQUENCE: 345

Asp Gly Asn Pro Asp Pro Asn Ala Asn Pro Asn Val Asp Pro Asn
1               5                  10                 15

<210> SEQ ID NO 346
<211> LENGTH: 15
<212> TYPE: PRT
<213> ORGANISM: Artificial Sequence
<220> FEATURE:
<223> OTHER INFORMATION: CSP Peptide

<400> SEQUENCE: 346

Gly Asn Pro Asp Pro Asn Ala Asn Pro Asn Val Asp Pro Asn Ala
1               5                  10                 15

<210> SEQ ID NO 347
<211> LENGTH: 15
<212> TYPE: PRT
<213> ORGANISM: Artificial Sequence
<220> FEATURE:
<223> OTHER INFORMATION: CSP Peptide

<400> SEQUENCE: 347

Asn Pro Asp Pro Asn Ala Asn Pro Asn Val Asp Pro Asn Ala Asn
1               5                  10                 15

<210> SEQ ID NO 348
<211> LENGTH: 15
<212> TYPE: PRT
<213> ORGANISM: Artificial Sequence
<220> FEATURE:
<223> OTHER INFORMATION: CSP Peptide

<400> SEQUENCE: 348

Pro Asp Pro Asn Ala Asn Pro Asn Val Asp Pro Asn Ala Asn Pro
1               5                  10                 15

<210> SEQ ID NO 349
<211> LENGTH: 15
<212> TYPE: PRT
<213> ORGANISM: Artificial Sequence
<220> FEATURE:
<223> OTHER INFORMATION: CSP Peptide

<400> SEQUENCE: 349

Asp Pro Asn Ala Asn Pro Asn Val Asp Pro Asn Ala Asn Pro Asn
1               5                  10                 15
```

```
<210> SEQ ID NO 350
<211> LENGTH: 15
<212> TYPE: PRT
<213> ORGANISM: Artificial Sequence
<220> FEATURE:
<223> OTHER INFORMATION: CSP Peptide

<400> SEQUENCE: 350

Pro Asn Ala Asn Pro Asn Val Asp Pro Asn Ala Asn Pro Asn Val
1               5                   10                  15

<210> SEQ ID NO 351
<211> LENGTH: 15
<212> TYPE: PRT
<213> ORGANISM: Artificial Sequence
<220> FEATURE:
<223> OTHER INFORMATION: CSP Peptide

<400> SEQUENCE: 351

Asn Ala Asn Pro Asn Val Asp Pro Asn Ala Asn Pro Asn Val Asp
1               5                   10                  15

<210> SEQ ID NO 352
<211> LENGTH: 15
<212> TYPE: PRT
<213> ORGANISM: Artificial Sequence
<220> FEATURE:
<223> OTHER INFORMATION: CSP Peptide

<400> SEQUENCE: 352

Ala Asn Pro Asn Val Asp Pro Asn Ala Asn Pro Asn Val Asp Pro
1               5                   10                  15

<210> SEQ ID NO 353
<211> LENGTH: 15
<212> TYPE: PRT
<213> ORGANISM: Artificial Sequence
<220> FEATURE:
<223> OTHER INFORMATION: CSP Peptide

<400> SEQUENCE: 353

Asn Pro Asn Val Asp Pro Asn Ala Asn Pro Asn Val Asp Pro Asn
1               5                   10                  15

<210> SEQ ID NO 354
<211> LENGTH: 15
<212> TYPE: PRT
<213> ORGANISM: Artificial Sequence
<220> FEATURE:
<223> OTHER INFORMATION: CSP Peptide

<400> SEQUENCE: 354

Pro Asn Val Asp Pro Asn Ala Asn Pro Asn Val Asp Pro Asn Ala
1               5                   10                  15

<210> SEQ ID NO 355
<211> LENGTH: 15
<212> TYPE: PRT
<213> ORGANISM: Artificial Sequence
<220> FEATURE:
<223> OTHER INFORMATION: CSP Peptide

<400> SEQUENCE: 355

Asn Val Asp Pro Asn Ala Asn Pro Asn Val Asp Pro Asn Ala Asn
1               5                   10                  15
```

<210> SEQ ID NO 356
<211> LENGTH: 15
<212> TYPE: PRT
<213> ORGANISM: Artificial Sequence
<220> FEATURE:
<223> OTHER INFORMATION: CSP Peptide

<400> SEQUENCE: 356

Val Asp Pro Asn Ala Asn Pro Asn Val Asp Pro Asn Ala Asn Pro
1               5                   10                  15

<210> SEQ ID NO 357
<211> LENGTH: 15
<212> TYPE: PRT
<213> ORGANISM: Artificial Sequence
<220> FEATURE:
<223> OTHER INFORMATION: CSP Peptide

<400> SEQUENCE: 357

Pro Asn Ala Asn Pro Asn Val Asp Pro Asn Ala Asn Pro Asn Ala
1               5                   10                  15

<210> SEQ ID NO 358
<211> LENGTH: 15
<212> TYPE: PRT
<213> ORGANISM: Artificial Sequence
<220> FEATURE:
<223> OTHER INFORMATION: CSP Peptide

<400> SEQUENCE: 358

Asn Ala Asn Pro Asn Val Asp Pro Asn Ala Asn Pro Asn Ala Asn
1               5                   10                  15

<210> SEQ ID NO 359
<211> LENGTH: 15
<212> TYPE: PRT
<213> ORGANISM: Artificial Sequence
<220> FEATURE:
<223> OTHER INFORMATION: CSP Peptide

<400> SEQUENCE: 359

Ala Asn Pro Asn Val Asp Pro Asn Ala Asn Pro Asn Ala Asn Pro
1               5                   10                  15

<210> SEQ ID NO 360
<211> LENGTH: 15
<212> TYPE: PRT
<213> ORGANISM: Artificial Sequence
<220> FEATURE:
<223> OTHER INFORMATION: CSP Peptide

<400> SEQUENCE: 360

Asn Pro Asn Val Asp Pro Asn Ala Asn Pro Asn Ala Asn Pro Asn
1               5                   10                  15

<210> SEQ ID NO 361
<211> LENGTH: 15
<212> TYPE: PRT
<213> ORGANISM: Artificial Sequence
<220> FEATURE:
<223> OTHER INFORMATION: CSP Peptide

<400> SEQUENCE: 361

Pro Asn Val Asp Pro Asn Ala Asn Pro Asn Ala Asn Pro Asn Ala
1               5                   10                  15

```
<210> SEQ ID NO 362
<211> LENGTH: 15
<212> TYPE: PRT
<213> ORGANISM: Artificial Sequence
<220> FEATURE:
<223> OTHER INFORMATION: CSP Peptide

<400> SEQUENCE: 362

Asn Val Asp Pro Asn Ala Asn Pro Asn Ala Asn Pro Asn Ala Asn
1               5                   10                  15

<210> SEQ ID NO 363
<211> LENGTH: 15
<212> TYPE: PRT
<213> ORGANISM: Artificial Sequence
<220> FEATURE:
<223> OTHER INFORMATION: CSP Peptide

<400> SEQUENCE: 363

Val Asp Pro Asn Ala Asn Pro Asn Ala Asn Pro Asn Ala Asn Pro
1               5                   10                  15

<210> SEQ ID NO 364
<211> LENGTH: 15
<212> TYPE: PRT
<213> ORGANISM: Artificial Sequence
<220> FEATURE:
<223> OTHER INFORMATION: CSP Peptide

<400> SEQUENCE: 364

Asp Pro Asn Ala Asn Pro Asn Ala Asn Pro Asn Ala Asn Pro Asn
1               5                   10                  15

<210> SEQ ID NO 365
<211> LENGTH: 15
<212> TYPE: PRT
<213> ORGANISM: Artificial Sequence
<220> FEATURE:
<223> OTHER INFORMATION: CSP Peptide

<400> SEQUENCE: 365

Pro Asn Ala Asn Pro Asn Ala Asn Pro Asn Ala Asn Pro Asn Ala
1               5                   10                  15

<210> SEQ ID NO 366
<211> LENGTH: 15
<212> TYPE: PRT
<213> ORGANISM: Artificial Sequence
<220> FEATURE:
<223> OTHER INFORMATION: CSP Peptide

<400> SEQUENCE: 366

Asn Ala Asn Pro Asn Ala Asn Pro Asn Ala Asn Pro Asn Ala Asn
1               5                   10                  15

<210> SEQ ID NO 367
<211> LENGTH: 15
<212> TYPE: PRT
<213> ORGANISM: Artificial Sequence
<220> FEATURE:
<223> OTHER INFORMATION: CSP Peptide

<400> SEQUENCE: 367

Ala Asn Pro Asn Ala Asn Pro Asn Ala Asn Pro Asn Ala Asn Pro
1               5                   10                  15

<210> SEQ ID NO 368
```

```
<211> LENGTH: 15
<212> TYPE: PRT
<213> ORGANISM: Artificial Sequence
<220> FEATURE:
<223> OTHER INFORMATION: CSP Peptide

<400> SEQUENCE: 368

Asn Pro Asn Ala Asn Pro Asn Ala Asn Pro Asn Ala Asn Pro Asn
1               5                   10                  15

<210> SEQ ID NO 369
<211> LENGTH: 15
<212> TYPE: PRT
<213> ORGANISM: Artificial Sequence
<220> FEATURE:
<223> OTHER INFORMATION: CSP Peptide

<400> SEQUENCE: 369

Pro Asn Ala Asn Pro Asn Ala Asn Pro Asn Ala Asn Pro Asn Val
1               5                   10                  15

<210> SEQ ID NO 370
<211> LENGTH: 15
<212> TYPE: PRT
<213> ORGANISM: Artificial Sequence
<220> FEATURE:
<223> OTHER INFORMATION: CSP Peptide

<400> SEQUENCE: 370

Asn Ala Asn Pro Asn Ala Asn Pro Asn Ala Asn Pro Asn Val Asp
1               5                   10                  15

<210> SEQ ID NO 371
<211> LENGTH: 15
<212> TYPE: PRT
<213> ORGANISM: Artificial Sequence
<220> FEATURE:
<223> OTHER INFORMATION: CSP Peptide

<400> SEQUENCE: 371

Ala Asn Pro Asn Ala Asn Pro Asn Ala Asn Pro Asn Val Asp Pro
1               5                   10                  15

<210> SEQ ID NO 372
<211> LENGTH: 15
<212> TYPE: PRT
<213> ORGANISM: Artificial Sequence
<220> FEATURE:
<223> OTHER INFORMATION: CSP Peptide

<400> SEQUENCE: 372

Asn Pro Asn Ala Asn Pro Asn Ala Asn Pro Asn Val Asp Pro Asn
1               5                   10                  15

<210> SEQ ID NO 373
<211> LENGTH: 15
<212> TYPE: PRT
<213> ORGANISM: Artificial Sequence
<220> FEATURE:
<223> OTHER INFORMATION: CSP Peptide

<400> SEQUENCE: 373

Pro Asn Ala Asn Pro Asn Ala Asn Pro Asn Val Asp Pro Asn Ala
1               5                   10                  15

<210> SEQ ID NO 374
<211> LENGTH: 15
```

```
<212> TYPE: PRT
<213> ORGANISM: Artificial Sequence
<220> FEATURE:
<223> OTHER INFORMATION: CSP Peptide

<400> SEQUENCE: 374

Asn Ala Asn Pro Asn Ala Asn Pro Asn Val Asp Pro Asn Ala Asn
1               5                   10                  15

<210> SEQ ID NO 375
<211> LENGTH: 15
<212> TYPE: PRT
<213> ORGANISM: Artificial Sequence
<220> FEATURE:
<223> OTHER INFORMATION: CSP Peptide

<400> SEQUENCE: 375

Ala Asn Pro Asn Ala Asn Pro Asn Val Asp Pro Asn Ala Asn Pro
1               5                   10                  15

<210> SEQ ID NO 376
<211> LENGTH: 15
<212> TYPE: PRT
<213> ORGANISM: Artificial Sequence
<220> FEATURE:
<223> OTHER INFORMATION: CSP Peptide

<400> SEQUENCE: 376

Asn Pro Asn Ala Asn Pro Asn Val Asp Pro Asn Ala Asn Pro Asn
1               5                   10                  15

<210> SEQ ID NO 377
<211> LENGTH: 15
<212> TYPE: PRT
<213> ORGANISM: Artificial Sequence
<220> FEATURE:
<223> OTHER INFORMATION: CSP Peptide

<400> SEQUENCE: 377

Pro Asn Ala Asn Pro Asn Ala Asn Pro Asn Ala Asn Pro Asn Lys
1               5                   10                  15

<210> SEQ ID NO 378
<211> LENGTH: 15
<212> TYPE: PRT
<213> ORGANISM: Artificial Sequence
<220> FEATURE:
<223> OTHER INFORMATION: CSP Peptide

<400> SEQUENCE: 378

Asn Ala Asn Pro Asn Ala Asn Pro Asn Ala Asn Pro Asn Lys Asn
1               5                   10                  15

<210> SEQ ID NO 379
<211> LENGTH: 15
<212> TYPE: PRT
<213> ORGANISM: Artificial Sequence
<220> FEATURE:
<223> OTHER INFORMATION: CSP Peptide

<400> SEQUENCE: 379

Ala Asn Pro Asn Ala Asn Pro Asn Ala Asn Pro Asn Lys Asn Asn
1               5                   10                  15

<210> SEQ ID NO 380
<211> LENGTH: 15
<212> TYPE: PRT
```

```
<213> ORGANISM: Artificial Sequence
<220> FEATURE:
<223> OTHER INFORMATION: CSP Peptide

<400> SEQUENCE: 380

Asn Pro Asn Ala Asn Pro Asn Ala Asn Pro Asn Lys Asn Asn Gln
1               5                   10                  15

<210> SEQ ID NO 381
<211> LENGTH: 15
<212> TYPE: PRT
<213> ORGANISM: Artificial Sequence
<220> FEATURE:
<223> OTHER INFORMATION: CSP Peptide

<400> SEQUENCE: 381

Pro Asn Ala Asn Pro Asn Ala Asn Pro Asn Lys Asn Asn Gln Gly
1               5                   10                  15

<210> SEQ ID NO 382
<211> LENGTH: 15
<212> TYPE: PRT
<213> ORGANISM: Artificial Sequence
<220> FEATURE:
<223> OTHER INFORMATION: CSP Peptide

<400> SEQUENCE: 382

Asn Ala Asn Pro Asn Ala Asn Pro Asn Lys Asn Asn Gln Gly Asn
1               5                   10                  15

<210> SEQ ID NO 383
<211> LENGTH: 15
<212> TYPE: PRT
<213> ORGANISM: Artificial Sequence
<220> FEATURE:
<223> OTHER INFORMATION: CSP Peptide

<400> SEQUENCE: 383

Ala Asn Pro Asn Ala Asn Pro Asn Lys Asn Asn Gln Gly Asn Gly
1               5                   10                  15

<210> SEQ ID NO 384
<211> LENGTH: 15
<212> TYPE: PRT
<213> ORGANISM: Artificial Sequence
<220> FEATURE:
<223> OTHER INFORMATION: CSP Peptide

<400> SEQUENCE: 384

Asn Pro Asn Ala Asn Pro Asn Lys Asn Asn Gln Gly Asn Gly Gln
1               5                   10                  15

<210> SEQ ID NO 385
<211> LENGTH: 15
<212> TYPE: PRT
<213> ORGANISM: Artificial Sequence
<220> FEATURE:
<223> OTHER INFORMATION: CSP Peptide

<400> SEQUENCE: 385

Pro Asn Ala Asn Pro Asn Lys Asn Asn Gln Gly Asn Gly Gln Gly
1               5                   10                  15
```